US008628792B2

(12) United States Patent  
Utkhede et al.

(10) Patent No.: US 8,628,792 B2  
(45) Date of Patent: Jan. 14, 2014

(54) DRUG CORES FOR SUSTAINED RELEASE OF THERAPEUTIC AGENTS

(75) Inventors: Deepank Utkhede, Surrey (CA); Robert W. Shimizu, Laguna Niguel, CA (US); Rachna Jain, Milpitas, CA (US); Stephen Boyd, Murrieta, CA (US); Hanson S. Gifford, Woodside, CA (US); Eugene De Juan, Jr., San Francisco, CA (US); Cary J. Reich, Los Gatos, CA (US)

(73) Assignee: Mati Therapeutics, Inc., Austin, TX (US)

(*) Notice: Subject to any disclaimer, the term of this patent is extended or adjusted under 35 U.S.C. 154(b) by 0 days.

(21) Appl. No.: 13/367,823

(22) Filed: Feb. 7, 2012

(65) Prior Publication Data

US 2012/0187594 A1 Jul. 26, 2012

Related U.S. Application Data

(63) Continuation of application No. 12/231,986, filed on Sep. 5, 2008.

(60) Provisional application No. 61/049,317, filed on Apr. 30, 2008, provisional application No. 60/970,820, filed on Sep. 7, 2007, provisional application No. 60/970,699, filed on Sep. 7, 2007, provisional application No. 60/970,709, filed on Sep. 7, 2007.

(51) Int. Cl.
*A61F 2/00* (2006.01)
*B28B 11/12* (2006.01)

(52) U.S. Cl.
USPC .......................................... 424/423; 264/157

(58) Field of Classification Search
None
See application file for complete search history.

(56) References Cited

U.S. PATENT DOCUMENTS

| | | |
|---|---|---|
| 3,828,777 A | 8/1974 | Ness |
| 3,865,108 A | 2/1975 | Hartop |
| 3,949,750 A | 4/1976 | Freeman |
| 4,014,335 A | 3/1977 | Arnold |
| 4,205,128 A * | 5/1980 | Ishimatsu et al. ............. 435/182 |
| 4,281,654 A | 8/1981 | Shell et al. |
| 4,322,323 A | 3/1982 | Capozza |
| 4,660,546 A | 4/1987 | Herrick et al. |
| 4,886,488 A | 12/1989 | White |
| 4,888,074 A * | 12/1989 | Pocknell ....................... 156/217 |
| 4,915,684 A | 4/1990 | MacKeen et al. |
| 4,959,048 A | 9/1990 | Seder et al. |
| 5,041,081 A | 8/1991 | Odrich |
| 5,049,142 A | 9/1991 | Herrick et al. |
| 5,053,030 A | 10/1991 | Herrick et al. |
| 5,098,443 A | 3/1992 | Parel et al. |
| 5,116,371 A | 5/1992 | Christensen et al. |
| 5,128,058 A | 7/1992 | Ishii et al. |
| 5,133,159 A | 7/1992 | Nelson |
| 5,163,959 A | 11/1992 | Herrick |
| 5,171,270 A | 12/1992 | Herrick |
| 5,283,063 A | 2/1994 | Freeman |
| 5,318,513 A | 6/1994 | Leib et al. |
| 5,334,137 A | 8/1994 | Freeman |
| 5,395,618 A | 3/1995 | Darougar et al. |
| 5,417,651 A | 5/1995 | Guena et al. |
| 5,417,744 A * | 5/1995 | Gasmena ....................... 106/2 |
| 5,423,777 A | 6/1995 | Tajiri et al. |
| 5,426,166 A * | 6/1995 | Usifer et al. ................. 526/301 |
| 5,466,233 A | 11/1995 | Weiner et al. |
| 5,556,633 A | 9/1996 | Haddad et al. |
| 5,707,643 A | 1/1998 | Ogura et al. |
| 5,723,005 A | 3/1998 | Herrick |
| 5,741,292 A | 4/1998 | Mendius |
| 5,766,243 A | 6/1998 | Christensen et al. |
| 5,770,589 A | 6/1998 | Billson et al. |
| 5,773,019 A | 6/1998 | Ashton et al. |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,961,370 A | 10/1999 | Valle et al. |
| 5,962,383 A | 10/1999 | Doyel et al. |

(Continued)

FOREIGN PATENT DOCUMENTS

| | | |
|---|---|---|
| AU | 20023644336 | 7/2003 |
| EP | 0442745 A1 | 8/1991 |

(Continued)

OTHER PUBLICATIONS

Vozzi, Giovanni, et al., Biomaterials, 24 (2003) pp. 2533-2540.*
Free Online Dictionary, Room Temperature, accessed Sep. 5, 2012, p. 1.*
International Search Report and Written Opinion, issued in PCT/US2008/010497, mail date Mar. 6, 2009, 20 pages.
International Search Report and Written Opinion, issued in PCT/US2008/010502, mail date Mar. 5, 2009, 19 pages.
Communication Article 94(3) EPC Examination Report, issued in EP Patent Application 08830451.4, dated Nov. 5, 2010.
U.S. Appl. No. 10/825,047, Response filed Oct. 22, 2009 to Final Office Action mailed Jun. 9, 2009, 20 pgs.

(Continued)

*Primary Examiner* — Scott Long
*Assistant Examiner* — Lyndsey Beckhardt

(57) ABSTRACT

A solid drug core insert can be manufactured by injecting a liquid mixture comprising a therapeutic agent and a matrix precursor into a sheath body. The injection can be conducted at subambient temperatures. The mixture is cured to form a solid drug-matrix core. The therapeutic agent can be a liquid at about room temperature that forms a dispersion of droplets in the matrix material. A surface of the solid drug core is exposed, for example by cutting the tube, and the exposed surface of the solid drug core releases therapeutic quantities of the therapeutic agent when implanted into the patient. In some embodiments, the insert body inhibits release of the therapeutic agent, for example with a material substantially impermeable to the therapeutic agent, such that the therapeutic quantities are released through the exposed surface, thereby avoiding release of the therapeutic agent to non-target tissues.

27 Claims, 50 Drawing Sheets

(56) References Cited

U.S. PATENT DOCUMENTS

| | | |
|---|---|---|
| 5,993,407 A | 11/1999 | Moazed |
| 6,010,391 A | 1/2000 | Lewellen et al. |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson et al. |
| 6,117,441 A | 9/2000 | Moo-Young et al. |
| 6,149,684 A | 11/2000 | Herrick |
| 6,196,993 B1 | 3/2001 | Cohan et al. |
| 6,234,175 B1 | 5/2001 | Zhou et al. |
| 6,238,363 B1 | 5/2001 | Kurihashi |
| 6,254,562 B1 | 7/2001 | Fouere |
| 6,264,971 B1 | 7/2001 | Darougar et al. |
| 6,290,684 B1 | 9/2001 | Herrick |
| 6,306,114 B1 | 10/2001 | Freeman et al. |
| 6,331,313 B1 | 12/2001 | Wong et al. |
| 6,344,047 B1 | 2/2002 | Price |
| 6,371,122 B1 | 4/2002 | Mandelkorn |
| 6,375,972 B1 | 4/2002 | Guo et al. |
| 6,383,192 B1 | 5/2002 | Kurihashi |
| 6,428,502 B1 | 8/2002 | Lang |
| 6,455,062 B1 | 9/2002 | Olejnik et al. |
| 6,605,108 B2 | 8/2003 | Mendius et al. |
| 6,629,533 B1 | 10/2003 | Webb et al. |
| 6,645,963 B2 | 11/2003 | Higashiyama et al. |
| 6,699,282 B1 | 3/2004 | Sceusa |
| 6,706,034 B1 | 3/2004 | Bhat |
| 6,706,275 B1 | 3/2004 | Camp |
| 6,729,939 B2 | 5/2004 | Wrue |
| 6,756,049 B2 | 6/2004 | Brubaker et al. |
| 6,780,164 B2 | 8/2004 | Bergheim et al. |
| 6,840,931 B2 | 1/2005 | Peterson et al. |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker et al. |
| 6,994,684 B2 | 2/2006 | Murray et al. |
| 7,017,580 B2 | 3/2006 | Prescott et al. |
| 7,117,870 B2 | 10/2006 | Prescott |
| 7,135,009 B2 | 11/2006 | Tu et al. |
| 7,198,205 B1 * | 4/2007 | Solomon et al. ............... 239/337 |
| 7,204,253 B2 | 4/2007 | Mendius et al. |
| 7,204,995 B2 | 4/2007 | El-Sherif et al. |
| 2002/0002362 A1 * | 1/2002 | Humayun et al. ............ 604/521 |
| 2002/0032400 A1 | 3/2002 | Moazed |
| 2002/0055701 A1 | 5/2002 | Fischell et al. |
| 2002/0151960 A1 | 10/2002 | Mendius et al. |
| 2002/0193441 A1 | 12/2002 | Robertson |
| 2002/0198453 A1 | 12/2002 | Herrick, II |
| 2003/0130612 A1 | 7/2003 | Moazed |
| 2004/0102729 A1 | 5/2004 | Haffner et al. |
| 2004/0121014 A1 | 6/2004 | Guo et al. |
| 2004/0127843 A1 | 7/2004 | Tu et al. |
| 2004/0137068 A1 | 7/2004 | Bhushan |
| 2004/0141151 A1 | 7/2004 | Gillespie |
| 2004/0147870 A1 | 7/2004 | Burns et al. |
| 2004/0170685 A1 | 9/2004 | Carpenter et al. |
| 2004/0175410 A1 | 9/2004 | Ashton et al. |
| 2004/0180075 A1 | 9/2004 | Robinson et al. |
| 2004/0208910 A1 | 10/2004 | Ashton |
| 2004/0210182 A1 | 10/2004 | Fouere et al. |
| 2004/0236343 A1 | 11/2004 | Taylor et al. |
| 2004/0249333 A1 | 12/2004 | Bergheim et al. |
| 2004/0254516 A1 | 12/2004 | Murray |
| 2004/0265356 A1 | 12/2004 | Mosack |
| 2005/0048121 A1 | 3/2005 | East et al. |
| 2005/0095269 A1 | 5/2005 | Ainpour et al. |
| 2005/0129731 A1 | 6/2005 | Horres et al. |
| 2005/0192527 A1 | 9/2005 | Gharib |
| 2005/0197614 A1 | 9/2005 | Pritchard et al. |
| 2005/0220882 A1 | 10/2005 | Pritchard et al. |
| 2005/0232972 A1 | 10/2005 | Odrich et al. |
| 2005/0244469 A1 | 11/2005 | Whitcup et al. |
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 | 1/2006 | Prescott |
| 2006/0074370 A1 | 4/2006 | Zhou |
| 2006/0100700 A1 | 5/2006 | Bernard et al. |
| 2006/0106352 A1 | 5/2006 | Kurihashi |
| 2006/0122553 A1 | 6/2006 | Hanna |
| 2006/0149194 A1 * | 7/2006 | Conston et al. ............... 604/294 |
| 2007/0043332 A1 | 2/2007 | Malcolm et al. |
| 2007/0083146 A1 | 4/2007 | Murray |
| 2007/0123924 A1 | 5/2007 | Becker |
| 2007/0132125 A1 | 6/2007 | Rastogi et al. |
| 2007/0135914 A1 | 6/2007 | Herrick, II |
| 2007/0243230 A1 | 10/2007 | de Juan et al. |
| 2007/0269487 A1 | 11/2007 | de Juan et al. |
| 2007/0298075 A1 | 12/2007 | Borgia et al. |
| 2007/0299515 A1 | 12/2007 | Herrick, II |
| 2007/0299516 A1 | 12/2007 | Cui |
| 2008/0038317 A1 | 2/2008 | Chang et al. |
| 2008/0045878 A1 | 2/2008 | Bergheim et al. |
| 2008/0045911 A1 | 2/2008 | Borgia et al. |
| 2009/0092654 A1 | 4/2009 | de Juan, Jr. et al. |
| 2009/0104243 A1 | 4/2009 | Utkhede et al. |
| 2009/0104248 A1 | 4/2009 | Rapacki et al. |
| 2009/0105749 A1 | 4/2009 | de Juan, Jr. et al. |
| 2009/0118702 A1 | 5/2009 | Lazar |
| 2009/0280158 A1 | 11/2009 | Butuner |

FOREIGN PATENT DOCUMENTS

| | | |
|---|---|---|
| EP | 0621022 A1 | 10/1994 |
| EP | 0988844 A2 | 3/2000 |
| JP | 10-033584 | 2/1998 |
| JP | 2004-202276 | 7/2004 |
| JP | 2005-000628 | 1/2005 |
| JP | 2005-058622 | 3/2005 |
| JP | 2005-110765 | 4/2005 |
| JP | 2005-110930 | 4/2005 |
| JP | 2005-312835 | 11/2005 |
| JP | 2005-319190 | 11/2005 |
| JP | 2005-328922 | 12/2005 |
| JP | 2007-195819 | 8/2007 |
| WO | WO-98/33461 A1 | 8/1998 |
| WO | WO-98/42282 A1 | 10/1998 |
| WO | WO-99/37260 A1 | 7/1999 |
| WO | WO-99/44553 A1 | 9/1999 |
| WO | WO-99/64089 A1 | 12/1999 |
| WO | WO-99/65544 A1 | 12/1999 |
| WO | WO-00/27321 A1 | 5/2000 |
| WO | WO-00/62760 A1 | 10/2000 |
| WO | WO-02/11783 A1 | 2/2002 |
| WO | WO-02/058667 A2 | 8/2002 |
| WO | WO-02/083198 A2 | 10/2002 |
| WO | WO-03/017897 A2 | 3/2003 |
| WO | WO-03/022242 A1 | 3/2003 |
| WO | WO-03/057101 A1 | 7/2003 |
| WO | WO-2004/004614 A2 | 1/2004 |
| WO | WO-2004/024043 A2 | 3/2004 |
| WO | WO-2004/105658 A1 | 12/2004 |
| WO | WO-2004/112639 A2 | 12/2004 |
| WO | WO-2005/000154 A1 | 1/2005 |
| WO | WO-2005/086694 A2 | 9/2005 |
| WO | WO-2006/014434 A2 | 2/2006 |
| WO | WO-2006/014793 A1 | 2/2006 |
| WO | WO-2006/031658 A2 | 3/2006 |
| WO | WO-2006/044669 A2 | 4/2006 |
| WO | WO-2006/057859 A1 | 6/2006 |
| WO | WO-2006/096586 A1 | 9/2006 |
| WO | WO-2007/008262 A2 | 1/2007 |
| WO | WO-2007/115259 A2 | 10/2007 |
| WO | WO-2007/115261 A2 | 10/2007 |
| WO | WO-2007/149771 A2 | 12/2007 |
| WO | WO-2007/149832 A2 | 12/2007 |
| WO | WO-2008/056060 A2 | 5/2008 |
| WO | WO-2008/094989 A2 | 8/2008 |
| WO | WO-2009/012406 A1 | 1/2009 |

(56) References Cited

FOREIGN PATENT DOCUMENTS

| WO | WO-2009/035562 A2 | 3/2009 |
|----|-------------------|--------|
| WO | WO-2009/134371 A2 | 11/2009 |
| WO | WO-2009/137085 A1 | 11/2009 |

OTHER PUBLICATIONS

U.S. Appl. No. 11/571,147, Preliminary Amendment and Response filed Dec. 21, 2009 to Restriction Requirement mailed Jun. 26, 2009, 9 pgs.
U.S. Appl. No. 11/695,537, Non-Final Office Action mailed Sep. 18, 2009, 12 pgs.
U.S. Appl. No. 12/604,202, Preliminary Amendment filed Nov. 30, 2009, 6 pgs.
U.S. Appl. No. 10/825,047, Non-Final Office Action mailed Dec. 28, 2009, 22 pgs.
Oasis Product Catalog, Apr. 2009, 7 pgs.
Production Information for EaglePlug® TearFlow™, © 2009 EagleVision, Inc., Memphis, TN, 2009, 1 pg.
Production Information for the Micro Flow™ Punctal Occluder, Odyssey Medical, 2009, 1 pg.
U.S. Appl. No. 10/825,047, Final Office Action mailed Jun. 9, 2009, 14 pgs.
U.S. Appl. No. 11/571,147, Restriction Requirement mailed Jun. 26, 2009, 5 pgs.
Chinese Application U.S. Appl. No. 200580028979.2, Response filed Jun. 24, 2009 to Office Action mailed Dec. 12, 2008, (w/ English Translation of Claims), 15 pgs.
Chinese Application Serial No. 200580028979.2, Office Action mailed Aug. 7, 2009, 3 pgs.
U.S. Appl. No. 10/825,047, Response filed Apr. 22, 2009 to Non-Final Office Action mailed Oct. 22, 2008, 17 pgs.
U.S. Appl. No. 10/825,047, Response filed Aug. 18, 2008 to Restriction Requirement mailed Jul. 17, 2008, 10 pgs.
U.S. Appl. No. 10/825,047, Restriction Requirement mailed Jul. 17, 2008, 6 pgs.
U.S. Appl. No. 10/825,047, Non-Final Office Action mailed Oct. 22, 2008, 13 pgs.
U.S. Appl. No. 11/695,537, Notice mailed Nov. 28, 2008 Regarding a Noncompliant or Nonresponsive Amendment filed on Nov. 3, 2008, 3 pgs.
U.S. Appl. No. 11/695,537, Restriction Requirement mailed Oct. 3, 2008, 10 pgs.
U.S. Appl. No. 11/695,537, Response filed Nov. 3, 2008 to Restriction Requirement mailed Oct. 3, 2008, 15 pgs.
U.S. Appl. No. 11/695,537, Response filed Dec. 17, 2008 to Office Communication mailed Nov. 28, 2008, 8 pgs.
U.S. Appl. No. 11/695,545, Preliminary Amendment and Response filed Nov. 6, 2008 to Restriction Requirement mailed Oct. 6, 2008, 14 pgs.
U.S. Appl. No. 11/695,545, Restriction Requirement mailed Oct. 6, 2008, 10 pgs.
Chinese Application No. 200580028979.2, Office Action mailed Dec. 12, 2008, 7 pgs.
European Application Serial No. 05768122.3, Office Action mailed on Mar. 31, 2009, 3 pgs.
European Application Serial No. 05768122.3, Office Action mailed on Apr. 17, 2009, 6 pgs.
International Application Serial No. PCT/US07/65792, International Search Report mailed on Nov. 20, 2008, 2 pgs.
International Application Serial No. PCT/US07/65792, International Written Opinion mailed on Nov. 20, 2008, 5 pgs.
International Application Serial No. PCT/US2007/065789, International Search Report mailed on Aug. 13, 2008, 3 pgs.
International Application Serial No. PCT/US2007/065789, Written Opinion mailed on Aug. 13, 2008, 5 pgs.
International Application Serial No. PCT/US2008/010479, International Search Report mailed Dec. 15, 2008, 6 pgs.
International Application Serial No. PCT/US2008/010479, Written Opinion mailed Dec. 15, 2008, 7 pgs.
International Application Serial No. PCT/US2008/010487, International Search Report mailed May 25, 2009, 5 pgs.
International Application Serial No. PCT/US2008/010487, Written Opinion mailed May 25, 2009, 8 pgs.
Israel Application No. 194515, Office Action mailed Apr. 5, 2009, 1 pg.
De Juan, Jr., E., et al., "Expandable Nasolacrimal Drainage System Implants", U.S. Appl. No. 60/970,696, filed Sep. 7, 2007, 82 pgs.
De Juan, Jr., E., et al., "Manufacture of Expandable Nasolacrimal Drainage System Implants", U.S. Appl. No. 60/970,720, filed Sep. 7, 2007, 57 pgs.
De Juan, Jr., E., et al., "Multiple Drug Delivery Systems and Combinations of Drugs With Punctal Implants", U.S. Appl. No. 60/970 820, filed Sep. 7, 2007, 67 pgs.
Fukano, Y., et al., "Influence of Benzalkonium Chloride on the Penetration of Latanoprost into Rabbit Aqueous Humor After Ocular Instillations", *AAPS Journal*, vol. 8(S2), (Abstract No. 1397), 2006, 1 pg.
Goskonda, V. R., et al., "Permeability of Chemical Delivery Systems Across Rabbit Corneal (SIRC) Cell Line and Isolated Corneas: A Comparative Study", *Pharmaceutical Development and Technology*, 5(3), (Abstract Only), Jul. 2000, 1 pg.
Kaur, I. P., et al., "Chapter 25—Ocular Penetration Enhancers", *In: Enhancement in Drug Delivery*, Toutou, E., et al., Editors, CRC Press, Boca Raton, FL, 2007, 527-548.
Lazar, E., "Treatment Medium Delivery Device and Methods for Delivery of Such Treatment Mediums to the Eye Using Such a Delivery Device", U.S. Appl. No. 11/571,147, filed Dec. 21, 2006, 32 pgs.
Nakajima, M., et al., "Assessment of Drug Concentrations in Tears in Therapeutic Drug Monitoring: I. Determination of Valproic Acid in Tears by Gas Chromatography/Mass Spectrometry With EC/NCI Mode", *Therapeutic Drug Monitoring*, 22, 2000, 716-722.
Reich, C., et al., "Nasolacrimal Drainage System Implants for Drug Delivery", U.S. Appl. No. 60/970,709, filed Sep. 7, 2007, 103 pgs.
Reich, C., et al., "Manufacture of Drug Cores for Sustained Release of Therapeutic Agents", U.S. Appl. No. 60/970,699, filed Sep. 7, 2007, 66 pgs.
Official Action as issued for Russian Patent Application No. 2010112426, dated Jun. 7, 2012.

\* cited by examiner

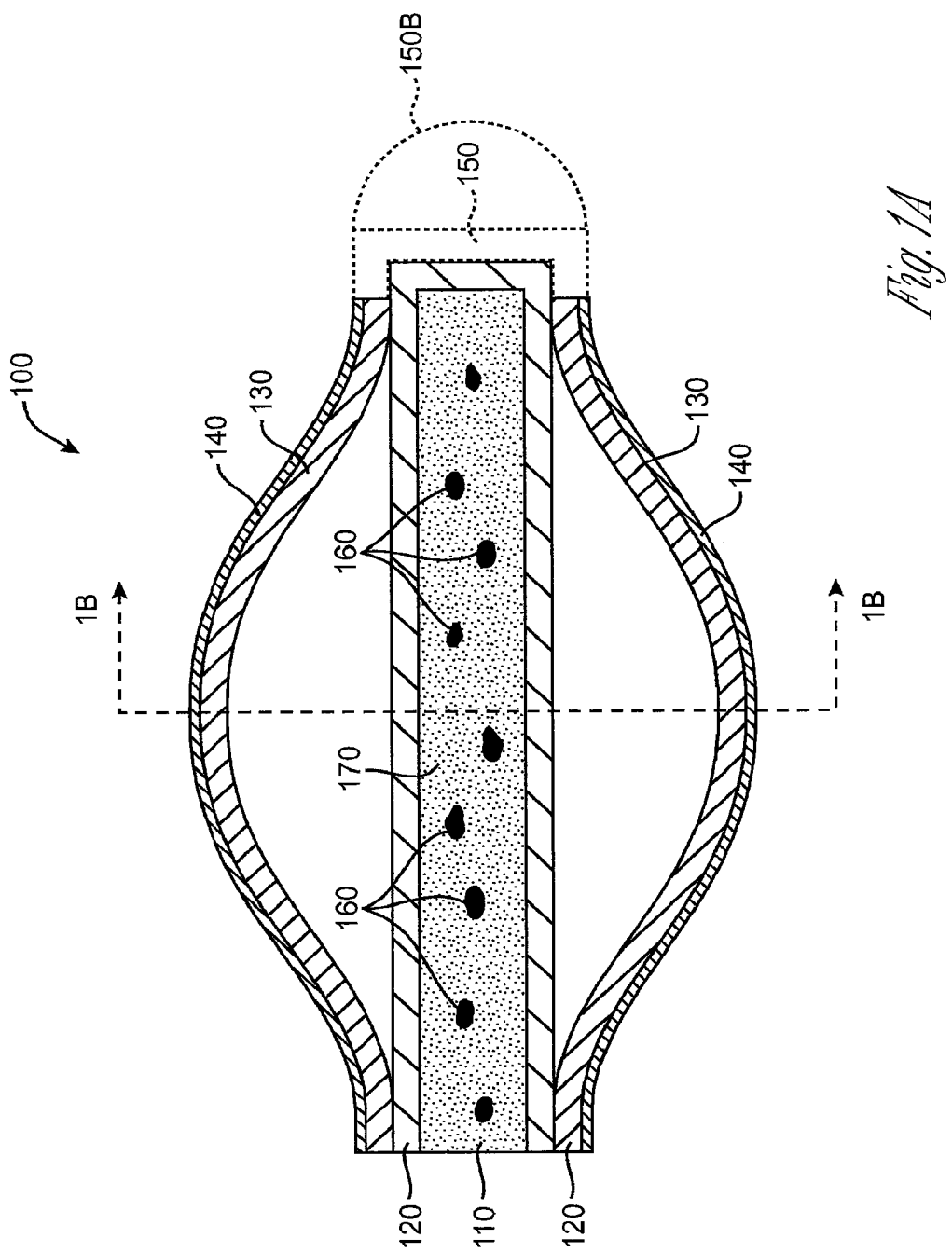

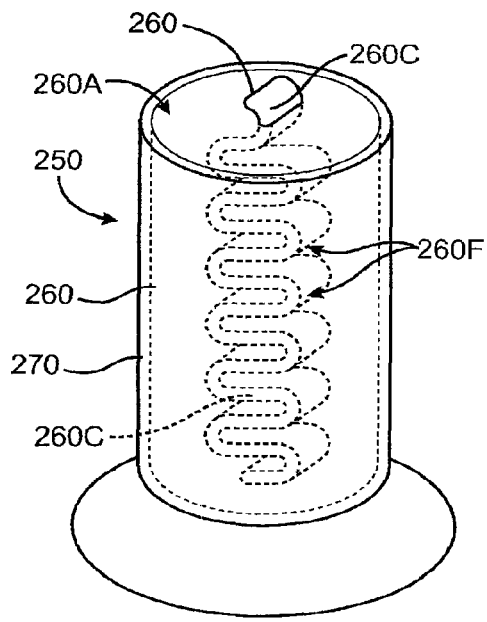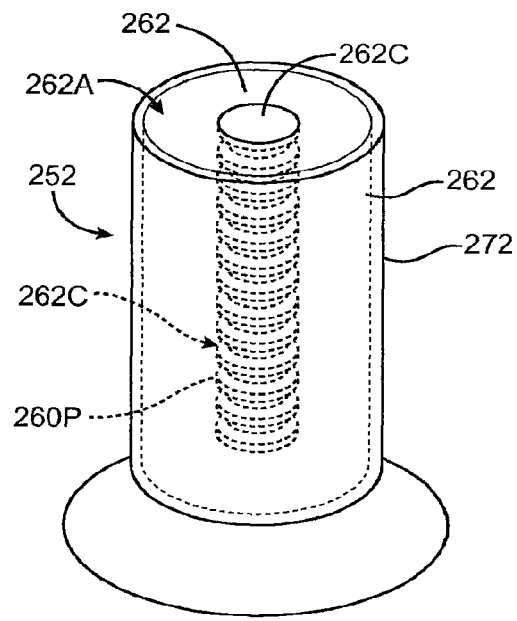
Fig.2F    Fig.2G
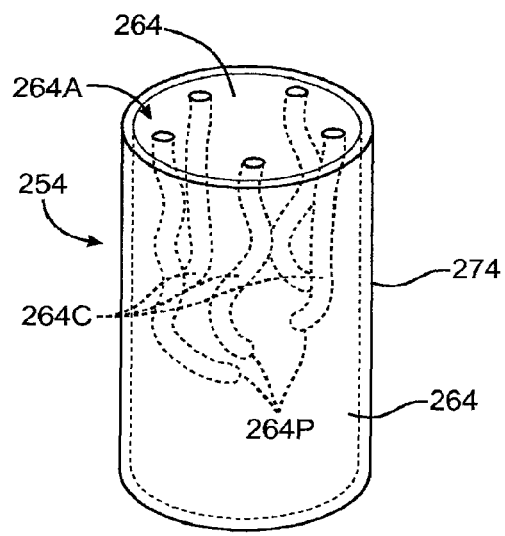
Fig.2H

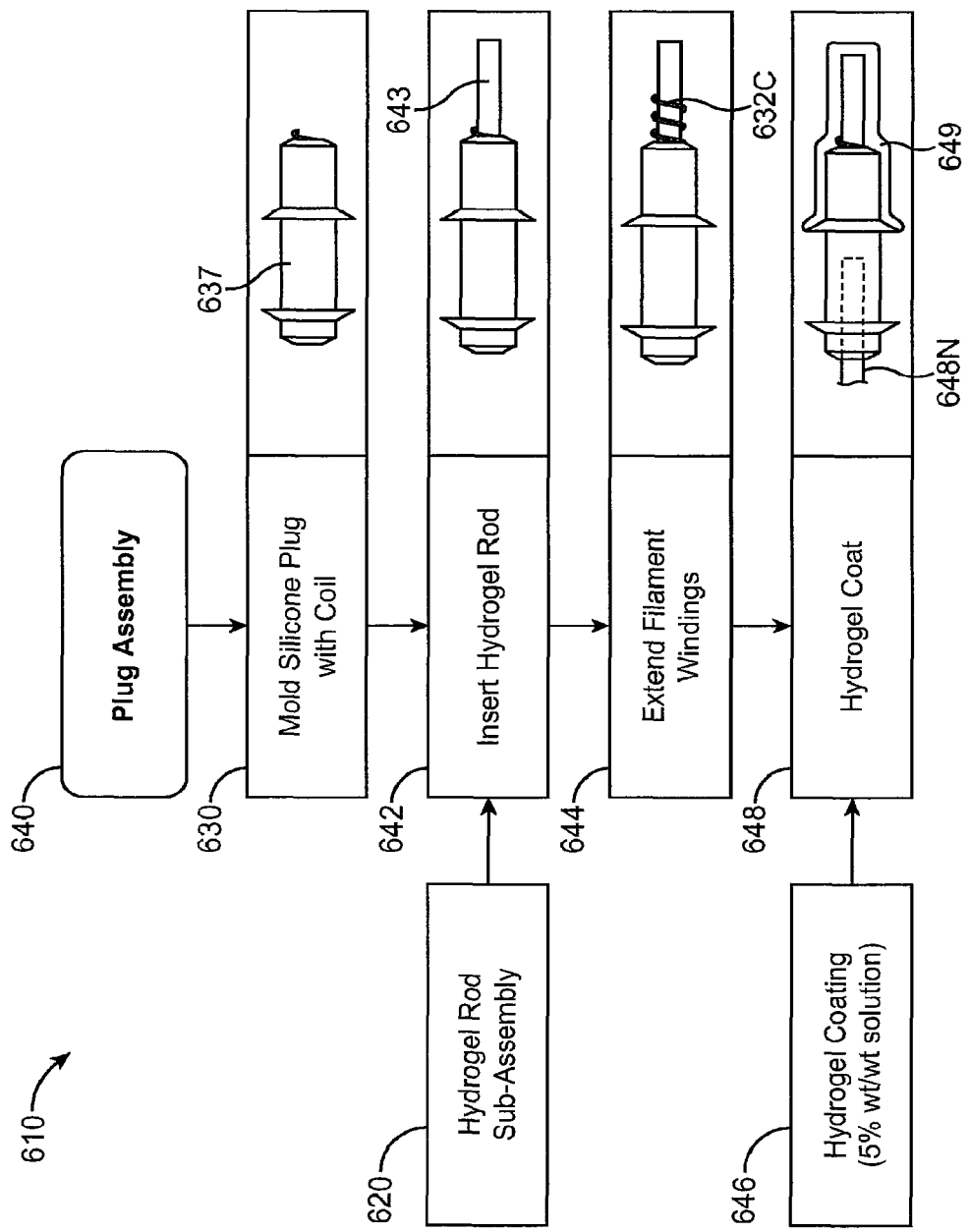

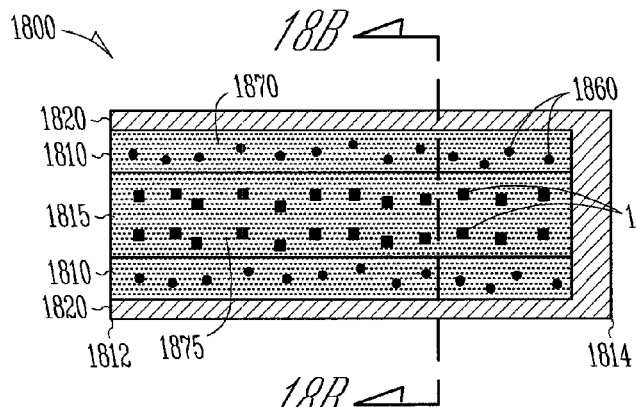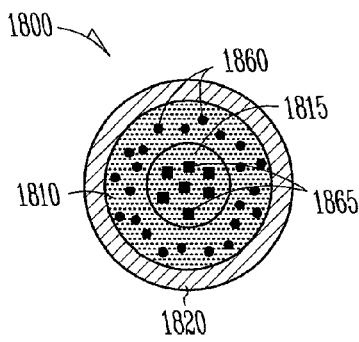
Fig.18A  Fig.18B
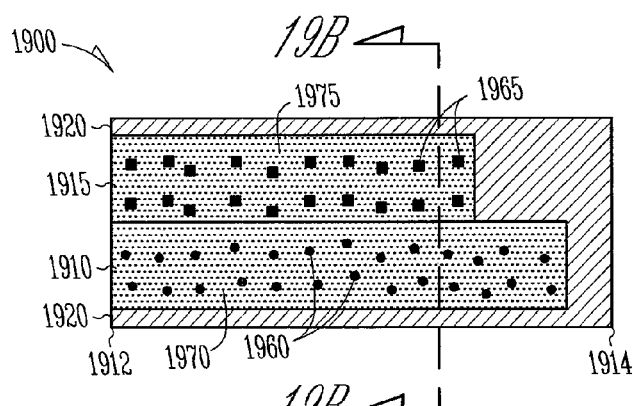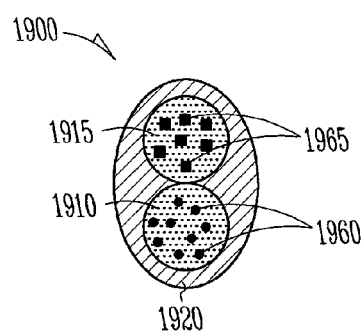
Fig.19A  Fig.19B
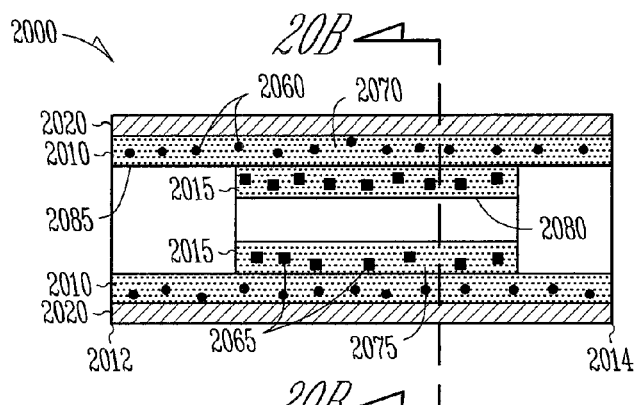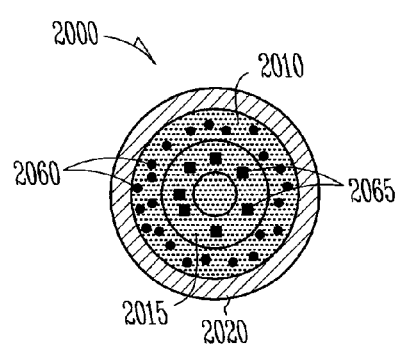
Fig.20A  Fig.20B

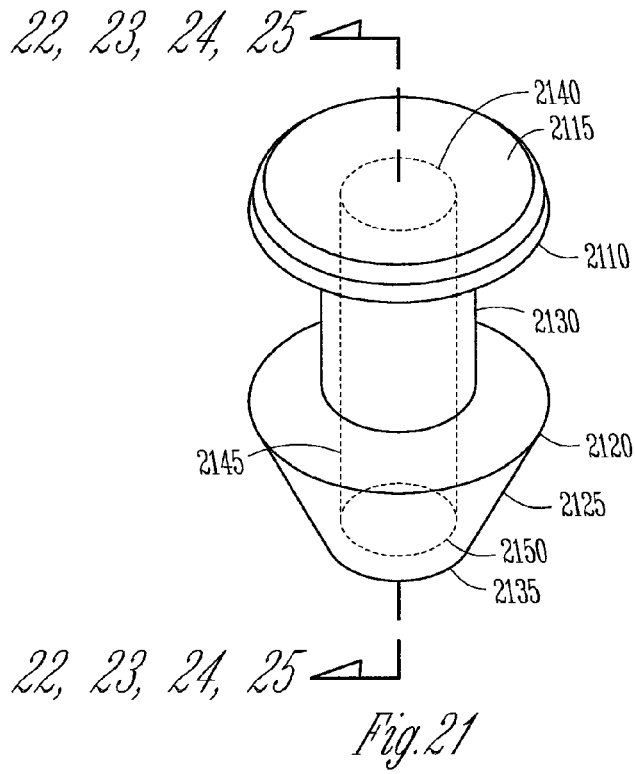
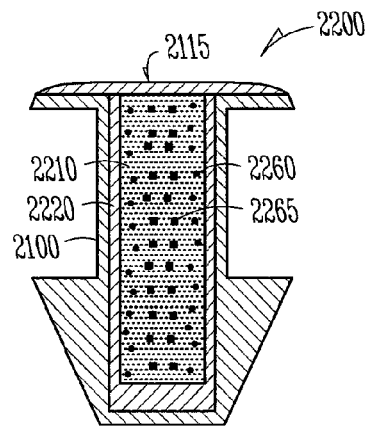
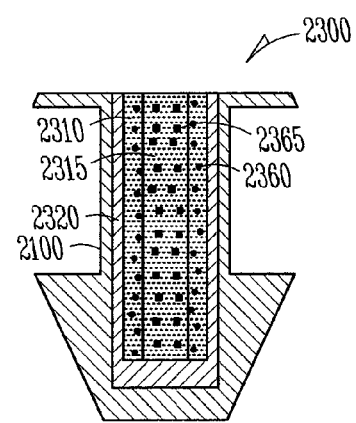
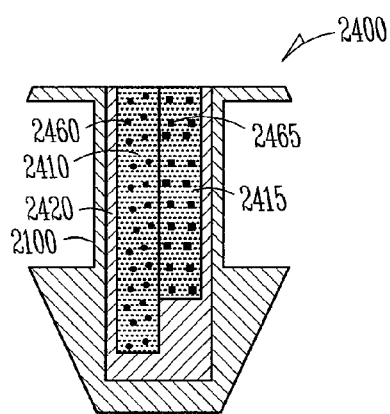
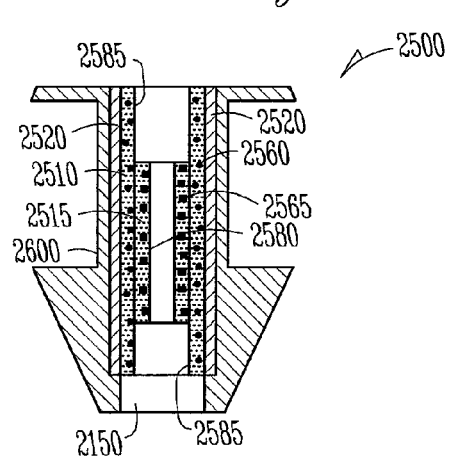

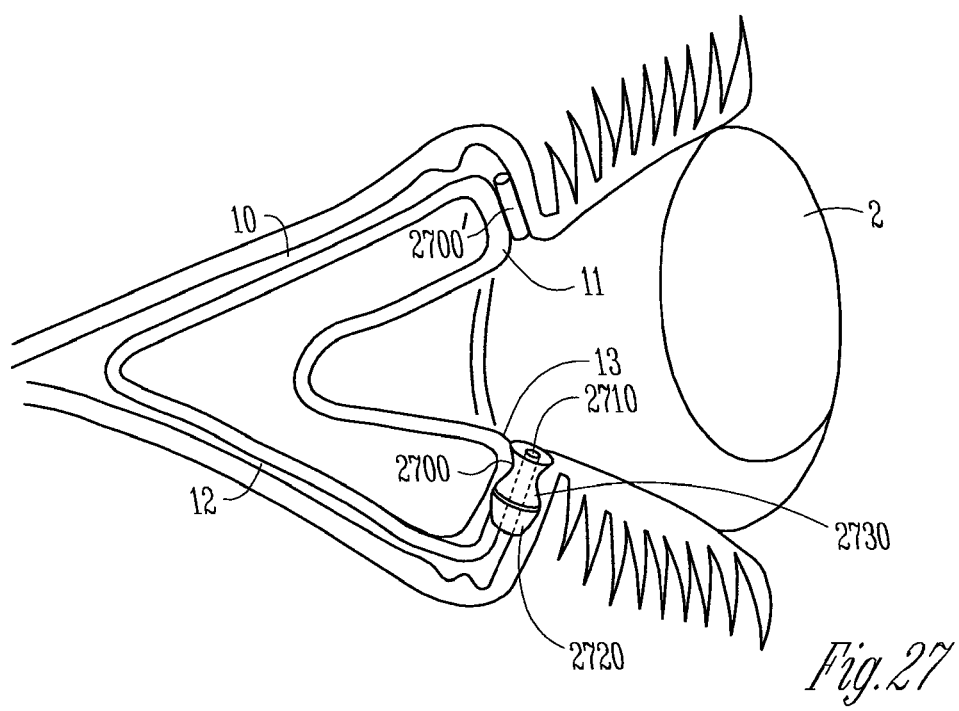

DRUG CORES FOR SUSTAINED RELEASE OF THERAPEUTIC AGENTS

CROSS-REFERENCES TO RELATED APPLICATIONS

This application is a divisional application under 35 U.S.C. §121 of U.S. patent application Ser. No. 12/231,986, filed Sep. 5, 2008, which claims the benefit of priority under 35 U.S.C. §119(e) to U.S. Provisional Patent Application Ser. Nos. 60/970,699, filed Sep. 7, 2007; 60/970,709, filed Sep. 7, 2007; 60/970,820, filed Sep. 7, 2007; and 61/049,317, filed Apr. 30, 2008, which are all incorporated herein by reference in their entireties.

The subject matter of this application is related to that of U.S. patent application Ser. No. 11/695,537, filed on Apr. 2, 2007, published as U.S. Patent Application Publication No. 2007/0269487 on Nov. 22, 2007, which claims the benefit of U.S. Provisional Application No. 60/871,864, filed on Dec. 26, 2006, the disclosures of which are incorporated herein by reference in their entireties.

The subject matter of this application is related to that of U.S. Pat. App. No. 61/057,246, filed on May 30, 2008 and U.S. Pat. App. No. 61/132,927, filed on Jun. 24, 2008, and U.S. patent application Ser. No. 12/231,989, filed Sep. 8, 2008, entitled "LACRIMAL IMPLANTS AND RELATED METHODS," and published as U.S. Patent Application Publication No. 2009/0104248 on Apr. 23, 2009.

BACKGROUND

A variety of challenges face patients and physicians in the area of drug delivery, for example, ocular drug delivery. In particular, the repetitive nature of the therapies (multiple injections, instilling multiple eye drop regimens per day), the associated costs, and the lack of patient compliance may significantly impact the efficacy of the therapies available, leading to reduction in vision and many times blindness.

Patient compliance in taking the medications, for example, instilling the eye drops, can be erratic, and in some cases, patients may not follow the directed treatment regime. Lack of compliance can include, failure to instill the drops, ineffective technique (instilling less than required), excessive use of the drops (leading to systemic side effects), and use of non-prescribed drops or failure to follow the treatment regime requiring multiple types of drops. Many of the medications may require the patient to instill them up to 4 times a day.

In addition to compliance, the cost of at least some eye drop medications is increasing, leading some patients on limited incomes to be faced with the choice of buying basic necessities or instead getting their prescriptions filled. Many times insurance does not cover the total cost of the prescribed eye drop medication, or in some cases eye drops containing multiple different medications.

Further, in many cases, topically applied medications have a peak ocular effect within about two hours, after which additional applications of the medications should be performed to maintain the therapeutic benefit. In addition, inconsistency in self-administered or ingested medication regimes can result in a suboptimal therapy. PCT Publication WO 06/014434 (Lazar), which is incorporated herein by reference in its entirety, may be relevant to these and/or other issues associated with eye drops.

One promising approach to ocular drug delivery is to place an implant that releases a drug in tissue near the eye. Although this approach can offer some improvement over eye drops, some potential problems of this approach may include implantation of the implant at the desired tissue location, retention of the implant at the desired tissue location, and sustaining release of the drug at the desired therapeutic level for an extended period of time. For example in the case of glaucoma treatment, visits to the treating physician can be months apart, and premature depletion and/or premature release of a drug from an implant can result in insufficient drug being delivered for a portion of the treatment period. This can result in the patient potentially suffering a reduction in vision or blindness.

In light of the above, it would be desirable to provide for the manufacture of improved drug delivery implants that overcome at least some of the above mentioned shortcomings.

SUMMARY

The present invention is directed to various embodiments of drug inserts and drug cores containing therapeutic agents for use in implant bodies adapted for disposition in a body tissue, fluid, cavity, or duct. The implant bodies can be adapted to be disposed in or adjacent to an eye of a patient. The implants release the agent to the body, for example, into an eye or surrounding tissues, or both, over a period of time, for treatment of a malcondition in the patient for which use of the therapeutic agent is medically indicated. The invention is also directed to various embodiments of methods of manufacture of the drug inserts and drug cores, and to methods of treatment of patients using implants containing the drug inserts or drug inserts.

In various embodiments, the invention provides a drug insert adapted for disposition within an implant, the implant being adapted for disposition within or adjacent to an eye of a patient, the drug insert comprising a drug core that can include a sheath body partially covering the drug core, the drug core comprising a therapeutic agent and a matrix wherein the matrix comprises a polymer, the sheath body being disposed over a portion of the drug core to control the release of the agent from said portion and so as to define at least one exposed surface of the drug core adapted to release the agent, or any combination thereof, when the implant is inserted into the patient, wherein an amount of the therapeutic agent in a volumetric portion of the drug core is similar to an amount of the therapeutic agent in any other equal volumetric portion of the drug core. For example, the therapeutic agent may be uniformly and homogeneously dispersed throughout the matrix, or the therapeutic agent at least in part forms solid or liquid inclusions within the matrix. For example, the amount of the therapeutic agent within the volumetric portion of the drug core may vary from the amount of the therapeutic agent within any other equal volumetric portion of the drug core by no greater than about 30%. For example, the amount of the therapeutic agent within the volumetric portion of the drug core varies from the amount of the therapeutic agent within any other equal volumetric portion of the drug core by no greater than about 20%. For example, the amount of the therapeutic agent within the volumetric portion of the drug core varies from the amount of the therapeutic agent within any other equal volumetric portion of the drug core by no greater than about 10%. For example, the amount of the therapeutic agent within the volumetric portion of the drug core varies from the amount of the therapeutic agent within any other equal volumetric portion of the drug core by no greater than about 5%. For example, the amount of the therapeutic agent within a volumetric portion of the drug core is the same as the amount of the therapeutic agent within any other equal volumetric portion of the drug core. In various embodiments, the drug insert can be adapted to release the agent to the eye, surrounding tissues, systemically, or any combination thereof, and/or for providing sustained release of a therapeutic agent to the eye or surrounding tissues, or systemically, or any combination thereof.

In various embodiments, the invention provides a plurality of the drug inserts as described above wherein each of the plurality of the inserts comprises a similar amount of the agent dispersed respectively therewithin. For example, the similar amount of agent dispersed respectively therein can vary no greater than about 30% therebetween. For example, the similar amount of agent dispersed respectively therein can vary no greater than about 20% therebetween. For example, the similar amount of agent dispersed respectively therein can vary no greater than about 10% therebetween. For example, the similar amount of agent dispersed respectively therein can vary no greater than about 5% therebetween.

In various embodiments, the invention provides a drug core comprising a therapeutic agent and a matrix wherein the matrix comprises a polymer, for disposition into a drug insert or an implant, the drug insert or the implant being adapted for disposition within or adjacent to an eye of a patient, wherein the therapeutic agent is uniformly homogeneously dispersed throughout the matrix, or the therapeutic agent at least in part forms solid or liquid inclusions within the matrix; wherein an amount of the therapeutic agent in a volumetric portion of the drug core is similar to an amount of the therapeutic agent in any other equal volumetric portion of the drug core. For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%. For example, the amount of the therapeutic agent within a volumetric portion of the drug core is the same as the amount of the therapeutic agent within any other equal volumetric portion of the drug core. In various embodiments, the drug insert can be adapted to release the agent to the eye, surrounding tissues, systemically, or any combination thereof, and/or for providing sustained release of a therapeutic agent to the eye or surrounding tissues, or systemically, or any combination thereof.

In various embodiments, the invention provides an implant for sustained delivery of a therapeutic agent to a patient, wherein the entire implant comprises a drug core comprising a therapeutic agent and a matrix, wherein the matrix comprises a polymer. A porous or absorbent material can alternatively be used to make up the entire implant or plug which can be saturated with the active agent.

In various embodiments, the invention provides a filled precursor sheath adapted for manufacture of a plurality of drug inserts therefrom by division of the filled precursor sheath, each drug insert being adapted for disposition within a respective implant, the implant being adapted for disposition within or adjacent to an eye of a patient, the filled precursor sheath comprising a precursor sheath body and a precursor drug core contained therewithin, the precursor drug core comprising a therapeutic agent and a matrix wherein the matrix comprises a polymer, wherein the therapeutic agent is uniformly and homogeneously dispersed throughout the matrix, or the therapeutic agent at least in part forms solid or liquid inclusions within the matrix, wherein an amount of the therapeutic agent in a volumetric portion of the precursor drug core is similar to an amount of the therapeutic agent in any other equal volumetric portion of the precursor drug core, the precursor sheath body being substantially impermeable to the agent, each of the plurality of inserts divided therefrom being adapted to release the agent, a respective sheath body of each of the plurality of inserts divided from the filled precursor sheath being disposed over a portion of a respective drug core of each of the plurality of inserts to inhibit release of the agent from said portion and so as to define at least one exposed surface of the drug core adapted to release the agent, when the insert is disposed in an implant and the implant is inserted into the patient. For example, an amount of the therapeutic agent in a volumetric portion of the precursor drug core can vary from an amount of the therapeutic agent in any other equal volumetric portion of the precursor drug core by no greater than about 30%. For example, an amount of the therapeutic agent in a volumetric portion of the precursor drug core can vary from an amount of the therapeutic agent in any other equal volumetric portion of the precursor drug core by no greater than about 20%. For example, an amount of the therapeutic agent in a volumetric portion of the precursor drug core can vary from an amount of the therapeutic agent in any other equal volumetric portion of the precursor drug core by no greater than about 10%. For example, an amount of the therapeutic agent in a volumetric portion of the precursor drug core can vary from an amount of the therapeutic agent in any other equal volumetric portion of the precursor drug core by no greater than about 5%. For example, the amount of the therapeutic agent within a volumetric portion of the drug core is the same as the amount of the therapeutic agent within any other equal volumetric portion of the drug core. In various embodiments, the drug insert can be adapted to release the agent to the eye, surrounding tissues, systemically, or any combination thereof, and/or for providing sustained release of a therapeutic agent to the eye or surrounding tissues, or systemically, or any combination thereof.

In various embodiments, the invention provides an implant body for disposition in or adjacent to an eye of a patient, the implant body comprising a channel therein adapted to receive a drug insert such that an exposed surface of the drug insert will be exposed to tear liquid when the drug insert is disposed within the implant and when the implant is disposed in or adjacent to the eye, the drug insert comprising a sheath body that is substantially impermeable to the agent, containing therewithin a drug core comprising a therapeutic agent and a matrix comprising a polymer, wherein the therapeutic agent is uniformly and homogeneously dispersed throughout the matrix, or the therapeutic agent at least in part forms solid or liquid inclusions within the matrix wherein an amount of the therapeutic agent in a volumetric portion of the drug core is similar to an amount of the therapeutic agent in any other equal volumetric portion of the drug core, the body comprising a biocompatible material and being adapted to be retained within or adjacent to the eye for a period of time. For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%. For example, the amount of the therapeutic agent within a volumetric portion of the drug core is the same as the amount of the therapeutic agent within any other equal volumetric portion of the drug core. In various embodiments, the drug insert can be adapted to release the agent to the eye, surrounding tissues, systemically, or any combination thereof, and/or for providing sustained release of a therapeutic agent to the eye or surrounding tissues, or systemically, or any combination thereof.

In various embodiments, the invention provides an implant body for disposition in or adjacent to an eye of a patient, the implant body comprising a channel therein adapted to receive a drug core such that an exposed surface of the drug core will be exposed to tear liquid when the drug core is disposed within the implant and when the implant is disposed in or adjacent to the eye, the drug core comprising a therapeutic agent and a matrix comprising a polymer, wherein an amount of the therapeutic agent in a volumetric portion of the drug core is similar to an amount of the therapeutic agent in any equal volumetric portion of the drug core, wherein the therapeutic agent is sufficiently soluble in the matrix such that therapeutic quantities of the agent will be released from the exposed surface of the drug core to tear liquid in contact with the exposed surface when the implant body is disposed in or adjacent to an eye, the body comprising a biocompatible material and being adapted to be retained within or adjacent to the eye for a period of time. For example, the amount of the therapeutic agent in a volumetric portion of the drug core can vary from the amount of the therapeutic agent in any equal volumetric portion of the drug core by no greater than about 30%. For example, the amount of the therapeutic agent in a volumetric portion of the drug core can vary from the amount of the therapeutic agent in any equal volumetric portion of the drug core by no greater than about 20%. For example, the amount of the therapeutic agent in a volumetric portion of the drug core can vary from the amount of the therapeutic agent in any equal volumetric portion of the drug core by no greater than about 10%. For example, the amount of the therapeutic agent in a volumetric portion of the drug core can vary from the amount of the therapeutic agent in any equal volumetric portion of the drug core by no greater than about 5%. In various embodiments, the drug core can be adapted to release the therapeutic agent to the eye, surrounding tissues, systemically, or any combination thereof, and/or for providing sustained release of a therapeutic agent to the eye or surrounding tissues, or systemically, or any combination thereof.

In various embodiments, the invention provides a method of manufacturing a drug insert for an implant body adapted for disposition within or adjacent to an eye of a patient, the insert comprising a drug core comprising a therapeutic agent and a matrix wherein the matrix comprises a polymer, wherein the therapeutic agent is uniformly and homogeneously dispersed throughout the matrix, or the therapeutic agent at least in part forms solid or liquid inclusions within the matrix wherein an amount of the therapeutic agent in a volumetric portion of the drug core is similar to an amount of the therapeutic agent in any other equal volumetric portion of the drug core, the sheath body being disposed over a portion of the drug core to inhibit release of the agent from said portion and so as to define at least one exposed surface of the drug core adapted to release the agent when the implant is inserted into the patient; the method comprising injecting, at a subambient temperature of less than about 20° C., a mixture comprising a matrix precursor and the agent into the sheath body such that the sheath body is substantially filled therewith; then, curing the mixture comprising the matrix precursor within the sheath body to form the drug insert such that a drug core having an exposed surface is formed therein. In various embodiments, the drug insert can be adapted to release the agent to the eye, surrounding tissues, systemically, or any combination thereof, and/or for providing sustained release of a therapeutic agent to the eye or surrounding tissues, or systemically, or any combination thereof.

In various embodiments, the invention provides a method of manufacturing a drug insert for an implant body adapted for disposition within or adjacent to an eye of a patient, the method comprising injecting, at a subambient temperature of less than about 20° C., a mixture comprising a therapeutic agent and a matrix precursor into a precursor sheath body, wherein the therapeutic agent is uniformly and homogeneously dispersed throughout the matrix, or the therapeutic agent at least in part forms solid or liquid inclusions within the matrix, wherein an amount of the therapeutic agent in a volumetric portion of the drug core is similar to an amount of the therapeutic agent in any other equal volumetric portion of the drug core, the precursor sheath body being substantially impermeable to the agent, such that the precursor sheath is substantially filled therewith to provide a filled precursor sheath; then, curing the mixture such that a precursor drug core is formed within the precursor sheath body, and then, dividing the filled precursor sheath to form a plurality of drug inserts therefrom, wherein each drug insert comprises a drug core and a sheath body, the sheath body being disposed over a portion of the drug core to inhibit release of the agent from said portion and so as to define at least one exposed surface of the drug core, when the insert is disposed with an implant and the implant is inserted into the patient; each insert being adapted fit within a respective implant body and to release, through the exposed surface of the insert, therapeutic quantities of the agent to tear liquid; wherein each of the plurality of drug inserts is of substantially the same length, wherein an amount of the agent in each of the plurality of inserts divided from the filled precursor sheath is similar.

For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%. For example, the amount of the agent in each of the plurality of inserts can vary by no greater than about 30% therebetween. For example, the amount of the agent in each of the plurality of inserts can vary by no greater than about 20% therebetween. For example, the amount of the agent in each of the plurality of inserts can vary by no greater than about 10% therebetween. For example, the amount of the agent in each of the plurality of inserts can vary by no greater than about 5% therebetween.

In further embodiments, the method of manufacturing a drug insert further comprises, after the curing step as described herein, extruding the drug core from the sheath body prior to or after dividing the filled sheath body into a plurality of drug insert, thereby forming the drug cores free of the sheath body material.

In various embodiments, the above methods are employed to manufacture an implant for sustained delivery of a therapeutic agent to a patient, wherein the entire implant comprises a drug core comprising a therapeutic agent and a matrix, wherein the matrix comprises a polymer. A porous or absorbent material can alternatively be used to make up the entire implant or plug which can be saturated with the active agent. In other embodiments, a therapeutic agent and a matrix as described herein are added to a mold to form the drug core; the drug core is then cured, then used as an implant for sustained delivery of the therapeutic agent to a patient.

In various embodiments, the invention provides a drug insert made by a method of the invention.

In various embodiments, the invention provides a method of treating a malcondition in a patient in need thereof; comprising disposing an implant comprising a drug insert of the invention, or a drug core of the invention, or a drug core obtained by division of a filled precursor sheath of the invention, or a drug implant of the invention, or a drug insert prepared by the method of the invention, wherein the therapeutic agent is adapted to treat the malcondition, in or adjacent to an eye of the patient such that the drug is released into a body tissue or fluid.

In various embodiments, the invention provides the use of a drug insert of the invention, or a drug core of the invention, or a drug core obtained by division of a filled precursor sheath of the invention, or a drug implant of the invention, or a drug insert prepared by the method of the invention, in the manufacture of an implant adapted for treatment of a malcondition in a patient in need thereof.

In various embodiments, the invention provides a drug insert adapted for disposition within an punctual plug for providing sustained release of a latanoprost to the eye for treatment of glaucoma, the insert comprising a core and a sheath body partially covering the core, the core comprising the latanoprost and a matrix wherein the matrix comprises a silicone polymer, the latanoprost being contained within the silicone as droplets thereof, wherein an amount of the latanoprost in a volumetric portion of the drug core is similar to an amount of the latanoprost in any other equal volumetric portion of the drug core, the sheath body being disposed over a portion of the core to inhibit release of the latanoprost from said portion, an exposed surface of the core not covered by the sheath body being adapted to release the latanoprost to the eye.

In various embodiments, the invention provides a drug insert adapted for disposition within an punctual plug for providing sustained release of a cyclosporine to the eye for treatment of dry eye or inflammation, the insert comprising a core and a sheath body partially covering the core, the core comprising the cyclosporine and a matrix wherein the matrix comprises a polyurethane polymer, the cyclosporine being contained within the polyurethane, wherein an amount of the cyclosporine in a volumetric portion of the drug core is similar to an amount of the cyclosporine in any other equal volumetric portion of the drug core, the sheath body being disposed over a portion of the core to inhibit release of the cyclosporine from said portion, an exposed surface of the core not covered by the sheath body being adapted to release the cyclosporine to the eye.

In various embodiments, the invention provides a drug insert adapted for disposition within an implant, the implant being adapted for disposition within or adjacent to a body cavity, tissue, duct, or fluid, for providing sustained release of a therapeutic agent to the cavity, duct, tissue, or surrounding tissues or any combination thereof, the insert comprising a drug core and a sheath body partially covering the drug core, the drug core comprising a therapeutic agent and a matrix wherein the matrix comprises a polymer, wherein the therapeutic agent is uniformly and homogeneously dispersed throughout the matrix, or the therapeutic agent at least in part forms solid or liquid inclusions within the matrix, wherein an amount of the therapeutic agent in a volumetric portion of the drug core is similar to an amount of the therapeutic agent in any other equal volumetric portion of the drug core, the sheath body being disposed over a portion of the drug core to inhibit release of the agent from said portion and so as to define at least one exposed surface of the drug core adapted to release the agent to the cavity, duct, tissue, or surrounding tissues or any combination thereof, when the implant is inserted into the patient.

In various embodiments, the invention provides a drug insert adapted for disposition within an implant, the implant being adapted for disposition within or adjacent to an eye of a patient, for providing sustained release of a therapeutic agent systemically, the insert comprising a drug core and a sheath body partially covering the drug core, the drug core comprising a therapeutic agent and a matrix wherein the matrix comprises a polymer, wherein the therapeutic agent is uniformly and homogeneously dispersed throughout the matrix, or the therapeutic agent at least in part forms solid or liquid inclusions within the matrix, wherein an amount of the therapeutic agent in a volumetric portion of the drug core is similar to an amount of the therapeutic agent in any other equal volumetric portion of the drug core, the sheath body being disposed over a portion of the drug core to inhibit release of the agent from said portion and so as to define at least one exposed surface of the drug core adapted to release the agent systemically when the implant is inserted into the patient.

In various embodiments, the invention provides a drug core comprising a therapeutic agent and a matrix wherein the matrix comprises a polymer, for disposition as or into a drug insert or an implant, the drug insert or the implant being adapted for disposition within or adjacent to a body cavity, tissue, duct, or fluid, for providing sustained release of a therapeutic agent to the cavity, duct, tissue, or surrounding tissues or any combination thereof, wherein the therapeutic agent is uniformly homogeneously dispersed throughout the matrix, or the therapeutic agent at least in part forms solid or liquid inclusions within the matrix; wherein an amount of the therapeutic agent in a volumetric portion of the drug core is similar to an amount of the therapeutic agent in any other equal volumetric portion of the drug core.

In various embodiments, the invention provides a drug core comprising a therapeutic agent and a matrix wherein the matrix comprises a polymer, for disposition as or into a drug insert or an implant, the drug insert or the implant being adapted for disposition within or adjacent to an eye of a patient for providing sustained release of the therapeutic agent systemically, wherein the therapeutic agent is uniformly homogeneously dispersed throughout the matrix, or the therapeutic agent at least in part forms solid or liquid inclusions within the matrix; wherein an amount of the therapeutic agent in a volumetric portion of the drug core is similar to an amount of the therapeutic agent in any other equal volumetric portion of the drug core. The drug core may be formed into an implant or drug insert by molding the matrix with the therapeutic agent into an appropriate shape. The implant of this form has no sheath or outer implant body or housing.

Although it is not intended to be a limitation of the invention, it is believed the therapeutic agent transports through the matrix to its surface whereupon the agent becomes dispersed, dissolved or otherwise entrained with body fluid for delivery to target tissue. The transport may be the result of and/or influenced by diffusion, molecular interaction, domain formation and transport, infusion of body fluid into the matrix or other mechanisms. For delivery to the eye, therapeutic quantities of agent transport to the exposed surface of the matrix whereupon tear liquid will sweep away the agent for delivery to target tissue or tissues.

To better illustrate the invention described herein, a non-limiting list of exemplary aspects and embodiments of the invention is provided as follows.

Aspect A1 concerns a drug insert adapted for disposition within an implant, the implant being adapted for disposition within or adjacent to a body cavity, tissue, duct, or fluid, the insert comprising a drug core and a sheath body partially covering the drug core, the drug core comprising a therapeutic agent and a matrix, the matrix comprising a polymer, the sheath body being disposed over a portion of the drug core to inhibit release of the agent from said portion and so as to define at least one exposed surface of the drug core adapted to release the agent to the cavity, tissue, duct, or fluid, or any combination thereof when the implant is inserted into the patient, and wherein an amount of the therapeutic agent in a volumetric portion of the drug core is similar to an amount of the therapeutic agent in any other equal volumetric portion of the drug core.

Embodiment A2 concerns the drug insert of aspect A1 wherein the amount of the therapeutic agent within the volumetric portion of the drug core varies from the amount of the therapeutic agent within any other equal volumetric portion of the drug core by no greater than about 30%.

Embodiment A3 concerns the drug insert of aspect A1 wherein the amount of the therapeutic agent within the volumetric portion of the drug core varies from the amount of the therapeutic agent within any other equal volumetric portion of the drug core by no greater than about 20%.

Embodiment A4 concerns the drug insert of aspect A1 wherein the amount of the therapeutic agent within the volumetric portion of the drug core varies from the amount of the therapeutic agent within any other equal volumetric portion of the drug core by no greater than about 10%.

Embodiment A5 concerns the drug insert of aspect A1 wherein the amount of the therapeutic agent within the volumetric portion of the drug core varies from the amount of the therapeutic agent within any other equal volumetric portion of the drug core by no greater than about 5%.

Embodiment A6 concerns the drug insert of aspect A1 wherein the implant is a punctual plug.

Embodiment A7 concerns a plurality of the drug inserts of aspect A1 wherein each of the plurality of the inserts comprises a similar concentration of the agent relative to the other inserts of the plurality.

Embodiment A8 concerns the plurality of drug inserts of embodiment A7 wherein the similar concentration of agent varies no greater than about 30% therebetween.

Embodiment A9 concerns the plurality of drug inserts of embodiment A7 wherein the similar concentration of agent varies no greater than about 20% therebetween.

Embodiment A10 concerns the plurality of drug inserts of embodiment A7 wherein the similar concentration of agent varies no greater than about 10% therebetween.

Embodiment A11 concerns the plurality of drug inserts of embodiment A7 wherein the similar concentration of agent varies no greater than about 5% therebetween.

Embodiment A12 concerns the drug insert of aspect A1 wherein the exposed surface is adapted to release therapeutic quantities of the agent for a time period of at least several days into tear liquid when the implant is inserted into the patient.

Embodiment A13 concerns the plurality of drug inserts of embodiment A7 wherein the exposed surface of each of the plurality of drug inserts is adapted to release therapeutic quantities of the agent for a time period of at least several days into tear liquid when the implant is inserted into the patient, wherein the therapeutic quantity of the agent released by each of the plurality of drug insert is similar.

Embodiment A14 concerns the plurality of embodiment A13, wherein the therapeutic quantity of the agent released by each of the plurality of the inserts varies by no greater than about 30% therebetween.

Embodiment A15 concerns the plurality of embodiment A13, wherein the therapeutic quantity of the agent released by each of the plurality of the inserts varies by no greater than about 20% therebetween.

Embodiment A16 concerns the plurality of embodiment A13, wherein the therapeutic quantity of the agent released by each of the plurality of the inserts varies by no greater than about 10% therebetween.

Embodiment A17 concerns the plurality of embodiment A13, wherein the therapeutic quantity of the agent released by each of the plurality of the inserts varies by no greater than about 5% therebetween.

Embodiment A18 concerns the drug insert of aspect A1 wherein the drug core comprises about 0.1 wt % to about 50 wt % of the agent.

Embodiment A19 concerns the drug insert of aspect A1 wherein the matrix comprises a non-biodegradable silicone or a polyurethane, or combination thereof.

Embodiment A20 concerns the drug insert of aspect A1 wherein the sheath body comprises a polymer comprising at least one of polyimide, PMMA, or PET, wherein the polymer is extruded or cast; or a metal comprising stainless steel or titanium.

Embodiment A21 concerns the drug insert of aspect A1 wherein the agent comprises a glaucoma medication, a muscarinic agent, a beta blocker, an alpha agonist, a carbonic anhydrase inhibitor, a prostaglandin or prostaglandin analog; an anti-inflammatory agent; an anti-infective agent; a dry eye medication; or any combination thereof.

Embodiment A22 concerns the drug insert of embodiment A21 wherein the anti-inflammatory agent comprises a steroid, a soft steroid, or an NSAID and other compounds with analgesic properties.

Embodiment A23 concerns the drug insert of embodiment A21 wherein the anti-infective agent comprises an antibiotic, an antiviral, or an antimycotic.

Embodiment A24 concerns the drug insert of embodiment A21 wherein the dry eye medication comprises cyclosporine, antihistamine, mast cell stabilizer such as olapatadine, a demulcent, or sodium hyaluronate.

Embodiment A25 concerns the drug insert of aspect A1 wherein the agent comprises latanoprost, and the amount of the agent in the drug insert is about 10-50 µg.

Embodiment A26 concerns the drug insert of aspect A1 wherein the drug insert comprises a release rate modifying material comprising an inert filler material, a salt, a surfactant, a dispersant, a second polymer, an oligomer, or a combination thereof.

Embodiment A27 concerns the drug insert of aspect A1 wherein the drug core is substantially cylindrical in form, having an axis, wherein the exposed surface of the drug core is disposed on one end of the cylindrical form and a surface of the drug core covered by the sheath body constitutes a remainder of the surface of the cylindrical form.

Embodiment A28 concerns the drug insert of aspect A1 wherein the agent is dissolved in the matrix within the drug core.

Embodiment A29 concerns the drug insert of embodiment A28 wherein the agent comprises cyclosporine and the matrix comprises polyurethane.

Embodiment A30 concerns the drug insert of aspect A1 wherein the agent is present at least in part as a plurality of solid or liquid inclusions throughout the matrix, the inclusions comprising, at a temperature of less than about 25° C., droplets of the agent of no greater than about 100 μm diameter when the agent is a liquid at less than about 25° C., or particles of the agent of no greater than about 100 μm diameter when the agent is a solid at less than about 25° C.

Embodiment A31 concerns the drug insert of embodiment A30 wherein an average inclusion diameter and a size distribution of a plurality of inclusion diameters within a population of inclusions have an effect on a rate of release of the agent from the drug core to the patient.

Embodiment A32 concerns the drug insert of embodiment A30 wherein the inclusions have an average diameter of less than about 20 μm.

Embodiment A33 concerns the drug insert of embodiment A32 wherein a standard deviation of diameters of the inclusions is less than about 8 μm.

Embodiment A34 concerns the drug insert of embodiment A30 wherein the inclusions have an average diameter of less than about 15 μm.

Embodiment A35 concerns the drug insert of embodiment A34 wherein a standard deviation of diameters of the inclusions is less than about 6 μm.

Embodiment A36 concerns the drug insert of embodiment A30 wherein the inclusions have an average diameter of less than about 10 μm.

Embodiment A37 concerns the drug insert of embodiment A36 wherein a standard deviation of diameters of the inclusions is less than about 4 μm.

Embodiment A38 concerns the drug insert of embodiment A30 wherein a distribution of diameters of the inclusions is a monodisperse distribution.

Embodiment A39 concerns the drug insert of embodiment A30 wherein the inclusions predominantly comprise a cross-sectional size within a range from about 0.1 μm to about 50 μm.

Embodiment A40 concerns the drug insert of embodiment A30 wherein the agent forms inclusions in the matrix that are in a liquid physical state at less than about 25° C.

Embodiment A41 concerns the drug insert of embodiment A40 wherein substantially all the inclusions are droplets of the agent of less than about 30 μm in diameter within the matrix.

Embodiment A42 concerns the drug insert of embodiment A40 wherein the droplets have an average diameter of less than about 10 μm.

Embodiment A43 concerns the drug insert of embodiment A42 wherein a standard deviation of diameters of the inclusions is less than about 4 μm.

Embodiment A44 concerns the drug insert of embodiment A40 wherein the agent is latanoprost.

Embodiment A45 concerns the drug insert of embodiment A30 wherein the agent forms inclusions in the matrix that are in a solid physical state at less than about 25° C.

Embodiment A46 concerns the drug insert of embodiment A45 wherein substantially all the inclusions are particles of the agent of less than about 30 μm in diameter within the matrix.

Embodiment A47 concerns the drug insert of embodiment A45 wherein an average particle diameter within the matrix is about 5-50 μm.

Embodiment A48 concerns the drug insert of embodiment A45 wherein the agent is bimatoprost, olopatadine, or cyclosporine.

Embodiment A49 concerns the drug insert of aspect A1 wherein the core comprises two or more therapeutic agents.

Embodiment A50 concerns the drug insert of aspect A1 wherein the drug core comprises first and second drug cores.

Embodiment A51 concerns the drug insert of embodiment A50 wherein the drug insert comprises two drug cores disposed within the sheath body, a first drug core comprising a first agent and a first matrix, and a second drug core comprising a second agent and a second matrix, wherein the first agent and the second agent are different, and wherein the first matrix and the second matrix are either the same or differ from each other; the implant body comprising an aperture adapted to receive the first and the second cores disposed within the sheath body, the drug cores being adapted to be disposed, within the sheath, within the aperture of the implant body.

Embodiment A52 concerns the drug insert of embodiment A50 wherein the first matrix and the second matrix differ from each other with respect to at least one of a composition, an exposed surface area, a surfactant, a crosslinker, an additive, a matrix material, a formulation, a release rate modifying reagent, or a stability.

Embodiment A53 concerns the drug insert of embodiment A50 wherein the first drug core and the second drug core are disposed within the sheath body such that the first drug core has a surface exposed directly to tear liquid and the second drug core does not have a surface exposed directly to tear liquid when the drug insert is disposed within the implant body and the implant body is disposed in or adjacent to the eye of the patient.

Embodiment A54 concerns the drug insert of embodiment A50 wherein the first drug core and the second drug core are disposed side by side within the sheath body.

Embodiment A55 concerns the drug insert of embodiment A50, wherein the first drug core and the second drug core are each cylindrical in shape and disposed with the sheath body, the first drug core being positioned near a proximal end of an aperture in the implant body and the second drug core being positioned near a distal end of the aperture, when the drug insert is disposed within the implant body.

Embodiment A56 concerns the drug insert of embodiment A50, wherein the first drug core and the second drug core are each cylindrical in shape provided that the first drug core has a first central opening, the drug cores being positioned concentrically within the sheath body within an aperture of the implant body adapted to receive the drug insert, and the second drug core being configured to fit within the first central opening of the first drug core.

Embodiment A57 concerns the drug insert of embodiment A56 wherein the first and second drug cores are concentrically positioned within the aperture of the implant body, the first drug core having a first central opening exposing a first inner surface and the second drug core having a second central opening exposing a second inner surface, the second drug core being configured to fit within the first central opening of the first drug core, and wherein the aperture extends from a proximal end to a distal end of the implant body thereby being adapted to allow tear liquid to pass through the aperture and contact the first and second inner surfaces of the first and second central openings and release the first and second therapeutic agents into a canaliculus of the patient when the implant body is inserted into a patient.

Embodiment A58 concerns the drug insert of embodiment A50 wherein the first therapeutic agent has a release profile wherein the first agent is released at therapeutic levels throughout a first time period and the second therapeutic agent has a second release profile wherein the second agent is released at therapeutic levels throughout a second time period.

Embodiment A59 concerns the drug insert of embodiment A58 wherein the first time period and the second time period are between one week and five years.

Embodiment A60 concerns the drug insert of embodiment A58 wherein the first release profile and the second release profile are substantially the same.

Embodiment A61 concerns the drug insert of embodiment A58 wherein the first release profile and the second release profile are different.

Embodiment A62 concerns the drug insert of embodiment A50 wherein any inclusions in the first drug core and in the second drug core respectively have an average diameter of less than about 20 µm.

Embodiment A63 concerns the drug insert of embodiment A50 wherein any inclusions in the first drug core and in the second drug core respectively have a standard deviation of diameters of less than about 8 µm.

Embodiment A64 concerns the drug insert of embodiment A50 wherein the implant body comprises a central bore that extends from a proximal end to a distal end of the implant body so as to be adapted to allow a tear liquid to pass through the implant body and the first and second therapeutic agents are released into the tear liquid into a canaliculus of the patient when the implant body is disposed in or adjacent to the eye.

Embodiment A65 concerns the drug insert of embodiment A50 wherein the first agent provides a first effect and a side effect to the patient, and the second agent provides a second effect that mitigates or counters the side effect of the first agent.

Embodiment A66 concerns the drug insert of embodiment A50, further comprising disposing a medication-impregnated porous material within the first matrix, the second matrix, or both, wherein the medication-impregnated porous material is adapted so as to permit tear liquid to release the first agent, the second agent, or both, from the medication-impregnated porous material at therapeutic levels over a sustained period when a drug core-containing implant is disposed within a punctum, and wherein the medication-impregnated porous material is a gel material that can swell from a first diameter to a second diameter when in contact with tear liquid.

Embodiment A67 concerns the drug insert of embodiment A66 wherein in which the second diameter is about 50% greater than the first diameter.

Embodiment A68 concerns the drug insert of embodiment A66 wherein the medication-impregnated porous material is a HEMA hydrophilic polymer.

Embodiment A69 concerns the drug insert of aspect A1 wherein the matrix comprises a polyurethane polymer or copolymer.

Embodiment A70 concerns the drug insert of embodiment A69 wherein the polyurethane polymer or copolymer comprises an aliphatic polyurethane, an aromatic polyurethane, a polyurethane hydrogel-forming material, a hydrophilic polyurethane, or a combination thereof.

Embodiment A71 concerns the drug insert of embodiment A69 wherein the polyurethane polymer or copolymer comprises a hydrogel adapted to swell when contacted with an aqueous medium and the sheath body is adapted to be of sufficient elasticity to expand in response thereto.

Embodiment A72 concerns the drug insert of embodiment A71 wherein the swelling is adapted to retain the implant body within a punctual canal of the patient.

Embodiment A73 concerns the drug insert of embodiment A69 wherein the therapeutic agent comprises cyclosporine or olopatadine, a prodrug or a derivative of cyclosporine or olopatadine, or any combination thereof.

Embodiment A74 concerns the drug insert of embodiment A73 wherein a weight ratio of the cyclosporine or the olopatadine, or the cyclosporine prodrug or derivative, or the olopatadine prodrug or derivative, or the combination thereof, to the polyurethane polymer or copolymer is about 1 wt % to about 70 wt %.

Embodiment A75 concerns the drug insert of aspect A1 wherein a concentration of the agent in the core is similar in a portion of the drug core proximate to the exposed surface, a portion distal to the exposed surface, and a portion disposed between the proximate portion and the distal portion.

Embodiment A76 concerns the drug insert of embodiment A75 wherein the proximal portion is in length at least about one tenth a length of the drug core.

Embodiment A77 concerns the drug insert of aspect A1 wherein the drug insert or the implant is adapted for disposition within or adjacent to an eye of a patient.

Embodiment A78 concerns the drug insert of aspect A1 wherein: a) the therapeutic agent is uniformly and homogeneously dispersed throughout the matrix; or b) the therapeutic agent at least in part forms solid or liquid inclusions within the matrix.

The drug insert aspects and embodiments of aspect A1 and embodiments A2 through A76 can be combined in any manner, as long as the combination is not internally inconsistent. For example, embodiment A6 may be combined with any of embodiments A2 through A5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for this aspect and embodiment set.

Aspect B1 concerns a drug core comprising a therapeutic agent and a matrix for disposition into or as a drug insert or an implant, the drug insert or the implant being adapted for disposition within or adjacent to a body cavity, tissue, duct, or fluid of a patient, the matrix comprising a polymer, wherein an amount of the therapeutic agent in a volumetric portion of the drug core is similar to an amount of the therapeutic agent in any other equal volumetric portion of the drug core.

Embodiment B2 concerns a drug core of aspect B1 wherein the drug insert or the implant is adapted for disposition within or adjacent to an eye of a patient.

Embodiment B3 concerns a core of aspect B1 wherein: a) the therapeutic agent is uniformly and homogeneously dispersed throughout the matrix; or b) the therapeutic agent at least in part forms solid or liquid inclusions within the matrix.

Embodiment B4 concerns the drug core of aspect B1, wherein the amount of the therapeutic agent in a volumetric portion of the drug core varies from the amount of the therapeutic agent in any other equal volumetric portion of the drug core by no greater than about 30%.

Embodiment B5 concerns the drug core of aspect B1, wherein the amount of the therapeutic agent in a volumetric portion of the drug core varies from the amount of the therapeutic agent in any other equal volumetric portion of the drug core by no greater than about 20%.

Embodiment B6 concerns the drug core of aspect B1, wherein the amount of the therapeutic agent in a volumetric portion of the drug core varies from the amount of the therapeutic agent in any other equal volumetric portion of the drug core by no greater than about 10%.

Embodiment B7 concerns the drug core of aspect B1, wherein the amount of the therapeutic agent in a volumetric portion of the drug core varies from the amount of the therapeutic agent in any other equal volumetric portion of the drug core by no greater than about 5%.

Embodiment B8 concerns the drug core of aspect B1, wherein the therapeutic agent is uniformly homogeneously distributed throughout the matrix.

Embodiment B9 concerns the drug core of aspect B1, wherein the therapeutic agent at least in part forms solid or liquid inclusions within the matrix.

Embodiment B10 concerns the drug core of aspect B1, wherein the therapeutic agent at least in part forms solid or liquid inclusions within the matrix, wherein the inclusions have an average diameter of less than about 20 μm.

Embodiment B11 concerns the drug core of embodiment B10 wherein a standard deviation of diameters of the inclusions is less than about 8

Embodiment B12 concerns the drug core of aspect B1, wherein the therapeutic agent at least in part forms solid or liquid inclusions within the matrix, wherein the inclusions have an average diameter of less than about 10 μm.

Embodiment B13 concerns the drug core of embodiment B12 wherein a standard deviation of diameters of the inclusions is less than about 4 μm.

Embodiment B14 concerns the drug core of aspect B1, wherein the amounts of the therapeutic agent in equal volumetric portions at about the proximal portion, at about the middle portion and at about the distal portion of the drug core are similar.

Embodiment B15 concerns the drug core of embodiment B14, wherein the amounts of the therapeutic agent vary by no greater than about 30%.

Embodiment B16 concerns the drug core of embodiment B14, wherein the amounts of the therapeutic agent vary by no greater than about 20%.

Embodiment B17 concerns the drug core of embodiment B14, wherein the amounts of the therapeutic agent vary by no greater than about 10%.

Embodiment B18 concerns the drug core of embodiment B16, wherein the amounts vary by no greater than about 5%.

Embodiment B19 concerns the drug core of aspect B1, wherein the polymer comprises a non-biodegradable silicone or polyurethane, or combination thereof.

Embodiment B20 concerns the drug core of aspect B1, wherein the therapeutic agent comprises a glaucoma medication, a muscarinic agent, a beta blocker, an alpha agonist, a carbonic anhydrase inhibitor, a prostaglandin or prostaglandin analog; an anti-inflammatory agent; an anti-infective agent; a dry eye medication; or any combination thereof.

Embodiment B21 concerns the drug core of embodiment B20 wherein the anti-inflammatory agent comprises a steroid, a soft steroid, or an NSAID and/or other compounds with analgesic properties.

Embodiment B22 concerns the drug core of embodiment B20 wherein the anti-infective agent comprises an antibiotic, an antiviral, or an antimycotic.

Embodiment B23 concerns the drug core of embodiment B20 wherein the dry eye medication comprises cyclosporine, antihistamines and mast cell stabilizers, olapatadine, a demulcent, or sodium hyaluronate.

Embodiment B24 concerns the drug core of aspect B1, wherein the polymer comprises silicone.

Embodiment B25 concerns the drug core of aspect B1, wherein the therapeutic agent comprises cyclosporine and the polymer comprises a polyurethane.

Embodiment B26 concerns the drug core of aspect B1 comprising a release rate modifying material comprising an inert filler material, a salt, a surfactant, a dispersant, a second polymer, an oligomer, or a combination thereof.

Embodiment B27 concerns the drug core of aspect B1 disposed within a sheath body.

Embodiment B28 concerns the drug core of aspect B1 which has been formed into a shape of an implant body for disposition in or adjacent to a body cavity, tissue, duct, or fluid of a patient.

The drug core aspects and embodiments of aspect B1 and embodiments B2 through B28 can be combined in any manner, as long as the combination is not internally inconsistent. For example, embodiment B6 may be combined with any of embodiments B2 through B5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for this aspect and embodiment set.

Aspect C1 concerns a filled precursor sheath comprising a precursor sheath body containing a precursor drug core, the drug core comprising a therapeutic agent and a matrix, the matrix comprising a polymer, the precursor sheath body being substantially impermeable to the agent, wherein an amount of the therapeutic agent in a volumetric portion of the precursor drug core is similar to an amount of the therapeutic agent in any other equal volumetric portion of the precursor drug core.

Embodiment C2 concerns the filled precursor sheath of aspect C1 adapted for manufacture of a plurality of drug inserts by division of the filled precursor sheath, each drug insert being adapted for disposition within a respective implant, the implant being adapted for disposition within or adjacent a body cavity, tissue, duct or fluid.

Embodiment C3 concerns the filled precursor sheath of aspect C1 wherein the implant is adapted for disposition within or adjacent to an eye of a patient.

Embodiment C4 concerns the precursor sheath of aspect C1 wherein an amount of the therapeutic agent in a volumetric portion of the precursor drug core varies from an amount of the therapeutic agent in any other equal volumetric portion of the precursor drug core by no greater than about 30%.

Embodiment C5 concerns the precursor sheath of aspect C1 wherein an amount of the therapeutic agent in a volumetric portion of the precursor drug core varies from an amount of the therapeutic agent in any other equal volumetric portion of the precursor drug core by no greater than about 20%.

Embodiment C6 concerns the precursor sheath of aspect C1 wherein an amount of the therapeutic agent in a volumetric portion of the precursor drug core varies from an amount of the therapeutic agent in any other equal volumetric portion of the precursor drug core by no greater than about 10%.

Embodiment C7 concerns the precursor sheath of aspect C1 wherein an amount of the therapeutic agent in a volumetric portion of the precursor drug core varies from an amount of the therapeutic agent in any other equal volumetric portion of the precursor drug core by no greater than about 5%.

Embodiment C8 concerns the precursor sheath of aspect C1 wherein the amount of the agent in a first insert of the plurality of inserts is similar to the amount of agent in any other insert of the plurality of inserts.

Embodiment C9 concerns the precursor sheath of embodiment C8 wherein the amount of the agent in the first insert varies by no greater than about 30% compared with the amount of agent in any other insert.

Embodiment C10 concerns the precursor sheath of embodiment C8 wherein the amount of the agent in the first insert varies by no greater than about 20% compared with the amount of agent in any other insert.

Embodiment C11 concerns the precursor sheath of embodiment C8 wherein the amount of the agent in the first insert varies by no greater than about 10% compared with the amount of agent in any other insert.

Embodiment C12 concerns the precursor sheath of embodiment C8 wherein the amount of the agent in the first insert varies by no greater than about 5% compared with the amount of agent in any other insert.

Embodiment C13 concerns the precursor sheath of aspect C1 wherein the implant comprises a punctual plug and each of the plurality of inserts is adapted for disposition within a respective plurality thereof.

Embodiment C14 concerns the precursor sheath of embodiment C13 wherein each exposed surface of each drug insert divided therefrom is adapted to release therapeutic quantities of the agent for a time period of at least several days into tear fluid, when the insert is disposed within a punctual plug and the punctual plug is disposed within a punctum of a patient.

Embodiment C15 concerns the precursor sheath of aspect C1 wherein the drug core comprises about 0.1 wt % to about 50 wt % of the agent.

Embodiment C16 concerns the precursor sheath of aspect C1 wherein the matrix comprises a non-biodegradable silicone or a polyurethane, or combination thereof.

Embodiment C17 concerns the precursor sheath of aspect C1 wherein the sheath body comprises a polymer comprising at least one of polyimide, PMMA, PET, wherein the polymer is extruded or cast, or stainless steel, or titanium.

Embodiment C18 concerns the precursor sheath of aspect C1 wherein the agent comprises wherein the agent comprises a glaucoma medication, a muscarinic agent, a beta blocker, an alpha agonist, a carbonic anhydrase inhibitor, a prostaglandin or prostaglandin analog; an anti-inflammatory agent; an anti-infective agent; a dry eye medication; or any combination thereof.

Embodiment C19 concerns the precursor sheath of embodiment C18 wherein the anti-inflammatory agent comprises a steroid, a soft steroid, or an NSAID and/or other compounds with analgesic properties.

Embodiment C20 concerns the precursor sheath of embodiment C18 wherein the anti-infective agent comprises an antibiotic, an antiviral, or an antimycotic.

Embodiment C21 concerns the precursor sheath of embodiment C18 wherein the dry eye medication comprises cyclosporine, antihistamines and mast cell stabilizers, olapatadine, a demulcent, or sodium hyaluronate.

Embodiment C22 concerns the precursor sheath of aspect C1 wherein the agent comprises latanoprost, and the amount of the agent in each of the plurality of drug inserts is about 10-50 μg.

Embodiment C23 concerns the precursor sheath of aspect C1 wherein the drug insert comprises a release rate modifying material comprising an inert filler material, a salt, a surfactant, a dispersant, a second polymer, an oligomer, or a combination thereof.

Embodiment C24 concerns the precursor sheath of aspect C1 adapted for division by cutting with a blade or with a laser.

Embodiment C25 concerns the precursor sheath of aspect C1 wherein the agent is dissolved in the matrix.

Embodiment C26 concerns the precursor sheath of aspect C1 wherein the agent is dispersed as a plurality of solid or liquid inclusions throughout the matrix, the inclusions comprising, at a temperature of less than about 25° C., droplets of the agent of no greater than about 100 μm diameter when the agent is a liquid at less than about 25° C., or particles of the agent of no greater than about 100 μm diameter when the agent is a solid at less than about 25° C.

Embodiment C27 concerns the precursor sheath of embodiment C26 wherein the inclusions have an average diameter of less than about 20 μm.

Embodiment C28 concerns the precursor sheath of embodiment C27 wherein a standard deviation of diameters of the inclusions is less than about 8 μm.

Embodiment C29 concerns the precursor sheath of embodiment C26 wherein the inclusions have an average diameter of less than about 10 μm.

Embodiment C30 concerns the precursor sheath of embodiment C29 wherein a standard deviation of diameters of the inclusions is less than about 4 μm.

Embodiment C31 concerns the precursor sheath of embodiment C26 wherein a size distribution of diameters of the plurality of inclusions is monodisperse.

Embodiment C32 concerns the precursor sheath of aspect C1 wherein: a) the therapeutic agent is uniformly and homogeneously dispersed throughout the matrix; or b) the therapeutic agent at least in part forms solid or liquid inclusions within the matrix.

The filled precursor sheath aspects and embodiments of aspect C1 and embodiments C2 through C32 can be combined in any manner, as long as the combination is not internally inconsistent. For example, embodiment C6 may be combined with any of embodiments C2 through C5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for this aspect and embodiment set.

Aspect D1 concerns an implant body for disposition in or adjacent to a body cavity, tissue, duct, or fluid of a patient, the implant body comprising a channel therein adapted to receive a drug insert such that an exposed surface of the insert will be exposed to the body cavity, tissue, duct or fluid when the insert is disposed within the implant and when the implant is disposed in or adjacent to the body cavity, tissue, duct or fluid, the drug insert comprising a sheath body that is substantially impermeable to the agent, the sheath body containing a drug core comprising a therapeutic agent and a matrix comprising a polymer, wherein an amount of the therapeutic agent in a volumetric portion of the precursor drug core is similar to an amount of the therapeutic agent in any other equal volumetric portion of the precursor drug core.

Embodiment D2 concerns an implant body of aspect D1 wherein the implant is adapted for disposition within or adjacent to an eye of a patient.

Embodiment D3 concerns the implant body of aspect D1, wherein the amount of the therapeutic agent in a volumetric portion of the drug core varies from the amount of the therapeutic agent in any other equal volumetric portion of the drug core by no greater than about 30%.

Embodiment D4 concerns the implant body of aspect D1, wherein the amount of the therapeutic agent in a volumetric portion of the drug core varies from the amount of the therapeutic agent in any other equal volumetric portion of the drug core by no greater than about 20%.

Embodiment D5 concerns the implant body of aspect D1, wherein the amount of the therapeutic agent in a volumetric portion of the drug core varies from the amount of the therapeutic agent in any other equal volumetric portion of the drug core by no greater than about 10%.

Embodiment D6 concerns the implant body of aspect D1, wherein the amount of the therapeutic agent in a volumetric portion of the drug core varies from the amount of the therapeutic agent in any other equal volumetric portion of the drug core by no greater than about 5%.

Embodiment D7 concerns the implant of aspect D1, wherein the exposed surface is capable of releasing the therapeutic quantities into at least one of a sclera, a cornea or a vitreous when disposed in or adjacent to the eye of the patient.

Embodiment D8 concerns the implant of aspect D1 comprising a punctual plug adapted for disposition within a punctum of a patient for release of the agent into tear liquid.

Embodiment D9 concerns the implant of aspect D1, wherein the therapeutic agent is soluble in the matrix.

Embodiment D10 concerns the implant of aspect D1 wherein the therapeutic agent forms inclusions within the matrix but is sufficiently soluble in or transportable through the matrix such that when the implant is disposed adjacent to an eye, the exposed surface is capable of releasing therapeutic quantities of the agent to the tear liquid for a period of time when the implant is disposed in or adjacent to the eye.

Embodiment D11 concerns the implant of aspect D1 wherein a rate of release of the agent is determined in part by a concentration of the agent that dissolves in the matrix.

Embodiment D12 concerns the implant of aspect D1 wherein the matrix comprises a crosslinked water insoluble solid material that contains the inclusions.

Embodiment D13 concerns the implant of embodiment D12 wherein the crosslinked water insoluble solid material comprises a silicone or a polyurethane.

Embodiment D14 concerns the implant of aspect D1 wherein the matrix further comprises an effective amount of a release rate varying material, the release rate varying material comprising at least one of a crosslinker, an inert filler material, a surfactant, a dispersant, a second polymer, or an oligomer, or any combination thereof.

Embodiment D15 concerns the implant of aspect D1 wherein the drug core comprises from about 5% to about 50% of the therapeutic agent.

Embodiment D16 concerns the implant of embodiment D10 wherein the inclusions of agent are in physical form liquid or solid.

Embodiment D17 concerns the implant of aspect D1 wherein the sheath body comprises a polymer comprising at least one of polyimide, PMMA, PET, wherein the polymer is extruded or case, or stainless steel, or titanium.

Embodiment D18 concerns the implant of aspect D1 wherein the implant body comprises at least one of a silicone or a hydrogel.

Embodiment D19 concerns the implant of aspect D1 wherein the agent is dispersed as a plurality of solid or liquid inclusions throughout the matrix, the inclusions comprising, at a temperature of less than about 25° C., droplets of the agent of no greater than about 200 μm diameter when the agent is a liquid at less than about 25° C., or particles of the agent of no greater than about 200 μm diameter when the agent is a solid at less than about 25° C.

Embodiment D20 concerns the implant of embodiment D19 wherein the inclusions have an average diameter of less than about 20 μm.

Embodiment D21 concerns the implant of embodiment D20 wherein a standard deviation of diameters of the inclusions is less than about 8 μm.

Embodiment D22 concerns the implant of embodiment D19 wherein the inclusions have an average diameter of less than about 15 μm.

Embodiment D23 concerns the implant of embodiment D22 wherein a standard deviation of diameters of the inclusions is less than about 6 μm.

Embodiment D24 concerns the implant of embodiment D19 wherein the inclusions have an average diameter of less than about 10 μm.

Embodiment D25 concerns the implant of embodiment D24 wherein a standard deviation of diameters of the inclusions is less than about 4 μm.

Embodiment D26 concerns the implant of embodiment D19 wherein a size distribution of diameters of the plurality of inclusions is monodisperse.

Embodiment D27 concerns the implant of embodiment D19 wherein the inclusions comprise a cross-sectional size within a range from about 0.1 μm to about 50 μm.

Embodiment D28 concerns the implant of embodiment D19 wherein the agent forms inclusions in the matrix that are in a liquid physical state at less than about 25° C.

Embodiment D29 concerns the implant of embodiment D19 wherein the agent forms inclusions in the matrix that are in a solid physical state at less than about 25° C.

Embodiment D30 concerns the implant of aspect D1 wherein: a) the therapeutic agent is uniformly and homogeneously dispersed throughout the matrix; or b) the therapeutic agent at least in part forms solid or liquid inclusions within the matrix.

The implant body aspects and embodiments of aspect D1 and embodiments D2 through D30 can be combined in any manner, as long as the combination is not internally inconsistent. For example, embodiment D6 may be combined with any of embodiments D2 through D5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for this aspect and embodiment set.

Aspect E1 concerns a method of manufacturing a drug insert for an implant body adapted for disposition within or adjacent to a body cavity, tissue, duct, or fluid of a patient, the insert comprising a drug core and a sheath body partially covering the drug core, the drug core comprising a therapeutic agent and a matrix the matrix comprising a polymer, the sheath body being disposed over a portion of the drug core to inhibit release of the agent from said portion and so as to define at least one exposed surface of the drug core adapted to release the agent when the implant is inserted into the patient, the method comprising injecting into the sheath body, at a temperature of less than about 25° C., a mixture comprising a matrix precursor and the therapeutic agent such that the sheath body is substantially filled therewith; then, curing the mixture within the sheath body to form within the sheath body the drug core wherein an amount of the therapeutic agent in a volumetric portion of the drug core is similar to an amount of the therapeutic agent in any other equal volumetric portion of the drug core.

Aspect E2 concerns a method of manufacturing a drug insert for an implant body adapted for disposition within or adjacent to a body cavity, tissue, duct, or fluid of a patient, the method comprising injecting into a precursor sheath body, at a temperature of less than about 25° C., a mixture comprising a therapeutic agent and a precursor matrix such that the precursor sheath is substantially filled therewith, the precursor sheath body being substantially impermeable to the agent, curing the mixture in the precursor sheath body to provide a cured, filled precursor sheath body containing a precursor drug core; and dividing the cured filled precursor sheath to form a plurality of drug inserts, each drug insert being adapted to fit within a respective implant body, wherein each drug insert comprises a drug core and a sheath body, the sheath body being disposed over a portion of the drug core to inhibit release of the agent from said portion and so as to define at least one exposed surface of the drug core adapted to release the agent when the insert is disposed with an implant and the implant is inserted into the patient, and wherein an amount of the therapeutic agent in a volumetric portion of the drug core is similar to an amount of the therapeutic agent in any other equal volumetric portion of the drug core.

Embodiment E3 concerns a method of manufacturing a drug insert of aspect E2 wherein each of the plurality of drug inserts is of substantially the same length, and wherein an amount of the agent in a first insert of the plurality is similar to the amount of agent in any other insert of the plurality.

Embodiment E4 concerns the method of manufacturing a drug insert according to aspect E1, aspect E2, or embodiment E3 wherein the implant is adapted for disposition in or adjacent to an eye of a patient.

Embodiment E5 concerns the method of aspect E1 or E2 wherein the amount of the therapeutic agent in a volumetric portion of the drug core varies from the amount of the therapeutic agent in any other equal volumetric portion of the drug core by no greater than about 30%.

Embodiment E6 concerns the method of aspect E1 or E2 wherein the amount of the therapeutic agent in a volumetric portion of the drug core varies from the amount of the therapeutic agent in any other equal volumetric portion of the drug core by no greater than about 20%.

Embodiment E7 concerns the method of aspect E1 or E2 wherein the amount of the therapeutic agent in a volumetric portion of the drug core varies from the amount of the therapeutic agent in any other equal volumetric portion of the drug core by no greater than about 10%.

Embodiment E8 concerns the method of aspect E1 or E2 wherein the amount of the therapeutic agent in a volumetric portion of the drug core varies from the amount of the therapeutic agent in any other equal volumetric portion of the drug core by no greater than about 5%.

Embodiment E9 concerns the method of aspect E2 wherein the amount of the agent in each of the plurality of inserts varies by no greater than about 30% therebetween.

Embodiment E10 concerns the method of aspect E2 wherein the amount of the agent in each of the plurality of inserts varies by no greater than about 20% therebetween.

Embodiment E11 concerns the method of aspect E2 wherein the amount of the agent in each of the plurality of inserts varies by no greater than about 10% therebetween.

Embodiment E12 concerns the method of aspect E2 wherein the amount of the agent in each of the plurality of inserts varies by no greater than about 5% therebetween.

Embodiment E13 concerns the method of aspect E2 wherein dividing the precursor insert comprises cutting the precursor insert with a blade or with a laser.

Embodiment E14 concerns the method of aspect E1 or E2 wherein the implant comprises a punctual plug adapted to be disposed within the punctum of the patient.

Embodiment E15 concerns the method of embodiment E14 wherein the exposed surface is adapted to release therapeutic quantities of the agent for a time period of at least several days into tear fluid when the insert is disposed in the punctual plug and the punctual plug is disposed within a punctum of a patient.

Embodiment E16 concerns the method of aspect E1 or E2 wherein the mixture further comprises a solvent in which the matrix precursor and the agent are soluble, and wherein curing comprises at least partial removal of the solvent following injection into the sheath body or precursor sheath body respectively.

Embodiment E17 concerns the method of embodiment E16 wherein curing comprises heating, vacuum treatment, or both.

Embodiment E18 concerns the method of embodiment E16 wherein the solvent comprises a hydrocarbon, an ester, a halocarbon, an alcohol, an amide, or a combination thereof.

Embodiment E19 concerns the method of embodiment E16 wherein the solvent comprises a halocarbon and the agent comprises cyclosporine.

Embodiment E20 concerns the method of aspect E1 or E2 wherein curing the mixture comprises heating the mixture to a temperature, at a relative humidity, for a period of time.

Embodiment E21 concerns the method of embodiment E20 wherein the temperature comprises a range from about 20° C. to about 100° C., the relative humidity comprises a range from about 40% to about 100%, and the period of time comprises a range from about 1 minute to about 48 hours.

Embodiment E22 concerns the method of embodiment E21 wherein the temperature is at least about 40° C., the relative humidity is at least about 80%, or both.

Embodiment E23 concerns the method of aspect E1 or E2 wherein curing comprises a step of polymerization or cross-linking, or both, of the matrix precursor.

Embodiment E24 concerns the method of embodiment E23 comprising polymerization or cross-linking, or both, in the presence of a catalyst.

Embodiment E25 concerns the method of embodiment E24 wherein the catalyst comprises a tin compound or a platinum compound.

Embodiment E26 concerns the method of embodiment E24 wherein the catalyst comprises at least one of a platinum with vinyl hydride system or a tin with alkoxy system.

Embodiment E27 concerns the method of aspect E1 or E2 wherein the mixture is prepared by a method comprising sonication.

Embodiment E28 concerns the method of aspect E1 or E2 wherein injecting comprises injecting under a pressure of at least about 40 psi.

Embodiment E29 concerns the method of aspect E1 or E2 wherein the temperature comprises a temperature of about −50° C. to about 25° C.

Embodiment E30 concerns the method of aspect E1 or E2 wherein the temperature comprises a temperature of about −20° C. to about 0° C.

Embodiment E31 concerns the method of aspect E1 or E2 wherein the mixture is injected such that the sheath body or precursor sheath body, respectively, is filled at a rate of no greater than about 0.5 cm/sec.

Embodiment E32 concerns the method of aspect E1 or E2 wherein each drug insert is sealed at one end thereof, a second end providing the exposed surface.

Embodiment E33 concerns the method of embodiment E32 wherein each drug insert is sealed at one end thereof with a UV-curable adhesive, a cyanoacrylate, an epoxy, by pinching, with a heat weld, or with a cap.

Embodiment E34 concerns the method of embodiment E33 further comprises irradiating the drug insert with a UV-curable adhesive with UV light.

Embodiment E35 concerns the method of embodiment E33 further comprising, after sealing one end thereof, inserting each drug insert into a channel of an implant body adapted to receive the insert therein.

Embodiment E36 concerns the method of aspect E1 or E2 wherein the insert comprises about 0.1 wt % to about 50 wt % of the agent.

Embodiment E37 concerns the method of aspect E1 or E2 wherein the matrix comprises a non-biodegradable silicone or a polyurethane.

Embodiment E38 concerns the method of aspect E1 or E2 wherein the sheath or precursor sheath comprises at least one of polyimide, PMMA, PET, stainless steel, or titanium.

Embodiment E39 concerns the method of aspect E1 or E2 wherein the agent comprises a glaucoma medication, a muscarinic agent, a beta blocker, an alpha agonist, a carbonic anhydrase inhibitor, or a prostaglandin or prostaglandin analog; an antiinflammatory agent; an anti-infective agent; a dry eye medication; or any combination thereof.

Embodiment E40 concerns the method of embodiment E39 wherein the anti-inflammatory agent comprises a steroid, a soft steroid, or an NSAID and/or any other compound with analgesic properties.

Embodiment E41 concerns the method of embodiment E39 wherein the anti-infective agent comprises an antibiotic, an antiviral, or an antimicotic.

Embodiment E42 concerns the method of embodiment E39 wherein the dry eye medication comprises cyclosporine, olapatadine, delmulcents, or sodium hyaluronate.

Embodiment E43 concerns the method of aspect E1 or E2 wherein the agent comprises latanoprost, the matrix comprises silicone or polyurethane, and the amount of the agent in each of the plurality of drug inserts is about 10-50 µg.

Embodiment E44 concerns the method of aspect E1 or E2 wherein the agent comprises cyclosporine, the matrix comprises silicone or polyurethane, and a relative amount of the agent in each of the plurality of drug inserts is ranges from about 1% to about 50% of the core.

Embodiment E45 concerns the method of aspect E1 or E2 wherein the drug insert comprises a release rate modifying material comprising an inert filler material, a salt, a surfactant, a dispersant, a second polymer, an oligomer, or a combination thereof.

Embodiment E46 concerns the method of aspect E1 or E2 wherein the drug core is substantially cylindrical in form, having an axis, wherein a surface of the drug core is not covered by the sheath is disposed on one end on the cylindrical form and is the drug core covered by the sheath is disposed on a remainder of the surface of the cylindrical form.

Embodiment E47 concerns the method of aspect E1 or E2 wherein the agent is dissolved in the matrix.

Embodiment E48 concerns the method of embodiment E47 wherein the agent comprises cyclosporine and the matrix comprises polyurethane.

Embodiment E49 concerns the method of aspect E1 or E2 wherein the agent is dispersed as a plurality of solid or liquid inclusions within the matrix, the inclusions comprising, at a temperature of less than about 25° C., droplets of the agent of no greater than about 200 µm diameter when the agent is a liquid at less than about 25° C., or particles of the agent of no greater than about 200 µm diameter when the agent is a solid at less than about 25° C.

Embodiment E50 concerns the method of embodiment E49 wherein the inclusions have an average diameter of less than about 20 µm.

Embodiment E51 concerns the method of embodiment E50 wherein a standard deviation of diameters of the inclusions is less than about 8 µm.

Embodiment E52 concerns the method of embodiment E49 wherein the inclusions have an average diameter of less than about 15 µm.

Embodiment E53 concerns the method of embodiment E52 wherein a standard deviation of diameters of the inclusions is less than about 6 µm.

Embodiment E54 concerns the method of embodiment E49 wherein the inclusions wherein the inclusions have an average diameter of less than about 10 µm.

Embodiment E55 concerns the method of embodiment E54 wherein a standard deviation of diameters of the inclusions is less than about 4 µm.

Embodiment E56 concerns the method of embodiment E49 wherein a distribution of diameters of the inclusions is a monodisperse distribution.

Embodiment E57 concerns the method of embodiment E49 wherein the mixture is prepared by a process comprising sonication.

Embodiment E58 concerns the method of embodiment E49 wherein the inclusions comprise a cross-sectional size within a range from about 0.1 µm to about 50 µm.

Embodiment E59 concerns the method of embodiment E49 wherein the agent forms inclusions within the matrix that are in physical state a liquid at less than about 25° C.

Embodiment E60 concerns the method of embodiment E59 wherein substantially all the inclusions are droplets of the agent of less than about 50 µm in diameter within the matrix.

Embodiment E61 concerns the method of embodiment E59 wherein an average droplet diameter within the matrix is about 5-50 µm.

Embodiment E62 concerns the method of embodiment E59 wherein the agent is latanoprost.

Embodiment E63 concerns the method of embodiment E49 wherein the physical state of the agent is a solid at less than about 25° C.

Embodiment E64 concerns the method of embodiment E63 wherein the agent forms inclusions in the matrix and the physical state of the inclusions is a solid at less than about 25° C.

Embodiment E65 concerns the method of embodiment E63 wherein substantially all the inclusions are particles of the agent of less than about 50 µm in diameter within the matrix.

Embodiment E66 concerns the method of embodiment E63 wherein an average particle diameter within the matrix is about 5-50 µm.

Embodiment E67 concerns the method of embodiment E63 wherein the agent is bimatoprost, olopatadine, or cyclosporine.

Embodiment E68 concerns the method of aspect E1 or E2 wherein each drug insert comprises two or more therapeutic agents.

Embodiment E69 concerns the method of aspect E1 or E2 wherein each drug core comprises first and second drug cores.

Embodiment E70 concerns the method of embodiment E69 wherein the first and second drug cores are positioned side by side and together form a cylinder which is the drug core within the sheath body.

Embodiment E71 concerns the method of embodiment E69 wherein the drug core comprises two drug cores, a first drug core comprising a first agent and a first matrix, and a second drug core comprising a second agent and a second matrix, wherein the first agent and the second agent are different, and wherein the first matrix and the second matrix are either the same or differ from each other, the implant body comprising an aperture adapted to receive the drug insert comprising the first and the second drug cores, the method further comprising disposing the drug cores within the insert prior to disposing the insert within the aperture of the implant body.

Embodiment E72 concerns the method of embodiment E71 wherein the first matrix and the second matrix differ from each other with respect to at least one of a composition, an exposed surface area, a surfactant, a crosslinker, an additive, a matrix material, a formulation, or a stability.

Embodiment E73 concerns the method of embodiment E71 wherein the first drug core and the second drug core are disposed within the sheath such that the first drug core has a surface exposed directly to tear liquid and the second drug core has a surface exposed the first drug core.

Embodiment E74 concerns the method of embodiment E71 wherein the first drug core and the second drug core are disposed side by side within the sheath.

Embodiment E75 concerns the method of embodiment E71 wherein the first drug core and the second drug core are each cylindrical in shape and disposed with the drug core, the first drug core being positioned near a proximal end of an aperture in the implant body adapted to receive the drug core and the second drug core being positioned near a distal end of the aperture.

Embodiment E76 concerns the method of embodiment E71 wherein the first drug core and the second drug core are each cylindrical in shape and are positioned concentrically within an aperture of the implant body adapted to receive the drug cores, the first drug core having a first central opening and the second drug core being configured to fit within the first central opening of the first drug core.

Embodiment E77 concerns the method of embodiment E71 wherein the first and second drug cores are concentrically positioned within the aperture, the first drug core having a first central opening exposing a first inner surface and the second drug core having a second central opening exposing a second inner surface, the second drug core being configured to fit within the first central opening of the first drug core, and wherein the aperture extends from a proximal end to a distal end of the implantable body adapted to allow a tear or tear film fluid to pass through the aperture and contact the first and second inner surfaces of the first and second central openings and release the first and second therapeutic agents into a canaliculus.

Embodiment E78 concerns the method of embodiment E71 wherein the insert is adapted such that when it is implanted the first therapeutic agent releases at therapeutic levels throughout a first time period and the second therapeutic agent releases at therapeutic levels throughout a second time period.

Embodiment E79 concerns the method of embodiment E71 wherein the first therapeutic agent releases at therapeutic levels throughout a first time period and the second therapeutic agent releases at therapeutic levels throughout a second time period.

Embodiment E80 concerns the method of embodiment E79 wherein the first time period and the second time period are between one week and five years.

Embodiment E81 concerns the method of embodiment E79 wherein the first time period and the second time period are substantially the same.

Embodiment E82 concerns the method of embodiment E79 wherein the first time period and the second timer period are different.

Embodiment E83 concerns the method of embodiment E71 further comprising disposing a head coupled to the implant body covering the aperture, the head being permeable to the first and second therapeutic agents.

Embodiment E84 concerns the method of embodiment E71, wherein the therapeutic levels are drop administered quantities or less.

Embodiment E85 concerns the method of embodiment E71, wherein the therapeutic levels are less than 10% of drop administered quantities.

Embodiment E86 concerns the method of embodiment E71, further comprising disposing a medication-impregnated porous material within the first matrix, the second matrix, or both, the medication-impregnated porous material being adapted such that tear liquid releases the first agent, the second agent, or both, therefrom at therapeutic levels over a sustained period when a drug core-containing implant is disposed within a punctum, wherein the medication-impregnated porous material is a gel material that can swell from a first diameter to a second diameter.

Embodiment E87 concerns the method of embodiment E86 wherein in which the second diameter is about 50% greater than the first diameter.

Embodiment E88 concerns the method of embodiment E86 wherein the medication-impregnated porous material is a HEMA hydrophilic polymer.

Embodiment E89 concerns the method of embodiment E71 wherein the implant body comprises a central bore that extends from a proximal end to a distal end of the implant body adapted to allow a tear liquid to pass through the implant body and release the first and second therapeutic agents into a canaliculus.

Embodiment E90 concerns the method of embodiment E71 wherein the first agent provides a first effect and a side effect to the patient, and the second agent provides a second effect that mitigates or counters the side effect of the first agent.

Embodiment E91 concerns the method of aspect E1 or E2 wherein the matrix comprises a polyurethane polymer or copolymer.

Embodiment E92 concerns the method of embodiment E91 wherein the polyurethane polymer or copolymer comprises an aliphatic polyurethane, an aromatic polyurethane, a polyurethane hydrogel-forming material, a hydrophilic polyurethane, or a combination thereof.

Embodiment E93 concerns the method of embodiment E91 wherein the polyurethane polymer or copolymer comprises a hydrogel adapted to swell when contacted with an aqueous medium and the sheath is adapted to be of sufficient elasticity to expand in response thereto.

Embodiment E94 concerns the method of embodiment E93 wherein the swelling is adapted to retain the plug within the punctual canal.

Embodiment E95 concerns the method of embodiment E91 wherein the therapeutic agent comprises cyclosporine or olopatadine, a prodrug or a derivative of cyclosporine or olopatadine or any combination thereof.

Embodiment E96 concerns the method of embodiment E95 wherein a weight ratio of the cyclosporine or the olopatadine or the cyclosporine prodrug or derivative, or the olopatadine prodrug or derivative, or the combination thereof, to the polyurethane polymer or copolymer is about 1 wt % to about 70 wt %.

Embodiment E97 concerns the method of embodiment E95 wherein the polyurethane polymer or copolymer, and a quantity or a concentration of the cyclosporine or olopatadine, or the prodrug or derivative of cyclosporine or olopatadine, or combination thereof, therein, is selected to provide a release profile of the agent into tear liquid of the patient.

Embodiment E98 concerns the method of embodiment E91 wherein the drug core further comprises a second therapeutic agent.

Embodiment E99 concerns the method of embodiment E91, comprising forming the mixture by melting and mixing the polyurethane polymer or copolymer and the therapeutic agent.

Embodiment E100 concerns the method of embodiment E99 wherein the therapeutic agent is in molten form in the mixture.

Embodiment E101 concerns the method of embodiment E99 wherein the therapeutic agent is in solid form in the mixture.

Embodiment E102 concerns the drug insert made by a method of aspect E1 or E2.

Embodiment E103 concerns the method of aspect E1 or E2, wherein the temperature comprises a temperature of less than about 25° C.

Embodiment E104 concerns the method of aspect E1 or E2, wherein the temperature comprises a temperature of less than about 15° C.

Embodiment E105 concerns the method of aspect E1 or E2, wherein the temperature comprises a temperature of less than about 10° C.

Embodiment E106 concerns the method of aspect E1 or E2, wherein the temperature comprises a temperature of less than about 5° C.

Embodiment E107 concerns the method of aspect E1 or E2 wherein: a) the therapeutic agent is uniformly and homogeneously dispersed throughout the matrix; or b) the therapeutic agent at least in part forms solid or liquid inclusions within the matrix.

The method of manufacturing aspects and embodiments of aspects E1 and E2 and embodiments E3 through E107 can be combined in any manner, as long as the combination is not internally inconsistent. For example, embodiment E6 may be combined with any of embodiments E3 through E5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for this aspect and embodiment set.

Aspect F1 concerns a method of treating a malcondition in a patient in need thereof, comprising disposing in the patient an implant comprising a drug insert of any one of aspect A1 and embodiments A2-A78 or a drug core of any one of aspect B1 and embodiments B2-B28, or a drug core obtained by division of a filled precursor sheath of any one of aspect C1 and embodiments C2-C32, or a drug implant of any one of aspect D1 and embodiments D2-D30, or a drug insert of embodiment E102, wherein the therapeutic agent is adapted to treat the malcondition, in or adjacent to an eye of the patient such that the drug is released into a body tissue or fluid.

Embodiment F2 concerns the method of aspect F1 wherein the malcondition comprises glaucoma, and the agent is a prostaglandin analog.

Embodiment F3 concerns the method of embodiment F2 wherein the matrix comprises a non-biodegradable silicone or polyurethane polymer.

Embodiment F4 concerns the method of embodiment F2 wherein the prostaglandin analog is latanoprost.

Embodiment F5 concerns the method of aspect F1 wherein the malcondition comprises dry eye or eye inflammation and the agent is cyclosporine or olopatadine or a prodrug or derivative of cyclosporine or olopatadine.

Embodiment F6 concerns the method of embodiment F5 wherein the matrix comprises polyurethane.

Aspect G1 concerns a drug insert adapted for disposition within a lacrimal implant for providing sustained release of latanoprost to an eye of a patient in need of treatment of glaucoma, the drug insert comprising a drug core and a sheath body partially covering the drug core, the drug core comprising latanoprost and a matrix, the matrix comprising a silicone polymer, the sheath body being disposed over a portion of the drug core to inhibit release of the latanoprost from that portion and so as to define at least one exposed surface of the drug core not covered by the sheath body thereby being adapted to release the latanoprost to the eye, wherein an amount of the latanoprost in a volumetric portion of the drug core is similar to an amount of the latanoprost in any other equal volumetric portion of the drug core.

Embodiment G2 concerns the drug insert of aspect G1 wherein the amount of the latanoprost in a volumetric portion of the drug core varies from the amount of the latanoprost in any other equal volumetric portion of the drug core by no greater than about 30%.

Embodiment G3 concerns the drug insert of aspect G1 wherein the amount of the latanoprost in a volumetric portion of the drug core varies from the amount of the latanoprost in any other equal volumetric portion of the drug core by no greater than about 20%.

Embodiment G4 concerns the drug insert of aspect G1 wherein the amount of the latanoprost in a volumetric portion of the drug core varies from the amount of the latanoprost in any other equal volumetric portion of the drug core by no greater than about 10%.

Embodiment G5 concerns the drug insert of aspect G1 wherein the amount of the latanoprost in a volumetric portion of the drug core varies from the amount of the latanoprost in any other equal volumetric portion of the drug core by no greater than about 5%.

Embodiment G6 concerns the drug insert of aspect G1, wherein the latanoprost is dispersed within the silicone as droplets thereof.

The drug insert aspects and embodiments of aspect G1 and embodiments G2 through G6 can be combined in any manner, as long as the combination is not internally inconsistent. For example, embodiment G6 may be combined with any of embodiments G2 through G5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for an aspect and embodiment set.

Aspect H1 concerns a drug insert adapted for disposition within an punctual plug for providing sustained release of a cyclosporine to the eye for treatment of dry eye or inflammation, the insert comprising a drug core and a sheath body partially covering the core, the drug core comprising the cyclosporine and a matrix, the matrix comprising a polyurethane polymer, the sheath body being disposed over a portion of the core to inhibit release of the cyclosporine from said portion and so as to define at least one exposed surface of the drug core not covered by the sheath body being adapted to release the cyclosporine to the eye, wherein an amount of the cyclosporine in a volumetric portion of the drug core is similar to an amount of the cyclosporine in any other equal volumetric portion of the drug core.

Embodiment H2 concerns the drug insert of aspect H1 wherein the amount of the cyclosporine in a volumetric portion of the drug core varies from the amount of the cyclosporine in any other equal volumetric portion of the drug core by no greater than about 30%.

Embodiment H3 concerns the drug insert of aspect H1 wherein the amount of the cyclosporine in a volumetric portion of the drug core varies from the amount of the cyclosporine in any other equal volumetric portion of the drug core by no greater than about 20%.

Embodiment H4 concerns the drug insert of aspect H1 wherein the amount of the cyclosporine in a volumetric portion of the drug core varies from the amount of the cyclosporine in any other equal volumetric portion of the drug core by no greater than about 10%.

Embodiment H5 concerns the drug insert of aspect H1 wherein the amount of the cyclosporine in a volumetric portion of the drug core varies from the amount of the cyclosporine in any other equal volumetric portion of the drug core by no greater than about 5%.

Embodiment H6 concerns the drug insert of aspect H1, wherein the cyclosporine is dissolved within the polyurethane.

The drug insert aspects and embodiments of aspect H1 and embodiments H2 through H6 can be combined in any manner, as long as the combination is not internally inconsistent. For example, embodiment H6 may be combined with any of embodiments H2 through H5. These combinations are intended to provide the same concepts and meanings as multiply-dependent claims have and also the concepts and meanings that multiply-dependent claims upon other multiply-dependent claims have, so that any and all combinations of preceding and succeeding subject matter are included for an aspect and embodiment set.

Further aspects and embodiments include the following.

The drug insert of any one of aspect A1 and embodiments A1-A78, or the drug core of any one of aspect B1 and embodiments B2-B28, or the drug core obtained by division of a filled precursor sheath of any one of aspects C1 and embodiments C2-C32, or the drug implant of any one of aspect D1 and embodiments D2-D30, or the drug insert of embodiment E102, adapted for providing sustained release of a therapeutic agent to the eye or surrounding tissues, or systemically, or any combination thereof.

A drug core of any of aspect A1 and embodiments A2-A78 which has been formed into a shape of an implant body for disposition in or adjacent to a body cavity, tissue, duct, or fluid of a patient.

Another aspect of the invention concerns the use of a drug insert of any one of aspect A1 and embodiments A2-A78, or a drug core of any one of aspect B1 or embodiments B2-B28, or a drug core obtained by division of a filled precursor sheath of any one of aspect C1 or embodiments C2-C32, or a drug implant of any one of aspect D1 or embodiments D2-D30, or a drug insert of E102, in the manufacture of an implant adapted for treatment of a malcondition in a patient in need thereof.

Another aspect of the invention concerns an implant comprising a polymer and a therapeutic agent disposed therein, wherein an amount of the therapeutic agent in a volumetric portion of the implant is similar to an amount of the therapeutic agent in any other equal volumetric portion of the implant.

A further aspect of the invention concerns a method of manufacturing an implant comprising a polymer and a therapeutic agent disposed therein, wherein an amount of the therapeutic agent in a volumetric portion of the implant is similar to an amount of the therapeutic agent in any other equal volumetric portion of the implant, in which the method comprises injecting a mixture comprising a polymer and a therapeutic agent into a mold, the method comprising injecting said mixture at a temperature less than about 25° C.

BRIEF DESCRIPTION OF THE DRAWINGS

FIG. 1A shows a top cross sectional view of a sustained release implant to treat an optical defect of an eye, according to an embodiment of the present invention.

FIG. 2F shows a perspective view of a sustained release implant comprising a core with folds, according to an embodiment of the present invention.

FIG. 2G shows a perspective view of a sustained release implant with a core comprising a channel with an internal surface, according to an embodiment of the present invention.

FIG. 2H shows a perspective view of a sustained release implant with a core comprising porous channels to increase drug migration, according to an embodiment of the invention.

FIG. 2I shows a perspective view of a sustained release implant with a convex exposed drug core surface, according to an embodiment of the present invention.

FIG. 6D shows a method of assembling the punctual plug component in accordance with the method of in FIG. 6A.

FIG. 18A shows a sectional view of a sustained release implant having a first drug core with a first therapeutic agent and a second drug core with a second therapeutic agent to treat an eye, the first and second drug cores being in a concentric configuration, according to an embodiment of the present invention.

FIG. 18B shows a side cross-sectional view of the sustained release implant of FIG. 18A.

FIG. 19A shows a sectional view of a sustained release implant having a first drug core with a first therapeutic agent and a second drug core with a second therapeutic agent to treat an eye, the first and second drug cores being in a side by side configuration, according to an embodiment of the present invention.

FIG. 19B shows a side cross-sectional view of the sustained release implant of FIG. 19A.

FIG. 20A shows a sectional view of a sustained release implant having a first drug core with a first therapeutic agent and a second drug core with a second therapeutic agent to treat an eye, the first and second drug cores being in a concentric configuration with a hollow center to allow fluid flow through the implant, according to an embodiment of the present invention.

FIG. 20B shows a side cross-sectional view of the sustained release implant of FIG. 20A.

FIG. 22 shows one embodiment of a therapeutic implant to treat an eye having a punctual plug and a sustained release implant having a drug core with a first therapeutic agent and a second therapeutic agent.

FIGS. 23-25 show different embodiments of therapeutic implants to treat an eye having a punctual plug and a sustained release implant having a first drug core with a first therapeutic agent and a second drug core having a second therapeutic agent.

FIG. 27 shows therapeutic implants containing first and second therapeutic agents as applied to the eye.

DETAILED DESCRIPTION

Definitions

Figure 1B:
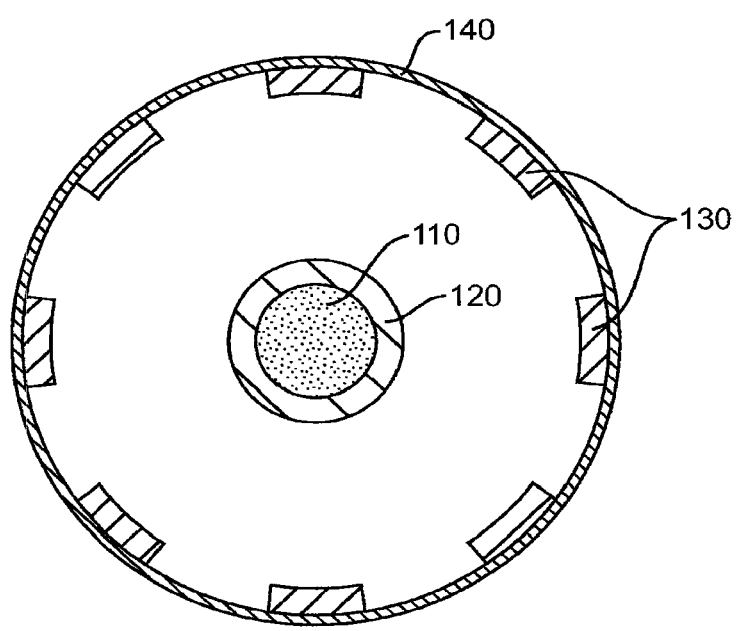
FIG. 1B shows a side cross sectional view of the sustained release implant of FIG. 1A.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc, Springfield, Mass., 1993, *The American Heritage Dictionary of the English Language*, Houghton Mifflin, Boston Mass., 1981, and *Hawley's Condensed Chemical Dictionary*, 14th edition, Wiley Europe, 2002.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise.

"Subject" or "patient" as used herein, includes mammals such as humans, non-human primates, rats, mice, dogs, cats, horses, cows and pigs.

A "therapeutic agent" is a medicinal compound or mixture thereof that is effective and medically indicated for treatment of a malcondition in a patient.

"Treating" or "treatment" within the meaning herein refers to an alleviation of symptoms associated with a disorder or disease, or inhibition of further progression or worsening of those symptoms, or prevention or prophylaxis of the disease or disorder. Similarly, as used herein, an "effective amount" in the context of a therapeutic agent, or a "therapeutically effective amount" of a therapeutic agent refers to an amount of the agent that alleviates, in whole or in part, symptoms associated with the disorder or condition, or halts or slows further progression or worsening of those symptoms, or prevents or provides prophylaxis for the disorder or condition. In particular, an "effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects. When the term "effective amount" is used in the context of a functional material, such as an effective amount of a dispersant, what is meant is that the amount of the functional material used is effective to achieve the desired result.

An "implant" as the term is used herein refers to a physical device adapted for insertion within or adjacent to a portion of a patient's body, not necessarily by surgical emplacement. For example, insertion of an implant such as a punctual plug through the punctum into the canaliculus of the eye of a patient need not involve surgical intervention, similarly with the emplacement of a device adapted to be held under an eyelid in contact with the orb of the eye. An implant is formed of biocompatible materials to the extent the materials actually come in contact with body tissues or fluids when disposed in their operative location. As defined herein, an implant is adapted to receive a "drug insert", that is, a structure that contains the therapeutic agent to be administered to the particular patient for treatment of the particular condition, and which is adapted to release the therapeutic agent to the target tissues or organs over a period of time. Release of therapeutic quantities of an agent over a period of time is referred to as "sustained release" or "controlled release", as is well known in the art.

By the terms "eye and surrounding tissues" is meant not just the orb of the eye, but surrounding conjunctival membranes, tear ducts, canaliculi (ducts draining tear liquid to the sinus), eyelids, and associated body structures.

A "polymer" as the term is used herein, refers to an organic macromolecule containing one or more repeating units, as is well known in the art. A "copolymer" refers to a polymer in which there are at least two types of repeating units included. A copolymer can be a block copolymer, in which there are segments containing multiple repeating units of one type, bonded to segments containing multiple repeating units of a second type. A "polymer" or "polymeric material" can be a silicone, a polyurethane, a polyamide, a polyester, a polysaccharide, a polyimide, or the like, or any copolymer thereof. When a polymeric material is to come in contact with a body tissue or fluid, the polymeric material is biocompatible.

A "matrix" is a material comprising an organic polymer in which the therapeutic agent is dispersed, the combination of which materials, referred to as a "core", serves as the reservoir of the agent from which the agent is released over a period of time.

The term "precursor" as used in the context of this invention and as applied to any particular item means an intermediate or forerunner or prior article, device, item, or compound that is subsequently manipulated to form a final article, device, item or compound, or the like. For example, a "precursor sheath" is the elongated tube that, when filled with matrix and then cut, forms the sheath of the insert. In another example in the language used herein, a "matrix precursor" is "cured" to form the matrix. The matrix precursor can itself be a polymer, and can be cured, for example, by crosslinking. Or, the matrix precursor can be a polymer dissolved in a solvent, and curing includes removal of the solvent to provide the polymeric matrix material. Or, the matrix precursor can be a monomer, and curing can involve polymerization of the monomer, and can also involve removal of a solvent, and crosslinking of a polymer formed by polymerization. In a further example, a precursor drug core is a cured matrix containing the therapeutic agent that can be cut into appropriate lengths to form a drug core. A typical application of the precursor drug core is the filled precursor sheath. The filled precursor sheath is a precursor sheath body containing the precursor drug core that can be cut into appropriate lengths thereby producing a drug insert of the invention.

The terms "agent", "therapeutic agent", or "drug" as used herein refer to a medicinal material, a compound or a mixture thereof, suitable and medically indicated for treatment of a malcondition in a patient. The agent can be in a solid physical form or a liquid physical form at about room temperature or at about body temperature, depending on the melting point of the material. Examples of therapeutic agents are provided herein; for treatment of malconditions of the eye, specific examples of types or classes of agents that can be included in the inventive inserts include a glaucoma medication, a muscarinic agent, a beta blocker, an alpha agonist, a carbonic anhydrase inhibitor, or a prostaglandin or prostaglandin analog; an antiinflammatory agent; an anti-infective agent; a dry eye medication; or any combination thereof. More specifically, an example of a glaucoma medication is a prostaglandin or a prostaglandin analog. An example of a muscarinic agent is pilocarpine. An example of a beta blocked is betaxolol. An example of an alpha agonist is brimonidine. Examples of a carbonic anhydrase inhibitor are dorzolamide or brinzolamide. Examples of an antiinflammatory agent include a steroid, a soft steroid, or an non-steroidal antiinflammatory drug (NSAID) such as ibuprofen. An example of an analgesic includes, salicylic acid and acetaminophen. An antibiotic (antibacterial) can be a beta-lactam antibiotic, a macrocyclic antibiotic such as erythromycin, a fluoroquinolone, or the like. An antiviral compound can be a reverse transcriptase inhibitor or a viral protease inhibitor. An antimycotic can be a triazole antifungal compound. A dry eye medication can be cyclosporine, olapatadine, a delmulcent, or sodium hyaluronate.

In various embodiments, the therapeutic agent is contained in the matrix such that an amount of the therapeutic agent in a volumetric portion of the drug core is similar to an amount of the therapeutic agent in any other equal volumetric portion of the drug core. For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%. In addition, the concentration of the therapeutic agent in a volumetric portion of the drug core can be the same as any other equal volumetric portion of the drug core, in certain embodiments including those embodiments wherein the agent is present as a uniform, homogeneous dispersion and in embodiments wherein the agent is present in solid or liquid inclusions throughout the matrix.

The agent can be dissolved in the matrix in some embodiments, when the chemical identities of the agent and the matrix, and the concentration of the agent in the matrix, are such that dissolution is achieved. For example, as is known in the art, certain lipophilic steroid derivatives can dissolve at significant concentrations in silicones. In this event, the agent is referred to as being "dissolved" in the polymer, or as being uniformly, homogeneously dispersed throughout the matrix or "dispersed at a molecular level" in the polymer, just as a compound can be dissolved in a solvent, to form a "solid solution" of the agent in the polymeric material of the matrix.

In other embodiments, the agent does not completely dissolve in the matrix, but is present as domains or "inclusions" of the agent within the polymeric matrix. The inclusions can be liquid or solid at about room temperature or at about the temperature of the human body. After the matrix precursor has been cured to form the matrix, the inclusions are non-uniformly distributed in the now-solid or near solid matrix, and are thus prevented at least to some extent from recombining with each other, such as by liquid droplet accretion. This form is referred to as a "heterogeneous" distribution of the agent in the matrix. When inclusions of the agent are present, it is believed that a certain proportion of the agent may also be dissolved in the matrix. However, dissolution is not necessary for operation and function of the invention. Furthermore, the heterogeneous distribution of the agent with the matrix can be managed on a macroscopic level as discussed in connection with the definition of the terms "concentration" and "similar" given below.

A "concentration" of a therapeutic agent, as the term is used herein, refers to a concentration of the agent within a macroscopic portion of the matrix-agent core, that is controlled to have a degree of reproducibility from sample to sample of the core. A concentration of the agent in a macroscopic portion of the core can vary, but only within limits, relative to that in any other equal macroscopic portion of the core. The term does not relate to concentrations at the molecular level, where discontinuous and/or irregular domains or inclusions of the agent in concentrated form may be present, but rather refers to bulk concentrations of the agent in volumes of the core that are greater than at least about 0.1 mm$^3$, for example, a cubic sample of core about 100 μm on a side, or a 0.1 mm thick slice of a core with cross-sectional area of about 1 mm$^2$.

The term "similar", as in a "similar" concentration of a therapeutic agent, means that within a defined margin, the quantity, such as the concentration of the agent, for example in units of μg/mm$^3$, only varies within a certain degree from measurement to measurement. The degree of variation is controlled or regulated to provide a degree of uniformity of core material, such that pluralities of cores or inserts are medically suitable in that the dose of the agent they can provide to the tissue is within certain limits from sample to sample. For example, a "similar" concentration between two equal volumes of core material, or between two inserts prepared by from a filled precursor sheath, can vary by no greater than about 30%, or can vary by no greater than about 20%, or can vary by no greater than about 10%, or can vary by no greater than about 5%. The term "similar" also includes solid solutions and uniform homogeneous dispersions, defined herein. These concern situations where the concentration of the therapeutic agent is the same in different portions of the core or between a plurality of cores. This is a subcategory of the more general category "similar."

The inclusions can be of various sizes, and various distributions of sizes of a plurality of the inclusions are possible, as are defined herein. When it is stated that the inclusions are no greater than about 100 µm in diameter, what is meant is that the largest inclusion observed within a drug insert of the invention has a greatest dimension of no greater than about 100 µm. When a particular size distribution of inclusions is recited, what is meant is that a predominant proportion of all the inclusions are of the stated dimension. When an average size or "average diameter" of inclusions within a population of inclusions is stated, what is meant is a numerical average of the greatest dimensions of all the inclusions. When a "standard deviation" of the distribution of inclusion diameters within in a population of inclusions is stated, what is meant that the distribution of inclusion diameters is normal or near normal, and that the standard deviation is a measure of the spread of the values, as is well known in the art. A small standard deviation relative to the average diameter denotes a tight distribution of inclusion diameters, a feature of various embodiments of the present invention.

In various embodiments, the inclusions can have an average diameter of less than about 20 µm, and a standard deviation of diameters of the inclusions is less than about 8 µm. Or, the inclusions can have an average diameter of less than about 15 µm, and a standard deviation of diameters of the inclusions is less than about 6 µm. Or, the inclusions can have an average diameter of less than about 10 µm, and a standard deviation of diameters of the inclusions is less than about 4 µm. A relative uniformity of inclusion size distribution, and a relative uniformity of the amount of agent dispersed per unit volume of the core within the insert, are features of various embodiments according to the present invention.

The size distribution of inclusion diameters can be monodisperse, and can be tightly so. By "monodisperse" is meant herein that the size distribution of the diameters of the plurality of inclusions is relatively tightly clustered around the average inclusion diameter, even if the distribution is not a normal distribution. For example, the distribution can have a fairly sharp upper size limit of inclusions of greater than average diameter, but can trail off in the distribution of inclusions of less than average diameter. Nevertheless, the size distribution can be tightly clustered, or monodisperse.

A "polyurethane" refers to a variety of polymer or copolymer containing repeating units bonded covalently through urethane, i.e., carbamate, bonds, —N—C(O)—O— wherein the N and O atoms are attached to an organic radical. The organic radical can be aliphatic, aromatic, or mixed; can contain other functional groups. Each radical, other than the radicals at the ends of the molecular chains, is bonded via two (or more) urethane groups to other radicals. A polyurethane polymer contains only urethane-type groups joining the repeating units. A polyurethane copolymer, such as a polyurethane-silicone copolymer or a polyurethane-carbonate copolymer, contains urethane and other types of groups joining the repeating units, i.e., silicone and carbonate type groups respectively.

A polyurethane-silicone copolymer contains segments of polyurethane chains and segments of silicone chains, as is well known in the art. A polyurethane-carbonate copolymer contains urethane segments and carbonate (—O—C(O)O—) segments. An example of a polyurethane-carbonate copolymer is Carbothane TPU® (Lubrizol).

A 'hydrogel' as the term is used herein refers to a polymeric material that has absorbed greater than 100 wt %, for example up to 500-2000 wt %, of water within the polymeric structure and has consequently swelled substantially in physical size. A hydrogel possesses physical integrity, has tensile strength, and is not substantially fluid. A "hydrogel-forming polymer" is a polymeric material capable of forming a hydrogel upon contact with water. Examples include TG-500 and TG-2000.

"TG-500" and "TG-2000" are polyurethane hydrogel-forming polymers manufactured by the Thermedics Polymer Products division of Lubrizol Advanced Materials, Inc., of Wilmington, Mass. They are described by the manufacturer as aliphatic, polyether based thermoplastic polyurethanes capable of forming hydrogels. Such hydrogel-forming polymers can absorb greater than 100 wt %, for example up to 500-2000 wt % of water, and consequently swell in physical dimensions.

A "hydrophilic polymer" is a polymer that can be wetted by water, i.e., does not have a water-repellant surface. A hydrophilic polymer can absorb water to a small degree, for example about 0-100 wt % of water, but does not greatly swell in volume as does a hydrogel-forming polymer.

"Cyclosporine" is an immunosuppressant drug widely used in post-allogeneic organ transplant to reduce the activity of the patient's immune system and so the risk of organ rejection. It has been studied in transplants of skin, heart, kidney, lung, pancreas, bone marrow and small intestine. Initially isolated from a Norwegian soil sample, Cyclosporin A, the main form of the drug, is a cyclic nonribosomal peptide of 11 amino acids (an undecapeptide) produced by the fungus *Tolypocladium inflatum Gams*. The structure of cyclosporine is:

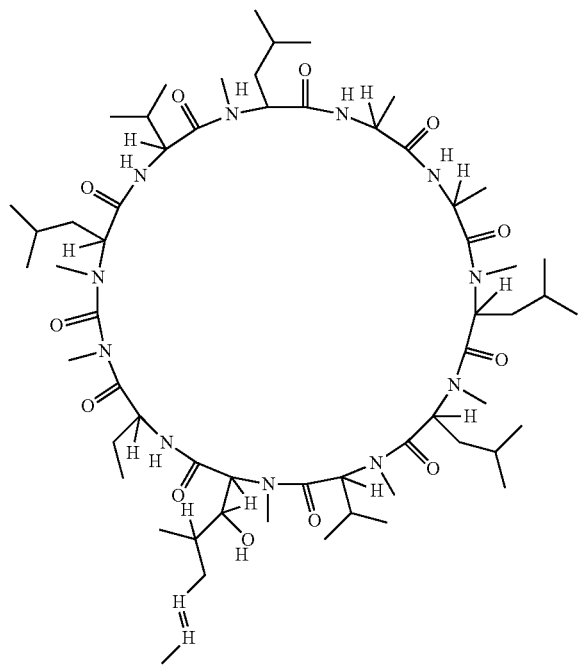

"Olopatadine", the structure of which is shown below, is a NSAID that can be administered in the form of a hydrochloride salt:

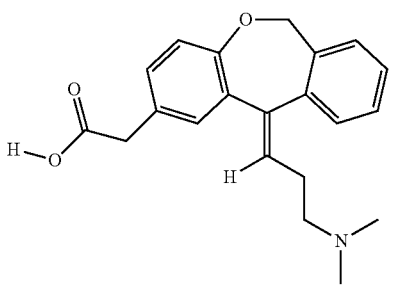 [SMILES: CN(C)CC/C=C1\c2ccccc2COc2ccc(CC(=O)O)cc21]

A "prodrug" is a substance, for example, that releases a therapeutic agent such as cyclosporine or olopatidine, or a biologically active derivative of either of these substances, when administered to a mammal. A prodrug can be a chemical derivative that contains a bond that is cleavable by an endogenous enzyme of the mammalian circulatory system such as an esterase or a phosphatase. For example, an amide NH of cyclosporine can be substituted with an ester group, providing a carbamate of structure ROC(O)N-cyclosporine. An endogenous esterase can cleave the ester bond, yielding an N-carboxyamide, which can spontaneously decarboxylate to yield cyclosporine. An ester of olopatidine, which can be cleaved by an endogenous esterase to yield olopatidine, is an example of an olopatidine prodrug. By formation of prodrugs, the polarity (hydrophobicity/hydrophilicity) of cyclosporine or olopatidine can be modified.

A "derivative" is a substance chemically allied to the therapeutic agent, and retaining at least some of the therapeutic agent's biological activity, but which need not be metabolized to the agent itself in the mammalian body to provide the desired beneficial result.

A "release profile", as in a "defined release profile", refers to a rate of release as a function of time of the therapeutic agent from an inventive plug into the eye, which can be defined or determined by selection of a particular polyurethane polymer or copolymer for a particular therapeutic agent. The release profile will in turn govern both the concentration of the agent in the eye and surrounding tissue over the time period during which the plug releases the agent.

DETAILED DESCRIPTION

The present invention is directed to various embodiments of drug inserts and drug cores containing therapeutic agents for use in implant bodies adapted for disposition in a body tissue, fluid, cavity, or duct. The implant bodies can be adapted to be disposed in or adjacent to an eye of a patient. The implants release the agent to the body, for example, into an eye or surrounding tissues, or both, over a period of time, for treatment of a malcondition in the patient for which use of the therapeutic agent is medically indicated. The invention is also directed to various embodiments of methods of manufacture of the drug inserts, and to methods of treatment of patients using implants containing the drug inserts.

In various embodiments, the invention provides a drug core adapted for disposition within a sheath and hence within an implant. The implant is adapted for disposition within or adjacent to an eye of a patient, for providing sustained release of a therapeutic agent to the eye or surrounding tissues or both.

The drug core comprises a therapeutic agent and a matrix wherein the matrix comprises a polymer, wherein an amount of the therapeutic agent in a volumetric portion of the drug core is similar to an amount of the therapeutic agent in any other equal volumetric portion of the drug core.

The insert comprises a drug core and a sheath body partially covering the drug core. For example, the amount of the therapeutic agent within the volumetric portion of the drug core varies from the amount of the therapeutic agent within any other equal volumetric portion of the drug core by less than about 30%. For example, the amount of the therapeutic agent within the volumetric portion of the drug core varies from the amount of the therapeutic agent within any other equal volumetric portion of the drug core by less than about 20%. For example, the amount of the therapeutic agent within the volumetric portion of the drug core varies from the amount of the therapeutic agent within any other equal volumetric portion of the drug core by less than about 10%. For example, the amount of the therapeutic agent within the volumetric portion of the drug core varies from the amount of the therapeutic agent within any other equal volumetric portion of the drug core by less than about 5%.

The sheath body is disposed over a portion of the drug core to inhibit release of the agent from said portion and so as to define at least one exposed surface of the drug core adapted to release the agent to the eye or surrounding tissues, or both, when the implant is inserted into the patient.

In various embodiments, the invention provides a plurality of the drug inserts as described above wherein each of the plurality of the inserts comprises a similar amount of the agent dispersed respectively therewithin. For example, the similar amount of agent dispersed respectively therein can vary no greater than about 30% therebetween. For example, the similar amount of agent dispersed respectively therein can vary no greater than about 20% therebetween. For example, the similar amount of agent dispersed respectively therein can vary no greater than about 10% therebetween. For example, the similar amount of agent dispersed respectively therein can vary no greater than about 5% therebetween.

The exposed surface of the core is adapted to release therapeutic quantities of the agent into body tissues or fluids, for example into tear liquid, for a time period of at least several days into tear liquid when the implant is inserted into the patient. The sheath, which is impermeable to the agent, serves to block, at least in part, exposure of non-target tissues to the agent. For example, when the drug insert is disposed within an implant inserted into the canaliculus of the eye, the sheath acts to inhibit the release of the agent to the therapeutic target, e.g., the eye, while blocking release to non-target tissue, such as the interior of the canaliculus, or the nasal sinus.

In an embodiment, the drug core can be substantially cylindrical in form, having an axis, wherein the exposed surface of the drug core is disposed on one end of the cylindrical form and a surface of the drug core covered by the sheath body constitutes a remainder of the surface of the cylindrical form.

In a plurality of drug inserts of the invention, the therapeutic quantity of the agent released by each of the drug inserts is similar from one insert to another. For example, among a plurality of drug inserts of the invention, the therapeutic quantity of the agent released by each of the plurality of the inserts can vary by no greater than about 30% therebetween, or by no greater than about 20% therebetween, or by no greater than about 10% therebetween, or by no greater than about 5% therebetween. In some embodiments, among a plurality of drug inserts of the invention, the therapeutic quantity of the agent released by each of the plurality of the inserts can be the same.

The drug core or drug insert can have various relative contents of the therapeutic agent therein. For example, the drug core can include about 0.1 wt % to about 50 wt % of the agent. The agent is dispersed within the matrix, the matrix comprising a polymer, to form a composite material that can be disposed within the sheath. For example, the matrix can be formed of a non-biodegradable silicone or a polyurethane, or combination thereof. The sheath is formed of a substantially drug-impermeable substance to block release of the agent except through an exposed surface. It can be formed of any suitable biocompatible material, such as a polymer comprising at least one of polyimide, PMMA, or PET, wherein the polymer is extruded or cast; or a metal comprising stainless steel or titanium.

A therapeutic agent for use in the inventive insert or core can include anti-glaucoma medications, (e.g. adrenergic agonists, adrenergic antagonists (beta blockers), carbonic anhydrase inhibitors (CAIs, systemic and topical), parasympathomimetics, prostaglandins such as latanoprost, and hypotensive lipids, and combinations thereof), antimicrobial agent (e.g., antibiotic, antiviral, antiparasitic, antimycotic, etc.), a corticosteroid or other anti-inflammatory (e.g., an NSAID or other analgesic and pain management compounds) such as cyclosporine or olopatidine, a decongestant (e.g., vasoconstrictor), an agent that prevents of modifies an allergic response (e.g., an antihistamine, cytokine inhibitor, leucotriene inhibitor, IgE inhibitor, immunomodulator such as cyclosporine), a mast cell stabilizer, cycloplegic, mydriatic or the like.

Examples of agents further include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as cyclosporine, olopatidine, hydrocortisone, hydrocortisone acetate, dexamethasone 21-phosphate, fluocinolone, medrysone, methylprednisolone, prednisolone 21-phosphate, prednisolone acetate, fluorometholane, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present punctum plugs, include triamcinolone acetonide and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdata.fda.gov/scripts/cder/drugsatfda/index. The present punctum plugs can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

In various embodiments, a agent can be cyclosporine, or a prodrug or derivative thereof, or olopatidine, or a prodrug or derivative thereof, and, optionally, a second agent selected from the above-listed therapeutic agents.

In various embodiments, the agent can be a prostaglandin analog, such as latanoprost, bimatoprost, or travoprost, and the amount of the agent in the drug insert can be about 10-50 µg.

In various embodiments, the therapeutic agent is contained in the matrix such that an amount of the therapeutic agent in a volumetric portion of the drug core is similar to an amount of the therapeutic agent in any other equal volumetric portion of the drug core. For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%. In addition, the concentration of the therapeutic agent in a volumetric portion of the drug core can be the same as any other equal volumetric portion of the drug core, in certain embodiments including those embodiments wherein the agent is present as a uniform, homogeneous dispersion and in embodiments wherein the agent is present in solid or liquid inclusions throughout the matrix.

In various embodiments, the agent can be dissolved in the matrix within the drug core, i.e., at an effective concentration for use as with an implant, wherein the agent is sufficiently soluble in the polymer such that no inclusions or concentrated domains of the agent are present. This is known in the art as a solid solution, i.e. a uniform, homogeneous dispersion on the molecular level, wherein the solid polymer plays the role of a solvent, and no liquid solvent is present. For example, when the agent comprises cyclosporine and the matrix comprises polyurethane, a solid solution is formed at useful concentrations of the cyclosporine in the insert. This solubility is believed to result, at least in part, from interaction of the abundant amide bonds found in the cyclosporine molecule, which is a cyclic peptide, with the amide-like urethane bonds of the polyurethane polymer.

In various embodiments, the agent is insufficiently soluble in the matrix to form a solid solution. In these embodiments, the agent can be distributed at least in part as a plurality of solid or liquid inclusions throughout the matrix, the inclusions comprising, at a temperature of about 20° C., droplets of the agent of no greater than about 100 µm diameter when the agent is a liquid at about 20° C., or particles of the agent of no greater than about 100 µm diameter when the agent is a solid at about 20° C.; wherein the inclusions of the agent are dispersed throughout each drug core.

As discussed above, the size and size distribution of the inclusions can have an effect on a rate of release of the agent from the drug core to the patient. For example, smaller, more uniform inclusions can serve to infuse the bulk matrix with the agent more effectively, at a higher rate, due to a more favorable surface area to volume ratio. Accordingly, inventive methods provide for control or regulation of the average inclusion diameter or the distribution of inclusion diameters. For example, the inclusions can have an average diameter of less than about 20 µm. Inclusions of this average diameter can have a standard deviation of diameters of the inclusions of less than about 8 µm. For example, the inclusions can have an average diameter of less than about 15 µm. Inclusions of this average diameter can have a standard deviation of diameters of the inclusions of less than about 6 µm. Or, the inclusions can have an average diameter of less than about 10 µm. Inclusions of this average diameter can have a standard deviation of diameters of the inclusions of less than about 4 µm. In various embodiments, the distribution of diameters of the inclusions can be a monodisperse distribution. In various embodiments, the inclusions predominantly comprise a cross-sectional size within a range from about 0.1 µm to about 50 µm. It is believed that tight, or monodisperse, distributions of inclusion diameter are favorable from the point of view of therapeutic aspects of the drug core or a drug insert containing the core.

Various embodiments of the invention also provide a drug core or an insert containing a drug core wherein the agent forms inclusions in the matrix that are in a liquid physical state at about 20° C. For example, substantially all the inclusions can be droplets of the agent of less than about 30 µm in diameter within the matrix. And, the droplets can have an average diameter of less than about 10 µm, or can have a standard deviation of diameters of the inclusions is less than about 4 µm. An example of an agent in a liquid physical state at about 20° C. is latanoprost.

Various embodiments of the invention also provide a drug core or an insert containing a drug core wherein the agent forms inclusions in the matrix that are in a solid physical state at about 20° C. For example, substantially all the inclusions can be particles of the agent of less than about 30 µm in diameter within the matrix. For example, an average particle diameter within the matrix can be about 5-50 µm. Examples of agents in a solid physical state at about 20° C. include bimatoprost, olopatadine, or cyclosporine.

In various embodiments the drug insert or drug core can comprise two or more therapeutic agents, or can comprise a plurality of drug cores. Such a plurality of drug cores can also be termed a plurality of drug sub-cores which together form the total drug core. In this context first and second drug cores can also be termed first and second drug sub-cores for clarity purposes. For example, a drug insert of the invention can include two drug cores disposed within the sheath body, a first drug core comprising a first agent and a first matrix, and a second drug core comprising a second agent and a second matrix, wherein the first agent and the second agent are different, and wherein the first matrix and the second matrix are either the same or differ from each other; the implant body comprising an aperture adapted to receive the first and the second cores disposed within the sheath body, the drug cores being adapted to be disposed, within the sheath, within the aperture of the implant body. The first matrix and the second matrix can differ from each other with respect to at least one of a composition, an exposed surface area, a surfactant, a crosslinker, an additive, a matrix material, a formulation, a release rate modifying reagent, or a stability. The first drug core and the second drug core can be disposed within the sheath body such that the first drug core has a surface exposed directly to tear liquid and the second drug core does not have a surface exposed directly to tear liquid when the drug insert is disposed within the implant body and the implant body is disposed in or adjacent to the eye of the patient. Or, the first drug core and the second drug core can be disposed side by side within the sheath body. Or, the first drug core and the second drug core can each be cylindrical in shape and be disposed with the sheath body, the first drug core being positioned near a proximal end of an aperture in the implant body and the second drug core being positioned near a distal end of the aperture, when the drug insert is disposed within the implant body. Or, the first drug core and the second drug core can each be cylindrical in shape provided that the first drug core has a first central opening, the drug cores being positioned concentrically within the sheath body within an aperture of the implant body adapted to receive the drug insert, and the second drug core being configured to fit within the first central opening of the first drug core. Or, the first and second drug cores can be concentrically positioned within the aperture of the implant body, the first drug core having a first central opening exposing a first inner surface and the second drug core having a second central opening exposing a second inner surface, the second drug core being configured to fit within the first central opening of the first drug core, and wherein the aperture extends from a proximal end to a distal end of the implant body thereby being adapted to allow tear liquid to pass through the aperture and contact the first and second inner surfaces of the first and second central openings and release the first and second therapeutic agents into a canaliculus of the patient when the implant body is inserted into a patient.

In various embodiments, the first therapeutic agent can have a release profile wherein the first agent is released at therapeutic levels throughout a first time period and the second therapeutic agent can have a second release profile wherein the second agent is released at therapeutic levels throughout a second time period. For example, the first time period and the second time period can be between one week and five years. The first release profile and the second release profile can be substantially the same, or can be different.

In various embodiments, the first agent can provides a first effect and a side effect to the patient, and the second agent can provide a second effect that mitigates or counters the side effect of the first agent.

In various embodiments, any inclusions in the first drug core and in the second drug core respectively have an average diameter of less than about 20 µm, and can have a standard deviation of diameters of less than about 8 µm.

In various embodiments, the implant body can comprise a central bore that extends from a proximal end to a distal end of the implant body so as to be adapted to allow a tear liquid to pass through the implant body such that the first and second therapeutic agents are released into the tear liquid into a canaliculus of the patient when the implant body is disposed in or adjacent to the eye.

In various embodiments, the drug insert or the drug core can further include a medication-impregnated porous material within the first matrix, the second matrix, or both, wherein the medication-impregnated porous material is adapted so as to permit tear liquid to release the first agent, the second agent, or both, from the medication-impregnated porous material at therapeutic levels over a sustained period when a drug core-containing implant is disposed within a punctum or within a lacrimal canaliculus, and wherein the medication-impregnated porous material is a gel material that can swell from a first diameter to a second diameter when in contact with tear liquid. The second diameter can be about 50% greater than the first diameter. An example of a suitable material for the medication-impregnated porous material is a hydroxyethylmethacrylate (HEMA) hydrophilic polymer.

In various embodiments, the drug insert or drug core can comprise a polyurethane polymer or copolymer. For example, the polyurethane polymer or copolymer can be an aliphatic polyurethane, an aromatic polyurethane, a polyurethane hydrogel-forming material, a hydrophilic polyurethane, or a combination thereof. In various embodiments, the polyurethane polymer or copolymer can include a hydrogel adapted to swell when contacted with an aqueous medium and the sheath body is adapted to be of sufficient elasticity to expand in response thereto. For example, the swelling can be adapted to retain the implant body within a duct, such as within a punctual canal, of the patient.

In various embodiments, when the matrix comprises a polyurethane, the therapeutic agent comprises cyclosporine or olopatadine, a prodrug or a derivative of cyclosporine or olopatadine, or any combination thereof. For example, the cyclosporine or the olopatadine, or the cyclosporine prodrug or derivative, or the olopatadine prodrug or derivative, or the combination thereof, can be present in a weight ratio to the polyurethane polymer or copolymer of about 1 wt % to about 70 wt %. A concentration of the cyclosporine in the core can be similar in a portion of the drug core proximate to the exposed surface, a portion distal to the exposed surface, and a portion disposed between the proximate portion and the distal portion. For example, the proximal portion can be in length at least about one tenth a length of the drug core.

In various embodiments, the invention provides a drug core comprising a therapeutic agent and a matrix wherein the matrix comprises a polymer, for disposition into a drug insert or an implant. The drug insert or the implant is adapted for disposition within or adjacent to an eye of a patient for providing sustained release of the therapeutic agent to the eye or surrounding tissues or both. The therapeutic agent is contained in the matrix such that an amount of the therapeutic agent in a volumetric portion of the drug core is similar to an amount of the therapeutic agent in any other equal volumetric portion of the drug core. For example, the therapeutic agent may be either uniformly homogeneously dispersed throughout the matrix such as in a solid solution, or the therapeutic agent at least in part forms solid or liquid inclusions within the matrix. For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%. For example, the amount of the therapeutic agent in a volumetric portion of the drug core can be the same as the amount of therapeutic agent in any other equal volumetric portion of the drug core.

In various embodiments of the inventive drug insert for an implant for disposition in or adjacent to a patient's eye, the implant can be a lacrimal implant insertable into a lacrimal canaliculus, which is commonly referred to as a punctual plug, i.e., an implant adapted to insertion through a punctum of the eye to reside within the canaliculus of the eye, wherein the drug insert can come in contact with tear liquid and thereby release the therapeutic agent for contact with the eye or surrounding tissues or both.

In various embodiments, the core of the insert comprising the agent and a matrix, the matrix comprising a polymeric material, is surrounded by a sheath body. The sheath body is substantially impermeable to the agent, such that the agent is released to the tear liquid only through an exposed surface of the core that comes in contact with the tear liquid. The agent contained within the core serves as a reservoir in order to release therapeutic quantities or concentrations of the agent over a period of time, which can range from days to months. For example, in treatment of glaucoma, the drug insert can contain a prostaglandin analog such as latanoprost.

The drug core is adapted to be disposed within a larger structure, an implant, which is in turn adapted for disposition within the body tissue, cavity, or duct. In various embodiments, the implant can be a punctual plug adapted for emplacement within the canaliculus of the eye, that is, within the duct(s) that drain tears from the surface of the eye.

For example, various embodiments of the drug cores can be used in implants, such as punctual plugs, adapted for placement near the eye to treat a patient suffering from a malcondition of the eye through the release of one or more drugs from the core within the implant onto the surface of the eye, such as by diffusion into tear fluids. Although specific reference is made to punctual plugs with drug delivery capabilities for use within the canaliculus of the eye, various embodiments of the implants may be useful for sustained release of the drug and treatment of other structures near and/or within the eye, for example the sclera, the conjunctiva, the cul-de-sac of the eyelid, the trabecular meshwork, the ciliary body, the cornea, the choroid, the suprachoroidal space, the sclera, the vitreous humor, aqueous humor and retina. Also, the inventive implants with their cores can be used for release of therapeutic agents into tissues, body cavities, or ducts, other than an eye or adjacent structures. In various embodiments, the drug cores can be used for sustained release of therapeutic agents into the ears and/or Eustachian tubes, nasal and/or sinus cavities, urethra, skin, gastrointestinal tract (including colon, bowel duct, and the like), and in or near joints such as knee, finger, and intervertebral joints.

In various embodiments, a drug core comprising a composite of a therapeutic agent and a matrix is partially contained within or surrounded by a sheath, the sheath being substantially impermeable to the agent. The sheath can cover part, but not all, of the surface of the core comprising the drug and the matrix material, the core having an exposed surface such that the therapeutic agent can be released therethrough. The drug core and its sheath together are adapted for inclusion within an implant structure that is itself adapted for implantation within a body of a patient, such as within a body cavity, tissue, duct, or fluid. For example, the implant can be an ocular implant, adapted for disposition in or around the eye, such as a punctual plug, adapted to disposition within the canaliculus of the eye such that the agent can be released through the punctum of the eye to contact the orb and surrounding tissues.

The sheath can be composed of any suitable biocompatible material which is substantially impermeable to the therapeutic agent. For example, the sheath can be an impermeable polymeric material such as a polyimide, polymethylmethacrylate, or a polyester such as PET, or a biocompatible metal such as stainless steel or titanium, or an inorganic glass, such as formed from silicon oxide. The agent can be any therapeutic substance capable of at least some diffusion through the matrix, which comprises a polymer, such that the agent can be released into a body tissue or fluid. A matrix can comprise a polymeric material, for example, the matrix can include a silicone, a polyurethane, or any non-biodegradable polymer wherein the agent has at least sufficient solubility to diffuse therethrough. The matrix can comprise other materials, including but not limited to other types of polymers such as polyolefins, polyamides, polyesters, polyvinyl alcohol or acetate, ethylene-vinyl acetate copolymers, polysaccharides such as cellulose or chitin, or the like, provided the material is biocompatible. Accordingly, selection of a material for the matrix can be made at least in part based on the agent selected for the particular application intended, such that a sufficient degree of solubility of the agent in the matrix can be achieved for a therapeutic level of the agent in the target tissue can be maintained over a period of time.

Other substances, such as release rate modifying substances such as surfactants, dispersants, fillers, other polymers and oligomers, and the like, can be included with the matrix in the core.

The substantially impermeable sheath prevents the diffusion of the agent therethrough. Accordingly, the agent diffuses into surrounding body fluids, tissues, etc. largely via that portion of the core that is not covered by the sheath. The rate of diffusion of the agent into the surrounding body fluids, tissues, etc. is governed at least in part by the rate of diffusion of the agent through the matrix. Once a molecule of the agent reaches the exposed surface of the composite in contact with the environment, it can diffuse into the surrounding fluid or tissue. In certain embodiments, the therapeutic agent can initially be released into a tissue structure adjacent to the target, for example into a punctum of a patient located near the target ocular tissues, from where it can diffuse to the site of action.

In various embodiments, the agent can be soluble or substantially insoluble in the polymeric matrix material. In embodiments wherein the agent is soluble at the concentration used in the polymeric matrix material, the drug core comprises a homogeneous composite wherein the agent is dispersed at a molecular level within the polymeric matrix material. For example, a highly lipophilic agent such as ethynodiol diacetate can dissolve at significant concentrations in silicone polymer, such that a core can be a homogeneous dispersion of the agent in the matrix at the molecular level. For example, cyclosporine, a cyclic peptide analog, can dissolve in significant concentrations in polyurethane, a polymer that contains linkages resembling amide bonds. When a homogeneous dispersion of the agent in the matrix is present, the rate of release of the agent from the exposed surface of the core into the body fluid or tissue can be controlled by the rate of diffusion or transport of the agent through the matrix. In embodiments wherein the agent is soluble in the polymeric matrix material, the rate of release of the agent into the body tissue or fluid can be determined at least in part by the concentration of the agent dissolved in the matrix of the core. In various embodiments, the concentration of therapeutic agent dissolved in the matrix can be a saturation concentration The kinetics of such release can be zero order, first order, or a fractional order between zero and first orders.

In embodiments wherein the agent is only partially or sparingly soluble or insoluble in the matrix at the concentration used, the core comprises a heterogeneous composition wherein the drug substance is dispersed as solid or liquid inclusions throughout the polymeric matrix material. Where some solubility, however slight, exists, a certain amount of the drug will be dissolved in the matrix. In various embodiments, the inclusions can range in size from about 0.1 μm to about 100 μm. When inclusions of the agent in the matrix are present, the agent may be at least slightly soluble in the matrix to enable at least some diffusion of the agent from an inclusion to an exposed surface of the drug core such that the agent can further diffuse into body fluid or tissue, for example, the agent can diffuse into tear fluid. When the agent is insoluble in the matrix, the agent will form domains or inclusions as a separate phase within the matrix that may cooperate to enable microchannels for transport of drug to the matrix surface. In various embodiments, the agent can be transported via channels or pores in the matrix, which can be permeated by the body fluid. In various embodiments, the agent can be transported through pores or channels present in the matrix.

The agent is present in the core, dispersed in the matrix, in a concentration. The concentration is a concentration of the agent within a macroscopic portion of the matrix-agent core, that is controlled to be similar from sample to sample of the core. A similar concentration of the agent in a macroscopic portion of the core can vary, but only within limits, relative to that in any other equal macroscopic portion of the core. The term does not relate to concentrations at the molecular level, where domains or inclusions of the agent in concentrated form may be present, but rather refers to bulk concentrations of the agent in volumes of the core that are greater than at least about 0.1 mm$^3$, for example, a cubic sample of core about 100 μm on a side, or a 0.1 mm thick slice of a core with cross-sectional area of about 1 mm$^2$. The concentration can vary within no greater than about 30%, or no greater than about 20%, or no greater than about 10%, or no greater than about 5%.

In various embodiments, the inclusions can have an average diameter of less than about 20 µm, or less than about 15 µm, or less than about 10 µm. The distribution of diameters of the inclusions can be monodisperse, that is, relatively tightly grouped around the average diameter. If the distribution of inclusion diameters is a normal or near-normal distribution, and the monodispersity can be expressed in terms of a standard deviation, a standard deviation of diameters of the inclusions can be less than about 8 or less than about 6 µm, or less than about 4 µm.

Although it is not intended to be a limitation of the invention, the factors controlling the rate of release of the agent from the matrix to the patient, such as the release of an ocular drug into tear liquid, are believed to be complex and dependent on many variables. For example, a drug and a matrix material may together define a saturation concentration of the drug in that matrix. For some drug-matrix combinations, high concentrations of the drug can dissolve in the matrix. For others, a saturation concentration is lower. For still others, no solubility exists, and separate domain phases often manage rate of release. Another possible factor is the rate of mass transfer from inclusions to the surface of the matrix. Yet another possible factor is the rate of diffusion of the agent from the matrix into a body fluid, such as tear liquid.

A rate of release of the therapeutic agent at therapeutic quantities can be determined at least in part by a concentration of therapeutic agent in the matrix of the drug core. The therapeutic agent can be capable of sufficiently dissolving into the matrix from the inclusions, if present, so as to maintain the concentration of therapeutic agent dissolved in the matrix such that the rate of release is within a therapeutic window for the extended period. This can lead to a desirable zero order rate of release of the agent, as substantial reservoirs of the agent are present in the inclusions, while the limited solubility of the agent in the matrix is rate-determining in bringing the agent to the exposed surface of the core, where it can be released in tear fluids or other media. In embodiments wherein the agent is insoluble and forms inclusions in the matrix material, the rate of release of the agent into the body tissue or fluid can be determined at least in part by the concentration of the agent as it diffuses from the inclusions through separate domains in the matrix material to the point of exposure to the body tissue or fluid.

In various embodiment, the matrix includes a release rate varying material in a quantity sufficient to release the therapeutic agent from the drug core at the therapeutic quantities for an extended period when implanted for use. The release rate modifying material can include an inert filler material, a salt, a surfactant, a dispersant, a second polymer, an oligomer, or a combination thereof. For example, the core can include a surfactant or a dispersant material, or a filler, an oligomer, another polymer, or the like, in addition to the one or more drugs and the polymeric matrix material. Examples include polymers such as polyethyleneglycols (PEGs), sodium alginate, low molecular weight silicones or polyurethanes, etc. Non-polymeric additives can include hydrophilic solvents such as ethylene glycol or glycerol.

In various embodiments, the core comprises from about 5% to about 50% of the drug. Depending on the drug, and the rate of release of the drug from the polymer selected for the matrix, the concentration can control the period of time over which therapeutic quantities of the drug are released into body fluid, such as tear liquid.

In various embodiments, as discussed above, the core can include two or more drugs. In certain embodiments, both drugs are substantially soluble in the matrix material. In other embodiments, a first drug is substantially soluble in the matrix material and a second drug forms inclusions within the matrix material. In some embodiments, the implant comprise a single drug core with two therapeutic agents mixed within a matrix. In other embodiments, the implant comprise two drug cores, each with a single therapeutic agent.

In some embodiments, the second drug can be a counteractive agent to avoid a side effect of the first therapeutic agent. In one example, the first drug can be a cycloplegic drug, i.e., one that blocks accommodation (focusing) of the eye, e.g., atropine or scopolamine, and the second therapeutic agent cab be at least one of an anti-glaucoma drug or a miotic drug, selected to reduce the known glaucoma-inducing side effect of cycloplegic drugs or to cause pupil contraction counteracting the known mydriatic effects of atropine or scopolamine. The anti-glaucoma drug may comprise at least one of a sympathomimetic, a parasympathomimetic, a beta blocking agent, a carbonic anhydrase inhibitor, or prostaglandin analogue. In another example, the first therapeutic agent may be a steroid and the second therapeutic agent may be an antibiotic, wherein the steroids compromise the immune response, but the antibiotics provides protection against infection. In another example, the first therapeutic agent may be pilocarpine and the second therapeutic agent may be non-steroidal anti-inflammatory drug (NSAID). An analgesic may be a good compliment for the treatment.

In specific embodiments, the core insert comprises a single drug-matrix composite having two drugs contained therein. In other embodiments, the core insert comprises two separate drug-matrix composites ("subcores" or first and second cores), disposed adjacent to each other within the sheath. The two separate composites can be disposed in a concentric spatial configuration, in a sector configuration, or otherwise, provided that exposed surfaces of both composites are exposed to body tissue or fluid when disposed within the body tissue, cavity, or duct of the patient.

In some embodiments the therapeutic agents can be released with a profile that corresponds to a kinetic order of therapeutic agents release and the order can be within a range from about zero to about one. In specific embodiments, the range is from about zero to about one half, for example from about zero to about one quarter. The therapeutic agents may be released with a profile that corresponds to a kinetic order of therapeutic agents release and the order is within a range from about zero to about one half for at least about a month after the structure is inserted, for example the order can be within the range at least about 3 months after the structure is inserted.

In various embodiments, the invention provides a filled precursor sheath adapted for manufacture of a plurality of drug inserts therefrom by division of the filled precursor sheath, each drug insert being adapted for disposition within a respective implant, the implant being adapted for disposition within or adjacent to an eye of a patient, for providing sustained release of a therapeutic agent to the eye or surrounding tissues or both. The filled precursor sheath comprises a precursor sheath body and a precursor drug core contained therewithin, the precursor drug core comprising a therapeutic agent and a matrix wherein the matrix comprises a polymer and a therapeutic agent. In the precursor drug cores, an amount of the therapeutic agent in a volumetric portion of the precursor drug core is similar to an amount of the therapeutic agent in any other equal volumetric portion of the precursor drug core. The precursor sheath body is substantially impermeable to the agent. Each of the plurality of inserts divided therefrom is adapted to release the agent to the eye or surrounding tissues, or both, when in contact with tear liquid. A respective sheath body of each of the plurality of inserts divided from the filled precursor sheath is disposed over a portion of a respective drug core of each of the plurality of inserts to inhibit release of the agent from said portion and so as to define at least one exposed surface of the drug core adapted to release the agent to the eye or surrounding tissues, or both, when the insert is disposed in an implant and the implant is inserted into the patient. For example, an amount of the therapeutic agent in a volumetric portion of the precursor drug core can vary from an amount of the therapeutic agent in any other equal volumetric portion of the precursor drug core by no greater than about 30%. For example, an amount of the therapeutic agent in a volumetric portion of the precursor drug core can vary from an amount of the therapeutic agent in any other equal volumetric portion of the precursor drug core by no greater than about 20%. For example, an amount of the therapeutic agent in a volumetric portion of the precursor drug core can vary from an amount of the therapeutic agent in any other equal volumetric portion of the precursor drug core by no greater than about 10%. For example, an amount of the therapeutic agent in a volumetric portion of the precursor drug core can vary from an amount of the therapeutic agent in any other equal volumetric portion of the precursor drug core by no greater than about 5%.

In various embodiments, the filled precursor sheath can be adapted to provide any of the above-discussed drug inserts by division of the filled precursor sheath. In various embodiments, the precursor sheath can be divided by cutting with a blade or with a laser, or the like.

In various embodiments, the invention provides an implant body for disposition in or adjacent to an eye of a patient for release of a therapeutic agent over a period of time to the eye or surrounding tissues, or both. The implant body comprises a channel therein adapted to receive a drug insert such that an exposed surface of the insert will be exposed to tear liquid when the insert is disposed within the implant and when the implant is disposed in or adjacent to the eye. The drug insert comprises a sheath body that is substantially impermeable to the agent, containing therewithin a drug core comprising a therapeutic agent and a matrix comprising a polymer, wherein an amount of the therapeutic agent in a volumetric portion of the drug core is similar to an amount of the therapeutic agent in any other equal volumetric portion of the drug core. The implant body comprises a biocompatible material and being adapted to be retained within or adjacent to the eye for a period of time. For example, the amount of the therapeutic agent in a volumetric portion of the drug core can vary from the amount of the therapeutic agent in any other equal volumetric portion of the drug core by no greater than about 30%. For example, the amount of the therapeutic agent in a volumetric portion of the drug core can vary from the amount of the therapeutic agent in any other equal volumetric portion of the drug core by no greater than about 20%. For example, the amount of the therapeutic agent in a volumetric portion of the drug core can vary from the amount of the therapeutic agent in any other equal volumetric portion of the drug core by no greater than about 10%. For example, the amount of the therapeutic agent in a volumetric portion of the drug core can vary from the amount of the therapeutic agent in any other equal volumetric portion of the drug core by no greater than about 5%.

In various embodiments, an exposed surface of the drug core contained within the implant is capable of releasing the therapeutic quantities into at least one of a sclera, a cornea or a vitreous when disposed in or adjacent to the eye of the patient. For example, the implant can be a punctual plug adapted for disposition within a punctum of a patient for release of the agent into tear liquid.

In various embodiments of the inventive methods described above, the mixture can further comprise a solvent in which the matrix precursor and the agent are soluble, and curing can comprise at least partial removal of the solvent following injection into the sheath body or precursor sheath body respectively. Curing can involve heating, vacuum treatment, or both. The solvent can be a hydrocarbon, an ester, a halocarbon, an alcohol, an amide, or a combination thereof. For example, when the agent is cyclosporine, the solvent can be a halocarbon.

In various embodiments, curing the mixture can comprise heating the mixture to a temperature, at a relative humidity, for a period of time. For example, the temperature can include a range from about 20 degrees C. to about 100 degrees C., the relative humidity can include a range from about 40% to about 100%, and the period of time can include a range from about 1 minute to about 48 hours. More specifically, the temperature can be at least about 40° C., the relative humidity can be at least about 80%, or both. In various embodiments, curing can include a step of polymerization or cross-linking, or both, of the matrix, the matrix precursor, or both. For example, polymerization or cross-linking, or both, can be carried out in the presence of a catalyst. For instance, the catalyst can be a tin compound or a platinum compound, such as a platinum with vinyl hydride catalyst system or a tin with alkoxy catalyst system.

In various embodiments, the mixture can be prepared by a method comprising sonication. The matrix precursor and the agent can be mixed to provide a thoroughly dispersed emulsion-like composite, wherein the agent, if insoluble or slightly soluble in the matrix precursor, is dispersed in small particles or droplets.

In various embodiments, the step of injecting the mixture into the sheath can be carried out under a pressure of at least about 40 psi. The mixture can be injected such that the sheath body or precursor sheath body, respectively, is filled at a rate of no greater than about 0.5 cm/sec.

The injection or extrusion of the mixture including the agent and the matrix precursor or matrix can be carried out at room temperature (20° C.), or above room temperature, or can be carried out at subambient temperatures of less than 20° C. For example, the injection can be carried out wherein the subambient temperature comprises a temperature of about −50° C. to about 20° C., or wherein the subambient temperature comprises a temperature of about −20° C. to about 0° C.

Figure 15A:
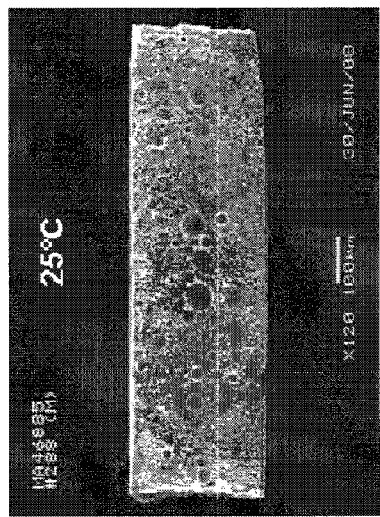
FIGS. 15 A-D shows scanning electron micrographs of longitudinal sections of a silicone/latanoprost drug insert prepared by a method of the invention; A, B,=extrusion at ambient and superambient temperatures; C, D=extrusion at subambient temperatures.
Figure 15B:
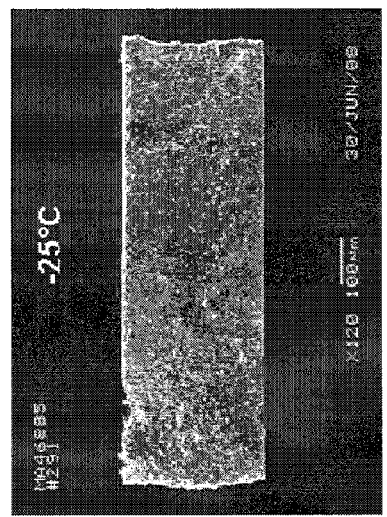
Figure 15C:
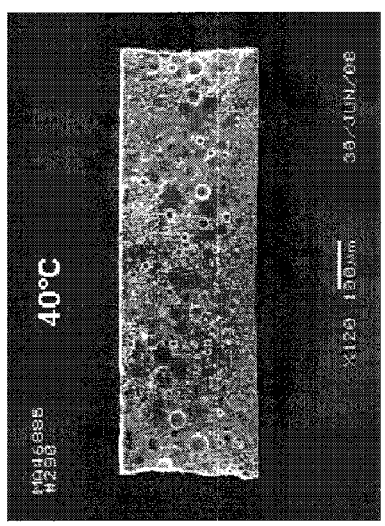
Figure 15D:
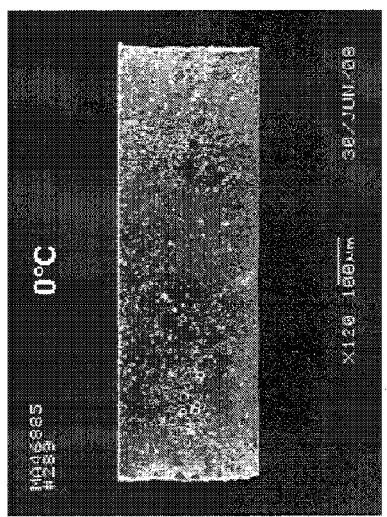
Figure 16:
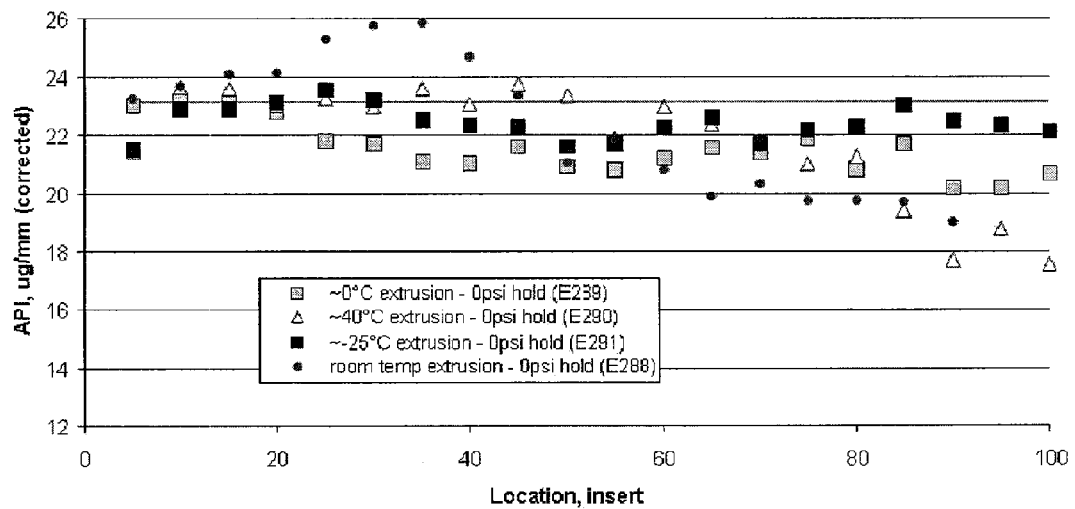
FIG. 16 shows a plot of latanoprost content per 1 mm section of a filled precursor sheath prepared by an extrusion method which was carried out at about 0 degrees, about −25, about 40, and room temperatures.

As discussed below, FIGS. 15 and 16 provide graphical evidence of the advantages of subambient extrusion, both in terms of uniformity of inclusion diameter, and in terms of uniformity of distribution of the therapeutic agent throughout the length of a filled precursor sheath. FIG. 15 shows electron micrographs of cryogenically section portions of a drug core wherein the extrusion was carried out at various temperatures. As can be seen, the average diameter of the included droplets of latanoprost is smaller when the extrusion is carried out at 0° C. or −25° C. than when the extrusion is carried out at 25° C. or at 40° C.

In a parallel experiment, described in Examples 12 and 13, average inclusion diameters; and diameter size distributions, were determined for extrusions carried out at room temperature and at −5° C. for a latanoprost-silicone mixture:

Cold extrusion (−5° C.): 0.006±0.002 mm (n=40 inclusion),

Room temp (22° C.): 0.019+0.019 mm (n=40 inclusion), showing that the cold extrusion technique produced inclusions of smaller average diameter and of more uniform size than when the extrusion was carried out at ambient temperature.

FIG. 16 shows graphically the content of latanoprost in a 10 cm precursor sheath filled with the latanoprost-silicone mixture, as discussed in Examples 12 and 13. As can be seen, cold extrusion at −25° C. and 0° C. (squares) unexpectedly produced a more uniform distribution of therapeutic agent latanoprost in the silicone matrix, after curing, along the entire length of the 10 cm precursor sheath, which was subsequently divided into 1 mm sections, and the latanoprost content of each sections (drug insert) determined. Extrusions carried out at room temperature (circles) and at 40° C. (triangles) were significantly more variable. The results are significant in terms of manufacturing medically useful devices, as it is desirable to maintain a uniform content of the therapeutic agent among a plurality of drug inserts manufactured by this method.

In various embodiments, each drug insert can be sealed at one end thereof, the second end thereby providing the exposed surface for release of the agent when the insert is disposed within an implant and inserted into a patient. Each drug insert can be sealed at one end thereof using a UV-curable adhesive, a cyanoacrylate, an epoxy, by pinching, with a heat weld, or with a cap. When a UV-curable adhesive is used, curing is carried out by irradiation with UV light.

In various embodiments, the inventive methods further comprise, after sealing one end thereof, inserting each drug insert into a channel of a respective implant body adapted to receive the insert therein.

In various embodiments, when the drug core comprises two drug cores, a first drug core comprising a first agent and a first matrix, and a second drug core comprising a second agent and a second matrix, wherein the first agent and the second agent are different, and wherein the first matrix and the second matrix are either the same or differ from each other, the implant body comprising an aperture adapted to receive the drug insert comprising the first and the second drug cores, the method can further comprise disposing the drug cores within the insert prior to disposing the insert comprising the drug cores within the aperture of the implant body.

In various embodiments, where the therapeutic agent comprises cyclosporine or olopatadine, a prodrug or a derivative of cyclosporine or olopatadine or any combination thereof, the matrix includes polyurethane, and a weight ratio of the cyclosporine or the olopatadine or the cyclosporine prodrug or derivative, or the olopatadine prodrug or derivative, or the combination thereof, to the polyurethane polymer or copolymer is about 1 wt % to about 70 wt %, the method can include forming the mixture by melting and mixing the polyurethane polymer or copolymer and the therapeutic agent. The therapeutic agent can be in molten form in the mixture, or can be in solid form in the mixture.

In some embodiments, the matrix comprises an inert filler material mixed with the therapeutic agent such that the exposed surface releases the therapeutic agent at therapeutic quantities for a sustained period of time.

In some embodiments, a salt is mixed with the matrix precursor such that the exposed surface of the matrix, after curing, releases the therapeutic agent at therapeutic quantities for a sustained period of time.

In some embodiments, a surfactant is mixed with the matrix precursor such that the exposed surface of the matrix, after curing, releases the therapeutic agent at therapeutic quantities for a sustained period of time.

In some embodiments a second polymer or an oligomer is mixed with the matrix precursor, and after curing to form the matrix, the presence of the second polymer or oligomer can serve to vary the rate of release of the therapeutic agent.

Various embodiments of the invention provide a punctum plug for insertion into a punctual canal of a patient, the plug comprising a drug core having a distal end and a proximal end, at least the distal end of the drug core having a cross section suitable for insertion through a punctum, the drug core comprising a polyurethane polymer or copolymer comprising a therapeutic agent deliverable into the eye or surrounding tissues; and a substantially impermeable sheath disposed over a portion of the drug core to define at least one exposed surface of the drug core, at least one exposed surface of the drug core being located near the proximal end to contact a tear or tear film fluid of a patient and release the therapeutic agent at therapeutic levels over a sustained period when the plug is implanted for use within the punctual canal of the patient. The inventive plug includes a core, in which the therapeutic agent is contained, that is formed from a polyurethane polymer or copolymer. The polyurethane polymer or copolymer of the core can be an aliphatic polyurethane, an aromatic polyurethane, a polyurethane hydrogel-forming material, a hydrophilic polyurethane, or a combination thereof. For example, the core can be formed of the polyurethane hydrogel-forming material TG-500 or TG-2000 aliphatic, polyether based thermoplastic polyurethanes capable of forming hydrogels. Such hydrogel-forming polymers can absorb greater than 100 wt %, for example up to 500-2000 wt % of water, and consequently swell in physical dimensions. Alternatively, the core can be formed of a hydrophilic polyurethane such as Pursil, which swells much less, to the extent of about 20-100%, upon contact with an aqueous medium. Other examples include Lubrizol products including Tecophilic grades such as HP-60D20, HP-60D35, HP-60D60, or HP-93A100.

In various embodiments, the therapeutic agent can comprise cyclosporine, or a prodrug or a derivative of cyclosporine. Cyclosporine, as is well-known in the art, is an immunomodulator, and can be used in the treatment of dry eye and inflammations of the eye, such as those resulting from an allergic response. The weight ratio of the cyclosporine or the cyclosporine prodrug or derivative, respectively, to the polyurethane polymer or copolymer can be about 1 wt % up to as high as about 70 wt %, or even greater. The rate of the release of the cyclosporine, or its prodrug or derivative, can be controlled by selection of the specific kind of polyurethane for the core and by modulating the polarity (hydrophobicity/hydrophilicity) of the therapeutic agent. Cyclosporine is a rather hydrophobic compound, but can be rendered more hydrophilic by incorporation of functional groups, such as groups that can be cleaved in vivo by endogenous enzymes like esterases, wherein the functional groups incorporated have hydrophilic moieties included.

In various embodiments, the therapeutic agent can be olopatidine, or a prodrug or a derivative of olopatidine. For instance, the agent can be olopatidine hydrochloride, also known as patanol. Used to treat allergic conjunctivitis (itching eyes), olopatadine inhibits the release of histamine from mast cells. It is a relatively selective histamine H1 antagonist that inhibits the in vivo and in vitro type 1 immediate hypersensitivity reaction including inhibition of histamine induced effects on human conjunctival epithelial cells.

The plug further includes a substantially impermeable sheath, to limit the zone or region of release of the therapeutic agent to the at least one exposed surface of the drug core, disposed immediately adjacent to the punctum of the eye such that the therapeutic agent is readily contacted by tear fluid and can thus diffuse over the surface of the eye. For example, cyclosporine can be released into the tear fluid to assist in treatment of the eye for dryness or for inflammation, such as caused by an allergic reaction. The sheath can also be adapted to provide a second exposed surface of the drug core is located near the distal end of the plug to release the therapeutic agent into the punctual canal, if such is desired. For example, a second therapeutic agent can be included, such as an antibiotic for treatment of infections of the punctual canal.

The sheath can be of sufficient elasticity or flexibility that when the core is adapted to swell when in contact with an aqueous medium, such as when the core is constructed of a hydrophilic or hydrogel-forming polyurethane polymer or copolymer, that the sheath can expand in response to the swelling of the hydrophilic or hydrogel-forming polyurethane polymer or copolymer. The swelling is adapted to assist in retaining the plug within the punctual canal.

The core can further contain a second bioactive agent, such as are listed below, such as for treatment of a secondary condition or to assist in treatment of the condition, for example, for which administration of cyclosporine or olopatidine, or both, is medically indicated.

The lacrimal implant can be any suitable shape adapted for insertion into the punctual canal of the eye. For example, the implant can be substantially cylindrical at the time of insertion into the canal, prior to swelling of any hydrogel-forming core of the plug. Or, the implant can be of a conical shape, or can be bent in the form of an "L", or can have any other shape which can be disposed within the punctual canal of a patient's eye such that the therapeutic agent can be released from the core into the tear fluid bathing the eye. Accordingly, the core of the implant, when the implant is disposed within the punctual canal, has access to the opening of the punctum such that the agent can diffuse into the tear fluid and thereby bathe the eye surface. In various embodiments, the core has access to the interior of the punctual canal for release of the agent thereto.

For example, the implant can be a shape termed the "bent-design" as disclosed in a patent application filed concurrently with this application. Or, the implant can be a design referred to as the "H-design", as disclosed in a patent application filed concurrently with this application. Or, the implant can be what is termed the "skeleton" design as disclosed in a patent application filed concurrently with this application.

In various embodiments, a method of manufacture of the inventive implant, comprising melting and mixing the polyurethane polymer or copolymer and adding the therapeutic agent to form a mixed melt, then, either casting the mixed melt within the sheath, or, casting the mixed melt to form the core, then disposing the sheath around the core, is provided.

The polyurethane selected to form the core of the implant can be thermoplastic such that the implant can be manufactured by a melt extrusion or casting process. For example, a melt of the core polyurethane can be prepared and the therapeutic agent can be incorporated therein. In various embodiments, the agent can melt at a temperature around the melting point of a suitable polyurethane polymer or copolymer, and the agent can itself be incorporated in a molten state, provided the melting point is at a temperature at or below the decomposition temperature of the polyurethane, and the melting point of the polyurethane is below a temperature at which the agent undergoes significant thermal decomposition. For example, cyclosporine melts at about 135° C., while TG-500 melts at about 170° C. and TG-2000 melts at about 115° C. Thus, a mixed melt can be prepared at about 135° C., or higher with TG-2000 wherein both the cyclosporine and the polyurethane core material are both in a molten state. A higher melting material like TG-500 can be used when the cyclosporine is stable for the time period it is held at the elevated temperate in the process used.

In various embodiments, the agent does not melt in the molten polyurethane, but is dispersed as a solid, which in be in the form of a fine powder, such as a microparticulate form. For example, olopatidine, which melts in excess of 200° C., can be dispersed in solid form in a melt of a polyurethane. The polyurethane melt containing the solid agent is then cast, optionally within a sheath, to provide the inventive plug.

Thus, melt mixing processes can be cast to form an inventive implant. For example, the mixed melt can be cast into a mold already lined with a higher melting sheath material, which can be a polyurethane that is not substantially permeable to diffusion of the cyclosporine. In this way the sheathed implant can be prepared. Alternatively, the core can be case in a mold, then the sheath material coated or cast on the surface of the implant, except for regions where the core material is to be left exposed. Or, the sheath material can be cast to cover the entire implant, then a portion removed to expose the core material in at least one location near the proximal end, where the cyclosporine can readily come into contact with tear fluid and thereby diffuse into the eye.

In various embodiments, a method of manufacture of the inventive implant, comprising dissolving the polyurethane polymer or copolymer and mixing in the therapeutic agent in a solvent to form a mixed solution, then, either casting the mixed solution within the sheath, then removing the solvent, or, casting the mixed solution to form the core, then removing the solvent, then disposing the sheath around the core, is provided.

The polyurethane selected to form the core of the implant can be soluble in an organic solvent, such as dichloromethane or tetrahydrofuran. Many therapeutic agent, for example, cyclosporine, are also soluble in many organic solvents, including dichloromethane or tetrahydrofuran. In this way a mixed solution can be prepared. This solution can then be used to cast the core of the implant, with removal of the solvent. The solvent can be removed by evaporation, which can be carried out under ambient conditions, or can involve the application of heat, reduced atmospheric pressure, or both. After removal of the solvent, the sheath can be coated or cast around the core, either leaving an exposed section of the core, or removing a portion of the sheath to provide an exposed section.

In various embodiments, a method of manufacture of an inventive implant comprises dissolving the polyurethane polymer or copolymer in a solvent, then adding a therapeutic agent in solid form, the agent being substantially insoluble in the solvent, then removing the solvent to cast the core. The solid form of the agent can be a fine powder, such as a microparticulate form, to provide for a favorable surface area/mass ratio. In various embodiments the implant comprises a dispersion of a solid form of the agent in the polyurethane polymer or copolymer.

The polyurethane polymer or copolymer making up the core can be an aliphatic polyurethane, an aromatic polyurethane, a polyurethane hydrogel-forming material, a hydrophilic polyurethane, or a combination thereof. The particular polyurethane used for the therapeutic agent can be selected to control the release profile of the agent over time.

The inventive implant can be used to treat a malcondition of the eye or of surrounding tissue. For example, the implant incorporating cyclosporine or olopatidine, or both, can be used to treat an eye malcondition involving dry eye or eye inflammation. The therapeutic agent can be released into the eye, as well as into surrounding tissue such as the interior of the punctual canal, over a period of time. The period of time can be about 1 week to about 6 months. When a swelling polyurethane is used, the swelling of the implant can be used to secure the plug within the punctual canal for the full time period over which the drug is adapted to be released.

In various embodiments, the invention provides a drug insert made by a method of the invention.

In various embodiments, the invention provides a method of treating a malcondition in a patient in need thereof, comprising disposing an implant comprising a drug insert of the invention, or a drug core of the invention, or a drug core obtained by division of a filled precursor sheath of the invention, or a drug implant of the invention, or a drug insert prepared by the method of the invention, wherein the therapeutic agent is adapted to treat the malcondition, in or adjacent to an eye of the patient such that the drug is released into a body tissue or fluid.

In various embodiments, the invention provides the use of a drug insert of the invention, or a drug core of the invention, or a drug core obtained by division of a filled precursor sheath of the invention, or a drug implant of the invention, or a drug insert prepared by the method of the invention, in the manufacture of an implant adapted for treatment of a malcondition in a patient in need thereof.

In various embodiments, the invention provides a drug insert adapted for disposition within an punctual plug for providing sustained release of a latanoprost to the eye for treatment of glaucoma, the insert comprising a core and a sheath body partially covering the core, the core comprising the latanoprost and a matrix wherein the matrix comprises a silicone polymer, the latanoprost being dispersed within the silicone as droplets thereof, wherein an amount of the latanoprost in a volumetric portion of the drug core is similar to an amount of the latanoprost in any other equal volumetric portion of the drug core, the sheath body being disposed over a portion of the core to inhibit release of the latanoprost from said portion, an exposed surface of the core not covered by the sheath body being adapted to release the latanoprost to the eye.

In various embodiments, the invention provides a drug insert adapted for disposition within an punctual plug for providing sustained release of a cyclosporine to the eye for treatment of dry eye or inflammation, the insert comprising a core and a sheath body partially covering the core, the core comprising the cyclosporine and a matrix wherein the matrix comprises a polyurethane polymer, the cyclosporine being dissolved within the polyurethane, wherein an amount of the cyclosporine in a volumetric portion of the drug core is similar to an amount of the cyclosporine in any other equal volumetric portion of the drug core, the sheath body being disposed over a portion of the core to inhibit release of the cyclosporine from said portion, an exposed surface of the core not covered by the sheath body being adapted to release the cyclosporine to the eye.

Discussion of the Figures

FIG. 1A shows a top cross sectional view of a sustained release implant 100 to treat an optical defect of an eye, according to embodiments of the present invention. Implant 100 includes a drug core 110. Drug core 110 is an implantable structure that retains a therapeutic agent. Drug core 110 comprises a matrix 170 that contains inclusions 160 of therapeutic agent. Inclusions 160 will often comprise a concentrated form of the therapeutic agent, for example a crystalline form of the therapeutic agent, and the therapeutic agent may over time dissolve into matrix 170 of drug core 110. Matrix 170 can comprise a silicone matrix or the like, and the mixture of therapeutic agent within matrix 170 can be non-homogeneous. In many embodiments, the non-homogenous mixture comprises a silicone matrix portion that is saturated with the therapeutic agent and an inclusions portion comprising inclusions of the therapeutic agent, such that the non-homogenous mixture comprises a multiphase non-homogenous mixture. In some embodiments, inclusions 160 comprise droplets of an oil of the therapeutic agent, for example Latanoprost oil. In some embodiments, inclusions 160 may comprise particles of the therapeutic agent, for example solid Bimatoprost particles in crystalline form. In many embodiments, matrix 170 encapsulates inclusions 160, and inclusions 160 may comprise microparticles have dimensions from about 1 μm to about 100 μm. The encapsulated inclusions dissolve into the surrounding solid matrix, for example silicone, that encapsulates the micro particles such that matrix 170 is substantially saturated with the therapeutic agent while the therapeutic agent is released from the core.

Drug core 110 is surrounded by a sheath body 120. Sheath body 120 is can be substantially impermeable to the therapeutic agent, so that the therapeutic agent is often released from an exposed surface on an end of drug core 110 that is not covered with sheath body 120. A retention structure 130 is connected to drug core 110 and sheath body 120. Retention structure 130 is shaped to retain the implant in a hollow tissue structure, for example, a punctum of a canaliculus as described above.

An occlusive element 140 is disposed on and around retention structure 130. Occlusive element 140 is impermeable to tear flow and occludes the hollow tissue structure and may also serve to protect tissues of the tissue structure from retention structure 130 by providing a more benign tissue-engaging surface. Sheath body 120 includes a sheath body portion 150 that connects to retention structure 130 to retain sheath body 120 and drug core 110. Sheath body portion 150 can include a stop to limit movement of sheath body 120 and drug core 110. In many embodiments, sheath body portion 150 can be formed with a bulbous tip 150B. Bulbous tip 150B can comprise a convex rounded external portion that provides atraumatic entry upon introduction into the canaliculus. In many embodiments, sheath body portion 150B can be integral with occlusive element 140.

FIG. 1B shows a side cross sectional view of the sustained release implant of FIG. 1A. Drug core 110 is cylindrical and shown with a circular cross-section. Sheath body 120 comprises an annular portion disposed on drug core 110. Retention structure 130 comprises several longitudinal struts 131. Longitudinal struts 131 are connected together near the ends of the retention structure. Although longitudinal struts are shown, circumferential struts can also be used. Occlusive element 140 is supported by and disposed over longitudinal struts 131 of retention structure 130 and may comprise a radially expandable membrane or the like.

Figure 1C:
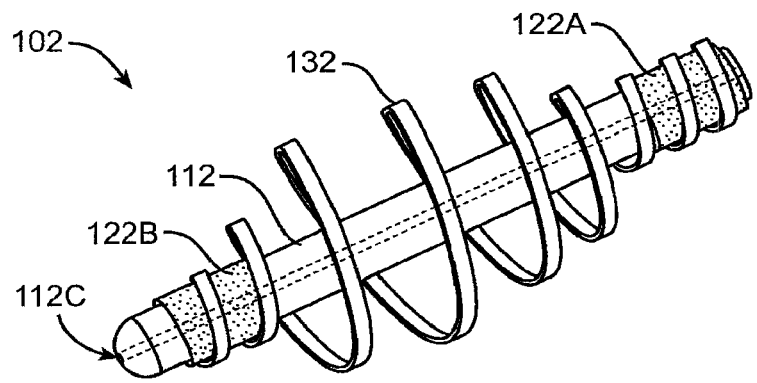
FIG. 1C shows a perspective view of a sustained release implant with a coil retention structure, according to an embodiment of the present invention.

FIG. 1C shows a perspective view of a sustained release implant 102 with a coil retention structure 132, according to an embodiment of the present invention. Retention structure 132 comprises a coil and retains a drug core 112. A lumen, for example channel 112C, may extend through the drug core 112 to permit tear flow through the lumen for the delivery of therapeutic agent for nasal and systemic applications of the therapeutic agent. In addition or in combination with channel 112C, retention structure 132 and core 112 can be sized to permit tear flow around the drug core and sheath body while the retention element holds tissue of the canaliculus away from the drug core. Drug core 112 may be partially covered. The sheath body comprises a first component 122A that covers a first end of drug cove 112 and a second component 122B that covers a second end of the drug core. An occlusive element can be placed over the retention structure and/or the retention structure can be dip coated as described above.

Figure 1D:
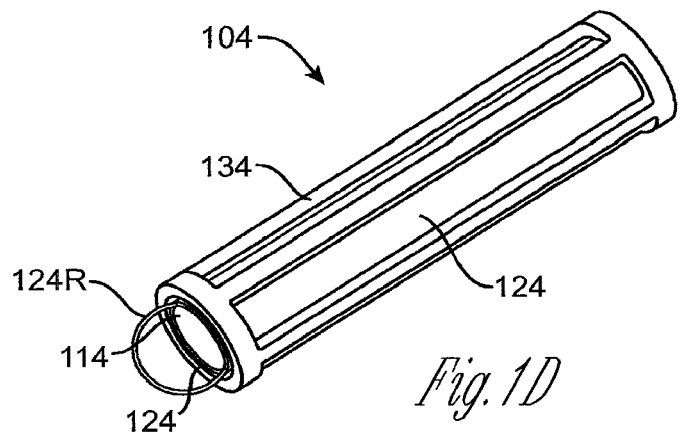
FIG. 1D shows a perspective view of a sustained release implant with a retention structure comprising struts, according to an embodiment of the present invention.

FIG. 1D shows a perspective view of a sustained release implant 104 with a retention structure 134 comprising struts, according to an embodiment of the present invention. Retention structure 134 comprises longitudinal struts and retains a drug core 114. Drug core 114 is covered with a sheath body 124 over most of drug core 114. The drug core releases therapeutic agent through an exposed end and sheath body 124 is annular over most of the drug core as described above. An occlusive element can be placed over the retention structure or the retention structure can be dip coated as described above. A protrusion that can be engaged with an instrument, for example a hook, a loop, a suture, or ring 124R, can extend from sheath body 124 to permit removal of the drug core and sheath body together so as to facilitate replacement of the sheath body and drug core while the retention structure remains implanted in the canaliculus. In some embodiments, a protrusion that can be engaged with an instrument comprising hook, a loop, a suture or a ring, can extend from retention structure 134 to permit removal of the sustained release implant by removing the retention structure with the protrusion, drug core and sheath body.

Figure 1E:
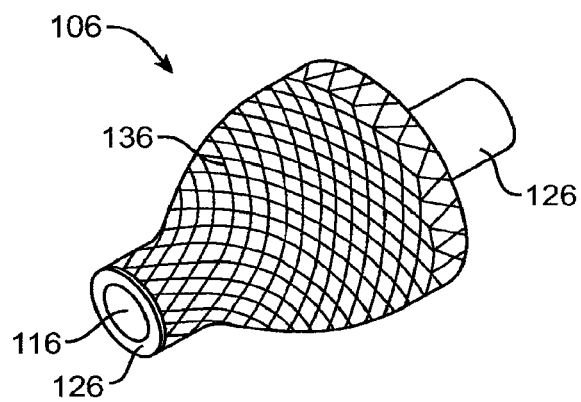
FIG. 1E shows a perspective view of a sustained release implant with a cage retention structure, according to an embodiment of the present invention.

FIG. 1E shows a perspective view of a sustained release implant 106 with a cage retention structure 136, according to an embodiment of the present invention. Retention structure 136 comprises several connected strands of metal and retains a drug core 116. Drug core 116 is covered with a sheath body 126 over most of drug core 116. The drug core releases therapeutic agent through an exposed end and sheath body 126 is annular over most of the drug core as described above. An occlusive element can be placed over the retention structure or the retention structure can be dip coated as described above.

Figure 1F:
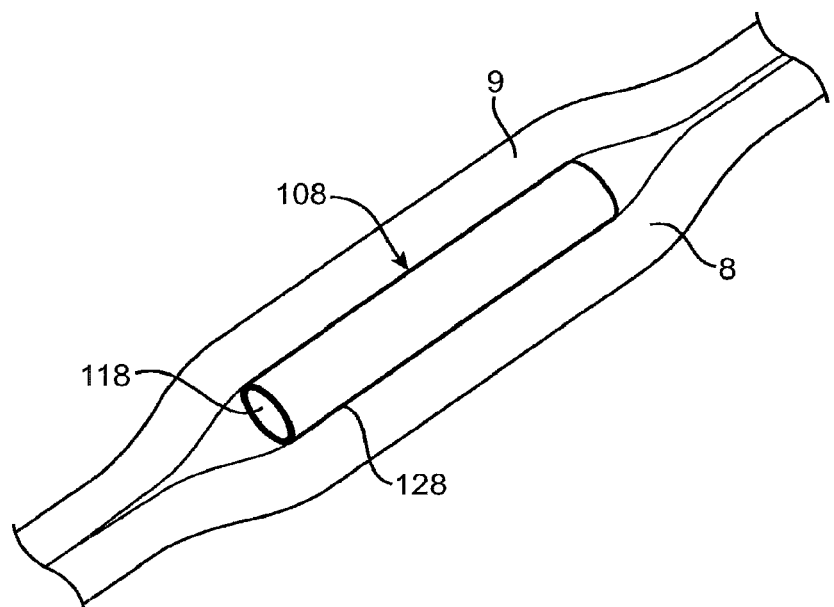
FIG. 1F shows a perspective view of a sustained release implant comprising a core and sheath, according to an embodiment of the present invention.

FIG. 1F shows a perspective view of a sustained release implant comprising a core and sheath, according to an embodiment of the present invention. Drug core 118 is covered with a sheath body 128 over most of drug core 118. The drug core releases therapeutic agent through an exposed end and sheath body 128 is annular over most of the drug core as described above. The rate of therapeutic agent release is controlled by the surface area of the exposed drug core and materials included within drug core 118. In many embodiments, the rate of elution of the therapeutic agent is strongly and substantially related to the exposed surface area of the drug core and weakly dependent on the concentration of drug disposed in the inclusions in the drug core. For circular exposed surfaces the rate of elution is strongly dependent on the diameter of the exposed surface, for example the diameter of an exposed drug core surface near an end of a cylindrical drug core. Such an implant can be implanted in ocular tissues, for example below conjunctival tissue layer 9 of the eye and either above sclera tissue layer 8, as shown in FIG. 1F, or only partially within the scleral tissue layer so as not to penetrate the scleral tissue. It should be noted that drug core 118 can be used with any of the retention structures and occlusive elements as described herein.

In an embodiment, the drug core is implanted between sclera 8 and conjunctiva 9 without sheath body 128. In this embodiment without the sheath body, the physical characteristics of the drug core can be adjusted to compensate for the increased exposed surface of drug core, for example by reducing the concentration of dissolved therapeutic agent in the drug core matrix as described herein.

Figure 1G:
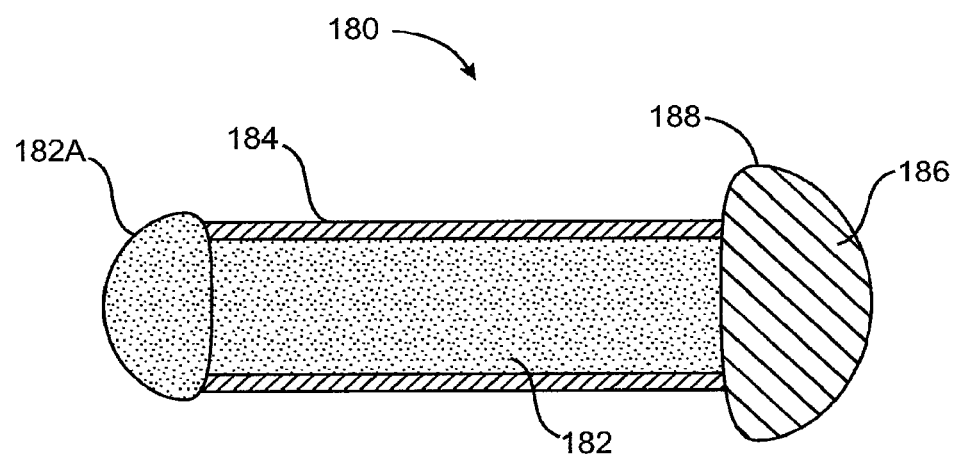
FIG. 1G schematically illustrates a sustained release implant comprising a flow restricting retention element, a core and a sheath, according to an embodiment of the present invention.

FIG. 1G schematically illustrates a sustained release implant 180 comprising a flow restricting retention structure 186, a core 182 and a sheath 184, according to an embodiment of the present invention. Sheath body 184 can at least partially cover drug core 182. Drug core 182 may contain inclusions of the therapeutic agent therein to provide a sustained release of the therapeutic agent. Drug core 182 can include an exposed convex surface area 182A. Exposed convex surface area 182A may provide an increased surface area to release the therapeutic agent. An occlusive element 188 can be disposed over retention structure 186 to block the flow of tear through the canaliculus. In many embodiments, retention structure 186 can be located within occlusive structure 188 to provide the occlusive element integrated with the retention structure. Flow restricting retention structure 186 and occlusive element 188 can be sized to block tear flow through the canaliculus.

The cores and sheath bodies described herein can be implanted in a variety of tissues in several ways. Many of the cores and sheaths described herein, in particular the structures described with reference to FIGS. 2A to 2J can be implanted alone as punctual plugs. Alternatively, many of the cores and sheath bodies described herein can comprise a drug core, sheath body, and/or the like so as to be implanted with the retention structures and occlusive elements described herein.

Figure 2A:
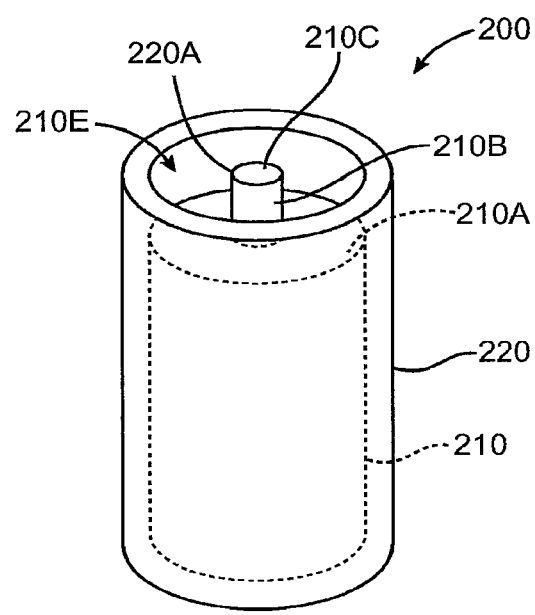
FIG. 2A shows a cross sectional view of a sustained release implant with core comprising an enlarged exposed surface area, according to an embodiment of the present invention.

FIG. 2A shows a cross sectional view of a sustained release implant 200 with core comprising an enlarged exposed surface area, according to an embodiment of the present invention. A drug core 210 is covered with a sheath body 220. Sheath body 220 includes an opening 220A. Opening 220 has a diameter that approximates the maximum cross sectional diameter of drug core 210. Drug core 210 includes an exposed surface 210E, also referred to as an active surface. Exposed surface 210E includes 3 surfaces: an annular surface 210A, a cylindrical surface 210B and an end surface 210C. Annular surface 210A has an outer diameter that approximates the maximum cross sectional diameter of core 210 and an inner diameter that approximates the outer diameter of cylindrical surface 210B. End surface 210C has a diameter that matches the diameter of cylindrical surface 210B. The surface area of exposed surface 210E is the sum of the areas of annular surface 210A, cylindrical surface 210B and end surface 210C. The surface area may be increased by the size of cylindrical surface area 210B that extends longitudinally along an axis of core 210.

Figure 2B:
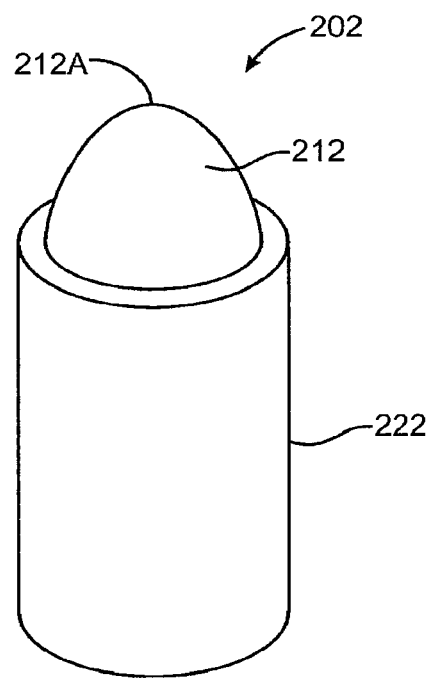
FIG. 2B shows a cross sectional view of a sustained release implant with a core comprising an enlarged exposed surface area, according to an embodiment of the present invention.

FIG. 2B shows a cross sectional view of a sustained release implant 202 with a core 212 comprising an enlarged exposed surface area 212A, according to an embodiment of the present invention. A sheath body 222 extends over core 212. The treatment agent can be released from the core as described above. Exposed surface area 212A is approximately conical, can be ellipsoidal or spherical, and extends outward from the sheath body to increase the exposed surface area of drug core 212.

Figure 2C:
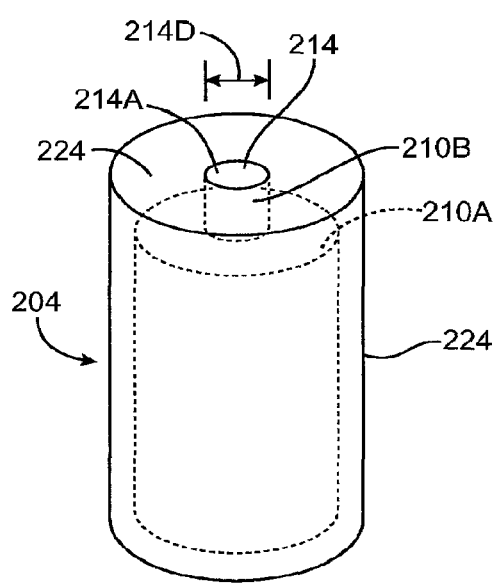
FIGS. 2C and 2D show perspective view and cross sectional views, respectively, of a sustained release implant with a core comprising a reduced exposed surface area, according to an embodiment of the present invention.
Figure 2D:
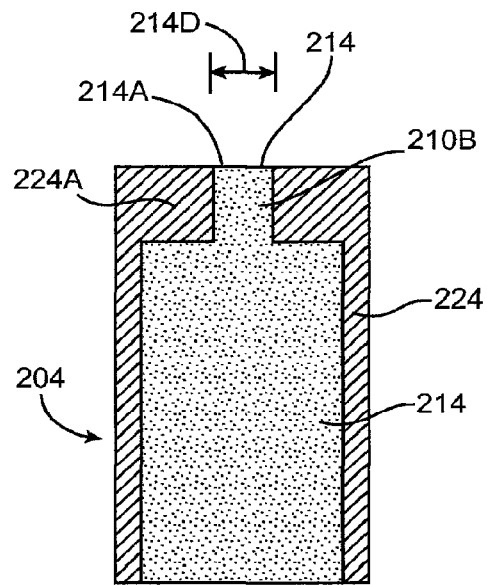

FIGS. 2C and 2D show perspective and cross sectional views, respectively, of a sustained release implant 204 with a drug core 214 comprising a reduced exposed surface area 214A, according to an embodiment of the present invention. Drug core 214 is enclosed within a sheath body 224. Sheath body 22 includes an annular end portion 224A that defines an opening through which drug core 214 extends. Drug core 214 includes an exposed surface 214A that releases the therapeutic agent. Exposed surface 214A has a diameter 214D that is less than a maximum dimension, for example a maximum diameter, across drug core 214.

Figure 2E:
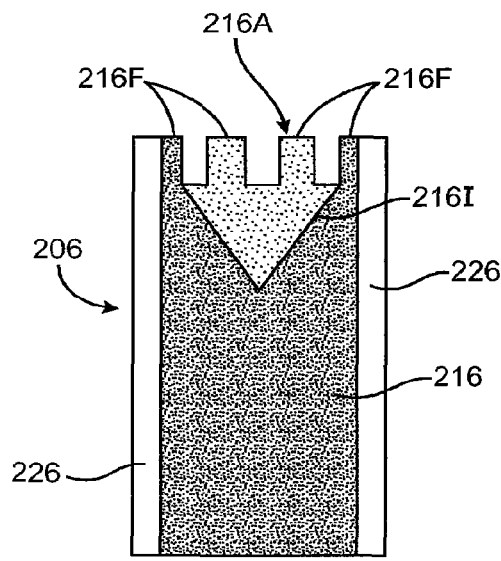
FIG. 2E shows a cross sectional view of a sustained release implant with a core comprising an enlarged exposed surface area with an indentation and castellation, according to an embodiment of the present invention.

FIG. 2E shows a cross sectional view of a sustained release implant 206 with a drug core 216 comprising an enlarged exposed surface area 216A with castellation extending therefrom, according to an embodiment of the present invention. The castellation includes several spaced apart fingers 216F to provide increased surface area of the exposed surface 216A. In addition to increased surface area provided by castellation, drug core 216 may also include an indentation 216I. Indentation 216I may have the shape of an inverted cone. Core 216 is covered with a sheath body 226. Sheath body 226 is open on one end to provide an exposed surface 216A on drug core 216. Sheath body 226 also includes fingers and has a castellation pattern that matches core 216.

FIG. 2F shows a perspective view of a sustained release implant 250 comprising a core with folds, according to an embodiment of the present invention Implant 250 includes a core 260 and a sheath body 270. Core 260 has an exposed surface 260A on the end of the core that permits drug migration to the surrounding tear or tear film fluid. Core 260 also includes folds 260F. Folds 260F increase the surface area of core that is exposed to the surrounding fluid tear or tear film fluid. With this increase in exposed surface area, folds 260F increase migration of the therapeutic agent from core 260 into the tear or tear film fluid and target treatment area. Folds 260F are formed so that a channel 260C is formed in core 260. Channel 260C connects to the end of the core to an opening in exposed surface 260A and provides for the migration of treatment agent. Thus, the total exposed surface area of core 260 includes exposed surface 260A that is directly exposed to the tear or tear film fluid and the surfaces of folds 260F that are exposed to the tear or tear film fluids via connection of channel 260C with exposed surface 260A and the tear or tear film fluid.

FIG. 2G shows a perspective view of a sustained release implant with a core comprising a channel with an internal surface, according to an embodiment of the present invention. Implant 252 includes a core 262 and sheath body 272. Core 262 has an exposed surface 262A on the end of the core that permits drug migration to the surrounding tear or tear film fluid. Core 262 also includes a channel 262C. Channel 262C increases the surface area of the channel with an internal surface 262P formed on the inside of the channel against the core. In some embodiment, the internal exposed surface may also be porous. Channel 262C extends to the end of the core near exposed surface 262A of the core. The surface area of core that is exposed to the surrounding tear or tear film fluid can include the inside of core 262 that is exposed to channel 262C. This increase in exposed surface area can increase migration of the therapeutic agent from core 262 into the tear or tear film fluid and target treatment area. Thus, the total exposed surface area of core 262 can include exposed surface 260A that is directly exposed to the tear or tear film fluid and internal surface 262P that is exposed to the tear or tear film fluids via connection of channel 262C with exposed surface 262A and the tear or tear film fluid.

FIG. 2H shows a perspective view of a sustained release implant 254 with a core 264 comprising channels to increase drug migration, according to an embodiment of the invention. Implant 254 includes core 264 and sheath body 274. Exposed surface 264A is located on the end of core 264, although the exposed surface can be positioned at other locations. Exposed surface 264 A permits drug migration to the surrounding tear or tear film fluid. Core 264 also includes channels 264C. Channels 264C extend to exposed surface 264. Channels 264C are large enough that tear or tear film fluid can enter the channels and therefore increase the surface area of core 264 that is in contact with tear or tear film fluid. The surface area of the core that is exposed to the surrounding fluid tear or tear film fluid includes the inner surfaces 264P of core 262 that define channels 264C. With this increase in exposed surface area, channels 264C increase migration of the therapeutic agent from core 264 into the tear or tear film fluid and target treatment area. Thus, the total exposed surface area of core 264 includes exposed surface 264A that is directly exposed to the tear or tear film fluid and internal surface 264P that is exposed to the tear or tear film fluids via connection of channels 262C with exposed surface 264A and the tear or tear film fluid.

FIG. 2I shows a perspective view of a sustained release implant 256 with a drug core 266 comprising a convex exposed surface 266A, according to an embodiment of the present invention. Drug core 266 is partially covered with a sheath body 276 that extends at least partially over drug core 266 to define convex exposed surface 266A. Sheath body 276 comprises a shaft portion 276S. Convex exposed surface 266A provides an increased exposed surface area above the sheath body. A cross sectional area of convex exposed surface 266A is larger than a cross sectional area of shaft portion 276S of sheath body 276. In addition to the larger cross sectional area, convex exposed surface 266A has a larger surface area due to the convex shape which extends outward from the core. Sheath body 276 comprises several fingers 276F that support drug core 266 in the sheath body and provide support to the drug core to hold drug core 266 in place in sheath body 276. Fingers 276F are spaced apart to permit drug migration from the core to the tear or tear film fluid between the fingers. Protrusions 276P extend outward on sheath body 276. Protrusions 276P can be pressed inward to eject drug core 266 from sheath body 276. Drug core 266 can be replaced with another drug core after an appropriate time, for example after drug core 266 has released most of the therapeutic agent.

Figure 2J:
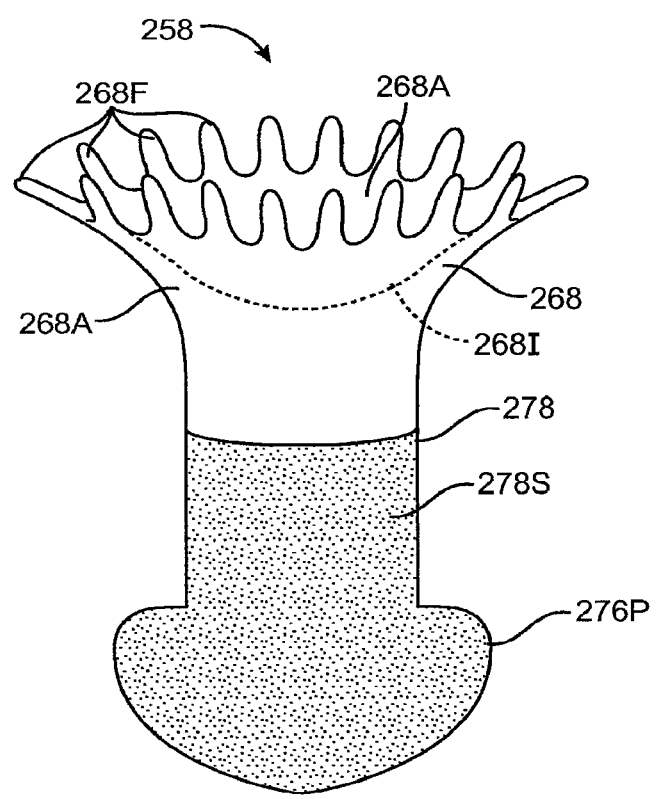
FIG. 2J shows a side view of a sustained release implant with a core comprising an exposed surface area with several soft brush-like members extending therefrom, according to an embodiment of the present invention.

FIG. 2J shows a side view of a sustained release implant 258 with a core 268 comprising an exposed surface area with several soft brush-like members 268F, according to an embodiment of the present invention. Drug core 268 is partially covered with a sheath body 278 that extends at least partially over drug core 268 to define exposed surface 268A. Sheath body 278 comprises a shaft portion 278S. Soft brush-like members 268F extend outward from drug core 268 and provide an increased exposed surface area to drug core 268. Soft brush-like members 268F are also soft and resilient and easily deflected such that these members do not cause irritation to neighboring tissue. Although drug core 268 can be made of many materials as explained above, silicone is a suitable material for the manufacture of drug core 268 also comprises soft brush like members 268F. Exposed surface 268A of drug core 268 also includes an indentation 268I such that at least a portion of exposed surface 268A is concave.

Figure 2K:
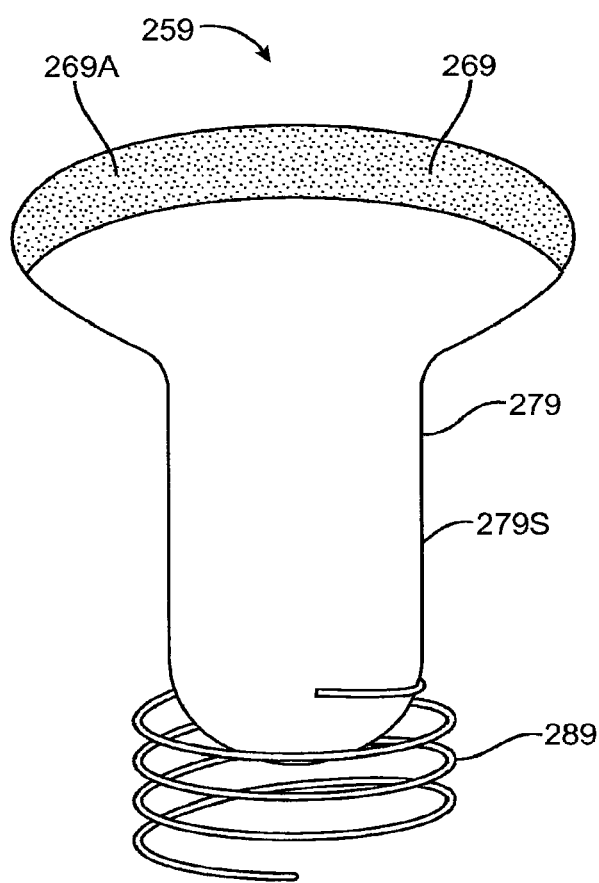
FIG. 2K shows a side view of a sustained release implant with a drug core comprising a convex exposed surface and a retention structure, according to an embodiment of the present invention.

FIG. 2K shows a side view of a sustained release implant 259 with a drug core 269 comprising a convex exposed surface 269A, according to an embodiment of the present invention. Drug core 269 is partially covered with a sheath body 279 that extends at least partially over drug core 269 to define convex exposed surface 269A. Sheath body 279 comprises a shaft portion 279S. Convex exposed surface 269 provides an increased exposed surface area above the sheath body. A cross sectional area of convex exposed surface 269A is larger than a cross sectional area of shaft portion 279S of sheath body 279. In addition to the larger cross sectional area, convex exposed surface 269A has a larger surface area due to the convex shape that extends outward on the core. A retention structure 289 can be attached to sheath body 279. Retention structure 289 can comprise any of the retention structures as describe herein, for example a coil comprising a super elastic shape memory alloy such as Nitinol™. Retention structure 289 can be dip coated to make retention structure 289 biocompatible.

Figure 2L:
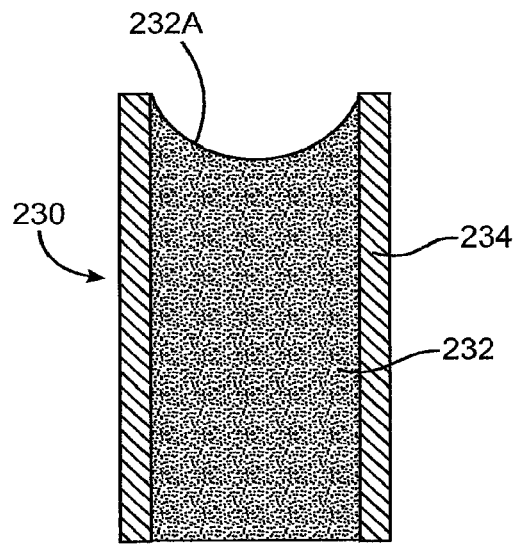
FIG. 2L shows a side view of a sustained release implant with a drug core comprising a concave indented surface to increase exposed surface area of the core, according to an embodiment of the present invention.

FIG. 2L shows a side view of a sustained release implant 230 with a drug core 232 comprising a concave indented surface 232A to increase exposed surface area of the core, according to an embodiment of the present invention. A sheath body 234 extends at least partially over drug core 232. Concave indented surface 232A is formed on an exposed end of drug core 232 to provide an increased exposed surface area of the drug core.

Figure 2M:
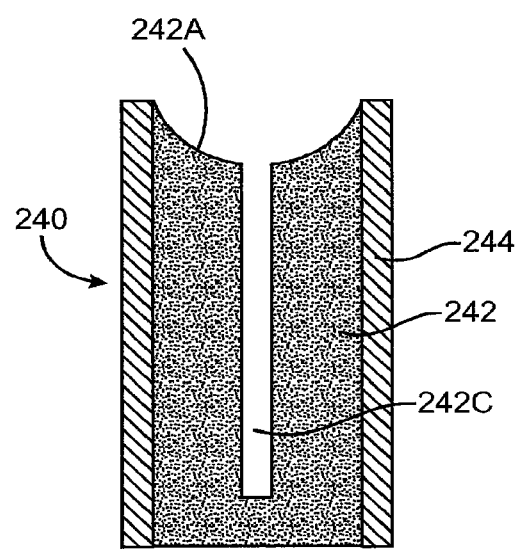
FIG. 2M shows a side view of a sustained release implant with a drug core comprising a concave surface with a channel formed therein to increase an exposed surface area of the core, according to an embodiment of the present invention.

FIG. 2M shows a side view of a sustained release implant 240 with a drug core 242 comprising a concave surface 242A with a channel 242C formed therein to increase an exposed surface area of the core, according to an embodiment of the present invention. A sheath body 244 extends at least partially over drug core 242. Concave indented surface 242A is formed on an exposed end of drug core 232 to provide an increased exposed surface area of the drug core. Channel 242C formed in drug core 242 to provide an increased exposed surface area of the drug core. Channel 242C can extend to concave indented surface 242A such that channel 242C and provide an increase in surface area of the core exposed to the tear or tear film.

Figure 3A:
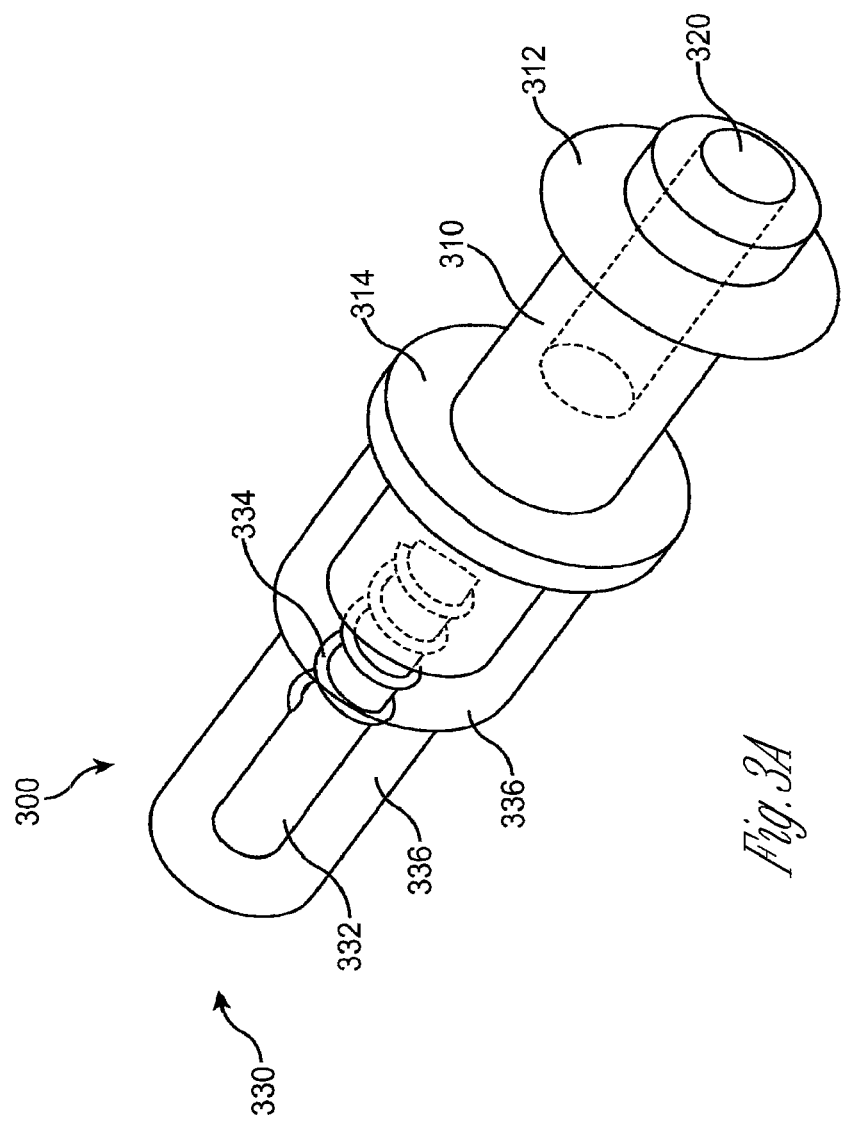
FIGS. 3A and 3B show an implant comprising a silicone body, a drug core and retention structures, according to embodiments of the present invention.
Figure 3B:
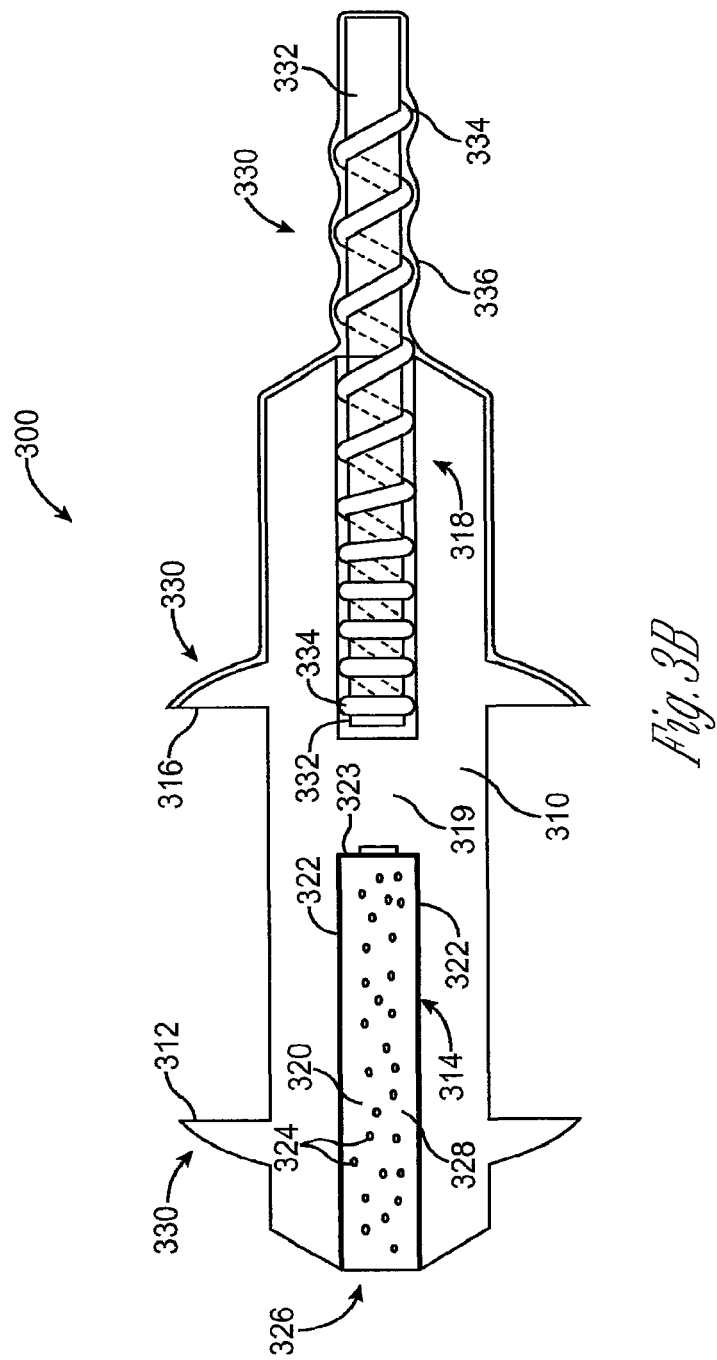

Referring now to FIGS. 3A and 3B an implant, for example a punctual plug 300, is shown which comprises a silicone body 310, a drug core 320 and a retention structures 330, according to embodiments of the present invention. Body 310 comprises a proximal channel 314 sized to receive drug core insert 320. Body 310 comprises a distal channel 318. Distal channel 318 can be sized to receive a hydrogel rod 332. A partition 319 may separate the proximal channel from the distal channel. A filament 334 can be embedded in body 310 and wrapped around hydrogel rod 332 to affix hydrogel rod 332 to body 310.

Drug core insert 320 may comprise a sheath 322, which is substantially impermeable to the drug so as to direct the drug toward an exposed surface 326 of the drug core. Drug core 320 may comprises a silicone matrix 328 with inclusions 324 of the drug encapsulated therein. The drug core insert and manufacture of the drug core insert are described in U.S. application Ser. Nos. 11/695,537 and 11/695,545, the full disclosures of which are incorporated herein by reference. In some embodiments, body 310 may comprise an annular rim 315 near exposed surface 326, that extends into proximal channel 314 and presses on sheath body 322 so as to indent the sheath body and decrease the exposed surface area of the drug core near the proximal end of the body. In some embodiments, optional annular rim 315 may press on the sheath body to retain the drug core in the channel without indentation of the sheath body.

Retention structures 330 may comprise hydrogel rod 332, hydrogel coating 336, protrusions 312 and protrusion 316. Hydrogel rod 332 can be inserted through the punctum into a canalicular lumen in a narrow profile configuration. After insertion into the lumen hydrogel rod 332 and hydrogel coating 336 can hydrate and expand to a wide profile configuration. Protrusions 312 and protrusion 316 can retain and/or stabilize implant 300 in the lumen, for example while the hydrogel coating and rod expand.

Figure 3C:
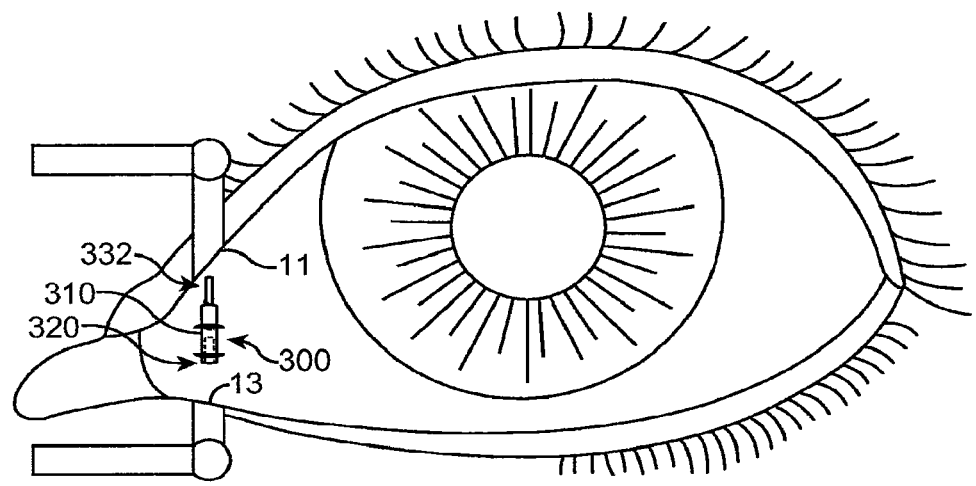
FIG. 3C shows insertion of the implant as in FIG. 3A into an upper canaliculus of an eye.

FIG. 3C shows insertion of punctual plug 300 as in FIG. 3A into an upper canaliculus of an eye. Punctual plug 300 can be oriented with hydrogel rod 332 aligned for placement in the upper canaliculus. Punctual plug 300 can be advanced into vertical portion 10V of the canaliculus such that the exposed surface of the drug core and proximal end of the implant are substantially aligned with the exterior of the punctual opening.

Figure 3D:
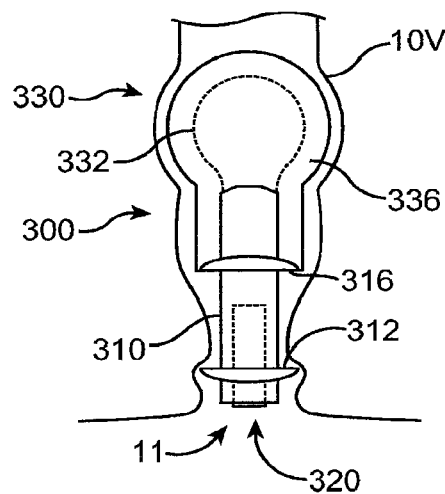
FIG. 3D shows an implant as in FIG. 3A in an expanded profile configuration following implantation in the canaliculus of the eye.

FIG. 3D shows a punctual plug as in FIG. 3A in an expanded profile configuration following implantation in the canaliculus of the eye. Hydrogel rod 332 and hydrogel coating 336 are shown in an expanded profile configuration.

FIG. 4 shows a drug core insert 400 suitable for use with an implant, according to embodiments of the present invention. Drug core insert comprises a first proximal end 402 and a distal end 404. Drug core insert 400 comprises a sheath body 410, for example a polyimide tube. Sheath body 410 can comprise a material that is substantially impermeable to the therapeutic agent such that flow of the therapeutic agent can be inhibited by the sheath body. Examples of materials that can be substantially impermeable to the therapeutic agent include polyimide, polymethylmethacrylate (PMMA) and polyethylene terephthalate (PET). Sheath body 410 comprises a first proximal end 412 and a second distal end 414. Drug core insert 400 comprises a drug core 420 comprising inclusions 424 encapsulated in a matrix material 426. An exposed surface 422 comprising an area on the proximal end of the drug core is capable of sustained release of the therapeutic agent at therapeutic levels, for example quantities. In many embodiments, the therapeutic agent is at least partially soluble in the matrix material 426 such that the therapeutic agent from the inclusions can penetrate the matrix material, for example via diffusion, and be released from matrix material into a tissue surface and/or bodily fluid in contact with exposed surface 422. A material 430 comprises distal end 404 of the drug core insert. In many embodiments, the polyimide tube comprises a cut length of tube in which the both ends of the tube have been cut to expose the drug core. Material 430 can be adhered on the distal end of the drug core inserted to inhibit flow of the therapeutic agent. In many embodiments, material 430 comprises an adhesive material that is substantially impermeable to the therapeutic agent, for example acrylic, cyanoacrylate, epoxy, urethane, hot melt adhesives and Loctite™ with UV curing.

Sheath body 410 is sized to fit within a channel of an implant. The distal end of drug core insert 404 can be inserted into the implant such that exposed surface 422 remains exposed when the drug core insert is inserted into the implant.

Figure 4A:
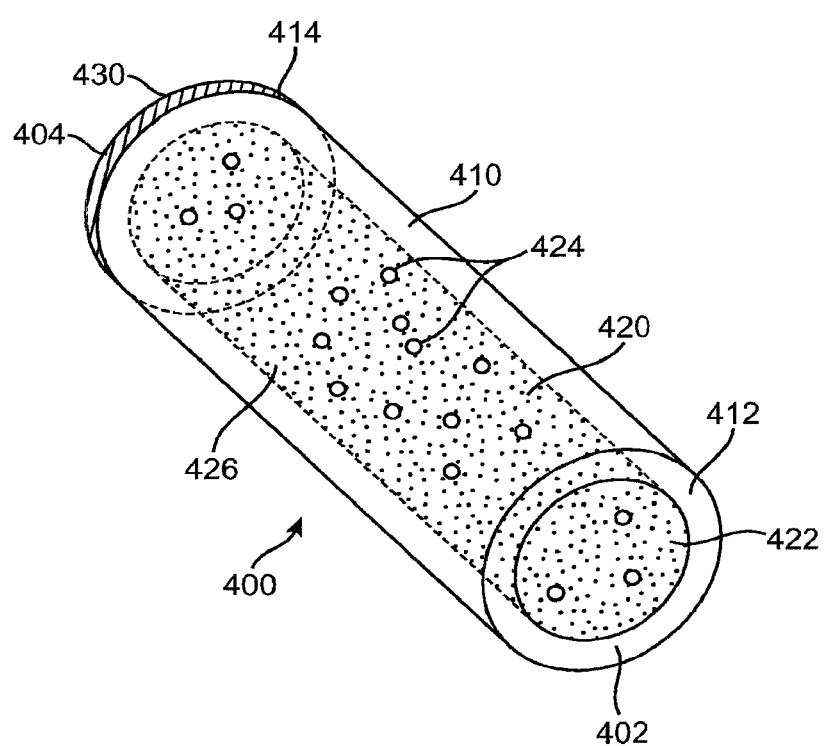
FIG. 4A shows a drug core insert suitable for use with an implant, according to embodiments of the present invention.
Figure 4B:
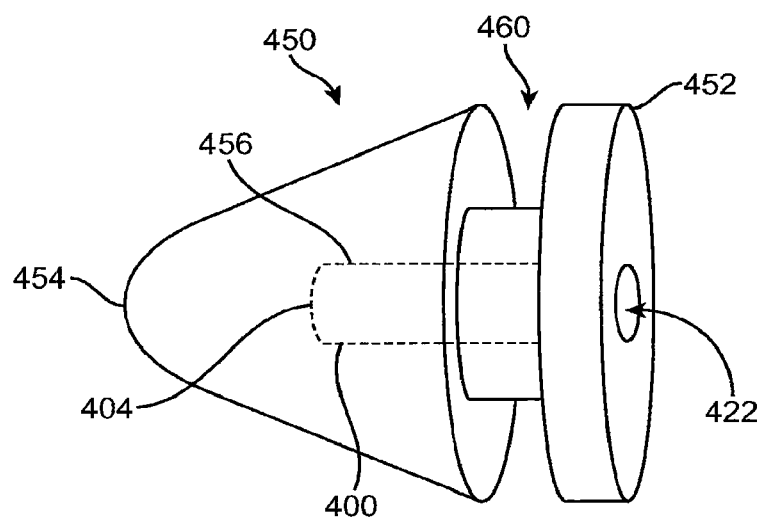
FIG. 4B shows an of implant suitable for use with a drug core insert, according to embodiments of the present invention.

FIG. 4B shows an example of implant 450 suitable for use with a drug core insert 400 as in FIG. 4A, according to embodiments of the present invention. Implant 450 comprises a proximal 452 and a distal end 454. Implant 450 comprises a retention structure 460 that includes an indentation to retain implant 450 in the punctum of the eye. Implant 450 comprises a channel 456 that extends from within the implant to an opening formed proximal end 452. Channel 456 can be sized to receive drug core insert 400. Drug core insert 400 can be inserted into channel 456 such that distal end 404 of drug core insert 400 is embedded within implant 450 while proximal end 402 comprising surface 422 is exposed. When implant 450 is placed in the punctum, surface 422 is exposed to the tear fluid of the eye such that the therapeutic agent can be delivered to the eye. In many embodiments, the punctual plug has a length of about 2 mm and a width of about 1 mm.

Many implants can be used with drug core insert 400. Some embodiments can employ a commercially available implant, for example the Soft Plug silicone punctum plug commercially Oasis Medical of Glendora Calif., the Tear Pool Punctual Plug commercially available form Medtronic, the "Parasol Punctual Occluder System" available from Odyssey of Memphis, Tenn., and/or the Eagle Vision Plug available from Eagle Vision of Memphis, Tenn. In some embodiments, the punctual plug may comprise a custom punctual plug, for example sized custom plugs that are selected in response to patient measurements. In some embodiments, the implant used with the drug core insert may comprise implants as described in U.S. application Ser. Nos. 11/695,537, filed on Apr. 2, 2007, entitled "DRUG DELIVERY METHODS, STRUCTURES, AND COMPOSITIONS FOR NASOLACRIMAL SYSTEM", published as U.S. patent Application Publication No. 2007/0269487 on Nov. 22, 2007; 11/695,545, filed on Apr. 2, 2007, entitled "NASOLACRIMAL DRAINAGE SYSTEM IMPLANTS FOR DRUG THERAPY", which issued as U.S. Pat. No. 7,998,497 on Aug. 16, 2011; 60/871,867, filed on Dec. 26, 2006, entitled "DRUG DELIVERY IMPLANTS FOR INHIBITION OF OPTICAL DEFECTS", the priority of which was claimed in PCT Application No. PCT/US2007/088701, which published as WO 2008/083118 on Jul. 10, 2008; and 10/825,047, filed Apr. 15, 2004, entitled "DRUG DELIVERY VIA PUNCTAL PLUG," published as U.S. Patent Application Publication No. 2005/0232972 on Oct. 20, 2005; the full disclosures of which are all incorporated herein by reference.

Figure 36:
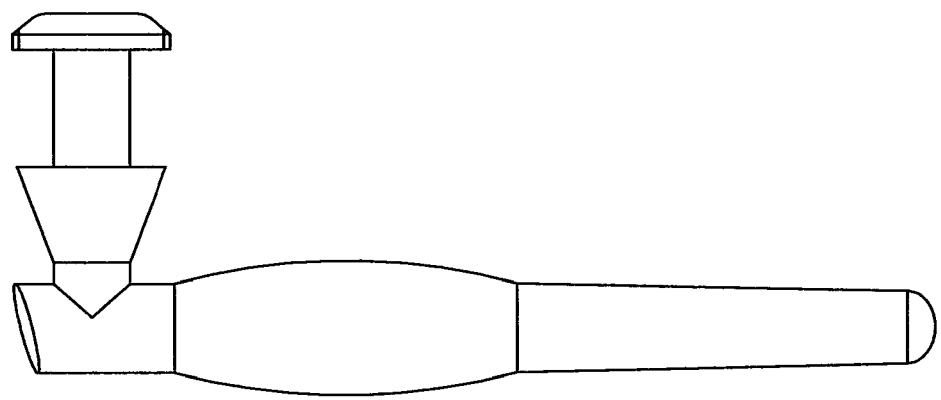
FIG. 36 shows one embodiment of the implant having the bent design.

In some embodiments, such as shown in FIG. 36 and discussed in U.S. patent application Ser. No. 12/231,989, filed Sep. 8, 2008, entitled "LACRIMAL IMPLANTS AND RELATED METHODS", and published as U.S. Patent Application Publication No. 2009/0104248 on Apr. 23, 2009, the implant can be insertable through a lacrimal punctum and into the associated canaliculus. The insertion of the implant through the lacrimal punctum and into the associated canaliculus can allow for one or more of: inhibition or blockage of tear flow therethrough (e.g., to treat dry eyes) or the sustained delivery of a drug or other therapeutic agent to an eye (e.g., to treat an infection, inflammation, glaucoma or other ocular disease or disorder), a nasal passage (e.g., to treat a sinus or allergy disorder) or an inner ear system (e.g., to treat dizziness or a migraine). The implant can comprise an implant body including first and second portions, and can extend from a proximal end of the first portion to a distal end of the second portion. In various examples, the proximal end can define a longitudinal proximal axis and the distal end can define a longitudinal distal axis. The implant body can be configured such that, when implanted within the lacrimal punctum and associated canaliculus, an at least 45 degree angled intersection exists between the proximal axis and the distal axis for biasing at least a portion of the implant body against at least a portion of a lacrimal canaliculus located at or more distal to a canaliculus curvature. In some examples, the implant body can be configured such that the angled intersection is between about 45 degrees and about 135 degrees. In this example, the implant body is configured such that the angled intersection is about 90 degrees (i.e., the intersection is about perpendicular). In various examples, a distal end of the first portion can be integral with the second portion at or near a proximal end of the second portion.

In certain examples, the implant body can include angularly disposed cylindrical-like structures comprising one or both of a first cavity disposed near the proximal end or a second cavity disposed near the distal end. In this example, the first cavity extends inward from the proximal end of the first portion, and the second cavity extends inward from the distal end of the second portion. A first drug-releasing or other agent-releasing drug core insert can be disposed in the first cavity to provide a sustained drug or other therapeutic agent release to an eye, while a second drug core insert can be disposed in the second cavity to provide a sustained drug or other therapeutic agent release to a nasal passage or inner ear system, for example. An implant body septum can be positioned between the first cavity and the second cavity, and can be used to inhibit or prevent communication of a material (e.g., agent) between the first drug core insert and the second drug core insert. In some embodiments, the implant body is solid and does not include one or more cavities or other voids.

Figure 4C:
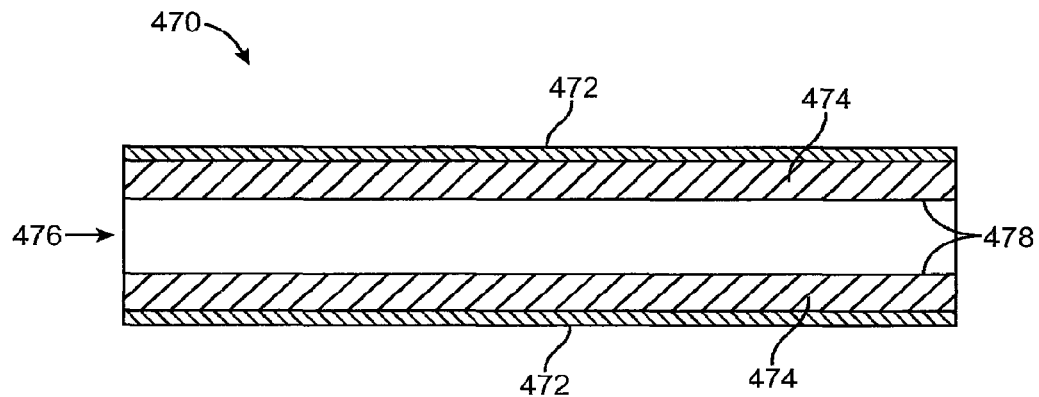
FIG. 4C shows an annular drug core insert suitable for use with an implant for systemic delivery of a therapeutic agent, according to embodiments of the present invention.

FIG. 4C shows an annular drug core insert 470 suitable for use with an implant for systemic delivery of a therapeutic agent. Drug core insert 470 comprises a sheath body 472 which is substantially impermeable to the therapeutic agent so as to inhibit flow of the therapeutic agent through the sheath body. Drug core insert 470 comprises a solid drug core 474. Drug core 474 comprises a matrix material with inclusions of the therapeutic agent dispersed therein, as described above. Drug core 474 comprises an exposed surface 478. Drug core 474 comprises a generally annular shape with a channel 476 formed therein, such that exposed surface 478 is inwardly directed and exposed to bodily fluids in the channel, for example the tear liquid when implanted in the channel. Therapeutic quantities, or levels, of the therapeutic agent can be released from inner exposed surface 478 to the bodily fluid within the channel.

Figure 4D:
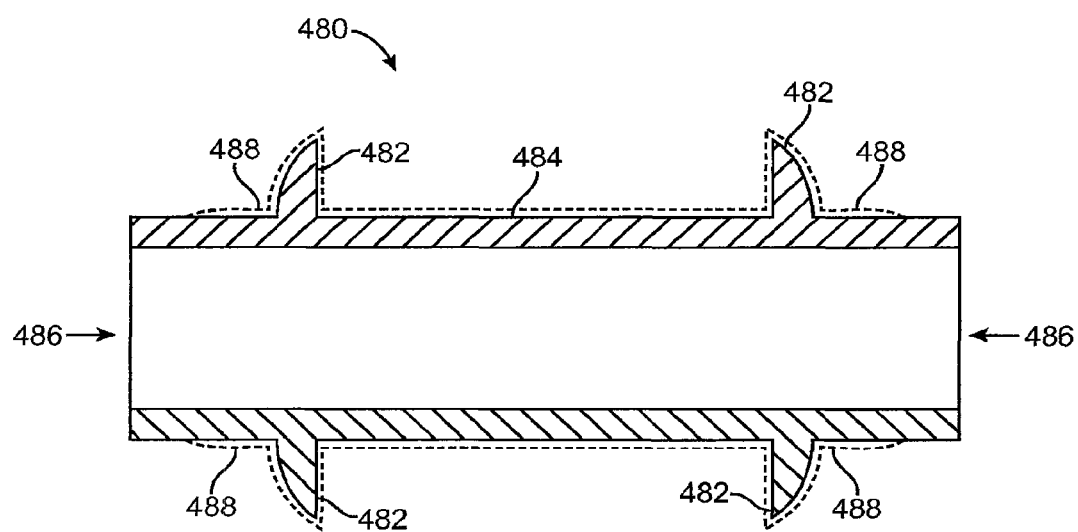
FIG. 4D shows an of implant suitable for use with a drug core insert as in FIG. 4C.

FIG. 4D shows an of implant 480 suitable for use with a drug core insert as in FIG. 4C. Implant 480 comprises a body 484, for example a molded silicone body, and retention structures 482. A channel 486 within body 484 is sized to receive drug core insert 470. Implant 480 may comprise a hydrogel coating 488 on the outside. Hydrogel coating 488 may be located near retention structure 488. In some embodiments, hydrogel coating 488 may be located away from the ends of implant 480, such that the hydrogel does not inhibit flow through channel 476 of the drug core insert when implanted in the patient. In some embodiments, the retention structure may comprise an expandable coil or stent like structure with a proximal portion embedded in body 484 and an exposed distal portion that expands to permit flow through the coil between the punctum and lacrimal sac, for example a shape memory capable of expansion to anchor the implant in the canaliculus.

Figure 4E:
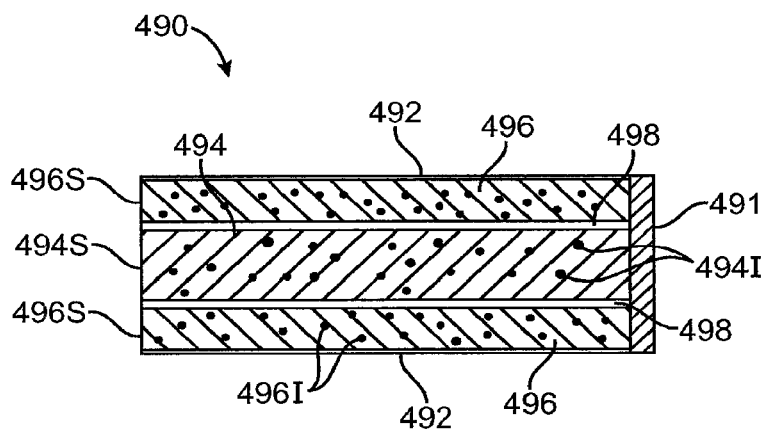
FIGS. 4E and 4F show a side cross-sectional view and an end view, respectively, of a drug core inserts with two drug cores, according to embodiments of the present invention.
Figure 4F:
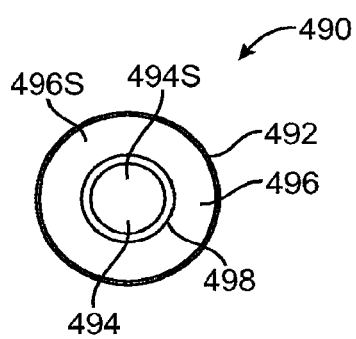

FIGS. 4E and 4F show a side cross-sectional view and an end view, respectively, of a drug core insert 490 comprising a first drug core 494 and a second drug core 496. First drug core 494 comprises inclusions 494I of a first therapeutic agent, and second drug core 496 comprises inclusions 496I of a second therapeutic agent. Therapeutic quantities of the first therapeutic agent are released through an exposed surface 494S of first drug core 494, and therapeutic quantities of a second therapeutic agent are released through an exposed surface 496S of second drug core 496.

Insert 490 comprises an outer sheath body 492 around drug core 496 and an inner sheath body 498 disposed between drug core 494 and drug core 496, so as to inhibit release of one drug core to the other drug core. The sheath body 492 and sheath body 498 may comprise materials substantially impermeable to the therapeutic agent, so as to inhibit release of the therapeutic agent away from the exposed surfaces. In some embodiments, the sheath bodies may comprise thin walled tubes.

In some embodiments, the drug core insert can be used with an implant for insertion in tissues in or near the eye, for example the sclera, the conjunctiva, the cul-de-sac of the eyelid, the trabecular meshwork, the ciliary body, the cornea, the choroid, the suprachoroidal space, the sclera, the vitreous humor, aqueous humor and retina.

In some embodiments, the drug core insert can be manufactured with a structure to facilitate removal of the drug core insert, for example a filament as described in U.S. Application Ser. Nos. 60/970,696, filed on Sep. 7, 2007, and 60/974,367 filed on Sep. 21, 2007 entitled "EXPANDABLE NASOLACRIMAL DRAINAGE SYSTEM IMPLANTS", the priorities of which are claimed in U.S. patent application Ser. No. 12/231,989, filed Sep. 8, 2008, entitled "LACRIMAL IMPLANTS AND RELATED METHODS", and published as U.S. Patent Application Publication No. 2009/0104248 on Apr. 23, 2009; the full disclosures of which are all incorporated herein by reference.

Figure 5A:
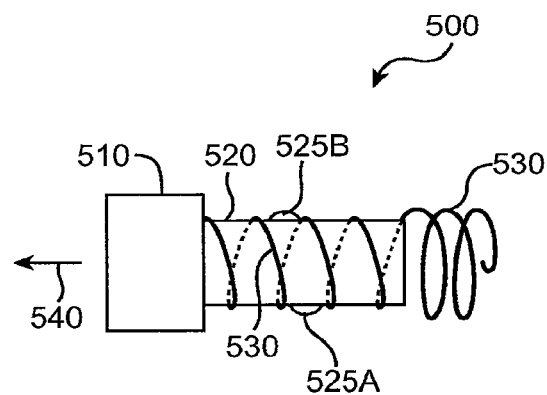
FIGS. 5A to 5C schematically illustrate replacement of a drug core and a sheath body, according to an embodiment of the present invention.
Figure 5B:
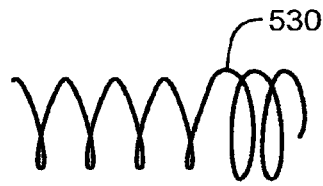
Figure 5C:
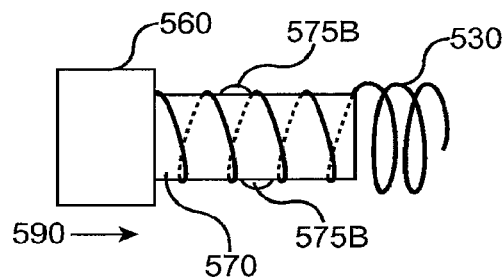

FIGS. 5A to 5C schematically illustrate replacement of a drug core 510 and a sheath body 520, according to an embodiment of the present invention. An implant 500 comprises drug core 510, sheath body 520 and a retention structure 530. Implant 500 can include an occlusive element support by and movable with retention structure 530. Often retention structure 530 can assume a first small profile configuration prior to implantation and a second large profile configuration while implanted. Retention structure 530 is shown in the large profile configuration and implanted in the canalicular lumen. Sheath body 520 includes extension 525A and extension 525B to attach the sheath body and drug core to retention structure 530 so that the sheath body and drug core are retained by retention structure 530. Drug core 510 and sheath body 520 can be removed together by drawing drug core 510 proximally as shown by arrow 530. Retention structure 530 can remain implanted in the canalicular tissue after drug core 510 and sheath body 520 have been removed as shown in FIG. 5B. A replacement core 560 and replacement sheath body 570 can be inserted together as shown in FIG. 5C. Such replacement can be desirable after drug core 510 has released effective amounts of therapeutic agent such that the supply of therapeutic agent in the drug core has diminished and the rate of therapeutic agent released is near the minimum effective level. Replacement sheath body 570 includes extension 575A and extension 575B. Replacement drug core 560 and replacement sheath body 570 can be advanced distally as shown by arrow 590 to insert replacement drug core 560 and replacement sheath body 570 into retention structure 530. Retention structure 530 remains at substantially the same location while replacement drug core 560 and replacement sheath body 570 are inserted into resilient member 530.

Figure 5D:
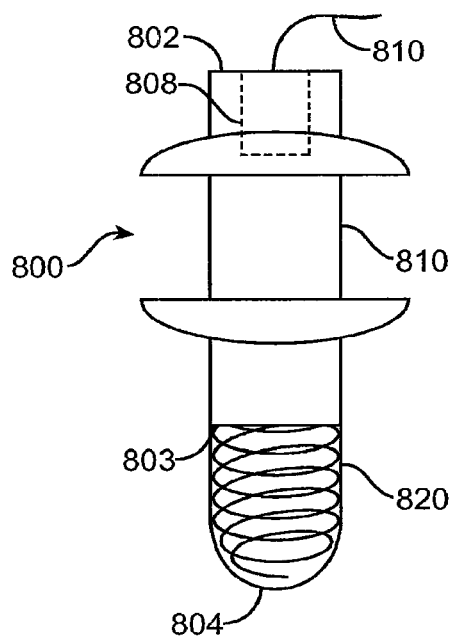
FIGS. 5D and 5E show an implant comprising a filament that extends from a drug core insert for removal the drug core insert from the implant, according to embodiments of the present invention.
Figure 5E:
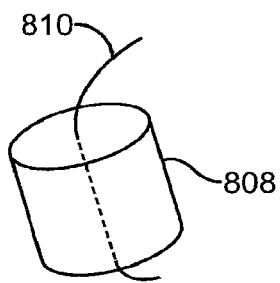

FIGS. 5D and 5E show an implant comprising 800 a filament 810 that extends from a drug core insert 808 for removal drug core insert 808 from implant 800, according to embodiments of the present invention. Implant 800 comprises a body 805 and expandable retention structure 820, as described above. Body 810 comprises a proximal end 802 and a distal end 803. Implant 800 extends from proximal end 802 to a distal end 804 of retention structure 820. Implant 800 comprises a channel to receive the drug core insert, as described above. Filament 810 extends from a proximal end of the drug core insert to a distal end of the drug core insert. Filament 810 can be molded into the drug core insert. Filament 840 may comprise many of the filaments described above, for example a suture, a thermoset polymer, a shape memory alloy, and the like.

Figure 5F:
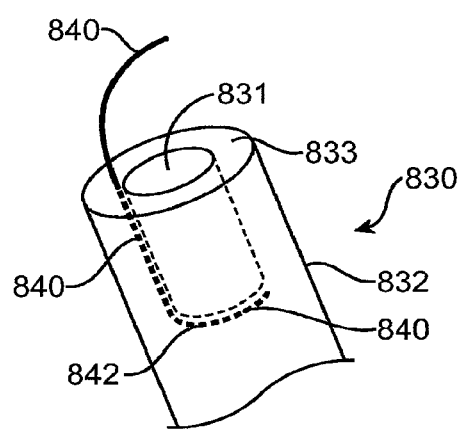
FIG. 5F shows an implant comprising a filament that extends along a drug core insert bonded to a distal end of the drug core insert for removal of the drug core insert from a body of the implant, according to embodiments of the present invention.

FIG. 5F shows an implant 830 comprising a filament 840 that extends along a drug core insert 831 bonded to a distal end of the drug core insert for removal of the drug core insert from a body 832 of the implant, according to embodiments of the present invention. Implant 830 comprises a proximal end 833. Filament 840 may be bonded to the distal end of drug core insert 831 with an adhesive 842. Filament 840 can be bonded to the distal end of drug core insert 831 in many ways, for example with cyanoacrylate, acrylic, epoxy, urethane and hot melt adhesives and the like.

Sheath Body

The sheath body comprises appropriate shapes and materials to control migration of the therapeutic agent from the drug core. The sheath body houses the core and can fit snugly against the core. The sheath body is made from a material that is substantially impermeable to the therapeutic agent so that the rate of migration of the therapeutic agent may be largely controlled by the exposed surface area of the drug core that is not covered by the sheath body. In many embodiments, migration of the therapeutic agent through the sheath body can be about one tenth of the migration of the therapeutic agent through the exposed surface of the drug core, or less, often being one hundredth or less. In other words, the migration of the therapeutic agent through the sheath body is at least about an order of magnitude less that the migration of the therapeutic agent through the exposed surface of the drug core. Suitable sheath body materials include polyimide, polyethylene terephthalate" (hereinafter "PET"), polymethylmethacrylate ("PMMA"), stainless steel (for example, type 316 stainless steel, tubing size 25XX), or titanium. The sheath body has a wall thickness from about 0.00025" to about 0.0015". In some embodiments, the wall thickness can be defined as the distance from the sheath surface adjacent the core to the opposing sheath surface away from the core. The total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected and/or extruded into the sheath body tube. The sheath body can also be dip coated around the core, for example dip coated around a pre-formed core.

The sheath body can be provided with additional features to facilitate clinical use of the implant. For example, the sheath may receive a drug core that is exchangeable while the retention structure and sheath body remain implanted in the patient. The sheath body may be rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body and/or retention structure may have a distinguishing feature, for example a distinguishing color, to show placement such that the placement of the sheath body and/or retention structure in the canaliculus or other body tissue structure can be readily detected by the patient. The retention element and/or sheath body may comprise at least one mark to indicate the depth of placement in the canaliculus such that the retention element and/or sheath body can be positioned to a desired depth in the canaliculus based on the at least one mark.

Retention Structure

The retention structure comprises an appropriate material that is sized and shaped so that the implant can be easily positioned in the desired tissue location, for example the canaliculus. The retention structure is mechanically deployable and typically expands to a desired cross sectional shape, for example with the retention structure comprising a super elastic shape memory alloy such as Nitinol™. Other materials in addition to Nitinol™ can be used, for example resilient metals or polymers, plastically deformable metals or polymers, shape memory polymers, and the like, to provide the desired expansion. In some embodiments polymers and coated fibers available from Biogeneral, Inc. of San Diego, Calif. may be used. Many metals such as stainless steels and non-shape memory alloys can be used and provide the desired expansion. This expansion capability permits the implant to fit in hollow tissue structures of varying sizes, for example canaliculae ranging from 0.3 min to 1.2 mm (i.e. one size fits all). Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm. The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the sheath body and drug core can be attached to one end of the retention structure as described above, in many embodiments the other end of retention structure is not attached to drug core and sheath body so that the retention structure can slide over the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A protrusion, for example a hook, a loop, or a ring, can extend from the retention structure to facilitate removal of the retention structure.

Occlusive Element

The occlusive element comprises an appropriate material that is sized and shaped so that the implant can at least partially inhibit, even block, the flow of fluid through the hollow tissue structure, for example lacrimal fluid through the canaliculus. The occlusive material shown is a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Therapeutic Agents

A "therapeutic agent" can comprise a drug and may be any of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins, prostaglandin analogs, and hypotensive lipids, and combinations thereof), antimicrobial agent (e.g., antibiotic, antiviral, antiparacytic, antifungal, etc.), a corticosteroid or other anti-inflammatory such as olopatadine (e.g., an NSAID), a decongestant (e.g., vasoconstrictor), an agent that prevents of modifies an allergic response (e.g., cyclosporine, an antihistamine, cytokine inhibitor, leucotriene inhibitor, IgE inhibitor, immunomodulator), a mast cell stabilizer, cycloplegic or the like. Examples of conditions that may be treated with the therapeutic agent(s) include but are not limited to glaucoma, pre and post surgical treatments, dry eye and allergies. In some embodiments, the therapeutic agent may be a lubricant or a surfactant, for example a lubricant to treat dry eye.

Exemplary therapeutic agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Such anti inflammatory steroids contemplated for use in the methodology of the present invention, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, -estradiol, progestational, progesterone, insulin, calcitonin, parathyroid hormone, peptide and vasopressin hypothalamus releasing factor); immunosuppressive agents such as cyclosporine, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandin, prostaglandin precursors, including antiglaucoma drugs including beta-blockers such as Timolol, betaxolol, levobunolol, atenolol, and prostaglandin analogues such as Bimatoprost, travoprost, Latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

For use in ophthalmic applications, some specific therapeutic agents that can be used include glaucoma medications (muscarinics, beta blockers, alpha agonists, carbonic anhydrase inhibitors, prostaglandins and their analogs), antiinflammatories (steroids, soft steroids, NSAIDs), anti infectives including antibiotics such as beta lactams, fluoro quinolones, etc.), antivirals, and antimicotics, dry eye medications (CsA, delmulcents, sodium hyaluronate), or combinations thereof.

The amount of drug associated with the drug-delivery device may vary depending on the particular agent, the desired therapeutic benefit and the time during which the device is intended to deliver the therapy. Since the devices of the present invention present a variety of shapes, sizes and delivery mechanisms, the amount of drug associated with the device will depend on the particular disease or condition to be treated, and the dosage and duration that is desired to achieve the therapeutic effect. Generally, the amount of drug is at least the amount of drug that upon release from the device, is effective to achieve the desired physiological or pharmacological effects.

Embodiments of the drug delivery devices of the present invention can be adapted to provide delivery of drug at a daily rate that is substantially below the therapeutically effective drop form of treatment so as to provide a large therapeutic range with a wide safety margin. For example, many embodiments treat the eye with therapeutic levels for extended periods that are no more than 5 or 10 percent of the daily drop dosage. Consequently, during an initial period of about seven days, more typically of about one to three days, the implant can elute the therapeutic agent at a rate that is substantially higher than the sustained release levels but still below the daily drop form dosage. For example, with an average sustained release level of 100 ng per day, and an initial release rate of 1000 to 1500 ng per day, the amount of drug initially released is less than the 2500 ng of drug that may be present in a drop of drug delivered to the eye. This use of sustained release levels substantially below the amount of drug in a drop and/or drops administered daily allows the device to release a therapeutically beneficial amount of drug to achieve the desired therapeutic benefit with a wide safety margin, while avoiding an inadequate or excessive amount of drug at the intended site or region.

An extended period of time may mean a relatively short period of time, for example minutes or hours (such as with the use of an anesthetic), through days or weeks (such as the use of pre-surgical or post-surgical antibiotics, steroids, or NSAIDs and the like), or longer (such as in the case of glaucoma treatments), for example months or years (on a recurring basis of use of the device).

For example, drug such as Timolol maleate, a beta1 and beta2 (non-selective) adrenergic receptor blocking agent can be used in the device for a release over an extended period of time such as 3 months. Three months is a relatively typical elapsed time between physician visits for a glaucoma patient undergoing topical drop therapy with a glaucoma drug, although the device could provide treatment for longer or shorter durations. In the three month example, a 0.25% concentration of Timolol translates to from 2.5 to 5 mg/1000 µL, typically being 2.5 mg/1000 µL. A drop of Timolol for topical application is usually in the range of 40-60 µL, typically being 50 µL. Thus, there may be 0.08-0.15 mg, typically being 0.125 mg of Timolol in a drop. There may be approximately 8% (e.g. 6-10%) of the drop left in the eye after 5 minutes, so about 10 µg of the drug is available at that time. Timolol may have a bioavailability of 30-50%, which means that from 1.5 to 7.5 µg, for example 4 µg of the drug is available to the eye. Timolol is generally applied twice a day, so 8 (or 3-15) µg is available to the eye each day. Therefore, a delivery device might contain from 270 to 1350 µg, for example 720 µg, of the drug for a 90 day, or 3 month, extended release. The drug would be contained within the device and eluted based on the design of the device, including the polymers used and the surface area available for drug elution. The drug can be similarly contained on the device and eluted for olopatadine hydrochloride (Patanol®) and other drugs in a manner similar to Timolol.

Commercially available solutions of Timolol maleate are available in 0.25% and 0.5% preparations, and the initial dosage can be 1 drop twice per day of 0.25% solution. A 0.25% concentration of Timolol is equivalent to 2.5 mg per 1000 µl. A sustained release quantity of Timolol released each day from the drug core can be from about 3 to 15 µg each day. Although the sustained release quantity delivered each day from the device may vary, a sustained release delivery of about 8 µg per day corresponds to about 3.2% of the 0.250 mg of Timolol applied with two drops of a 0.25% solution.

For example, in the case of Latanoprost (Xalatan), a prostaglandin F2α analogue, this glaucoma medication has concentrations that are about 1/50th that of Timolol. Therefore, the amount of drug on the implantable device, depending on the bioavailability, would be significantly less—approximately 5-135 µg and typically 10-50 µg—for Latanoprost and other prostaglandin analogues. This also translates to a device that can either be smaller than one required for a beta blocker delivery or can house more drug for a longer release period.

A drop of Xalatan contains about 2.5 µg of Latanoprost, assuming a 50 µL drop volume. Therefore, assuming that about 8% of 2.5 µg is present 5 minutes after instillation, only about 200 ng of drug remains on the eye. Based on the Latanoprost clinical trials, this amount is effective in lowering IOP for at least 24 hours. Pfizer/Pharmacia conducted several dose-response studies in support of the NDA for Xalatan. The doses ranged from 12.5 µg/mL to 115 µg/mL of Latanoprost. The current dose of Latanoprost, 50 µg/mL, given once per day, was shown to be optimal. However, even the lowest doses of 12.5 µg/mL QD or 15 µg/mL BID consistently gave about 60-75% of the IOP reduction of the 50 µg/mL QD dose. Based on the assumptions above, a 12.5 µg/mL concentration provides 0.625 µg of Latanoprost in a 50 µL drop, which results in only about 50 ng (8%) of drug remaining in the eye after 5 minutes.

In many embodiments, the concentrations of Latanoprost are about 1/100th, or 1 percent, that of Timolol, and in specific embodiments the concentrations of Latanoprost may be about 1/50th, or 2 percent, that of Timolol. For example, commercially available solution preparations of Latanoprost are available at concentrations 0.005%, often delivered with one drop per day. In many embodiments, the therapeutically effective concentration of drug released from the device per day can be about 1/100th of Timolol, about 30 to 150 ng per day, for example about 80 ng, assuming tear washout and bioavailability similar to Timolol. For example, the amount of drug on the implantable device, can be significantly less-approximately 1% to 2% of Timolol, for example 2.7 to 13.5 µg, and can also be about 3 to 20 µg, for Latanoprost and other prostaglandin analogues. Although the sustained release amount of Latanoprost released each day can vary, a sustained release of 80 ng per day corresponds to about 3.2% of the 2.5 µg of Latanoprost applied with a single drop of a 0.005% solution.

For example, in the case of Bimatoprost (Lumigan), a synthetic prostamide prostaglandin analogue, this glaucoma medication may have concentrations that are 1/20th or less than that of Timolol. Therefore, the amount of drug loaded on the extended release device for a 3 to 6 month extended release, depending on the bioavailability, can be significantly less, approximately 5-30 µg and typically 10-20 µg—for Bimatoprost and analogues and derivatives thereof. In many embodiments, the implant can house more drug for a longer sustained release period, for example 20-40 µg for a sustained release period of 6 to 12 months with Bimatoprost and its derivatives. This decrease in drug concentration can also translate to a device that can be smaller than one required for a beta blocker delivery.

Commercially available solution concentrations of Bimatoprost are 0.03% by weight, often delivered once per day. Although the sustained release amount of Bimatoprost released each day can vary, a sustained release of 300 ng per day corresponds to about 2% of the 15 μg of Bimatoprost applied with a single drop of a 0.03% solution. Work in relation with the present invention suggests that even lower sustained release doses of Bimatoprost can provide at least some reduction in intraocular pressure, for example 20 to 200 ng of Bimatoprost and daily sustained release dosages of 0.2 to 2% of the daily drop dosage.

For example, in the case of Travoprost (Travatan), a prostaglandin F2α analogue, this glaucoma medication may have concentrations that are 2% or less than that of Timolol. For example, commercially available solution concentrations are 0.004%, often delivered once per day. In many embodiments, the therapeutically effective concentration of drug released from the device per day can be about 65 ng, assuming tear washout and bioavailability similar to Timolol. Therefore, the amount of drug on the implantable device, depending on the bioavailability, would be significantly less. This also translates to a device that can either be smaller than one required for a beta blocker delivery or can house more drug for a longer release period. For example, the amount of drug on the implantable device, can be significantly less—approximately 1/100 of Timolol, for example 2.7 to 13.5 μg, and typically about 3 to 20 μg, for Travoprost, Latanoprost and other prostaglandin F2α analogues. Although the sustained release amount of Latanoprost released each day can vary, a sustained release of 65 ng per day corresponds to about 3.2% of the 2.0 μg of Travoprost applied with a single drop of a 0.004% solution.

In some embodiments, the therapeutic agent may comprise a corticosteriod, for example fluocinolone acetonide, to treat a target ocular tissue. In specific embodiments, fluocinolone acetonide can be released from the canaliculus and delivered to the retina as a treatment for diabetic macular edema (DME).

It is also within the scope of this invention to modify or adapt the devices to deliver a high release rate, a low release rate, a bolus release, a burst release, or combinations thereof. A bolus of the drug may be released by the formation of an erodable polymer cap that is immediately dissolved in the tear or tear film. As the polymer cap comes in contact with the tear or tear film, the solubility properties of the polymer enable the cap to erode and the drug is released all at once. A burst release of a drug can be performed using a polymer that also erodes in the tear or tear film based on the polymer solubility. In this example, the drug and polymer may be stratified along the length of the device so that as the outer polymer layer dissolves, the drug is immediately released. A high or low release rate of the drug could be accomplished by changing the solubility of the erodable polymer layer so that the drug layer released quickly or slowly. Other methods to release the drug could be achieved through porous membranes, soluble gels (such as those in typical ophthalmic solutions), microparticle encapsulations of the drug, or nanoparticle encapsulation, depending on the size of the drug molecule.

Drug Core

The drug core comprises the therapeutic agent and matrix materials to provide sustained release of the therapeutic agent. The matrix material can include a polymer, such as silicone or polyurethane. The therapeutic agent migrates from the drug core to the target tissue, for example the ciliary body of the eye. The therapeutic agent may optionally be only slightly soluble in the matrix so that a small amount of therapeutic agent is dissolved in the matrix and available for release from the surface of drug core 110, additional agent being present in the form of inclusions, which can be in a solid or a liquid physical state within the matrix. As the therapeutic agent diffuses from the exposed surface of the core to the tear or tear film, the rate of migration from the core to the tear or tear film can be related to the concentration of therapeutic agent dissolved in the matrix. In addition or in combination, the rate of migration of therapeutic agent from the core to the tear or tear film can be related to properties of the matrix in which the therapeutic agent dissolves. In specific embodiments, the rate of migration from the drug core to the tear or tear film can be based on a silicone formulation. In some embodiments, the concentration of therapeutic agent dissolved in the drug core may be controlled to provide the desired rate of release of the therapeutic agent. The therapeutic agent included in the core can include liquid, solid, solid gel, solid crystalline, solid amorphous, solid particulate, and/or dissolved forms of the therapeutic agent. In an embodiment, the drug core comprises a silicone matrix containing the therapeutic agent. The therapeutic agent may comprise liquid or solid inclusions, for example liquid latanoprost droplets or solid bimatoprost particles, respectively, dispersed in the silicone matrix. The average diameter, and the distribution of diameters throughout the population of droplets or particles, can be used to control the elution rate of the agent from the drug core into, for example, tear liquid in the eye.

In another embodiment, the therapeutic agent can be soluble at relatively high levels in the matrix, such that inclusions are not formed when the agent is present at therapeutically useful concentrations. For example, cyclosporine can be dissolved in a polyurethane matrix at high concentrations, and the cyclosporine is dispersed throughout the polyurethane matrix at molecular levels, i.e., a "solid solution" of the cyclosporine in the polyurethane matrix can be achieved.

When the inclusion is solid, various comminuted forms of the solid material can be used to achieve a particular average particle diameter and size distribution of diameters. Such solid powders can be obtained by any suitable method known in the art. See, for example, machines manufactured for the pharmaceutical industry by Glatt GmbH, at http://www.glatt.com/e/00_home/00.htm. In the milling process a range of sizes can be generated. Fluidized beds and coaters can be used to increase particle size to a desired dimension. Particle size will influence surface area and may affect dissolution. Inclusion size and associated size distribution can be used to control an elution rate of the agent from the drug core, both in the situation where the inclusions are solid, such as bimatoprost, and where the inclusions are liquid, such as latanoprost oil.

The drug core can comprise one or more biocompatible materials capable of providing a sustained release of the therapeutic agent. Although the drug core is described above with respect to an embodiment comprising a matrix with a substantially non-biodegradable silicone matrix with inclusions of the drug located therein that dissolve, the drug core can include structures that provide sustained release of the therapeutic agent, for example a biodegradable matrix, a porous drug core, liquid drug cores and solid drug cores. A matrix that contains the therapeutic agent can be formed from either biodegradable or non-biodegradable polymers. A non-biodegradable drug core can include silicone, acrylates, polyethylenes, polyurethane, polyurethane, hydrogel, polyester (e.g., DACRON® from E.I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® m Elgin Specialty Metals, Elgin, Ill.; CONICHROME® from Carpenter Metals Corp., Wyomissing, Pa.). A biodegradable drug core can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some embodiments the drug core can comprise at least one of hydrogel polymer.

Release of Therapeutic Agent at Effective Levels

The rate of release of the therapeutic agent can be related to the concentration of therapeutic agent in the drug core. In many embodiments, the drug core comprises non-therapeutic agents that are selected to provide a desired solubility of the therapeutic agent in the drug core. The non-therapeutic agent of the drug core can comprise polymers as described herein and additives. A polymer of the core can be selected to provide the desired solubility and/or dispersability of the therapeutic agent in the matrix. For example, the core can comprise hydrogel that may promote solubility or dispersability of hydrophilic treatment agent. In some embodiments, functional groups can be added to the polymer to provide the desired solubility or dispersity of the therapeutic agent in the matrix. For example, functional groups can be attached to silicone polymer.

In some embodiments, release rate modifying additives may be used to control the release kinetics of therapeutic agent. For example, the additives may be used to control the concentration of therapeutic agent by increasing or decreasing solubility of the therapeutic agent in the drug core so as to control the release kinetics of the therapeutic agent. The solubility may be controlled by providing appropriate molecules and/or substances that increase and/or decrease the solubility of the therapeutic agent to the matrix. The solubility of the therapeutic agent may be related to the hydrophobic and/or hydrophilic properties of the matrix and therapeutic agent. For example, surfactants, tinuvin, salts and water can be added to the matrix and may increase the solubility of hydrophilic therapeutic agent in the matrix. Salts can be water soluble, such as sodium chloride, or water-insoluble, such as titanium dioxide. In addition, oils and hydrophobic molecules and can be added to the matrix and may increase the solubility of hydrophobic treatment agent in the matrix. Alternatively, various oligomers and polymers, for example polysaccharides such as alginates, or proteins such as albumin, can be added. Solvents such as glycerol can also be used to modify the rate of release of the agent from the matrix into the tear liquid.

Instead of or in addition to controlling the rate of migration based on the concentration of therapeutic agent dissolved in the matrix, the surface area of the drug core can also be controlled to attain the desired rate of drug migration from the core to the target site. For example, a larger exposed surface area of the core will increase the rate of migration of the treatment agent from the drug core to the target site, and a smaller exposed surface area of the drug core will decrease the rate of migration of the therapeutic agent from the drug core to the target site. The exposed surface area of the drug core can be increased in any number of ways, for example by any of castellation of the exposed surface, a surface having exposed channels connected with the tear or tear film, indentation of the exposed surface, protrusion of the exposed surface. The exposed surface can be increased by the addition of salts that dissolve and leave cavities once the salt dissolves. Hydrogels may also be used, and can swell in size to provide a larger exposed surface area.

In addition, drug impregnated porous materials, such as meshes, may be used such as those disclosed in U.S. Patent Application Publication No. 2002/0055701 or layering of biostable polymers as described in U.S. Patent Application Publication No. 2005/0129731. Certain polymer processes may be used to incorporate drug into the devices of the present invention such as, so-called "self-delivering drugs" or PolymerDrugs (Polymerix Corporation, Piscataway, N.J.) are designed to degrade only into therapeutically useful compounds and physiologically inert linker molecules, further detailed in US Patent Publication No. 2005/0048121 (East), hereby incorporated by reference in its entirety. Such delivery polymers may be employed in the devices of the present invention to provide a release rate that is equal to the rate of polymer erosion and degradation and is constant throughout the course of therapy. Such delivery polymers may be used as device coatings or in the form of microspheres for a drug depot injectable (such as a reservoir of the present invention). A further polymer delivery technology may also be adapted to the devices of the present invention such as that described in U.S. Patent Application Publication No. 2004/0170685 (Carpenter), and technologies available from Medivas (San Diego, Calif.).

In specific embodiments, the drug core matrix comprises a solid material, for example silicone, that encapsulates inclusions of the drug. The drug comprises molecules which are very insoluble in water and slightly soluble in the encapsulating drug core matrix. The inclusions encapsulated by the drug core can be micro-particles having dimensions from about 1 µm to about 100 µm across. The drug inclusions can comprise crystals, for example bimatoprost crystals, and/or droplets of oil, for example with latanoprost oil. The drug inclusions can dissolve into the solid drug core matrix and substantially saturate the drug core matrix with the drug, for example dissolution of latanoprost oil into the solid drug core matrix. The drug dissolved in the drug core matrix is transported, often by diffusion, from the exposed surface of the drug core into the tear film. As the drug core is substantially saturated with the drug, in many embodiments the rate limiting step of drug delivery is transport of the drug from the surface of the drug core matrix exposed to the tear film. As the drug core matrix is substantially saturated with the drug, gradients in drug concentration within the matrix are minimal and do not contribute significantly to the rate of drug delivery. As surface area of the drug core exposed to the tear film is nearly constant, the rate of drug transport from the drug core into the tear film can be substantially constant. Work in relation with the present invention suggests that the solubility of the therapeutic agent in water and molecular weight of the drug can effect transport of the drug from the solid matrix to the tear. In many embodiments, the therapeutic agent is nearly insoluble in water and has a solubility in water of about 0.03% to 0.002% by weight and a molecular weight from about 400 grams/mol. to about 1200 grams/mol.

In many embodiments the therapeutic agent has a very low solubility in water, for example from about 0.03% by weight to about 0.002% by weight, a molecular weight from about 400 grams per mole (g/mol.) to about 1200 g/mol and is readily soluble in an organic solvent. Cyclosporin A (CsA) is a solid with an aqueous solubility of 27.67 µg/mL at 25° C., or about 0.0027% by weight, and a molecular weight (M.W.) of 1202.6 g/mol. Latanoprost (Xalatan) is a prostaglandin F2α analogue, a liquid oil at room temperature, and has an aqueous solubility of 50 µg/mL in water at 25° C., or about 0.005% by weight and a M.W. of 432.6 g/mol.

Bimatoprost (Lumigan) is a synthetic prostamide analogue, a solid at room temperature solubility in water of 300 µg/mL in water at 25° C., or 0.03% by weight, and has a M.W. of 415.6 g/mol.

Work in relation with the present invention indicates that naturally occurring surfactants in the tear film, for example surfactant D and phospholipids, may effect transport of the drug dissolved in the solid matrix from the core to the tear film. The drug core can be adapted in response to the surfactant in the tear film to provide sustained delivery of the drug into the tear film at therapeutic levels. For example, empirical data can be generated from a patient population, for example 10 patients whose tears are collected and analyzed for surfactant content. Elution profiles in the collected tears for a drug that is sparingly soluble in water, for example cyclosporine, can also be measured and compared with elution profiles in buffer and surfactant such that an in vitro model of tear surfactant is developed. An in vitro solution with surfactant based on this empirical data can be used to adjust the drug core in response to the surfactant of the tear film.

The drug cores may also be modified to utilize carrier vehicles such as nanoparticles or microparticles depending on the size of the molecule to be delivered such as latent-reactive nanofiber compositions for composites and nanotextured surfaces (Innovative Surface Technologies, LLC, St. Paul, Minn.), nanostructured porous silicon, known as BioSilicon®, including micron sized particles, membranes, woven fivers or micromachined implant devices (pSividia, Limited, UK) and protein nanocage systems that target selective cells to deliver a drug (Chimeracore).

In many embodiments, the drug insert comprises of a thin-walled polyimide tube sheath with a drug core comprising latanoprost dispersed in Nusil 6385 (MAF 970), a medical grade solid silicone that serves as the matrix for drug delivery. The distal end of the drug insert is sealed with a cured film of solid Loctite 4305 medical grade adhesive. The drug insert may be placed within the bore of the punctum plug, the Loctite 4305 adhesive does not come into contact with either tissue or the tear film. The inner diameter of the drug insert can be 0.32 mm; and the length can be 0.95 mm. Three Latanoprost concentrations in the finished drug product can be tested clinically: Drug cores can comprise 3.5, 7 or 14 µg latanoprost, with percent by weight concentrations of 5, 10 and 20% respectively. Assuming an overall elution rate of approximately 100 ng/day, the drug core comprising 14 µg of latanoprost is adapted to deliver drug for approximately at least 100 days, for example 120 days. The overall weight of the drug core, including latanoprost, can be ~70 µg. The weight of the drug insert including the polyimide sleeve can be approximately 100 µg.

In many embodiments, the drug core may elute with an initial elevated level of therapeutic agent followed by substantially constant elution of the therapeutic agent. In many instances, an amount of therapeutic agent released daily from the core may be below the levels found in drops and still provide a benefit to the patient. An elevated level of eluted therapeutic agent can result in a residual amount of therapeutic agent and/or residual effect of the therapeutic agent to provide relief to the patient. In embodiments where therapeutic level is about 80 ng per day, the device may deliver about 100 ng per day for an initial delivery period. The extra 20 ng delivered per day can have a beneficial immediate effect. As the amount of drug delivered can be precisely controlled, an initial elevated dose may not result in complications and/or adverse events to the patient.

Further, an implant may be used that includes the ability to release two or more drugs in combination, such as the structure disclosed in U.S. Pat. No. 4,281,654 (Shell). For example, in the case of glaucoma treatment, it may be desirable to treat a patient with multiple prostaglandins or a prostaglandin and a cholinergic agent or an adrenergic antagonist (beta blocker), such as Alphagan®, or prostaglandin and a carbonic anhydrase inhibitor.

In various embodiments, the implant may have at least one surface and release a therapeutic quantity of two therapeutic agents into tear or tear film fluid of the eye throughout a time period of at least one week when the implant is implanted with the at least one surface exposed to the tear or tear film fluid. For example, the implant can be adapted to release the therapeutic agents in therapeutic amounts over a period of time from about one to twelve months. The release rate of each of the therapeutic agents may be the same or each of the therapeutic agents may have different release rates.

In some embodiments, the implant comprise a single drug core with two therapeutic agents mixed within a matrix. In other embodiments, the implant comprise two drug cores, each with a single therapeutic agent.

In specific embodiments, at least a portion of the implant may be bioerodable, and the therapeutic agents can be released while the a portion of the implant erodes.

In some embodiments, the second therapeutic agent may comprise a counteractive agent to avoid a side effect of the first therapeutic agent. In one example, the second therapeutic agent may comprise at least one of an anti-glaucoma drug or a miotic drug. The anti-glaucoma drug may comprise at least one of a sympathomimetic, a parasympathomimetic, a beta blocking agent, a carbonic anhydrase inhibitor, or prostaglandin analogue. In another example, the first therapeutic agent may be steroids and the second therapeutic agent may be antibiotics, where the steroids compromise the immune response, but the antibiotics provides coverage for infection. In another example, the first therapeutic agent may be pilocarpine and the second therapeutic agent may be non-steroidal anti-inflammatory drug (NSAID). An analgesic may be a good compliment for the treatment.

In some embodiments the therapeutic agents can be released with a profile that corresponds to a kinetic order of therapeutic agents release and the order can be within a range from about zero to about one. In specific embodiments, the range is from about zero to about one half, for example from about zero to about one quarter. The therapeutic agents may be released with a profile that corresponds to a kinetic order of therapeutic agents release and the order is within a range from about zero to about one half for at least about a month after the structure is inserted, for example the order can be within the range at least about 3 months after the structure is inserted.

Figure 17:
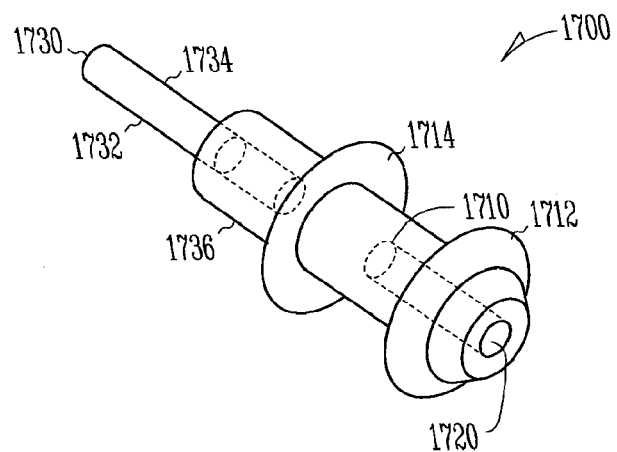
FIG. 17 shows an implant comprising a silicone body, a drug core and retention structures, according to embodiments of the present invention.

Referring now to FIG. 17, an implant, for example a punctual plug 1700, is shown which comprises a silicone body 1710, a drug core 1720 and a retention structures 1730, according to embodiments of the present invention. Body 1710 comprises a proximal channel 1714 sized to receive drug core insert 1720. A filament 1734 can be embedded in body 1710 and wrapped around hydrogel rod 1732 to affix hydrogel rod 1732 to body 1710. The drug core insert and manufacture of the drug core insert are described in U.S. application Ser. Nos. 11/695,537 and 11/695,545, the full disclosures of which are incorporated herein by reference. Although a drug core insert is shown, some embodiments may comprises a drug reservoir, a semi-permeable membrane, a drug coating or the like, as described in U.S. Pat. No. 6,196,993 (Cohan) and U.S. application Ser. Nos. 10/899,416 (Prescott); 10/899,417 (Prescott); 10/762,421 (Ashton); 10/762,439 (Ashton); 11/571,147 (Lazar) and 10/825,047 (Odrich), the full disclosures of which are herein incorporated by reference for all purposes. In some embodiments, the implant comprises a punctual plug without drug carried on the implant, for example an implant similar to punctual plug 1700 without channel 1714 and drug core insert 1720.

Retention structures 1730 may comprise hydrogel rod, hydrogel coating, and protrusions. Hydrogel rod 1732 can be inserted through the punctum into a canalicular lumen in a narrow profile configuration. After insertion into the lumen the hydrogel rod, hydrogel coating, or both, can hydrate expand to a wide profile configuration.

FIG. 18A shows a cross sectional view of a sustained release implant 1800 having two therapeutic agents to treat an eye, according to embodiments of the present invention. Implant 1800 has a proximal end 1812 in which the therapeutic agents are released and a distal end 1814. Implant 1800 includes two concentric drug cores 1810, 1815. First drug core 1810 is a cylindrical shaped structure with a central opening that includes a first therapeutic agent, and second drug core 1815 is a cylindrical shaped structure that includes a second therapeutic agent. Second drug core 1815 is configured to fit within the central opening of first drug core 1810, as shown in the figures. First drug core 1810 comprises a first matrix 1870 that contains first inclusions 1860 of the first therapeutic agent, and second drug core 1815 comprises a second matrix 1875 that contains second inclusions 1865 of the second therapeutic agent. First and second inclusions 1860, 1865 will often comprise a concentrated form of the first and second therapeutic agents, for example a liquid or solid form of the therapeutic agents, and the therapeutic agents may over time dissolve into first matrix 1870 of first drug core 1810 and second matrix 1875 of second drug core 1815. First and second matrixes 1870, 1875 can comprise a silicone matrix or the like, and the mixture of therapeutic agents within matrixes can be non-homogeneous. In many embodiments, the non-homogenous mixture comprises a silicone matrix portion that is saturated with the therapeutic agents and an inclusions portion comprising inclusions of the therapeutic agents, such that the non-homogenous mixture comprises a multiphase non-homogenous mixture. The first matrix may differ from the second matrix, including, for example, an exposed surface area, a surfactant, a cross-linking, an additive, and/or matrix materials including formulation and/or solubility. In some embodiments, first and second inclusions 1860, 1865 comprise droplets of an oil of the therapeutic agent, for example Latanoprost oil. In some embodiments, first and second inclusions 1860, 1865 may comprise particles of the therapeutic agents, for example solid bimatoprost particles. In many embodiments, first matrix 1870 contains first inclusions 1860 and second matrix 1875 contains second inclusions 1865. First and second inclusions 1860, 1865 may comprise microparticles having dimensions from about 0.1 μm to about 100 μm, or 200 μm. The contained inclusions at least partially dissolve into the surrounding solid matrix, for example silicone, that contains the micro particles such that first and second matrixes 1870, 1875 are substantially saturated with the therapeutic agent while the therapeutic agent is released from the core.

First and second drug cores 1810, 1815 are surrounded by a sheath body 1820, except at an exposed surface where the therapeutic agents are released, in this case at the proximal end 1812. Sheath body 1820 is substantially impermeable to the therapeutic agents, so that the therapeutic agents are released from the exposed surface on the open end of first and second drug cores 1810, 1815 that are not covered with sheath body 1820. In some embodiments, the implant may be incorporated into a different structure, such as a punctual plug.

FIG. 18B shows a side cross sectional view of the sustained release implant of FIG. 18A. First drug core 1810 with a first therapeutic agent is a cylindrical shaped structure and shown with a circular cross-section with an open center. Second drug core 1815 with a second therapeutic agent is a cylindrical shaped structure and shown with a circular cross-section and is configured to fit within first drug core 1810, as shown in the figures. Sheath body 1820 comprises an annular portion disposed on first drug core 310.

FIG. 19A shows a cross sectional view of a sustained release implant 1900 having therapeutic agents to treat an eye, according to embodiments of the present invention. Implant 1900 has a proximal end 1912 in which the therapeutic agents are released and a distal end 1914. Implant 1900 includes first and second drug cores 1910, 1915 that are positioned in a side by side configuration. First drug core 1910 is a cylindrical shaped structure that includes the first therapeutic agent and second drug core 1915 is a cylindrical shaped structure that includes the second therapeutic agent. First and second drug cores 1910 and 1915 are placed adjacent to each other and may have the same length, or different lengths, such as shown in the figure. First drug core 1910 comprises a first matrix 1970 that contains first inclusions 1960 of the first therapeutic agent and second drug core 415 comprises a second matrix 1975 that contains second inclusions 1965 of the second therapeutic agent. First and second inclusions 1960, 1965 will often comprise a concentrated form of the first and second therapeutic agents, for example a liquid or solid form of the therapeutic agents, and the therapeutic agents may over time dissolve into first matrix 1970 of first drug core 1910 and second matrix 1975 of second drug core 1915. First and second matrixes 1970, 1975 can comprise a silicone matrix or the like, and the mixture of therapeutic agents within matrixes can be non-homogeneous. In many embodiments, the non-homogenous mixture comprises a silicone matrix portion that is saturated with the therapeutic agents and an inclusions portion comprising inclusions of the therapeutic agents, such that the non-homogenous mixture comprises a multiphase non-homogenous mixture. The first matrix may differ from the second matrix, including, for example, an exposed surface area, a surfactant, a cross-linking, an additive, and/or matrix materials including formulation and/or solubility. In some embodiments, first and second inclusions 1960, 1965 comprise droplets of an oil of the therapeutic agent, for example Latanoprost oil. In some embodiments, inclusions may comprise particles of the therapeutic agent, for example solid bimatoprost particles. First and second inclusions 1960, 1965 may comprise microparticles having dimensions from about 0.1 μm to about 100 μm, or 200 μm. The contained inclusions at least partially dissolve into the surrounding solid matrix, for example silicone, that contains the micro particles such that first and second matrixes 1970, 1975 are substantially saturated with the therapeutic agent while the therapeutic agent is released from the core.

First and second drug cores 1910, 1915 are surrounded by a sheath body 1920, except at an exposed surface where the therapeutic agents are released, in this case at the proximal end 1912. Sheath body 1920 is substantially impermeable to the first and second therapeutic agents, so that the first and second therapeutic agents are released from the exposed surface on the open end of first and second drug cores 1910, 1915 that are not covered with sheath body 1920. In some embodiments, the implant may be incorporated into a different structure, such as a punctual plug.

FIG. 19B shows a side cross sectional view of the sustained release implant of FIG. 19A. First drug core 1910 with the first therapeutic agent is a cylindrical shaped structure and shown with a circular cross-section. Second drug core 1915 with the second therapeutic agent is also a cylindrical shaped structure and shown with a circular cross-section. First and second drug cores 1910, 1915 may have different diameters or the same diameter, as shown in the figures. Sheath body 1920 comprises an annular portion disposed around first and second drug cores 1910, 1915.

FIG. 20A shows a cross sectional view of a sustained release implant 2000 having therapeutic agents to treat an eye, according to embodiments of the present invention. Implant 2000 has a proximal end 2012 and a distal end 2014. Implant 2000 includes two concentric drug cores 2010, 2015 with hollow centers to allow fluid flow through the implant 2000. First drug core 2010 is a hollow cylindrical shaped structure that includes a first therapeutic agent and second drug core 2015 is a hollow cylindrical shaped structure that includes a second therapeutic agent. Second drug core 2015 is configured to fit within a central opening of first drug core 2010, as shown in the figures. First and second drug cores 2010, 2015 may have the same length, or different lengths, as shown in the figures. First drug core 2010 comprises a first matrix 2070 that contains first inclusions 2060 of the first therapeutic agent and second drug core 2015 comprises a second matrix 2075 that contains second inclusions 2065 of the second therapeutic agent. First and second inclusions 2060, 2065 will often comprise a concentrated form of the first and second therapeutic agents, for example a liquid or solid form of the therapeutic agents, and the therapeutic agents may over time dissolve into a first matrix 2070 of first drug core 2010 and a second matrix 2075 of second drug core 2015, respectively. First and second matrixes 2070, 2075 can comprise a silicone matrix or the like, and the mixture of therapeutic agents within matrixes can be non-homogeneous. In many embodiments, the non-homogenous mixture comprises a silicone matrix portion that is saturated with the therapeutic agents and an inclusions portion comprising inclusions of the therapeutic agents, such that the non-homogenous mixture comprises a multiphase non-homogeneous mixture. The first matrix may differ from the second matrix, including, for example, an exposed surface area, a surfactant, a cross-linking, an additive, and/or matrix materials including formulation and/or solubility. In some embodiments, first and second inclusions 2060, 2065 comprise droplets of an oil of the therapeutic agent, for example latanoprost oil. In some embodiments, inclusions may comprise particles of the therapeutic agent, for example solid bimatoprost particles. First and second inclusions 2060, 2065 may comprise microparticles having dimensions from about 0.1 μm to about 100 μm, or about 200 μm. The contained inclusions at least partially dissolve into the surrounding solid matrix, for example silicone, that contains the micro particles such that first and second matrixes 2070, 2075 are substantially saturated with the therapeutic agent while the therapeutic agent is released from the core.

First drug core 2010 is surrounded on its outer surface by a sheath body 2020, having first drug core 2010 with an open inner surface 2085 and exposed proximal and distal end surfaces. Sheath body 2020 is substantially impermeable to the first therapeutic agents in first drug core 2010, so that the first therapeutic agents are released from the exposed surfaces of the drug core 2010. Second drug core 2015 is surrounded on its outer surface by first drug core 2010, with an open inner surface 2080 and exposed proximal and distal end surfaces. The second drug core 2015 is shorter than the first drug core 2010 so that portions of the inner surface 2085 are exposed. First therapeutic agents are released from the exposed surfaces of first drug core 2010 that are not covered by the sheath body 2020 and second drug core 2015, and second therapeutic agents are released from the exposed surfaces of second drug core 2015 that are not covered with first drug core 2010. In some embodiments, the implant may be incorporated into a different structure, such as a punctual plug.

FIG. 20B shows a side cross sectional view of the sustained release implant of FIG. 20A with concentric drug cores. First drug core 510 with the first therapeutic agent is shown with a circular cross-section with a first open center portion. Second drug core 2015 with the second therapeutic agent is shown with a circular cross-section with a second open center and is configured to fit within the first open center portion of first drug core 2010, while allowing flow through the center of the second drug core 2015, as shown in the figures. Sheath body 2020 comprises an annular portion disposed on first drug core 2010.

The drug cores disclosed above comprise the first and second therapeutic agents and materials to provide sustained release of the first and second therapeutic agents. The first and second therapeutic agents migrate from the drug core to the target tissue, for example ciliary body of the eye. The ocular surface could be targeted for cyclosporine A (control inflammation) and mucin inducers for dry eyes. The uvea could be targeted by steroids, NSAIDs and CSA for uveitis. The first and second therapeutic agents may optionally be only slightly soluble in the matrix so that the release rate remains "zero order" for the lifetime of the release of the first and second therapeutic agents when dissolved in the matrix and available for release from the exposed surfaces of the drug cores. As the first and second therapeutic agents differs from the exposed surfaces of the drug cores to the tear or tear film, the rate of migration from the drug cores to the tear or tear film is related to the concentration of first and second therapeutic agents dissolved in the matrixes. In some embodiments, the concentration of first and second therapeutic agents dissolved in the drug cores may be controlled to provide the desired rate of release of the first and second therapeutic agents. In some embodiments the desired rate of release of the first therapeutic agent may be the same as the desired rate of release of the second therapeutic agent. In some embodiments the desired rate of release of the first therapeutic agent may be different than the desired rate of release of the second therapeutic agent. The first and second therapeutic agents included in the drug cores can include liquid, solid, solid gel, solid crystalline, solid amorphous, solid particulate, and/or dissolved forms of the therapeutic agents. In some embodiments, the drug cores comprise a silicone matrix containing the first and second therapeutic agents.

The drug cores can be made from any biocompatible material capable of providing a sustained release of the therapeutic agents. Although the drug cores are described above with respect to embodiments comprising a matrix with a substantially non-biodegradable silicone matrix with particles of the drugs located therein that at least partially dissolve, the drug cores can include any structure that provides sustained release of the first and second therapeutic agents, for example biodegradable matrix, a porous drug core, liquid drug cores and solid drug cores. In some embodiments, the drug cores have the same structure, while in other embodiments, the drugs cores have different structures. The structures can be adapted to release the first and second therapeutic agents in therapeutic amounts over a period of time from about one to twelve months after the structure is inserted into the eye. In some embodiments the release rate for the first and second therapeutic agents may be the same or similar. In other embodiments the release rate for the first and second therapeutic agents may be different, with one therapeutic agent being released at a higher rate than the other therapeutic agent. A matrix that contains the first and second therapeutic agents can be formed from either biodegradable or non-biodegradable polymers. Examples of biodegradable polymers may include poly(L,-lactic acid) (PLLA), poly(L-glycolic acid) (PLGA), polyglycolide, poly-L-lactide, poly-D-lactide, poly (amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid), collagen matrices and combinations thereof. The devices of the present invention may be fully or partially biodegradable or non-biodegradable. Examples of non-biodegradable materials are various commercially available biocompatible polymers including but not limited to silicone, polyethylene terephthalate, acrylates, polyethylenes, polyolefins, including ultra high molecular weight polyethylene, expanded polytetrafloroethylene, polypropylene, polycarbonate urethane, polyurethanes, polyamides, sheathed collagen. Additional examples of polymers may include cyclodextrans, chitans, hyaluronic acid, chrondroitin sulfate and any cross limited derivatives of these polymers. In some embodiments the drug cores may comprise a hydrogel polymer, either degradable or non-degradable. In some embodiments, the therapeutic agents can be comprised in a drug eluting material used as a coating, such as those commercially available from Surmodics of Eden Prairie, Minn., and Angiotech Pharmaceuticals of British Columbia, Canada, and the like.

The first and second therapeutic agents can comprise any substance, for example a drug, that effects the eye. In some embodiments, the first and second therapeutic agents work together in treating the eye. In other embodiments, the first therapeutic agent can counteract possible side effects of the second therapeutic agent. The additional counteractive therapeutic agent can be comprised within the core that releases the therapeutic agent that treats the eye, such as shown in FIG. 2A, or separate drug cores can be provided to separately release the additional counteractive therapeutic agent, such as shown in FIGS. 3A, 4A and 5A.

For example, one possible side effect of a cycloplegic therapeutic agent is pupil dilation that can result in photophobia. Therefore, a miotic therapeutic agent is released into the eye to counteract the pupil dilation caused by the cycloplegic. Cycloplegic therapeutic agents may include atropine, cyclopentolate, succinylcholine, homatropine, scopolamine, and tropicamide. Miotic therapeutic agents may include echothiophate, pilocarpine, physostigmine salicylate, diisopropylfluorophosphate, carbachol, methacholine, bethanechol, epinephrine, dipivefrin, neostigmine, echothiopateiodide and demecium bromide. Other suitable therapeutic agents include mydriatics such as hydroxyamphetamine, ephedrine, cocaine, tropicamide, phenylephrine, cyclopentolate, oxyphenonium and eucatropine. In addition, anti-cholinergics may be employed such as, pirenzepine. Examples of applicable therapeutic agents may be found in U.S. Patent Application Publication Nos. 2006/0188576 and 2003/0096831, hereby incorporated by reference in their entirety.

Another potential side effect of cycloplegic therapeutic agents is glaucoma, possibly related to the dilation of the pupil. Therefore, the second therapeutic agent is an anti-glaucoma agent released to counteract a possible glaucoma inducing side effect of the first therapeutic agent used to treat the eye. Suitable anti-glaucoma therapeutic agents include: sympathomimetics such as Apraclonidine, Brimonidine, Clonidine, Dipivefrine, and Epinephrine; parasympathomimetics such as Aceclidine, Acetylcholine, Carbachol, Demecarium, Echothiophate, Fluostigmine, Neostigmine, Paraoxon, Physostigmine, and Pilocarpine; carbonic anhydrase inhibitors such as Acetazolamide, Brinzolamide, Diclofenamide, Dorzolamide, and Methazolamide, beta blocking agents such as Befunolol, Betaxolol, Carteolol, Levobunolol, Metipranolol, and Timolol; prostaglandin analogues such as Bimatoprost, Latanoprost, Travoprost, and Unoprostone; and other agents such as Dapiprazole, and Guanethidine. In a preferred embodiment, atropine is released as a first therapeutic agent to treat developmental myopia in children, and bimatoprost and/or latanoprost is released as a second therapeutic agent for anti-glaucoma treatment.

Other non-limiting examples of the active agents or medications which are appropriate for use with the invention include, for example only: topical prostaglandin derivatives such as latanoprost, travaprost and bimatoprost used for the topical treatment of glaucoma. Also a treatment for corneal infections is appropriate using ciprofloxacin, moxifloxacin or gatifloxacin. Systemic medications useful for this invention are those used for hypertension such as atenolol, nifedipine or hydrochlorothiazide. Any other chronic disease requiring chronic medication could be used. The active agents or medications may by antiinfective agents. For example for bacteria use fluoroquinolones, β lactan, aminoglycosides or cephalasporins. For antiviral agents use antimycotics. For anti-inflammatory agents use gluco corticoid steroid, NSAIDs and other analgesics.

The treatment of allergic conjunctivitis and rhinitis are also applications for the invention, e.g. using antihistamine and anti-allergy medication such as olopatadine and cromalyn sodium in or on the implant.

This list of active agents is not comprehensive in that many other agents can be used with the present invention. For example, a treatment for dry eye by topical cyclosporin is particularly interesting for administration by the present invention, in which a therapeutic amount of cyclosporin may be delivered each day that is less than the daily drop administered quantity, for example, the therapeutic amount may be 5 to 10% of the drop administered quantity of cyclosporin or Restasis®, commercially available from Allergan. There are many other active agents can also be administered using the method and apparatus of the invention. The active agents may be lubricants and emollients like PVA, PVP, modified cellulose molecules like carboxymethyl cellulose and hydroxypropyl methyl cellulose, also Hyaluronic acid and mucin stimulators.

It should be noted that some therapeutic agents will have more than one effect on the eye. For example, anti-glaucoma therapeutic agents can also cause pupil constriction. Thus in some embodiments, the second therapeutic agent can counteract more than one side effect of the first therapeutic agent that is released to treat the eye.

The first and second therapeutic agents are released at therapeutic levels to provide a desired treatment response when the implants disclosed above are implanted in a tissue or near the eye. The first and second therapeutic agents are preferably released at a uniform rate, for example a rate that corresponds to zero order kinetics, although the therapeutic agents can be released at rates that correspond to other orders of reaction kinetics, for example first order. In many embodiments, the kinetic order of the reaction will vary from zero order to first order as the first and second therapeutic agents are released. Thus, the first and second therapeutic agents are released with a profile that corresponds to a range of kinetic orders that varies from about zero to about one. Ideally, the drug cores are removed before the rate at which the first and second therapeutic agents are released changes significantly so as to provide uniform delivery of the first and second therapeutic agents. As a uniform rate of delivery is desired, it may be desirable to remove and/or replace the drug cores before the reaction kinetics transition entirely to first order. In other embodiments, first or higher order release kinetics may be desirable during some or all of the treatment, so long as the first and second therapeutic agents release profile remains within a safe and effective range. In some embodiments the drug cores may release first and second therapeutic agents at an effective rate for the period of 1 week to 5 years, more particularly in the range of 3-24 months. As pointed out above, in some embodiments it may be desirable for the drugs cores to have similar release rates for the first and second therapeutic agents. In other embodiments, it may be desirable for the drug cores to have different release rates for the first and second therapeutic agents, depending on the therapeutic agents used.

The rate of release of the first and second therapeutic agents can be related to the concentration of first and second therapeutic agents dissolved in the drug cores. In many embodiments, the drug cores comprise additional non-therapeutic agents that are selected to provide a desired solubility of the first and second therapeutic agents in the drug cores. The non-therapeutic agent of the drug cores can comprise polymers as described above and additives. A polymer of the drug core can be selected to provide the desired solubility of the first and second therapeutic agents in the matrix. For example, the drug core can comprise hydrogel that may promote solubility of hydrophilic treatment agents. In some embodiments, functional groups can be added to the polymer to modulate the release kinetics of one or both of the therapeutic agents. For example, functional groups can be attached to silicone polymer. In some embodiments different ions may generate different salts with different solubility.

In some embodiments, additives may be used to control the concentration of the first and second therapeutic agents by increasing or decreasing solubility of the therapeutic agents in the drug cores. The solubility may be controlled by providing appropriate molecules and/or substances that increase and/or decrease the solubility of the dissolved form of the therapeutic agents to the matrixes. The solubility of the dissolved form of the therapeutic agents may be related to the hydrophobic and/or hydrophilic properties of the matrix and therapeutic agents. For example, surfactants, salts, hydrophilic polymers can be added to the matrix to modulate the release kinetics. In addition, oils and hydrophobic molecules can be added to the matrix to modulate the release kinetics of the matrix.

Instead of or in addition to controlling the rate of migration based on the concentration of the first and second therapeutic agents dissolved in the matrix, the surface area of the drug cores can also be controlled to attain the desired rate of drug migration from the core to the target site. For example, a larger exposed surface area of the drug cores will increase the rate of migration of the first and second therapeutic agents from the drug core to the target site, and a smaller exposed surface area of the drug core will decrease the rate of migration of the first and second therapeutic agents from the drug core to the target site. The exposed surface area of the drug cores can be increased in any number of ways, for example by making the exposed surface tortuous or porous, thereby increasing the surface area available to the drug cores.

The sheath body of the implants disclosed above comprise appropriate shapes and materials to control migration of the first and second therapeutic agents from the drug cores. The sheath body houses the drug cores and can fit snugly against the cores. The sheath body is made from a material that is substantially impermeable to the therapeutic agents so that the rate of migration of the therapeutic agents may be largely controlled by the exposed surface area of the drug cores that are not covered by the sheath body. Typically, migration of the therapeutic agents through the sheath body will be about one tenth of the migration of the therapeutic agents through the exposed surface of the drug cores, or less, often being one hundredth or less. In other words, the migration of the therapeutic agents through the sheath body is at least about an order of magnitude less that the migration of the therapeutic agents through the exposed surface areas of the drug cores. Suitable sheath body materials include polyimide, polyethylene terephthalate" (hereinafter "PET"). The sheath body has a wall thickness from about 0.00025" to about 0.0015". The total diameter of the sheath that extends across the drug cores range from about 0.2 mm to about 1.2 mm. The drug cores may be formed by dip coating the drugs cores in the sheath material. Alternatively, the sheath body can be a tube and the drug cores introduced into the sheath as a liquid or slid into the sheath body tube.

The sheath body can be provided with additional features to facilitate clinical use of the implant. For example, the sheath may replaceable receive drug cores that are exchangeable while the retention element and sheath body remain implanted in the patient. The sheath body is often rigidly attached to the retention element as described above, and the drugs cores are exchangeable while the retention element retains the sheath body. For example, the sheath body can be provided with external protrusions that apply force to the sheath body when squeezed and eject the drug cores from the sheath body. Another drug core can then be positioned in the sheath body.

In another embodiment, the therapeutic implant includes an implantable body that is sized and shaped for insertion into the patient body. The implantable body has a first receptacle and a second receptacle. The first receptacle includes a first therapeutic agent and a first surface for releasing the first therapeutic agent. The second receptacle includes a second therapeutic agent and a second surface for releasing the second therapeutic agent. The first and second therapeutic agents may be any therapeutic agent described herein. The first and second therapeutic agents may be released at therapeutic levels through the first and second surfaces of the first and second receptacles over a sustained period when the implant is implanted for use. As disclosed herein, the release rate and/or the release period of the first and second therapeutic agents may be the same or different. In other embodiments, the first and second receptacles be shaped and positioned within the sustained release implants and therapeutic implants described in the present application.

Figure 21:
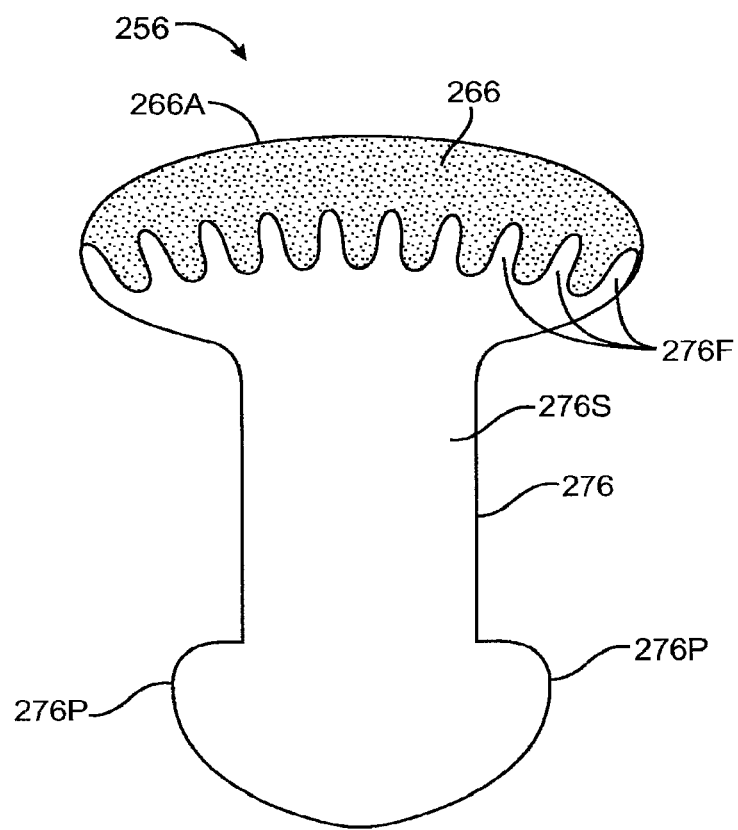
FIG. 21 schematically illustrates a lacrimal insert in the shape of a punctual plug for use in a therapeutic implant.

FIG. 21 schematically illustrates one embodiment of a lacrimal insert in the shape of a punctual plug 2100 for use in a therapeutic implant configured to hold a sustained release implant with at least one drug core containing first and second therapeutic agents. The punctual plug 2100 includes a collarette 2110 at a proximal end which rests on the exterior of the punctum 11, 13 (see FIG. 34), a bulb 2120 with a tapered portion 2125 terminating in a tip 2135 at a distal end that blockingly projects into the canaliculus 10, 12 (see FIG. 34), and a body portion 2130 connecting the collarette 2110 and the bulb 2120. The punctual plug 2100 is approximately 2.0 mm in length. The bulb 2120 is designed to prevent the punctual plug 2100 from being easily dislodged from the canaliculus 10, 12, and may be tapered for ease of insertion into the punctum 11, 13. The collarette 2110 is designed to have a diameter to prevent the punctual plug 2100 from completely entering the canaliculus 10, 12, and is preferably smooth to minimize irritation of the eye. The body portions 2130 of the punctual plug 2100 is essentially a non-functional connection between the collarette 2110 and the bulb 2120 portions. The collarette 2110 includes an aperture 2140 extending into the body portion 2130 into which an implant 2145 is placed. The size of the aperture 2140 is selected to hold the implant in place during treatment. In some embodiments, a sheath body of the implant may be omitted and the drug core(s) may be inserted directly into the aperture 2140 of the punctual plug 2100. In some embodiments, the tip 2135 is closed, in other embodiments, an opening 2150 in the tip 2135 at the distal end allows access to the aperture 2140, allowing fluid flow through the punctual plug. In some embodiments, an optional non-porous head 2115 is provided over the collarette 2110 to enclose the aperture 2140. In accord with one aspect of the invention, the body 2110 and head 2115 are made of different materials, with the body 2110 may be molded or otherwise formed from a flexible material, such as silicone, that is impermeable to the therapeutic agents, and the head 2115 being made from a biocompatible, preferably soft and flexible second material which is permeable to the medication. When the punctual plug 2100 is in place, the therapeutic agents are deployed from the drug core(s) into the tears of the lacrimal lake where the therapeutic agents mix, as eye drops do, with the tears and penetrates the eye to have the intended pharmacological effect. The size of the aperture 2140 is selected to hold the implant in place during treatment.

FIGS. 22-25 show different embodiments of therapeutic implants having a structure, such as a punctual plug 2100. Other structures suitable for incorporation with the present invention are described in U.S. Pat. App. Pub. Nos. 2006/0020253, entitled "Implantable device having controlled release of medication and method of manufacturing the same", published in the name of Prescott on Jan. 26, 2006; and U.S. Pat. No. 7,117,870, entitled "Lacrimal insert having reservoir with controlled release of medication and method of manufacturing the same", issued on Oct. 10, 2006 in the name of Prescott, the full disclosures of which are incorporated herein by reference. The reservoir can include any of the therapeutic agents described herein to treat the eye, for example medications to treat optical defects of the eye.

FIG. 22 schematically illustrates one embodiment of a therapeutic implant 2200 having a punctual plug 2100 and a sustained release implant containing first and second therapeutic agents. In the embodiment shown, the sustained release implant is sustained release implant 2200 discussed above having drug core 2210 with first inclusions 2260 of a first therapeutic agent and second inclusions 2265 of a second therapeutic agent. This embodiment of the therapeutic implant 2200 further includes the optional head 2115 at a proximal end that is permeable to the first and second therapeutic agents. When the therapeutic implant 2200 is in place, the first and second therapeutic agents are deployed from proximal end of the drug core through the permeable head into the tears of the lacrimal lake where the first and second therapeutic agents mix, as eye drops do, with the tears and penetrates the eye to have the intended pharmacological effect. The size of the aperture 2240 is selected to hold the sustained release implant in place during treatment. In the embodiment shown, the sheath body is also within the aperture 2140. In other embodiments, the sheath body 2220 may be omitted and the drug core 2210 may be inserted directly into the aperture 2140 of the punctual plug 2100.

FIG. 23 schematically illustrates one embodiment of a therapeutic implant 2300 having a punctual plug 2100 and a sustained release implant having first and second concentric drug cores with first and second therapeutic agents. In the embodiment shown, the sustained release implant is sustained release implant 2300 having an outer first drug core 2310 with first inclusions 2360 of a first therapeutic agent and an inner second drug core 2315 with second inclusions 2365 of a second therapeutic agent. When the therapeutic implant 2300 is in place, the first and second therapeutic agents are deployed from the drug cores at the exposed or proximal end and into the tears of the lacrimal lake where the first and second therapeutic agents mix, as eye drops do, with the tears and penetrates the eye to have the intended pharmacological effect. The size of the aperture 2140 is selected to hold the sustained release implant in place during treatment. In some embodiments, the sheath body 2320 of the implant 2300 may be omitted and the first and second drug cores 2310, 2315 may be inserted directly into the aperture 2140 of the punctual plug 2100. Optionally, a head 2115 may be used that is permeable to the first and second therapeutic agents, wherein first and second therapeutic agents are deployed from first and second drug cores 2310, 2315 through permeable head 2115.

FIG. 24 schematically illustrates one embodiment of a therapeutic implant 2400 having a punctual plug 2100 and a sustained release implant having first and second drug cores containing first and second therapeutic agents. In the embodiment shown, the sustained release implant is sustained release implant 2400 having a first drug core 2410 with first inclusions 2460 of a first therapeutic agent next to a second drug core 2415 with second inclusions 2465 of a second therapeutic agent. When the therapeutic implant 2400 is in place, the first and second therapeutic agents are deployed from the drug cores at the exposed or proximal ends and into the tears of the lacrimal lake where the first and second therapeutic agents mix, as eye drops do, with the tears and penetrates the eye to have the intended pharmacological effect. The size of the aperture 2140 is selected to hold the implant 2400 in place during treatment. In some embodiments, the sheath body 2420 of the implant 400 may be omitted and the first and second drug cores 2410, 2415 may be inserted directly into the aperture 2140 of the punctual plug 2100. Optionally, a head 2115 may be used that is permeable to the first and second therapeutic agents, wherein first and second therapeutic agents are deployed from the first and second drug cores 2410, 2415 through the permeable head 2115.

FIG. 25 schematically illustrates one embodiment of a therapeutic implant 2500 having a punctual plug 2100 and a sustained release implant having first and second concentric drug cores in a flow-through configuration, with each drug core containing a therapeutic agent. In the embodiment shown, the sustained release implant is sustained release implant 2500 having an outer first drug core 2510 with first inclusions 2560 of a first therapeutic agent and an inner second drug core 2515 with second inclusions 2565 of a second therapeutic agent. In the embodiment shown, the punctual plug 2100 includes an opening 2150 in the tip 2135 at the distal end allowing fluid flow through the body of the punctual plug 2100 from the proximal end to the distal end and through first and second drug cores 2510, 2515. When the therapeutic implant 2500 is in place, the first and second therapeutic agents are deployed from the drug cores 2510, 2515 at the exposed ends and exposed inner surfaces 2585, 2580 as the fluid flows through. The size of the aperture 2140 of the punctual plug 2100 is selected to hold the implant in place during treatment and the opening 2150 is sized to allow sufficient flow through the implant 2100 and first and second drug cores 2510, 2515. In some embodiments, the sheath body of the implant may be omitted and first and second drug cores 510, 2515 may be inserted directly into the aperture 2140 of the punctual plug 2100. Optionally, a head 2115 may be used that is permeable to the first and second therapeutic agents. Other flow-through structures suitable for incorporation with the present invention are described in U.S. patent application Ser. No. 11/695,545, entitled "Nasolacrimal Drainage System Implants for Drug Therapy, filed Apr. 2, 2007, and issued as U.S. Pat. No. 7,998,497 on Aug. 16, 2011, the full disclosure of which is incorporated herein by reference.

Figure 26A:
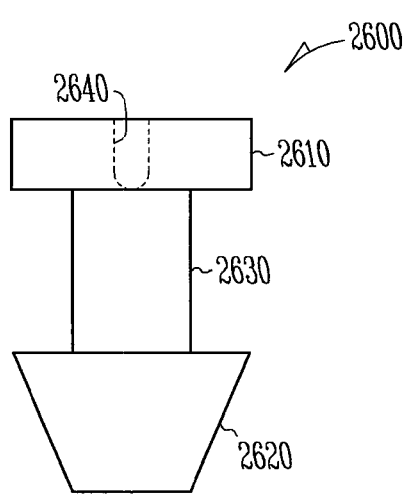
FIGS. 26A-26C show different embodiments of therapeutic implants to treat an eye that encompass punctual plugs made of a medication-impregnable porous material having with two therapeutic agents.
Figure 26B:
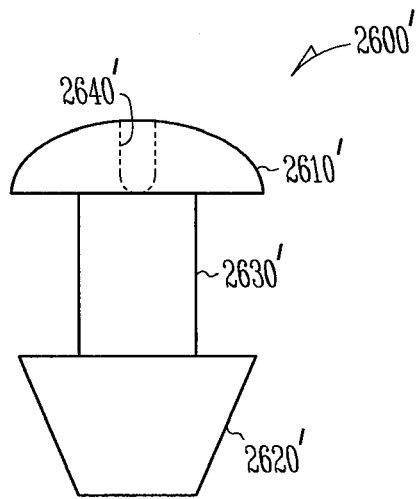
Figure 26C:
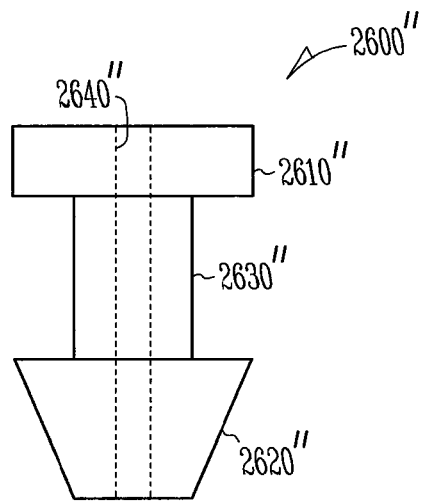

FIGS. 26A-26C show therapeutic implants 2600, 2600', 2600" that encompass punctual plugs and structures that release first and second therapeutic agents, according to an embodiment of the present invention. Structures suitable for incorporation with the present invention are described in U.S. Pat. No. 3,949,750, entitled "Punctum plug and method for treating keratoconjunctivitis sicca and other ophthalmic aliments using same", issued in the name of Freeman on Apr. 13, 1976, the full disclosure of which is incorporated herein by reference. The head portion can include any two of the therapeutic agents described herein to treat the eye.

In the treatment of ophthalmic ailments where it is desired to prevent or decrease the drainage of lacrimal fluid and/or medication from the eye, the punctual aperture in one or both of the upper and lower lids are to be blocked by therapeutic implants, two respective embodiments of which are shown in FIGS. 26A and 26B. Referring initially to the embodiment of FIG. 26A, the therapeutic implant 2600 has a blunted tip or barb portion 2620 at a distal end, a middle neck or waist portion 26130 of somewhat smaller diameter than the tip, and a smooth disc-like head portion 2610 at a proximal end of relatively larger diameter. The therapeutic implant 2600' of FIG. 26B is of generally similar dimensions to the first-described embodiment with a blunted tip or barb portion 2620', a cylindrical middle portion 2630' of substantially the same dimension, and a dome-shaped head portion 2610' of somewhat smaller diameter than its counterpart in the embodiment of FIG. 26A. The head portion 2610, 2610' of both embodiments may be provided, if desired as an alternative to grasping it with forceps, with a central bore opening 2640, 2640' adapted to receive the projecting tip of an inserter tool to provide a releasable grip on the therapeutic implant as it is manipulated for insertion, as hereinafter described.

FIG. 26C shows a hollow therapeutic implant 2600" that is of generally similar dimensions to the first-described embodiment having a blunted tip or barb portion 2620", a middle neck or waist portion 2630" of somewhat smaller diameter than the tip, a smooth disc-like head portion 2610" of relatively larger diameter and a central bore 2640" extending through the plug. The central bore 2640" allows fluid flow from a proximal end to distal end of the therapeutic implant 2600".

In some embodiments of the invention, the two therapeutic agents as described herein are incorporated in a punctual plug as described in U.S. App. Pub. No. 2005/0197614, the full disclosure of which is incorporated herein by reference. A gel can be used to form the therapeutic implant 2600, 2600', 2600" and the gel can swell from a first diameter to a second diameter in which the second diameter is about 50% greater than the first diameter. The gel can be used to entrap the first and second therapeutic agents, for example within a microporous structure in which the agents are uniformly dispersed, and the gel can slowly elute the first and second therapeutic agents into the patient. Various therapeutic agents have been describe herein and additional therapeutic agents are described in U.S. Provisional Application No. 60/550, 132, entitled "Punctum Plugs, Materials, And Devices", the full disclosure of which is incorporated herein by reference, and may be combined with the gels and devices described herein.

In other embodiments of the invention, the entire body or only portions of the therapeutic implants 2600, 2600', 2600" may be made of a medication-impregnable porous material such as HEMA hydrophilic polymer, or may be otherwise adapted as with capillaries or the like, to store and slowly dispense ophthalmic drugs to the eye as they are leached out by the lacrimal fluids. For example, the head portion 2610, 2610', 2610" of each embodiment may be medication-impregnable porous material impregnated with first and second therapeutic agents.

FIG. 27 shows therapeutic implants containing first and second therapeutic agents as applied to the eye. In the embodiment shown, a therapeutic implant 2700 is designed for insertion into the lower punctual aperture 13 of the eye 2, and along the canaliculus 12 communicating with the aperture. The therapeutic implant 2700 includes a collarette 2710 at a proximal end, a flared portion 2720 at a distal end, a neck portion 2730. The collarette 2710 is designed for seating against the aperture 13. Examples of suitable therapeutic implants 2700 containing two therapeutic agents have been described above, and include therapeutic implants 2200, 2300, 2400, 2500, 2600, 2600' and 2600". The therapeutic implant 2700 may be used to block fluid flow, or may have a hollow portion allowing fluid flow. In the embodiment shown in FIG. 27, the therapeutic implant 2700 is shown as being a hollow like a straw shape for the passage of tears. Examples of these include therapeutic implants 2500 and 2600". Unlike the tear stopping therapeutic implants 2200, 2300, 2400, 2600 and 2600', the hollow therapeutic implants 2500 and 2600" provide a very different drug administering method, scheme and structure. The hollow therapeutic implant is particularly useful in that the active agents are available at the inner surface or interior of the therapeutic implant, and is uniquely structured to pass tears and thus administer the active therapeutic agents to the tear stream in a fashion that is controlled by the flow of tears which thus act as the carrier for the therapeutic agents.

FIG. 27 further shows an implant 2700' containing first and second therapeutic agents that is a substantially cylindrical in shape that has been inserted into the upper punctum aperture 11, to block the flow of tears to canaliculus 10, while lower punctual plug 2700 passes the tears to canaliculus 12. Examples of suitable implants 2700' containing two therapeutic agents may be any one of the implants disclosed herein, or it may be an occlusive plug of some inert biocompatible material.

The therapeutic implant 2700 and implant 2700' can be used in any desired combination, either separately or in combination (shown in FIG. 27). For example, implant 2700' can be positioned in the lower canaliculus and therapeutic implant 2700 can be positioned in the upper canaliculus. Alternatively, two of the same therapeutic implants 2700 or 2700' can be positioned in both canaliculi.

FIGS. 28, 29A-29D, 30A, and 30B show embodiments of various drug delivery core elements for use in a therapeutic implant that can be tailored to each individual patient based on their needs. The core elements of the therapeutic implant are pie slice shaped and can be assembled into cylindrical shaped drug cores with many different configurations with many different therapeutic agents. Doing this can achieve therapeutic implant configurations to maximize individual patient management. This approach can tailor treatment to use multiple therapeutic agents for disease management. The approach can also tailor the dose of the therapeutic agent based on the genetic and/or physiological condition of the patient.

Figure 28:
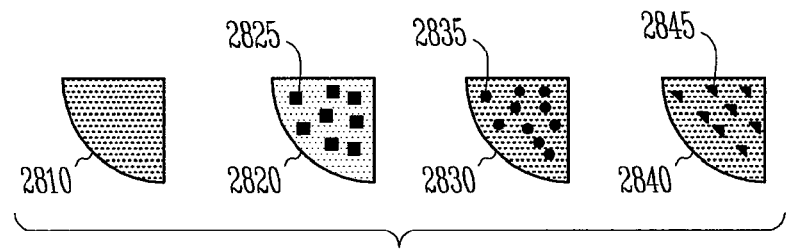
FIG. 28 shows various core elements that are combinable into a cylindrical shaped drug core.

FIG. 28 shows various core elements, or drug cores, that are combinable into a, for example, cylindrical shaped drug core according to embodiments of the present invention. The drug core need not be cylindrical, but a cylindrical drug core is preferred for ease of manufacture. Drug core 2810 is a blank core element that does not contain a therapeutic agent, drug core 2820 contains a therapeutic agent 2825 with a concentration X, drug core 2830 contains a therapeutic agent 2835 with a concentration Y, and drug core 2840 contains a therapeutic agent 2845 with a concentration Z. The cores and the therapeutic agents may be any of the cores and therapeutic agents disclosed herein. While the drug cores are shown as pie slice shaped (sectors), the drug cores are not limited to any particular shape. Since the drug cores 2810, 2820, 2830, and 2840, or any combination thereof, together can form a right cylindrical shape, (for example, see FIGS. 29A-D) each drug core in this instance is a right prismatic shape with the particular cross-section, for example, a sector cross-section. The drug cores may have many different combinable shapes, for example square, rectangular, oval, jig saw puzzle piece, to name a few.

Each individual drug core comprises a matrix that contains the therapeutic agent, which can be present as a solid solution, or can be present as inclusions. Inclusions will often comprise a concentrated form of the therapeutic agent, for example a crystalline form of the therapeutic agent, and the therapeutic agent may over time dissolve into matrix of the drug core. A certain concentration of the agent can be dissolved in the matrix in equilibrium with the inclusions of the agent. The concentration of dissolved agent can be a saturation concentration. The matrix can comprise a silicone matrix, or a polyurethane matrix, or the like. In many embodiments, the non-homogenous mixture comprises a silicone matrix portion that is saturated with the therapeutic agent and an inclusions portion comprising inclusions of the therapeutic agent, such that the non-homogenous mixture comprises a multiphase non-homogenous mixture. The first matrix may differ from the second matrix, including, for example, an exposed surface area, a surfactant, a cross-linking, an additive, and/or matrix materials including formulation and/or solubility. In some embodiments, inclusions comprise droplets of an oil of the therapeutic agent, for example latanoprost oil. In some embodiments, inclusions may comprise particles of the therapeutic agent, for example solid bimatoprost particles in crystalline form. In many embodiments, matrix encapsulates inclusions, and inclusions may comprise microparticles have dimensions from about 0.1 µm to about 100 µm, or about 200 µm. The encapsulated inclusions dissolve into the surrounding solid matrix, for example silicone, that encapsulates the micro particles such the matrix is substantially saturated with the therapeutic agent while the therapeutic agent is released from the core.

FIGS. 29A-29D show different embodiments of a cylindrical shaped drug core using the core elements of FIG. 28 surrounded by a sheath body 2920. Sheath body 2920 is can be substantially impermeable to the therapeutic agents, so that the therapeutic agents are often released from an exposed surface on an end of the cylindrical shaped drug core that is not covered with sheath body 2920. In some embodiments, the sheath body may be omitted and the cylindrical shaped drug core be place directly into the implant, such as placement in an aperture of a punctual plug. While only four embodiments are shown for the cylindrical shaped drug core, any suitable drug cores and therapeutic agents may be used.

Figure 29A:
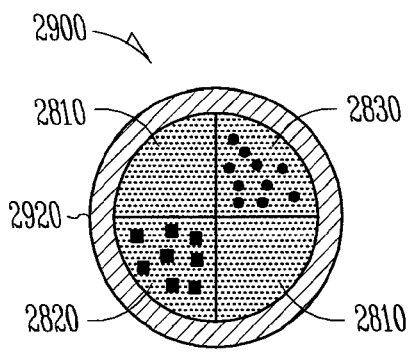
FIGS. 29A-29D show different embodiments of a cylindrical shaped drug core using the core elements of FIG. 28.

FIG. 29A shows one embodiment of a cylindrical shaped drug core 2900 assembled using two core elements 2810 (blank cores), one core element 2820 and one core element 2830. The cylindrical shaped drug core 2900 is then able to deliver therapeutic agent 2825 with a concentration X and therapeutic agent 2835 with a concentration Y.

Figure 29B:
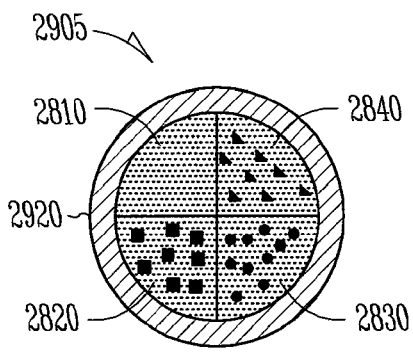

FIG. 29B shows one embodiment of a cylindrical shaped drug core 2905 assembled using one core element 2810 (blank core), one core element 2820, one core element 2830 and one core element 2840. The cylindrical shaped drug core 2905 is then able to deliver therapeutic agent 2825 with a concentration X, therapeutic agent 2935 with a concentration Y and therapeutic agent 2845 with a concentration Z.

Figure 29C:
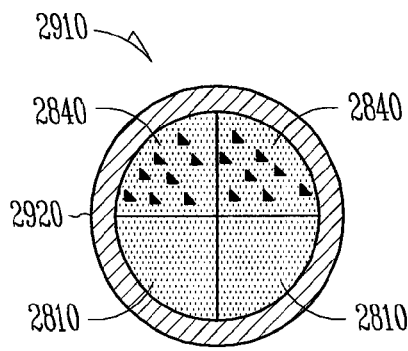

FIG. 29C shows one embodiment of a cylindrical shaped drug core 2910 assembled using two core elements 2810 (blank core) and two core elements 2840. The cylindrical shaped drug core 2910 is then able to deliver two doses therapeutic agent 2845 with a concentration Z.

Figure 29D:
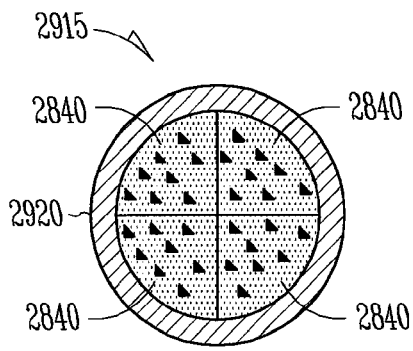

FIG. 29D shows one embodiment of a cylindrical shaped drug core 2915 assembled using four core elements 2840. The cylindrical shaped drug core 2915 is then able to deliver four doses therapeutic agent 2845 with a concentration Z.

Figure 30A:
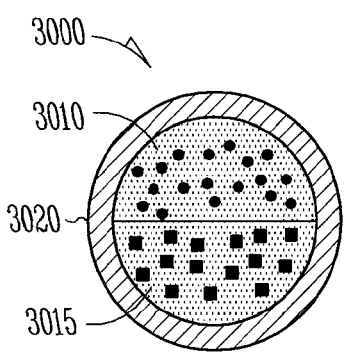
FIGS. 30A and 30B show other embodiments of a cylindrical shaped drug core assembled from core elements of different shapes.
Figure 30B:
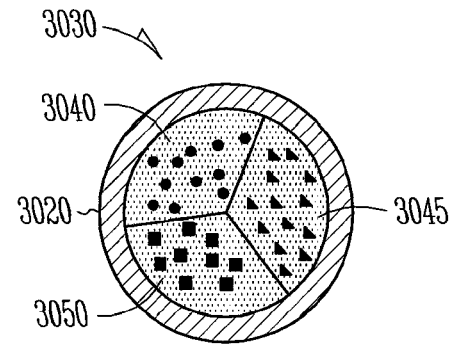

FIGS. 30A and 30B show other embodiments of a cylindrical shaped drug core assembled from core elements of different shapes. FIG. 30A shows a cylindrical shaped drug core 3000 made from two core elements 3010, 3015 that are semicircular in shape surrounded by a sheath body 3020. FIG. 30B shows a cylindrical shaped drug core 3030 made from three core elements 3040, 3045 and 3050 surrounded by sheath body 3020. While embodiments may include a plurality of core elements of substantially even sizes as shown, other embodiments may include core elements of two or more differing sizes. For example, a semicircular core element 3010 may be combined with two ¼ circular core elements 2830 and 2840. A wide variety of different sizes and uneven shapes may also be combined with a variety of geometries, with or without sheath body material (or other material that is substantially impermeable to one or more of the therapeutic agents) being disposed between the adjacent drug core elements. For example, sheets of drug core material (including matrix and an associated agent) may formed separately and stacked or layered, and/or may be formed sequentially by polymerizing the matrix over a substrate or underlying drug core element sheet. The multi-layered drug core element sheets could then be cut across the layers to a desired drug core length and/or width. An end and/or side of the sheet could be exposed in the implanted device, with the exposed end or side of each layered drug core element having a surface area dependent on a thickness of the associated drug core layer or sheet.

Figure 31:
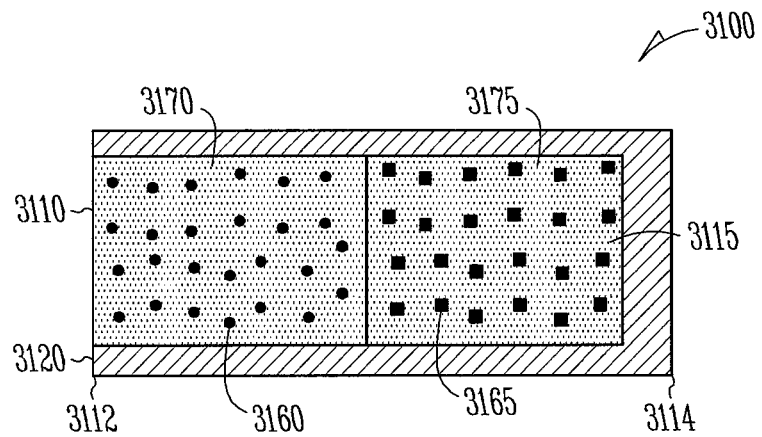
FIG. 31 shows a sectional view of a sustained release implant having a first drug core with a first therapeutic agent and a second drug core with a second therapeutic agents to treat an eye, the first and second drug cores being in a stacked configuration, according to an embodiment of the present invention.

FIG. 31 shows a sectional view of a sustained release implant 3100 having a first drug core 3110 with a first therapeutic agent 3160 and a second drug core 3115 with a second therapeutic agent 3165 to treat an eye, the first and second drug cores being in a stacked configuration, according to an embodiment of the present invention.

FIG. 31 shows a cross sectional view of a sustained release implant 3100 having two therapeutic agents to treat an eye 2, according to embodiments of the present invention. Implant 3100 has a proximal end 3112 in which the therapeutic agents are released and a distal end 3114. Implant 3100 includes two drug cores 3110, 3115. First drug core 3110 is a cylindrical shaped structure that includes a first therapeutic agent, and second drug core 3115 is a cylindrical shaped structure that includes a second therapeutic agent. The first drug core 3110 and the second drug core 3115 are assembled in a stacked configuration, as shown in the figures, with the first drug core 3110 being positioned near the proximal end 3112. First drug core 3110 comprises a first matrix 3170 that contains first inclusions 3160 of the first therapeutic agent, and second drug core 3115 comprises a second matrix 3175 that contains second inclusions 3165 of the second therapeutic agent. First and second inclusions 3160, 3165 will often comprise a concentrated form of the first and second therapeutic agents, for example a liquid or solid form of the therapeutic agents, and the therapeutic agents may over time dissolve into first matrix 3170 of first drug core 3110 and second matrix 3175 of second drug core 3115. First and second matrixes 3170, 3175 can comprise a silicone matrix or the like, and the mixture of therapeutic agents within matrixes can be non-homogeneous. In many embodiments, the non-homogenous mixture comprises a silicone matrix portion that is saturated with the therapeutic agents and an inclusions portion comprising inclusions of the therapeutic agents, such that the non-homogenous mixture comprises a multiphase non-homogeneous mixture. The first matrix may differ from the second matrix, including, for example, an exposed surface area, a surfactant, a cross-linking, an additive, and/or matrix materials including formulation and/or solubility. In some embodiments, first and second inclusions 3160, 3165 comprise droplets of an oil of the therapeutic agent, for example latanoprost oil. In some embodiments first and second inclusions 3160, 3165 may comprise particles of the therapeutic agents, for example solid bimatoprost particles. In many embodiments, first matrix 3170 contains first inclusions 3160 and second matrix 3175 contains second inclusions 3165. First and second inclusions 3160, 3165 may comprise microparticles having dimensions from about 0.1 µm to about 100 µm, or about 200 µm. The contained inclusions at least partially dissolve into the surrounding solid matrix, for example silicone, that contain the micro particles such that first and second matrixes 3170, 3175 are substantially saturated with the therapeutic agent while the therapeutic agent is released from the core.

First and second drug cores 3110, 3115 are surrounded by a sheath body 3120, except at an, exposed surface where the therapeutic agents are released, in this case at the proximal end 3112. Sheath body 3120 is substantially impermeable to the therapeutic agents, so that the therapeutic agents are released from the exposed surface on the open end of first and second drug cores 3110, 3115 that are not covered with sheath body 3120. In some embodiments, the sheath body is similar to sheath body 3120 disclosed above, and a retention structure and an occlusive element, such as retention element and occlusive element as discussed above, may be connected to the sheath body. In other embodiments, the implant may be incorporated into a different structure, such as a punctual plug (see FIG. 32).

Figure 32:
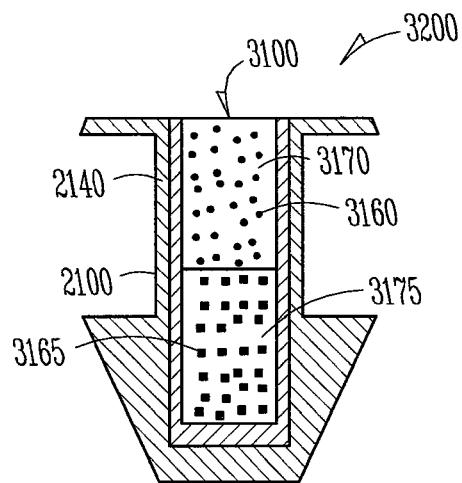
FIG. 32 shows one embodiment of a therapeutic implant to treat an eye having a punctual plug and a sustained release implant having a first drug core with a first therapeutic agent and a second drug core having a second therapeutic agent, the first and second drug cores being in a stacked configuration, according to an embodiment of the present invention.

FIG. 32 schematically illustrates one embodiment of a therapeutic implant 3200 having a punctual plug and a sustained release implant having first and second stacked drug cores with first and second therapeutic agents. In the embodiment shown, the sustained release implant is sustained release implant 3100 having a proximal first drug core 3110 with first inclusions 3160 of a first therapeutic agent and a distal second drug core 3115 with second inclusions 3165 of a second therapeutic agent. When the therapeutic implant 3200 is in place, the first therapeutic agent is deployed from the proximal first drug core at the exposed or proximal end and into the tears of the lacrimal lake where the first therapeutic agent mixes, as eye drops do, with the tears and penetrates the eye to have the intended pharmacological effect. Subsequent to that, the second therapeutic agent is deployed from the distal second drug core, through the first drug core to the exposed or proximal end and into the tears of the lacrimal lake where the second therapeutic agent mixes, as eye drops do, with the tears and penetrates the eye to have the intended pharmacological effect. The size of the aperture 2140 is selected to hold the sustained release implant 3100 in place during treatment. In some embodiments, the sheath body 3120 of the implant 3100 may be omitted and the first and second drug cores 3110, 3115 may be inserted directly into the aperture 2140 of the punctual plug 2100. Optionally, a head 2115 may be used, such as shown in FIG. 22, that is permeable to the first and second therapeutic agents, wherein first and second therapeutic agents are deployed from first and second drug cores 3110, 3115 through permeable head 3115.

Figure 33:
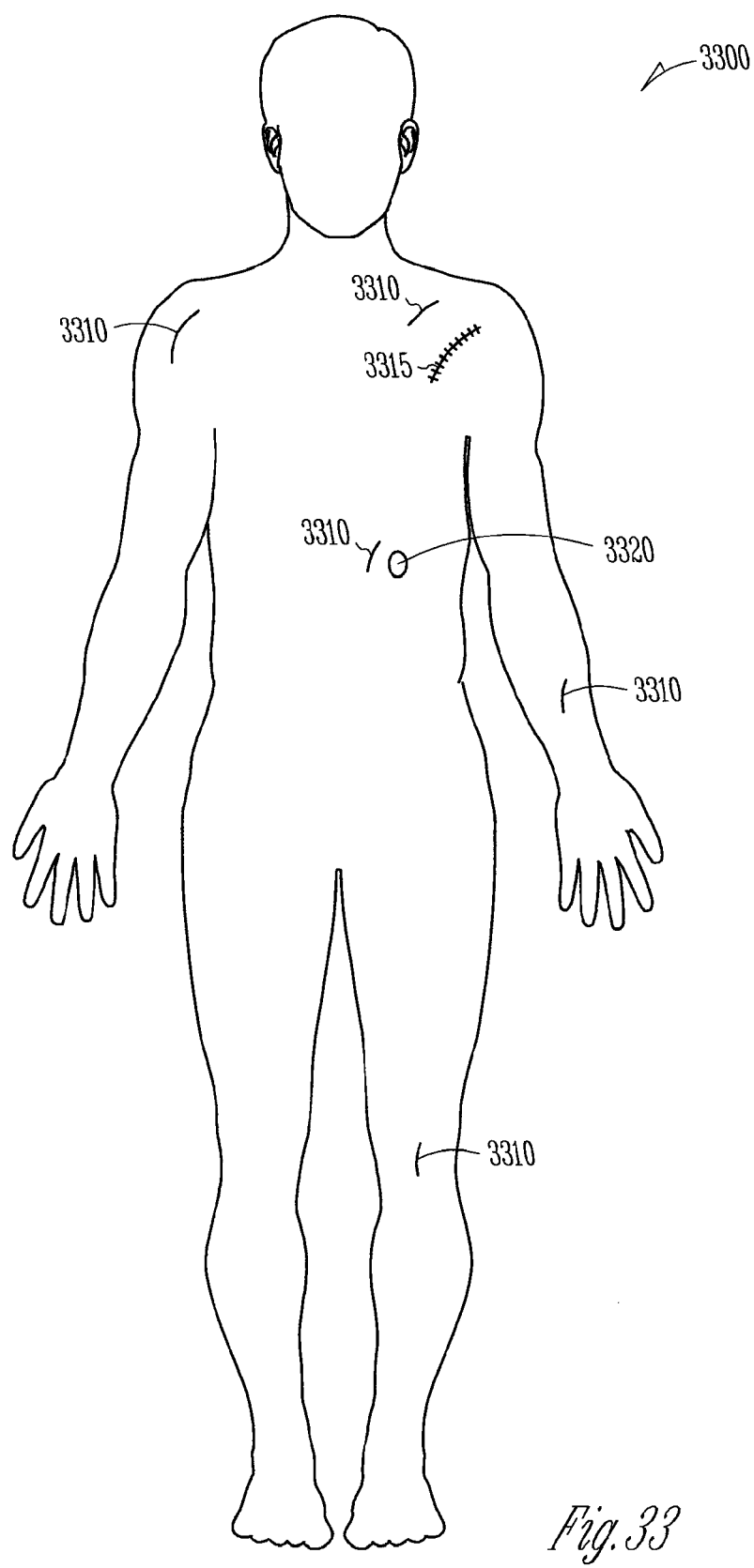
FIG. 33 shows one embodiment of a therapeutic implant to treat a body condition, the implant having a first therapeutic agent and a second therapeutic agent.

In other embodiments, referring to FIG. 33, the multiple drug delivery therapeutic implants 3310 may be implanted in other portions of a body 3300, not just in the punctum, to treat a body condition, as shown in FIG. 33. The therapeutic implants 3310 are sustained release implants with at least one drug core containing first and second therapeutic agents that is used to delivery multiple drugs to treat other conditions or diseases other than the eye. Therapeutic implant 3310 may include therapeutic implants having two or more therapeutic agents released from an exposed surface of core(s), such as the therapeutic implants described above. The therapeutic implant may be implanted by known means.

The first and second therapeutic agents are released at therapeutic levels to provide a desired treatment response when the implants are implanted in a body. The first and second therapeutic agents are preferably released at therapeutic levels over a sustained period. In some embodiments the drug cores may release first and second therapeutic agents at an effective rate for the period of 1 week to 5 years, more particularly in the range of 3-24 months. In some embodiments it may be desirable for the drugs cores to have similar release rates for the first and second therapeutic agents. In other embodiments, it may be desirable for the drug cores to have different release rates for the first and second therapeutic agents, depending on the therapeutic agents used. In some embodiments, the therapeutic level is less than a dose administered quantity or less or 5-10% of the dose administered quantity, typically being less than 10% and often being 5% or less than the dose administered quantity each day for an extended period of days. The dose administered quantity may be the oral dose or may be an injectable dose.

In use, the therapeutic implant 3310 is implanted in the body 3300, where a body fluid may contact the exposed surface of the drug core(s), releasing the first and second therapeutic agents. Depending on the implant location, any body fluid proximate the therapeutic implant, such as blood, may contact the exposed surface, releasing the first and second therapeutic agents from the implant. The therapeutic implant location may include body locations for local drug delivery to joints, such as proximate the shoulder, knee, elbow, or a trauma location 3315, or a trauma location 3320, other locations, such as the abdomen, for general drug delivery. The therapeutic implant 3310 may include one or more retention elements known in the art to retain the therapeutic implant 3310 near a body location, such as the body locations listed above.

In one embodiment, a therapeutic implant may be used in oncology, where chemotherapy involves use of a cocktail that is dependent upon the primary tumor type. Use of a local therapeutic implant drug delivery could allow an extra benefit of treating a tumor site post surgically, and minimizing the collateral damage to the rest of the body. An example would be lumpectomy for breast tumor or surgical treatment of prostate cancer, where the therapeutic implant would be implanted near the cancer site. In fact any solid tumor would be a target, with the therapeutic implant being implanted near the tumor.

In another embodiment, a therapeutic implant may be used for the delivery of multiple drugs, sometimes called cocktails, for the treatment of HIV. In this instance, the therapeutic implant would be treating a systemic disease. One example of the multiple drugs in the therapeutic implant is a protease inhibitor and a nucleic acid target.

Some treatments are contraindicated due to other disease states. An example is diabetics where surgeries including amputation are often required in patients where circulation and wound healing is impaired. The use of steroids could not be used systemically in these patients, but could be used locally. In this embodiment, the therapeutic implant is positioned post surgically in the body at the appropriate location for local delivery of a steroid and another drug, such as an antiinflammatory or anti-infective drug. In some embodiments, the steroid may be released at therapeutic levels for 8 or more weeks and the anti-inflammatory may be released at therapeutic levels for 2-4 weeks.

In joints, non-steroidal anti-inflammatory drugs (NSAIDs) may be used for the treatment of such things as osteoarthritis and rheumatoid arthritis. Delivery of NSAIDs locally would reduce the risk associated with systemic cox II inhibitors, such as gastrointestinal problems (problems in the stomach or intestine) the may include stomach ulcers or bleeding, and possibly life threatening perforations (rips or holes) in the wall of the stomach or intestine. In this embodiment, the therapeutic implant is positioned near the joint to deliver NSAIDs locally and may also include the delivery of a nutritional supplement, like glucosamine, and perhaps get a positive physiological response in local tissue.

In another embodiment, a therapeutic implant may be used for localized delivery of multiple drugs to a trauma site, such as delivering an analgesic and an antiinfectives.

Figure 34:
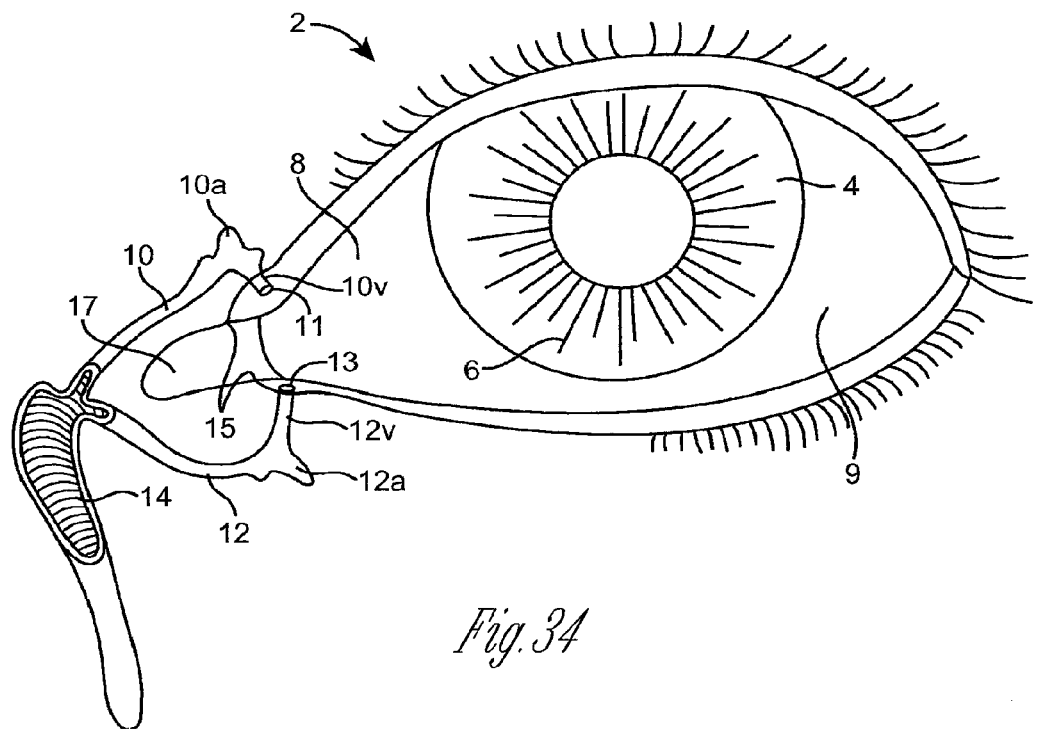
FIGS. 34 and 35 show anatomical tissue structures of the eye suitable for use with implants, according to embodiments of the present invention.
Figure 35:
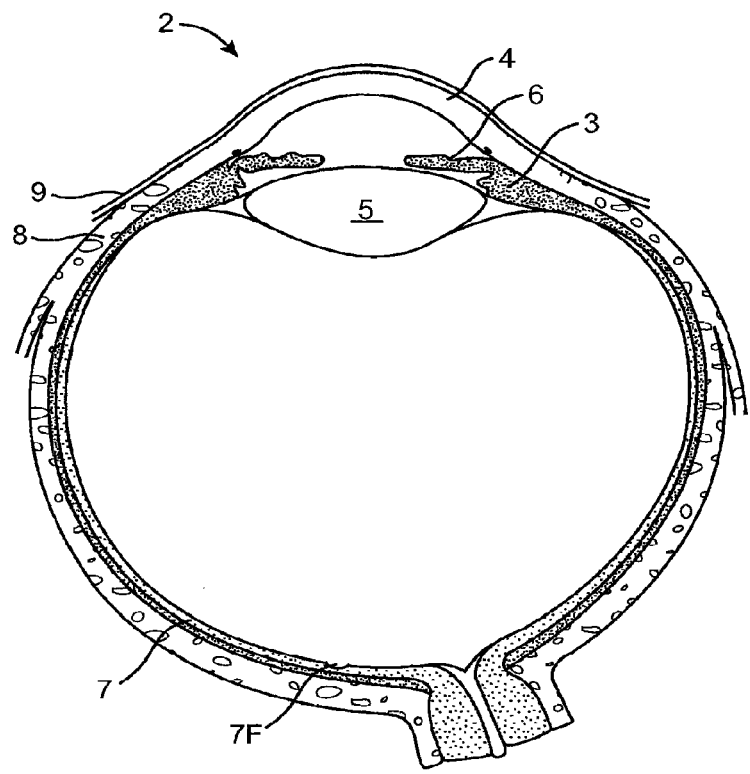

FIGS. 34 and 35 show anatomical tissue structures of an eye 2 suitable for treatment with implants, according to an embodiment of the present invention. Eye 2 includes a cornea 4 and an iris 6. A sclera 8 surrounds cornea 4 and iris 6 and appears white. A conjunctival layer 9 is substantially transparent and disposed over sclera 8. A crystalline lens 5 is located within the eye. A retina 7 is located near the back of eye 2 and is generally sensitive to light. Retina 7 includes a fovea 7F that provides high visual acuity and color vision. Cornea 4 and lens 5 refract light to form an image on fovea 7F and retina 7. The optical power of cornea 4 and lens 5 contribute to the formation of images on fovea 7F and retina 7. The relative locations of cornea 4, lens 5 and fovea 7F are also important to image quality. For example, if the axial length of eye 2 from cornea 4 to retina 7F is large, eye 2 can be myopic. Also, during accommodation, lens 5 moves toward cornea 4 to provide good near vision of objects proximal to the eye.

The anatomical tissue structures shown in FIG. 34 also include the lacrimal system, which includes an upper canaliculus 10 and a lower canaliculus 12, collectively the canaliculae, and a naso-lacrimal duct or sac 14. The upper canaliculus 10 and lower canaliculus 12 extend from the lacrimal sac 14 and terminate in an upper punctum 11 and a lower punctum 13, respectively, that also referred to as punctual apertures. The punctual apertures are situated on a slight elevation at the medial end of the lid margin at the junction 15 of the ciliary and lacrimal portions near the medial canthus 17. The punctual apertures are round or slightly ovoid openings surrounded by a connective ring of tissue. Each canaliculus extends from punctual openings 11, 13, and comprises a vertical position 10v, 12v of the respective canaliculus before turning horizontally to join its other canaliculus at the entrance of a lacrimal sac 14. The canaliculae are tubular and lined by stratified squamous epithelium surrounded by elastic tissue which permits the canaliculus to be dilated. The upper and lower canaliculi may each comprise an ampulla 10a, 12a, or small dilation, in the respective canaliculus.

Manufacture of Implants

Figure 6A:
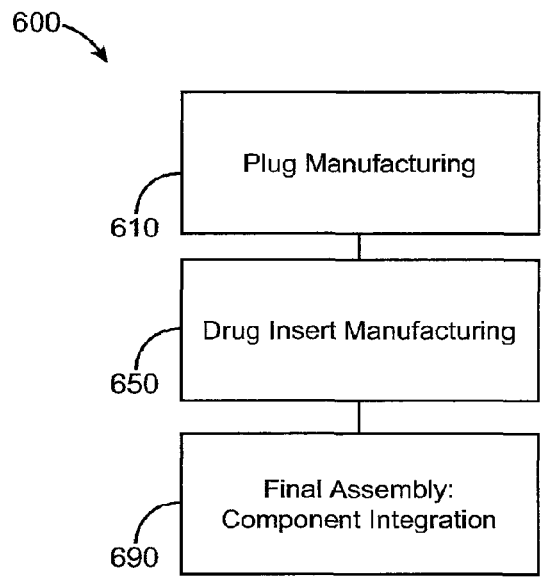
FIG. 6A shows a method of manufacturing a punctual plug, according to embodiments of the present invention.

FIG. 6A shows a method 600 of manufacturing an implant, according to embodiments of the present invention. A sub method 610 manufactures a punctual plug. A sub method 650 manufactures a drug core insert, for example as described above. A sub method 690 assembles the components into an integrated drug delivery system.

Figure 6B:
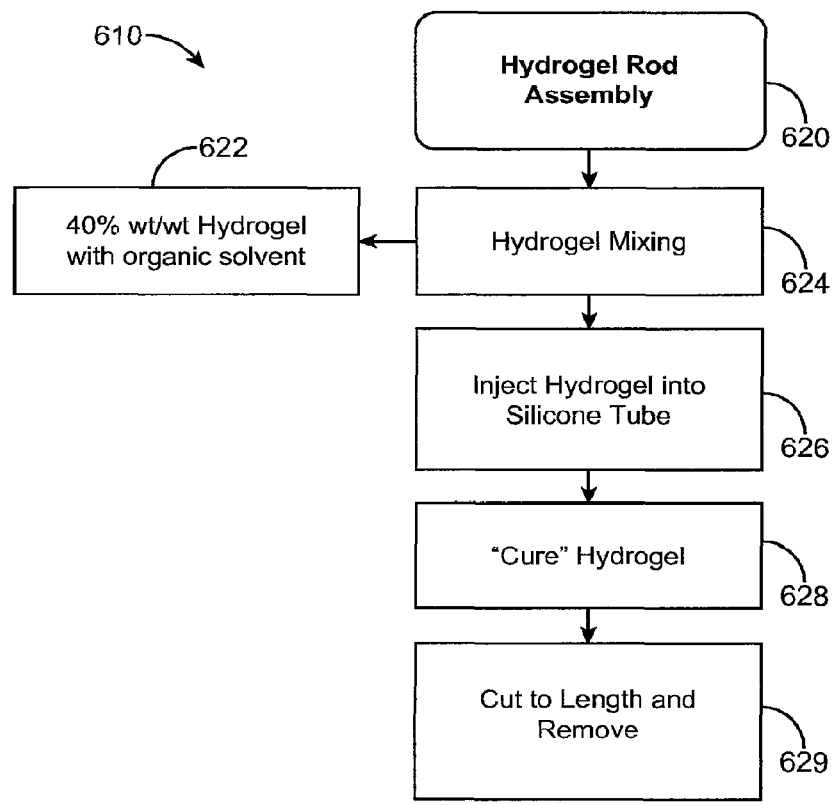
FIG. 6B shows a method of manufacturing a hydrogel rod in accordance with the method of FIG. 6A.

FIG. 6B shows a method 620 of manufacturing a hydrogel rod for the punctual plug in accordance with method 600 of FIG. 6A. In some embodiments, method 620 comprises a sub method, or sub-step, of method 610. A step 622 combines 40% by weight hydrogel with an organic solvent. In some embodiments, the percentage of hydrogel comprises a range from about 5% to about 50% hydrogel, for example from about 20% to about 40% hydrogel. A step 624 mixes the hydrogel with the solvent. In some embodiments, the hydrogel may dissolve in the organic solvent. A step 626 injects the hydrogel into a silicone tube. In many embodiments, the silicone tube is permeable to the organic solvent. The silicone tube comprises a mold to form the hydrogel. A step 628 cures the hydrogel. At least one of a heat or a pressure, in many embodiments both, can be used to drive off the solvent, for example through the permeable mold, to cure the hydrogel. A step 629 cuts the cured hydrogel to a desired length. The curing can be optimized with empirical process/validation studies with an adequate a sample size, for example 10 sample of cured hydrogels, to determine material variability and/or process variability over time. Process variable that can be optimized include time, pressure and temperature of curing. Tolerance analysis associated with the process can also be performed.

Figure 6C:
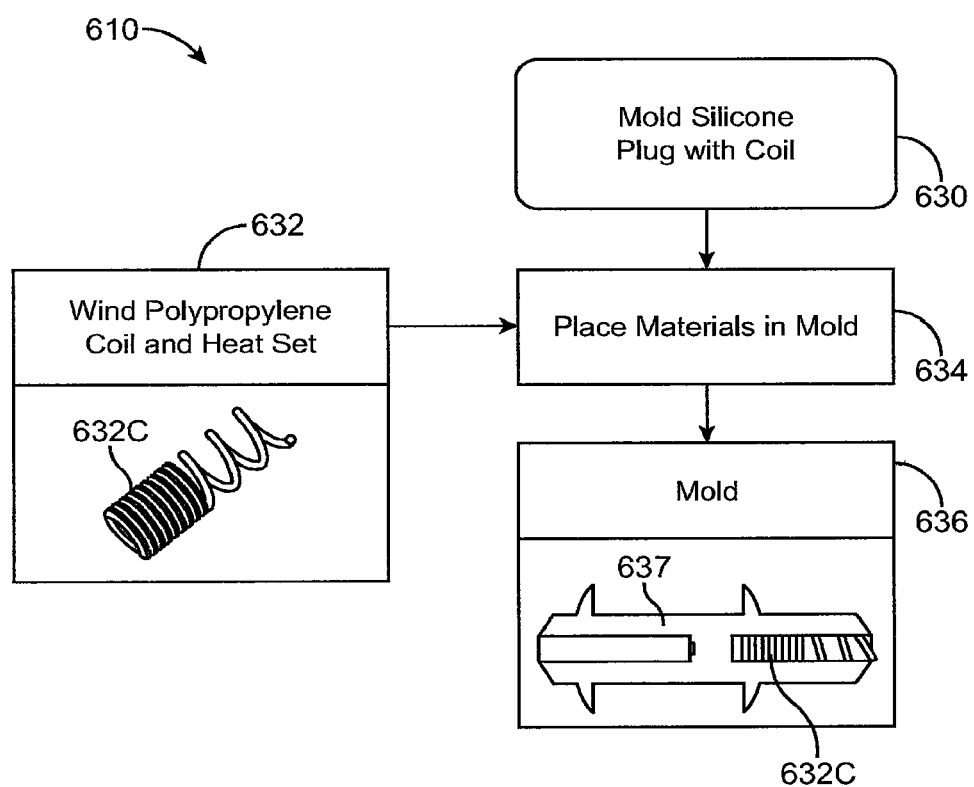
FIG. 6C shows a method of molding a silicone plug in accordance with the method of FIG. 6A.

FIG. 6C shows a method 630 of molding a silicone plug body 637 in accordance with method 600 of FIG. 6A. A step 632 winds a filament comprising a solid material, for example a coil 632C, and heat sets the filament. A step 634 places the filament comprising heat set coil 632C in a mold. A step 636 molds plug body 637 with coil 632C embedded therein. The plug body may comprise sleeves, tubes, retention structures and/or at least one chamber as described above. The filament may comprise at least one of a heat activated material, Nitinol, a shape memory material, a polymer, polypropylene, polyester, nylon, natural fibers, stainless steel, polymethylmethacrylate or polyimide. In some embodiments, the filament may comprise an absorbable thermoplastic polymer, for example at least one of polylactic acid (PLA), poly glycolic acid (PGA) or poly-lactic-co-glycolic acid (PLGA). The heat setting of the filament can be optimized by appropriately controlling the time and/or temperature of the heat filament based on empirical data from a sample of heat set filaments, for example 10 filaments. The molding of the plug at step 636 can be optimized in several ways, such as appropriate time and temperature, hard tooling of the mold, a multiple cavity mold, and mold equipment parameters. In some embodiments, a filament for removal of the drug core insert, as described above, can be molded with the plug body such that the filament is embedded in the plug body and positioned near the channel that receives the drug core insert.

FIG. 6D shows a method 640 of assembling the punctual plug components in accordance with method 600 of in FIG. 6A. Step 630 molds the punctual plug body 637 with a coil 632C. Step 620 molds a hydrogel rod. A step 642 inserts the hydrogel rod component into a channel of the plug body component. A step 644 extends windings of coil 632C over the hydrogel rod. A step 648 dip coats the hydrogel rod and plug body. A step 646 may prepare a hydrogel coating solution 646 comprising for example a 5% solution of hydrogel by weight. A needle 648N may be placed in a channel of the plug body to hold the body while the hydrogel rod and plug body are dipped in the solution.

Figure 6E:
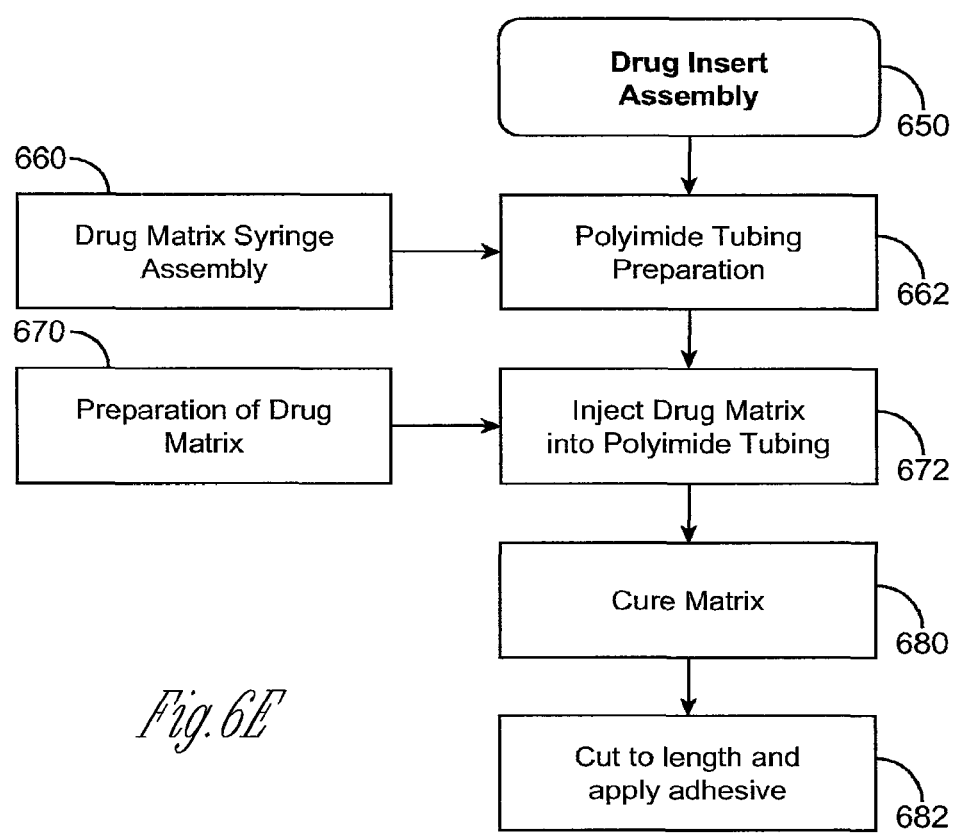
FIG. 6E shows a method of manufacturing a drug core insert, in accordance with the method of in FIG. 6A.

FIG. 6E shows a method 650 of manufacturing a drug core insert, in accordance with method 600 of in FIG. 6A. A step 661 prepares a syringe assembly to inject a drug matrix into a polyimide tubing. A step 662 prepares a polyimide tubing for injection. A step 670 prepares a drug core matrix for injection into the tubing. A step 672 injects the drug core matrix into the polyimide tubing. A step 680 cures the matrix inside the polyimide tubing. A step 682 cuts the polyimide tubing and cured matrix to a length and applies an adhesive.

Step 661 can use known commercially available syringes in the syringe assembly. The syringe assembly may comprise a syringe tube and cartridge assembly. The syringe tube and cartridge assembly may comprise a tube attached to a modified needle tip that attaches that attaches to a syringe. The syringe can be connected to a syringe pump or other mechanism to pressurize the tube. The syringe assembly can be used for injection of the drug core mixture and/or material into the polyimide tubing. In some embodiments, multiple syringes can be used, for example with the manufacture of drug inserts that comprise two or- more drug cores. In some embodiments, the syringe assembly may comprise a manifold with two or more injection pots that can be used to with separate syringes in which each syringe includes a different drug core mixture.

Step 662 can prepare the polyimide tubing for injection by attaching a 15 cm length of polyimide tubing to a luer. The luer can be connected to the syringe for injection of the drug core mixture and/or material. In some embodiments, the tubing connected to the syringe may comprise PMMA and/or PET. In many embodiments the tubing comprises a material that inhibits release of the therapeutic agent from the drug core through the tubing, for example a material that is substantially impermeable to the flow of the therapeutic agent through the tubing, such that the flow of therapeutic agent is directed toward the exposed end of the drug core. In some embodiments, for example drug core inserts comprising two or more concentric drug cores, the tubing may comprise concentric tubes, for example concentric polyimide tubes, with an outer tube arranged to receive and outer drug core mixture, and an inner tube arranged to receive an inner drug core mixture. With an annular drug core as described above, concentric tubes may be used to form the annular drug core, with an inner tube that can be removed after the drug core matrix material has solidified.

In some embodiments, a filament for removal of the drug core insert can be embedded in the drug core. The filament may be run through the sheath, for example tubing, and the mixture injected into the tubing. The matrix material is then cured with the filament embedded in the matrix.

Step 670 can prepare a drug core mixture comprising a therapeutic agent with a matrix material, for example silicone. In some embodiments, the therapeutic agent may comprise at least one of latanoprost, bimatoprost or travoprost Embodiments can use silicones that comprise dimethylsiloxane, for example Med-4011, Med-6385 and Med-6380 each of which is commercially available from NuSil of Lafayette, Calif. In some embodiments, two or more drug core mixtures are prepared, each for injection for a separate drug core, for example two mixtures one for an inner drug core and one for an outer drug core.

In a specific embodiment, step 670 can prepare a drug core mixture comprising inclusions of latanoprost oil in silicone. The therapeutic agent and drug core matrix material can be prepared prior to mixing the therapeutic agent with the drug core matrix material.

Preparation of Therapeutic Agent:

Latanoprost oil can be provided as a 1% solution in methyl acetate. An appropriate amount of the 1% solution can be placed in a dish. A stream of dry nitrogen can be used to evaporate the solution until only the latanoprost remains. The dish with latanoprost oil can be placed under vacuum for 30 minutes. In some embodiments, for example those which use bimatoprost available as crystals as the therapeutic agent, the evaporation and vacuum may not be used to prepare the therapeutic agent.

In some embodiments with solid therapeutic agent, for example bimatoprost crystals, the therapeutic agent can be ground and passed through a sieve, prior to mixing with the matrix material. In some embodiments, the sieve may comprise a 120 sieve (125 um) and/or a 170 sieve (90 um). Work in relation to embodiments of the present invention indicates that a sieve may remove a very small fraction of therapeutic agent and that many embodiments will work with inclusions of therapeutic agent having a size greater than the optional sieve. In many embodiments, the release rate is independent of the size and/or distribution of size of the inclusions, and the release rate can be independent of particle size for particles from about 0.1 um to about 100 um. In some embodiments, the size and/or distribution of sizes of the particles and/or inclusions can be characterized with at least one of a sieve, light scatter measurements of the core, light microscopy of the core, scanning electron microscopy of the core or transmission electron microscopy of sections of the core. A sieve can generally be used to create desirable particle sizes and/or exclude undesirable particle sizes before mixing with the matrix. The exemplary sieve comprises a fine mesh that passes only the desired size particles or smaller, thereby limiting the therapeutic agent to finer drug particles. This can be used to produce a more homogenous drug core and/or drug particle size that is easier to mix with the silicone matrix than one with excessively large particles, although significant variations among particle sizes may remain. A variety of sieves may be used. For example, a Sieve #120 can be used so that the largest particle diameter passed is about 0.0049 inches. Sieve #170 may pass particles of 0.0035 inch diameter or smaller. A Sieve #70 will allow a particle size of 0.0083 inch diameter to pass through. Sieves may optionally be used in series.

Preparation of Silicone:

Silicone, for example NuSil 6385, can be obtained from the manufacturer in a sealed container. An appropriate amount of silicone can be weighed based on the lot size of the build.

Combine Therapeutic Agent with Silicone:

The therapeutic agent, for example latanoprost, can be combined with silicone, based on the intended and/or measured percentage of therapeutic agent in the drug core matrix. The percent of latanoprost to silicone can be determined by the total weight of the drug matrix. The therapeutic agent, for example latanoprost, is incorporated into the silicone by weighing out the appropriate amount of the components. The following formula can be used to determine the percentage of therapeutic agent in the drug core matrix:

Percent Drug=(weight of drug)/(weight of drug+ weight of silicone)×100

For the specific example of latanoprost in silicone the percentage of latanoprost is silicone is given by:

(20 mg of latanoprost)/(20 mg of latanoprost+80 mg of silicone)×100=20%.

The therapeutic agent, for example latanoprost is combined and mixed with the silicone using known methods and apparatus for mixing silicones. In some embodiments, the therapeutic agent comprising latanoprost oil may form a micro emulsion comprising inclusions that may scatter light and appear white.

When a therapeutic agent such as latanoprost, which is in a liquid physical state at about room temperature (22° C.), and thus is also in a liquid physical state at human body temperature (37° C.), is used, the agent and the matrix material can be mixed by techniques that bring about a high degree of dispersion of the liquid latanoprost droplets in the matrix material in which it can be substantially insoluble. Mixing techniques should provide for a dispersion of the droplet within the matrix material, such that when curing takes place, the liquid therapeutic agent is present as relatively small, relatively homogeneously dispersed discrete droplets within the matrix of solid silicone material. For example, mixing can include sonication, i.e., the use of ultrasonic frequencies, such as are generated by an ultrasonic probe. The probe can be put in contact with the mixture of matrix material and liquid therapeutic agent to prepare an intimate mixture of the two substantially immiscible materials. See, for instance, Example 12 below.

Step 672 can inject the mixture of therapeutic agent and silicone into the tubing. A syringe, for example a 1 ml syringe, can be connected to the syringe tube and cartridge assembly. A drop of catalyst appropriate for the silicone, for example MED-6385 curing agent, can be placed into the syringe and the syringe is then filled with the uncured mixture of silicone and therapeutic agent, or silicone drug matrix. The mixture, i.e., mixture of the uncured silicone and agent still liquid enough to flow or pump, can be chilled to subambient temperatures. For example, the mixture can be chilled to temperatures of less than 20° C. For example, the mixtures can be chilled to 0° C., or to −25° C. The polyimide tube is injected with the drug/matrix mixture until the tube is filled. The tube and associated apparatus can also be chilled to maintain the subambient temperature of the mixture throughout the process of filling or injecting the sheath with the mixture. In various embodiments, the polyimide tube, or sheath, is filled with the drug matrix mixture under pressure, for example through use of a high pressure pump. For instance, the drug/matrix mixture, such as can be obtained in mixtures of latanoprost with MED-6385 Part A to which amounts of catalyst Part B have been added, can be pumped into the tube under at least about 40 psi pressure. The tube can be filled at any suitable rate, but preferably, at rates of less than about 0.5 linear cm/sec. It is believed by the inventors herein that filling the tube relatively rapidly under a relatively high head of pressure can reduce the degree of phase separation of the substantially immiscible latanoprost oil and silicone monomer material, such that upon polymerization ("curing") to provide the final silicone polymeric product, the latanoprost droplets are finely dispersed in the solid matrix in which they are only slightly soluble.

Curing takes place in the presence of the catalyst ("Part B") of the NuSil MED-6385, and can be carried out at temperatures of at least about 40° C., at relative humidity (RH) of at least about 80%, or both. Curing can be initiated directly after filling the tube and clamping the ends of the filled tube to prevent the formation of voids and loss of the precursor material from the tube ends.

After curing, which can be complete in about 16-24 hours at 40° C. and 80% RH, the clamps can be removed from the ends of the tubing, as the silicone is fully set up. The tubing can then be cut into sections of suitable length for use as drug inserts, for example, lengths of about 1 mm.

When the extrusion is carried out at subambient temperatures, small and more uniform inclusions of the agent can result. For example, when the agent is latanoprost, a liquid at room temperature, extrusion at −5° C. provides significantly smaller and more uniform inclusion droplets. In an example, cold extrusion yielded a drug core comprising a silicone matrix with latanoprost droplets of average diameter of 6 μm, with a standard deviation of diameter of 2 μm. In comparison, an extrusion carried out at room temperature yielded a drug core comprising a silicone matrix with latanoprost droplets of average diameter of 19 μm, with a standard deviation of droplet diameter of 19 μm. It is apparent that the cold extrusion technique provides smaller, more uniform inclusions than does extrusion at room temperature. This in turn results in a more uniform concentration of drug throughout the core, or the insert containing the core, which is desirable for medical applications as uniformity of dose is improved.

The open end of the polyimide tube can be closed off until the silicone begins to solidify. In some embodiments with two or more drug cores, two or more separate mixtures can each be separately injected from two or more syringes.

Step 680 cures the drug core matrix comprising the mixture silicone and therapeutic agent. The silicone is allowed to cure, for example for 12 hours. The amount of time and temperature of the cure may be controlled, and empirical data can be generated to determine ideal times and temperatures of the curing. Work in relation with embodiments of the present invention indicates that the silicone material and drug loading of the core, for example a percentage of therapeutic agent in the core, may effect the optimal time and temperature of the cure. In some embodiments, empirical data can be generated for each silicone matrix material and percentage of each therapeutic agent to determine an optimal amount of time to cure the injected mixture. In some embodiments with two or drug cores in a drug core insert, two or more mixtures can be cured together to cure the drug cores of the insert.

Table 1 shows drug insert silicones that may be used and associated cure properties, according to embodiments of the present invention. The drug core insert matrix material can include a base polymer comprising dimethyl siloxane, such as MED-4011, MED 6385 and MED 6380, each of which is commercially available from the NuSil company. The base polymer can be cured with a cure system such as a platinum-vinyl hydride cure system and/or a tin-alkoxy cure system, both commercially available from NuSil. In many embodiments, the cure system may comprise a known cure system commercially available for a known material, for example a known platinum vinyl hydride cure system with known MED-4011. In a specific embodiment shown in Table 1, 90 parts of MED-4011 can be combined with 10 parts of the crosslinker, such that the crosslinker comprises 10% of the mixture. A mixture with MED-6385 may comprise 2.5% of the crosslinker, and mixtures of MED-6380 may comprise 2.5% or 5% of the crosslinker.

TABLE 1

Drug Insert Silicone Selections

| Material | Base Polymer | Cure System | Crosslinker Percent | Curing Properties |
|---|---|---|---|---|
| MED-4011 | Dimethyl Siloxane Silica filler material | Platinum vinyl hydride system | 10% | Curing inhibited at high concentrations of latanoprost |
| MED-6385 | Dimethyl siloxane Diatomaceous earth filler material | Tin-Alkoxy | 2.5% | Very slight inhibition of curing at high concentrations of latanoprost |
| MED-6380 | Dimethyl siloxane without filler material | Tin-Alkoxy | 2.5% to 5% | Very slight inhibition of curing at high concentrations of latanoprost |

Work in relation with embodiments of the present invention suggests that the cure system and type of silicone material can effect the curing properties of the solid drug core insert, and may potentially effect the yield of therapeutic agent from the drug core matrix material. In specific embodiments, curing of MED-4011 with the platinum vinyl hydride system can be inhibited with high concentrations of latanoprost, for example over 20% latanoprost, such that a solid drug core may not be formed. In specific embodiments, curing of MED-6385 and/or MED 630 with the tin alkoxy system can be slightly inhibited with high concentrations, e.g. 20%, of latanoprost. This slight inhibition of curing can be compensated by increasing the time and/or temperature of the curing process. For example, embodiments of the present invention can make drug cores comprising 40% latanoprost and 60% MED-6385 with the tin alkoxy system using appropriate cure times and temperatures. Similar results can be obtained with the MED-6380 system the tin-alkoxy system and an appropriate curing time and/or temperature. In many embodiments, the solid drug core forms so as to form a solid structure, for example a solid cylinder, within the drug core that corresponds to the dimensions of the tube. Even with the excellent results for the tin alkoxy cure system, work in relation with embodiments of the present invention suggests that there may be an upper limit, for example above 50% latanoprost, at which the tin-alkoxy cure system may not produce a solid drug core. In many embodiments, the therapeutic agent comprises the prostaglandin analogue, for example latanoprost, in the drug solid drug core may be at least about 5%, for example a range from about 5% to 50%, and can be from about 20% to about 40% by weight of the drug core. In specific embodiments with moderate to high loading of the therapeutic agent in the drug core, the drug core may comprise from about 25% to about 50% of the therapeutic agent in the drug core, for example 50% latanoprost oil in the drug core and/or matrix material.

In some embodiments, the therapeutic agent may comprise a functional group that can, at least potentially, react with the cure system. In some embodiments, the therapeutic agent may comprise a prostaglandin analogue such as latanoprost, bimatoprost or travoprost, each of which may comprise an unsaturated carbon-carbon double bond that can potentially react with the platinum vinyl hydride cure system. These unsaturated carbon-carbon double bonds can be similar to the vinyl group in the platinum cure vinyl hydride system, and can potentially react with the vinyl hydride cure system via a hydrosilation reaction. Latanoprost comprise an unsaturated carbon-carbon double bond in one of the side chains. Bimatoprost and travoprost each comprise two unsaturated carbon-carbon double bonds, one in each side chain. Work in relation with embodiments of the present invention indicate that the hydrosilation reaction of the unsaturated double bond in the prostaglandin analogues with in the platinum vinyl hydride cure system does not significantly reduce the quantity of prostaglandin analogue available for release from the drug core.

In some embodiments, the therapeutic agent may comprise a prostaglandin analogue such as latanoprost, bimatoprost or travoprost, each of which may comprise hydroxyl groups that can potentially react with the tin alkoxy cure system. These hydroxyl groups can potentially react with the alkoxy groups via an alkoxy condensation reaction. Bimatoprost, latanoprost and travoprost each comprise a molecule with three hydroxyl groups that can potentially react via the alkoxy condensation reaction. Work in relation with embodiments of the present invention indicate that the alkoxy condensation reaction of the hydroxyl groups in the prostaglandin analogues with in the tin alkoxy cure system does not significantly reduce the quantity of prostaglandin analogue available for release from the drug core. Work in relation to embodiments of the present invention indicates that a negligible amount of therapeutic agent is consumed by solidification or otherwise not available, as extraction data of the therapeutic agent for solid cores shows that at least 95%, for example 97% or more, of therapeutic agent can be extracted from the drug core.

In some embodiments, the silicone material may comprise an inert filler to add rigidity to the cured matrix. Work in relation with embodiments of the present invention suggests that the filler material may increase the rate of release of the therapeutic agent. The MED-4011 and MED-6385 materials are commercially available with the filler material. The MED-4011 material may comprise an inert silica filler material to add rigidity to the cured silicone matrix. The MED-4385 may comprise inert diatomaceous earth filler material to add rigidity to the cured silicone matrix.

The inert filler material can increase the concentration of drug in the silicone of the component matrix as the filler material may not substantially absorb the therapeutic agent and the inert filler material can reduce the fraction of silicone in the material drug core matrix. In some embodiments, MED-4385 comprises approximately 25% diatomaceous earth filler and approximately 75% dimethyl siloxane. In a specific embodiment, the drug core may comprise 40% of the therapeutic agent and 60% of the material. The 60% of material, e.g. MED-4385, corresponds to 45% dimethyl siloxane base polymer and 15% inert diatomaceous earth filler. Assuming that very little therapeutic agent is absorbed into the inert filler material, the 40% of therapeutic agent is contained within the 45% of dimethyl siloxane base polymer, such that the concentration of therapeutic agent in the base polymer is 47% or about 50%. Consequently, the release rate of the therapeutic agent from the exposed surface of the silicone drug core insert can be increased slightly as the concentration of therapeutic agent in the silicone portion of the matrix material can be elevated due to the presence of the filler material. In some embodiments, the drug core may comprise a matrix material without a filler material, such that the therapeutic agent, for example latanoprost oil, comprises approximately 50% of the material in the cured solid drug core and may also comprise a concentration approximately 50% in the matrix base polymer.

In many embodiments, the size and/or distribution of sizes of the inclusions in the core can be characterized with at least one of light scatter measurements of the core, light microscopy of the core, scanning electron microscopy of the core or transmission electron microscopy of sections of the core.

Step 680 cuts the polyimide tubing with the cured solid matrix mixture to an intended length and may apply an adhesive to one end of the cut length of tubing. In many embodiments, the matrix material is cured so as to form a solid drug core structure, for example a cylindrical rod that corresponds to the shape of the tubing, such that the exposed surface of the cut solid drug core substantially retains its shape when implanted into the patient. In some embodiments with two or more drug cores in a drug core insert, the two or more drug cores can be cut together, for example the tubes and cores of concentric drug cores can be cut together.

Cut Drug Inserts to Length:

The polyimide tubing may be inserted into a fixture and cut to a section of the specified length. In some embodiments, the cut sections of polyimide tubing may be placed in a vacuum for 30 minutes. The cut section polyimide tubing comprising the drug core insert can be inspected and weighed following the vacuum and the weight may be recorded.

Close Off End of Drug Core Insert:

An adhesive can be applied to one end of the drug core insert. The adhesive may be applied as a liquid and cured under UV light, for example cured under UV light for five seconds. In specific embodiments, the adhesive may comprise Loctite 4305 UV adhesive. In many embodiments the material applied to one end of the drug core insert comprises a material that is substantially impermeable to the therapeutic agent such that release of the therapeutic agent through the covered end is inhibited. This inhibition of release from the drug core through the covered end can result in effective and/or efficient delivery of the drug through the exposed surface of the drug core on the opposite end, such that the drug is selectively released to the target tissue and/or bodily fluid, for example to the tear liquid tear film. In some embodiments, a filament may be bonded to the end as described above, to facilitate removal of the drug core insert from the implant.

In some embodiments, the end can be closed by heat welding, pinching the tube end closed, and covering the end of the tube with a cap comprising a material that is substantially impermeable to the therapeutic agent to inhibit release of the therapeutic agent through the cap. In embodiments with two or more drug cores in the drug core insert, the covered end may cover both cores, for example cover an inner cylindrical core and an outer annular core.

In some embodiments, with flow of the drug through the drug core, the end of the drug core may not be closed off, or the end may be partially closed, for example with a cap having an opening to let fluid flow though the channel in the core while the periphery of the cap covers an annular end of the core.

In some embodiments, the exposed end opposite the closed end can be shaped to increase surface area of the exposed end as described above. In some embodiments, a cone with a sharp tip, similar to a sharp pencil tip, can be inserted into the exposed surface to indent the exposed surface with an inverted cone shape that increases surface area. In some embodiments, the exposed end may be crimped to decrease the surface area.

Figure 6F:
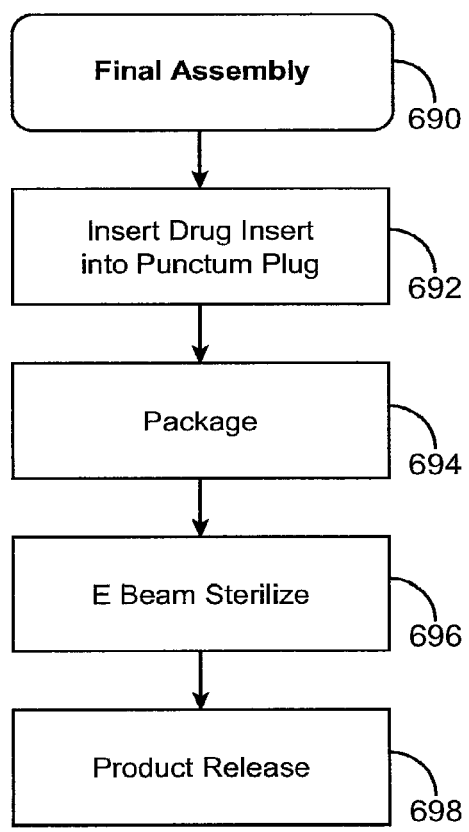
FIG. 6F shows method 690 of final assembly in accordance with method 600 of FIG. 6A.

FIG. 6F shows method 690 of final assembly in accordance with method 600 of FIG. 6A. A step 692 inserts a drug core component into a channel in the punctual plug. A step 694 packages the punctual plug with the drug core insert in the channel. A step 696 sterilizes the packaged plug and drug core insert. A step 698 releases the product.

Step 692 inserts the drug core into the implant, for example a punctual plug. The drug core can be inspected prior to insertion and may be part of the step of insertion. The inspection can comprise visual inspection to ensure that the sleeve comprising the cut tubing is completely filled with no voids or foreign particles in the silicone matrix, that the silicone is flush and the same length as the polyimide tube, that the adhesive comprising cyanoacrylate completely covers one end of the tube, and that the tube is the correct length. The drug insert and implant comprising the punctual plug can be loaded into a drug insertion tool and holding fixture. The drug insert can be loaded into the implant bore, or channel, using the plunger on the drug insertion tool. The drug insert insertion tool can be removed. The implant comprising the punctum plug can be inspected to verify that the drug core insert is fully seated in the bore, that the drug core insert is below the surface of the punctual plug flange, and that there is no visible damage to the implant/drug core assembly.

Step 694 packages the punctual plug with the drug core inserted into the channel. The punctual plug may be packaged with known packaging and methods, for example with an inner pouch, an outer Mylar pouch, a pouch sealer, argon gas, and an inflation needle. In specific embodiments, two completed drug delivery systems, each comprising the punctual plug implant with drug core insert, are placed in the inner pouch and sealed in the inner pouch. The sealed inner pouch is placed in an outer pouch. The outer pouch may extend about ¼ beyond a pouch sealer element. The number 25 gauge needle can be inserted into the pouch and under the sealing element with the Argon flowing. The sealer element can be clamped and the package allowed to inflate. The argon flow needle can be removed and the sealing operation repeated. The package can be inspected by pressing gently on the argon filled pouch to check for leaks. If a leak is detected, the inner pouch can be removed and repacked in a new Mylar outer pouch.

Step 696 can sterilize the packaged plug and drug core insert with known sterilization methods, for example with commercially available e-beam from Nutek Corporation of Hayward, Calif.

Step 698 can release the product in accordance with final testing and release procedures.

It should be appreciated that the specific steps illustrated in FIGS. 6A to 6E provide a particular method of manufacturing a plug with a drug core insert, according to some embodiments of the present invention. Other sequences of steps may also be performed according to alternative embodiments. For example, alternative embodiments of the present invention may perform the steps outlined above in a different order. Moreover, the individual steps illustrated in FIGS. 6A to 6E may include multiple sub-steps that may be performed in various sequences as appropriate to the individual step. Furthermore, additional steps may be added or removed depending on the particular applications. One of ordinary skill in the art would recognize many variations, modifications, and alternatives.

EXAMPLES

Example 1

Latanoprost Drug Core Elution Data

Drug cores as described above have been fabricated with different cross sectional sizes of 0.006 inches, 0.012 inches, and 0.025 inches, and drug concentrations of 5%, 10% and 20% in a silicone matrix. Theses drug cores can be made with a Syringe Tube and Cartridge Assembly, Mixing Latanoprost with Silicone, and Injecting the mixture into a polyimide tube which is cut to desired lengths and sealed. The length of the drug cores were approximately 0.80 to 0.95 mm, which for a diameter of 0.012 inches (0.32 mm) corresponds to total Latanoprost content in the drug cores of approximately 3.5 µg, 7 µg and 14 µg for concentrations of 5%, 10% and 20%, respectively.

Syringe Tube and Cartridge Assembly. 1. Take polyimide tubing of three different diameters 0.006 inches, 0.0125 inches and 0.025 inches. 2. Cut polyimide tubing of different diameters to ~15 cm length. 3. Insert Polyimide tubes into a Syringe Adapter. 4. Adhesive bond polyimide tube into luer adapter (Loctite, low viscosity UV cure). 5. Trim end of assembly. 6. Clean the cartridge assembly using distilled water and then with methanol and dry it in oven at 60° C.

Mix Latanoprost with Silicone. Prepare Latanoprost. Latanoprost is provided as a 1% solution in methylacetate. Place the appropriate amount of solution into a dish and using a nitrogen stream, evaporate the solution until only the Latanoprost remains. Place the dish with the Latanoprost oil under vacuum for 30 minutes. Combine Latanoprost with silicone. Prepare three different concentrations of Latanoprost (5%, 10% and 20%) in silicone Nusil 6385 and inject it into tubing of different diameters (0.006 in, 0.012 in and 0.025 inches) to generate 3×3 matrixes. The percent of Latanoprost to silicone is determined by the total weight of the drug matrix. Calculation: Weight of Latanoprost/(weight of Latanoprost+weight of silicone)×100=percent drug.

Inject tube. 1. Insert Cartridge and Polyimide tubes assembly into 1 ml syringe. 2. Add one drop of catalyst, (MED-6385 Curing Agent) in the syringe. 3. Force excess catalyst out of the polyimide tube with clean air. 4. Fill syringe with silicone drug matrix. 5, Inject tube with drug matrix until the tube is filled or the syringe plunger becomes too difficult to push. 6. Close off the distal end of the polyimide tube and maintain pressure until the silicone begins to solidify. 7. Allow to cure at room temperature for 12 hours. 8. Place under vacuum for 30 minutes. 9. Place tube in right size trim fixture (prepared in house to hold different size tubing) and cut drug inserts to length (0.80-0.95 mm).

Testing. Elution study (in vitro). 1. Place 10 plugs of same size and same concentration per centrifuge tube and add 1.5 ml of 7.4 pH buffer solution to it. 2. Change the solvent with fresh 7.4 pH buffer after appropriate time. 3. Take HPLC of the elutant at 210 nm with PDA detector 2996 using Sunfire C18, 3 mm×10 mm column (Waters Corporation, Milford, Mass.). Acetonitrile and water mixture is used for gradient elution. Calibration was done in house before and after each analysis, using in-house standards with precisely weighed concentration of Latanoprost. 4. Calculate the amount of drug release per day per device for different size tubings having different concentrations of Latanoprost. 5. Plot elution rate vs area and concentration for day 1 and day 14.

Figure 7A:
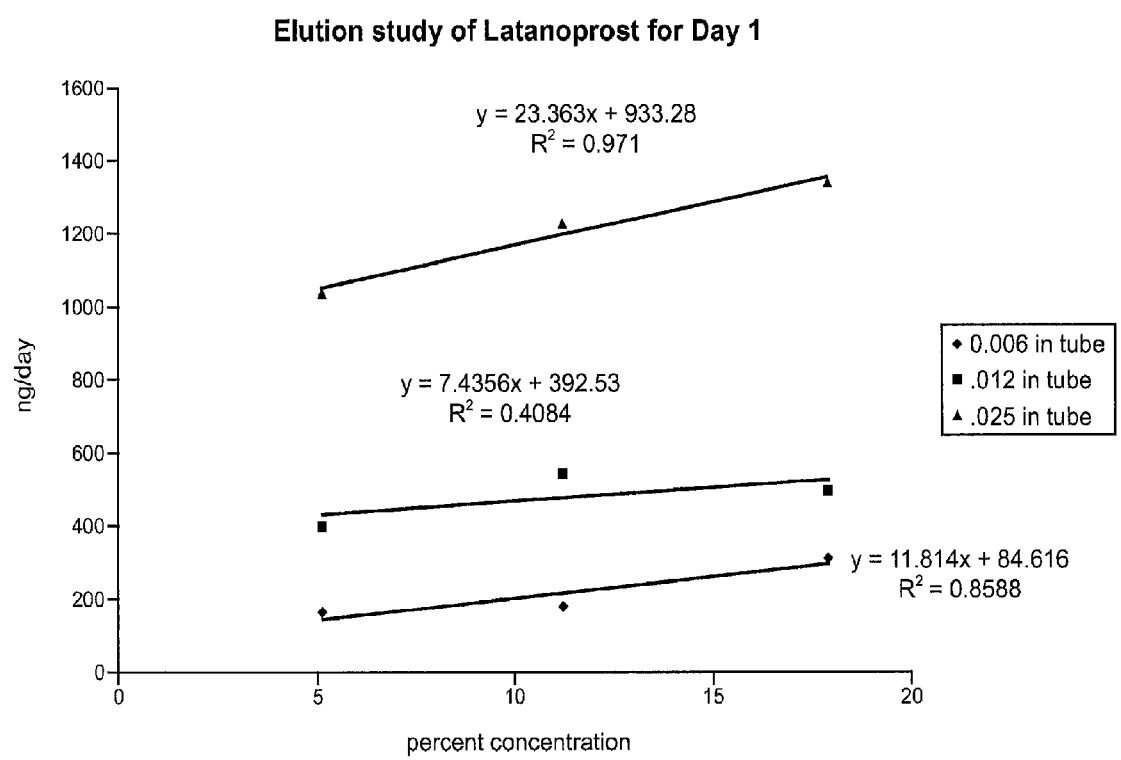
FIGS. 7A and 7B show elution data of latanoprost at day 1 and day 14, respectively, for the three core diameters of 0.006, 0.012 and 0.025 inches and three Latanoprost concentrations of approximately 5%, 11% and 18%, according to embodiments of the present invention.
Figure 7B:
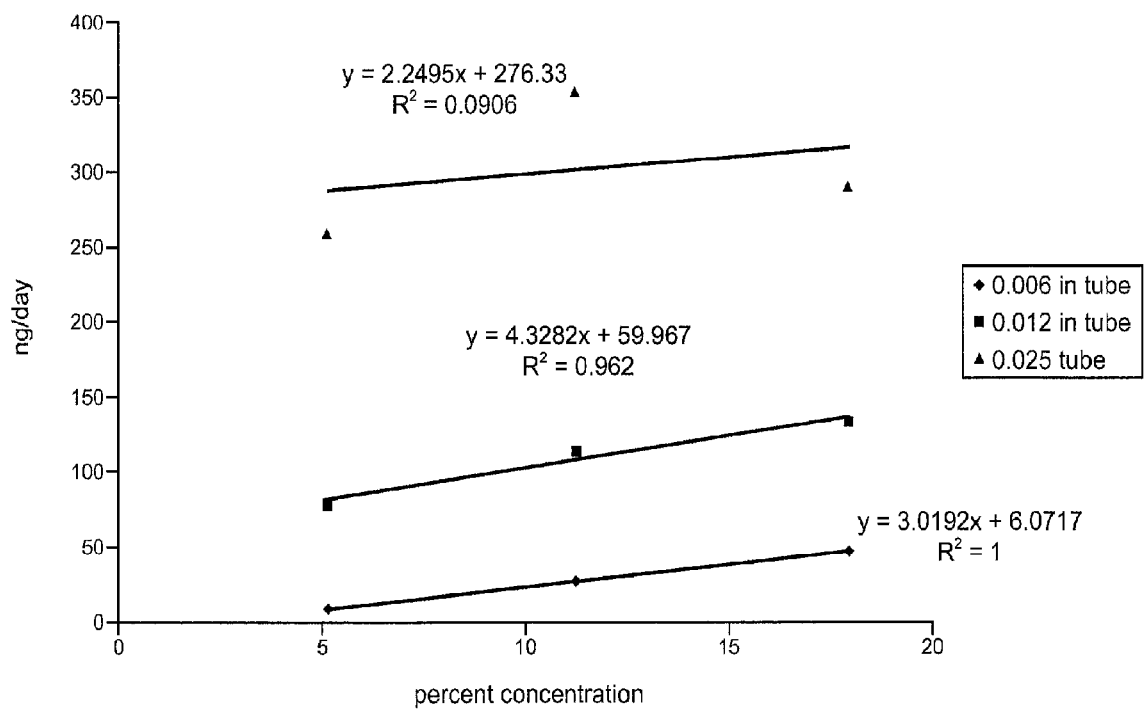

FIGS. 7A and 7B show elution data of Latanoprost at day 1 and day 14, respectively, for the three core diameters of 0.006, 0.012 and 0.025 inches and three Latanoprost concentrations of approximately 5%, 11% and 18%. Elution rate of the Latanoprost in nanograms (ng) per day is plotted versus percent concentration. These data show that the rate of elution is mildly dependent on the concentration and strongly dependent on the exposed surface area at both time periods. At day 1, the 0.006 inch, 0.012 inch and 0.025 inch diameter cores released about 200 ng, 400 ng and 1200 ng of Latanoprost, respectively, showing that the quantity of Latanoprost released increases with an increased size of the exposed surface area of the drug core. For each tube diameter, the quantity of Latanoprost released is compared to the concentration of drug in the drug core with a least square regression line. For the 0.006, 0.012 and 0.025 inch drug cores the slope of the regression lines are 11.8, 7.4 and 23.4, respectively. These values indicate that a doubling of concentration of the Latanoprost drug in the core does not lead to a doubling of the elution rate of the Latanoprost from the core, consistent with droplets of Latanoprost suspended in a drug core matrix and substantial saturation of the drug core matrix with Latanoprost dissolved therein, as described above.

At day 14, the 0.006 inch, 0.012 inch (0.32 mm) and 0.025 inch diameter cores released about 25 ng, 100 ng and 300 ng of Latanoprost, respectively, showing that the quantity of Latanoprost released increases with an increased size of the exposed surface area of the drug core at extended periods of time, and that the quantity of Latanoprost released is mildly dependent on the concentration of therapeutic agent in the core. For each tube diameter, the quantity of Latanoprost released is compared to the concentration of drug in the drug core with a least square regression line. For the 0.006, 0.012 and 0.025 inch drug cores the slope of the regression lines are 3.0, 4.3 and 2.2, respectively. For the 0.012 and 0.025 inch cores, these values indicate that a doubling of concentration of the Latanoprost drug in the core does not lead to a doubling of the elution rate of the Latanoprost from the core, consistent with droplets of Latanoprost suspended in a drug core matrix and substantial saturation of the drug core matrix with Latanoprost dissolved therein, as described above. However, for the 0.006 inch diameter core, there is an approximately first order relationship between the quantity of initially in the core and the amount of drug released at day 14, which can may be caused by depletion of Latanoprost drug droplets in the core.

Figure 7C:
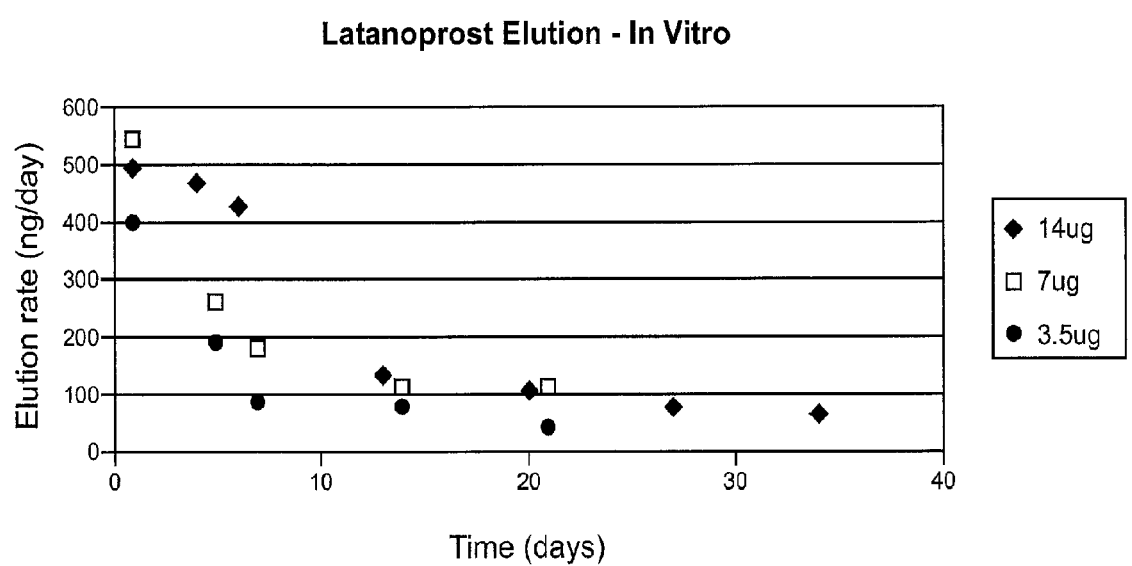
FIG. 7C shows elution data for Latanoprost from 0.32 mm diameter, 0.95 mm long drug cores with concentrations of 5, 10 and 20% and drug weights of 3.5, 7 and 14 µg, respectively, according to embodiments of the present invention.
Figure 7D:
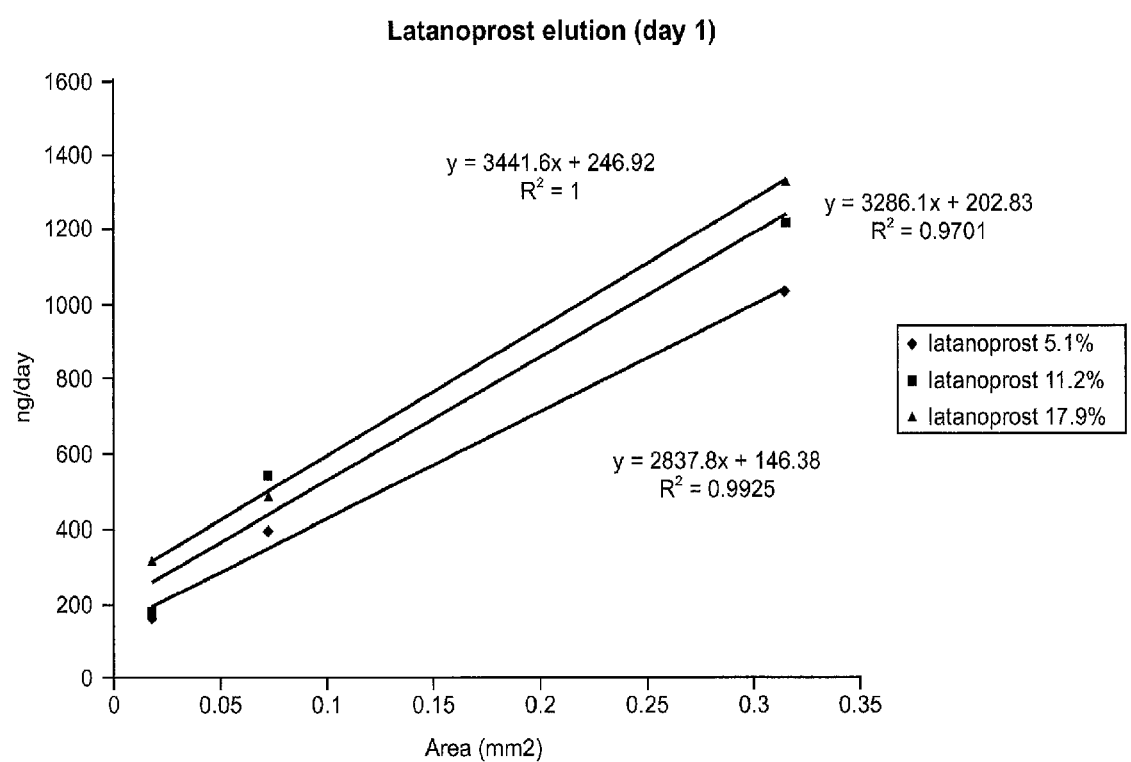
FIGS. 7D and 7E show dependence of the rate of elution on exposed surface area of the drug core for the three core diameters and the three concentrations as in FIGS. 7A and 7B Latanoprost at day 1 and day 14, respectively, according to embodiments of the present invention.
Figure 7E:
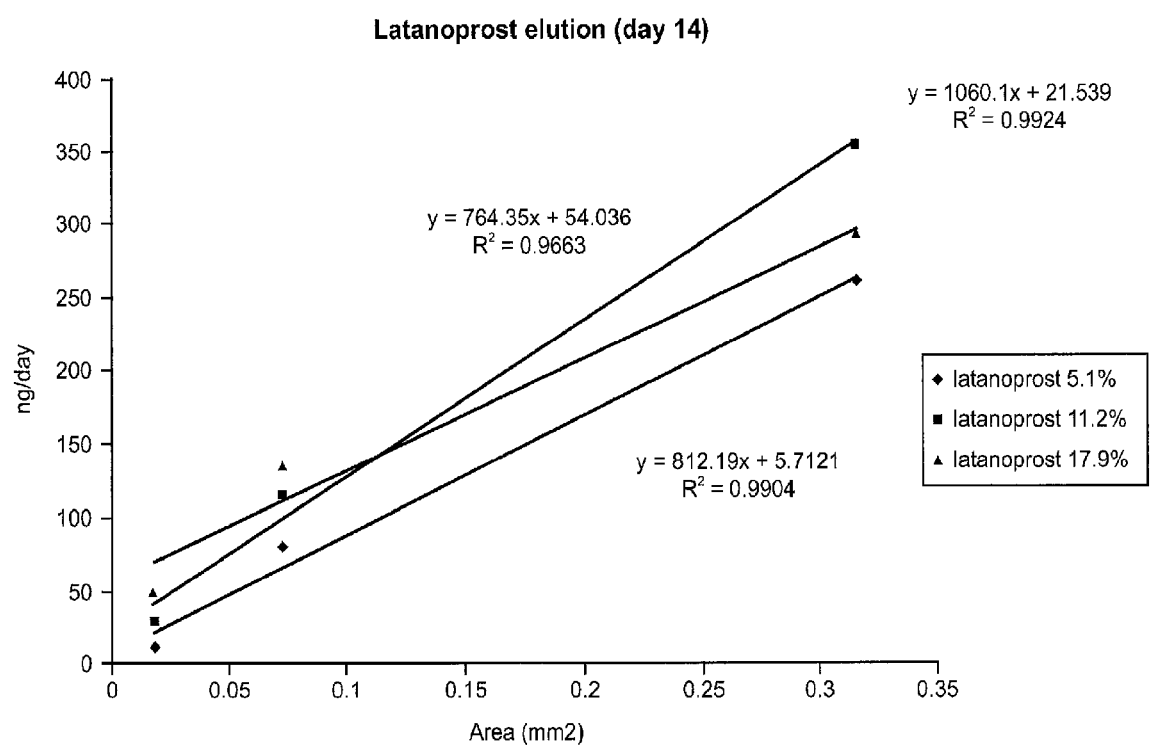

FIGS. 7D and 7E show dependence of the rate of elution on exposed surface area of the drug core for the three core diameters and the three concentrations as in FIGS. 7A and 7B Latanoprost at day 1 and day 14, respectively, according to embodiments of the present invention. Elution rate of the Latanoprost in nanograms (ng) per day is plotted versus the exposed surface area of the drug core in mm2 as determined by the diameter of the drug core. These data show that the rate of elution is mildly dependent on the concentration of drug in the core and strongly dependent on the exposed surface area at both one day and a 14 days. The exposed surface areas of the 0.006 inch, 0.012 inch and 0.025 inch diameter cores are approximately 0.02, 0.07, and 0.32 mm2, respectively. At day 1, the 0.02, 0.07, and 0.32 mm2, cores released about 200 ng, 400 ng and 1200 ng of Latanoprost, respectively, showing that the quantity of Latanoprost released increases with an increased size of the exposed surface area of the drug core. For each concentration of therapeutic agent in the drug core, the quantity of Latanoprost released is compared to the exposed surface area of the drug core with a least square regression line. For the 5.1%, 11.2%, and 17.9% drug cores the slope of the regression lines are 2837.8, 3286.1 and 3411.6, respectively, with $R^2$ coefficients of 0.9925, 0.9701 and 1, respectively. At day 14, the 0.02, 0.07, and 0.32 mm2, cores released about 25 ng, 100 ng and 300 ng of Latanoprost, respectively showing that the quantity of Latanoprost released increases with an increased size of the exposed surface area of the drug core. For the 5.1%, 11.2%, and 17.9% drug cores the slope of the regression lines are 812.19, 1060.1 and 764.35, respectively, with $R^2$ coefficients of 0.9904, 0.9924 and 0.9663, respectively. These values indicate the elution rate of the Latanoprost from the core increases linearly with the surface area of the drug core, consistent with a drug sheath that can control the exposed surface area, as described above. The weak dependence of Latanoprost elution on concentration in the drug core is consistent with droplets of Latanoprost suspended in a drug core matrix and substantial saturation of the drug core matrix with Latanoprost dissolved therein, as described above.

FIG. 7C shows elution data for Latanoprost from 0.32 mm diameter, 0.95 mm long drug cores with concentrations of 5, 10 and 20% and drug weights of 3.5, 7 and 14 µg, respectively, according to embodiments of the present invention. The drug cores were manufactured as described above. The elution rate is plotted in ng per day from 0 to 40 days. The 14 µg core shows rates of approximately 100 ng per day from about 10 to 40 days. The 7 µg core shows comparable rates from 10 to 20 days. These data are consistent with droplets of Latanoprost suspended in a drug core matrix and substantial saturation of the drug core matrix with Latanoprost dissolved therein, as described above.

Table 2 shows the expected parameters for each drug concentration. As shown in FIG. 7C, in vitro results in a buffered saline elution system show that the plug initially elutes approximately 500 ng of Latanoprost per day, dropping off rapidly within 7-14 days to approximately 100 ng/day, depending on the initial concentration of drug.

TABLE 2

Drug Elution Properties

| Total Latanoprost content | 14 µg | 7 µg | 3.5 µg |
|---|---|---|---|
| In vitro elution rate | See FIG. 7C | See FIG. 7C | See FIG. 7C |
| Duration | ~100 days | ~45 days | ~25 days |

In many embodiments, the duration of the drug core can be determined based on the calculated time when ~10% of the original amount of drug remains in drug insert, for example where the elution rate levels out and remains substantially constant at approximately 100 ng/day.

Example 2

Cyclosporin Drug Core Elution Data

Figure 8:
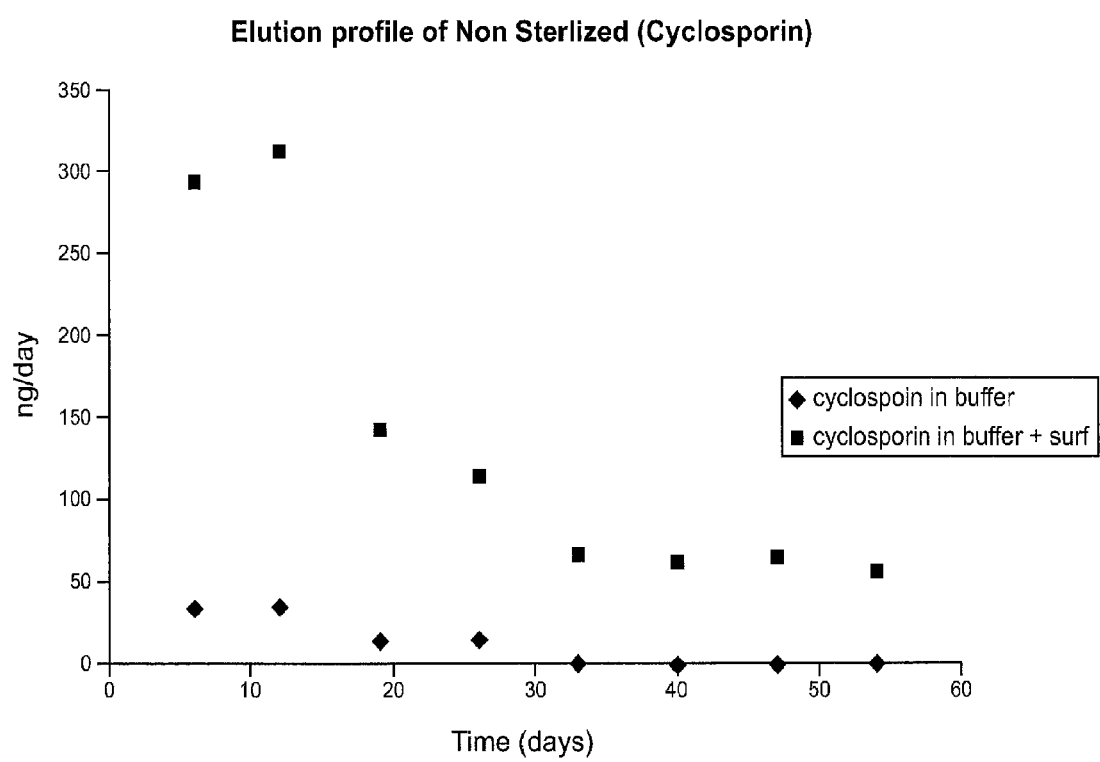
FIG. 8 shows elution profiles of cyclosporine from drug cores into a buffer solution with surfactant and a buffer solution with surfactant, according to embodiments of the present invention.

Drug cores as described in Example 1 were made with cyclosporin having a concentration of 21.2%. FIG. 8A shows elution profiles of cyclosporin from drug cores into a buffer solution without surfactant and into a buffer solution with surfactant, according to embodiments of the present invention. The buffer solution was made as described above. The solution with surfactant includes 95% buffer and 5% surfactant, UP-1005 Ultra Pure Fluid from Dow Corning, Midland Mich. Work in relation with embodiments of the present invention indicates that in at least some instances, surfactants may be used in in vitro to model in situ elution from the eye as the eye can include natural surfactants, for example Surfactant Protein D, in the tear film. The elution profile of cyclosporin into surfactant is approximately 50 to 100 ng per day from 30 to 60 days. Empirical data from tears of a patient population, for example 10 patients, can be measured and used to refine the in vitro model with appropriate amounts of surfactant. The drug core matrix may be modified in response to the human tear surfactant as determined with the modified in vitro model. The drug core can be modified in many ways in response to the human tear film surfactant, for example with an increased exposed surface area and/or additives to increase an amount of cyclosporine drug dissolved in the core, as described above, to increase elution from the core to therapeutic levels, if appropriate.

Example 3

Bimatoprost Bulk Elution Data

Bulk samples of 1% Bimatoprost having a known diameter of 0.076 cm (0.76 mm) were prepared. The height of each sample was determined from the weight and known diameter of the sample.

TABLE 3

Bulk Sample Size

| Sample | wt (mg) | Diameter (cm) | calculated height (cm) | Exposed Surface Area (cm^2) |
|---|---|---|---|---|
| 14-2-10 | 1.9 | 0.076 | 0.42 | 0.109 |
| 14-2-11 | 1.5 | 0.076 | 0.33 | 0.088 |
| 14-2-12 | 1.9 | 0.076 | 0.42 | 0.109 |

Figure 9:
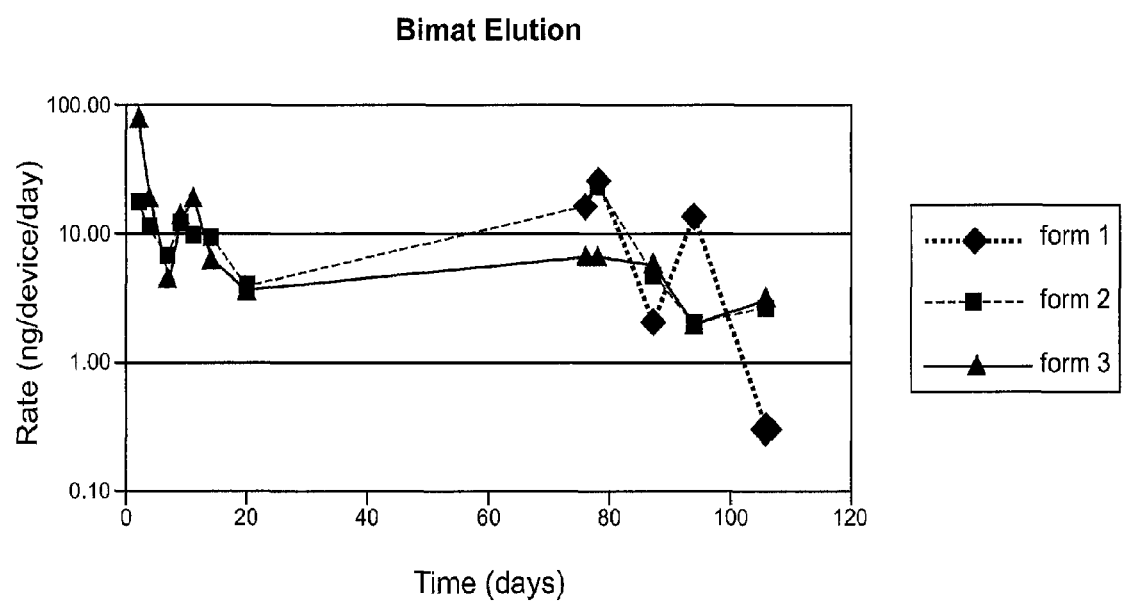
FIG. 9 shows normalized elution profiles in nano-grams per device per day over 100 days for bulk sample of silicone with 1% Bimatoprost, according to embodiments of the present invention.

The calculated heights ranged from 0.33 cm to 0.42 cm. The exposed surface area on each end of each bulk sample was approximately 0.045 cm2, providing volumes of 0.019 cm3 and 0.015 cm3 for the 0.42 and 0.33 cm samples, respectively. The exposed an exposed surface area of samples calculated from the height and diameter without a drug sheath was approximately 0.1 cm2. Three formulations were evaluated: 1) silicone 4011, 1% Bimatoprost, 0% surfactant; 2) silicone 4011, 1% Bimatoprost, approximately 11% surfactant; and 3) silicone 4011, 1% Bimatoprost, approximately 33% surfactant. The elution data measured for the bulk samples with formulation 1, 2 and 3 were normalized to ng per device per day (ng/device/day) assuming a surface area of the bulk device is 0.1 cm2 and the surface area of the clinical device is 0.00078 cm2 (0.3 mm diameter). FIG. 9A shows normalized elution profiles in ng per device per day over 100 days for bulk sample of silicone with 1% Bimatoprost, assuming an exposed surface diameter of 0.3 mm on the end of the device, according to embodiments of the present invention. The normalized elution profile is about 10 ng per day. The data show approximately zero order release kinetics from about ten days to about 90 days for each of the formulations. These data are consistent with particles of Bimatoprost suspended in a drug core matrix and substantial saturation of the drug core matrix with Bimatoprost dissolved therein, as described above. Similar formulations can be used with drug core sheaths and a shaped exposed surface of the core exposed to the tear to increase the exposed surface area as described above and deliver the drug in therapeutic amounts over an extended period.

In some embodiments, the core can comprise a 0.76 mm diameter core with an exposed surface diameter of 0.76 mm, corresponding to an exposed surface area of 0.0045 cm2. The core can be covered with a sheath to define the exposed surface of the core as described above The normalized elution profile for such a device, based on the bulk sample data above, is approximately 6 times (0.0045 cm2/0.00078 cm2) the elution profile for the device with a 0.3 mm diameter exposed surface area. Thus, a zero order elution profile with an elution rate of about 60 ng per day can be obtained over a period of about 90 days. If the exposed surface area is increased to about 0.0078 cm2, for example with many of the exposed surface shapes as described above, the zero order elution rat is about 100 ng per day over a period of about 90 days. The concentration can also be increased from 1%. Similar elution profiles can be obtained with Latanoprost.

Example 4

Latanoprost Elution Data

Figure 10:
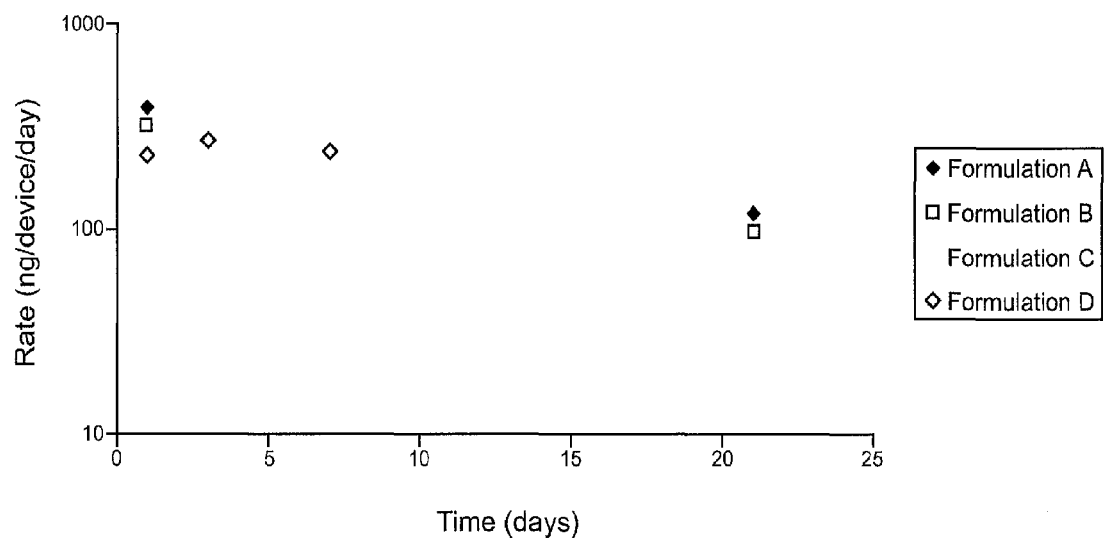
FIG. 10 shows profiles of elution of Latanoprost from the cores for four formulations of Latanoprost, according to embodiments of the present invention.

Drug cores were manufactured as described above in Example 1 with Latanoprost and silicone 4011, 6385 and/or NaCl. Four formulations were manufactured as follows: A) silicone 4011, approximately 20% Latanoprost, and approximately 20% NaCL; B) silicone 4011, approximately 20% Latanoprost, and approximately 10% NaCl; C) silicone 4011, approximately 10% Latanoprost, and approximately 10% NaCl; and D) silicone 6385, approximately 20% Latanoprost. FIG. 10A shows profiles of elution of Latanoprost form the cores for four formulations of Latanoprost, according to embodiments of the present invention. The results show initial rates of approximately 300 ng per device per day that decreases to about 100 ng per device per day by 3 weeks (21 days). The results shown are for non-sterile drug cores. Similar results have been obtained with sterile drug cores of Latanoprost. These data are consistent with droplets of Latanoprost suspended in a drug core matrix and substantial saturation of the drug core matrix with Latanoprost dissolved therein, as described above.

Example 5

Drug Release as a Function of Crosslinking

Figure 11A:
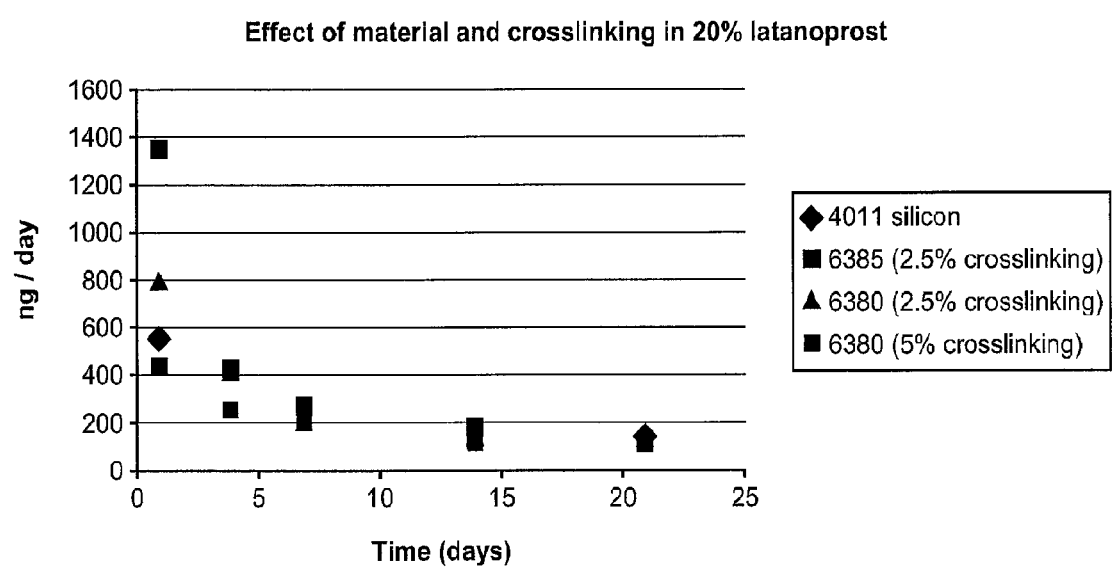
FIG. 11A shows the effect on elution of material and crosslinking on drug cores with 20% latanoprost, according to embodiments of the present invention.

FIG. 11A shows the effect on elution of material and crosslinking on drug cores with 20% latanoprost, according to embodiments of the present invention. Drug cores were manufactured as described above with manufacturing methods as in FIG. 6E and Table 1. The drug cores comprised 4011 silicone, 6385 silicone with 2.5% crosslinker, 6380 with 2.5% crosslinker and 6380 with 5% crosslinker. The therapeutic agent in all samples comprised approximately 20% latanoprost. The 6380 material with 5% crosslinker provided the lowest elution rate at all time points. As the 6380 material with 5% crosslinker elutes at a lower rate than the 6385 material with 2.5% crosslinker, increased crosslinker and concomitant crosslinking appears to decrease the rate of elution. The 6385 material with 2.5% crosslinker provides the highest elution rates at 1, 4, 7 and 14 days. The 6380 material with 2.5% crosslinker has slightly lower elution rate at 1, 4, 7 and 14 days than the 6385 material. Both the 6385 and 6380 materials elute faster than the 4011 material that does not include a filler material. The 4011, 6380 and 6385 materials comprise dimethyl siloxane as the base polymer. As noted above, the 6385 material comprises diatomaceous earth filler material, and the 6380 material comprises silica filler material, indicating, based on the above elution rates, that the inert filler material can increase the rate of elution.

Example 6

Effect of Drug Concentration on the Elustion of Latanoprost

Figure 11B:
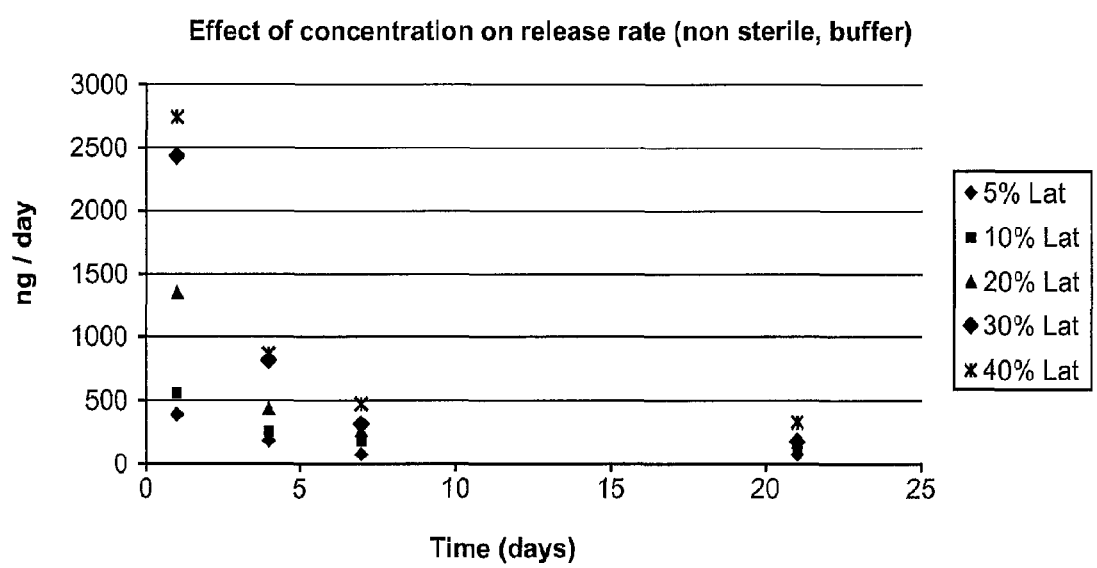
FIG. 11B shows the effect of drug concentration on the elution of latanoprost, according to embodiments of the present invention.

FIG. 11B shows the effect of drug concentration on the elution of latanoprost, according to embodiments of the present invention. Drug cores were manufactured as described above with manufacturing methods as in FIG. 6E and Table 1. The drug cores comprised 6385 material with 5, 10, 20, 30 and 40% latanoprost, respectively. The amount of tin-alkoxy cure system was 2.5% in all samples. The release of latanoprost is weakly dependent on the concentration of latanoprost at all time periods with 40% the latanoprost material eluting at the highest rate and 5% latanoprost eluting at the lowest rate. The elution rate for all samples falls below 500 ng per day by 7 days and continues to be released at therapeutic levels thereafter.

Example 7

Effect of Covering One End of the Drug Core Insert

Figure 11C:
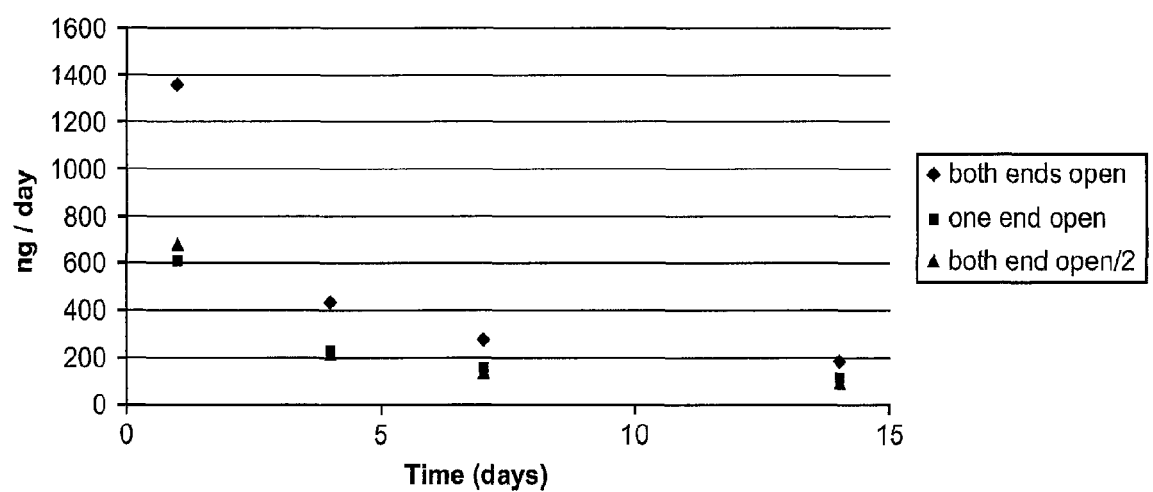
FIG. 11C shows the effect of covering one end of the drug core insert, according to embodiments of the present invention.

FIG. 11C shows the effect of covering one end of the drug core insert, according to embodiments of the present invention. Drug cores were manufactured as described above with manufacturing methods as in FIG. 6E and Table 1. The drug cores comprised 6385 material with 20% latanoprost. The elution rate of cut tubes as described above was measured with both ends of each cut tube open, referred to as both ends open. The elution rate of cut tubes with one end exposed and one end covered with uv cured Loctite, as described above, was measured, referred to as one end open. For comparison, the elution rate for the drug core inserts with both ends open divided by two is shown, referred to as "both ends open/2". The both ends open/2 values are very close to the one end open data at all time points, indicating that covering one end of the drug core insert with an adhesive material that is substantially impermeable to the therapeutic agent can inhibit the release of therapeutic agent from the drug core, such that the drug is effectively delivered through the exposed surface of the drug core on the open end of the tube.

Example 8

Elution of Fluorescein and the Effect of Surfactant on Fluorescein Elution

Figure 12:
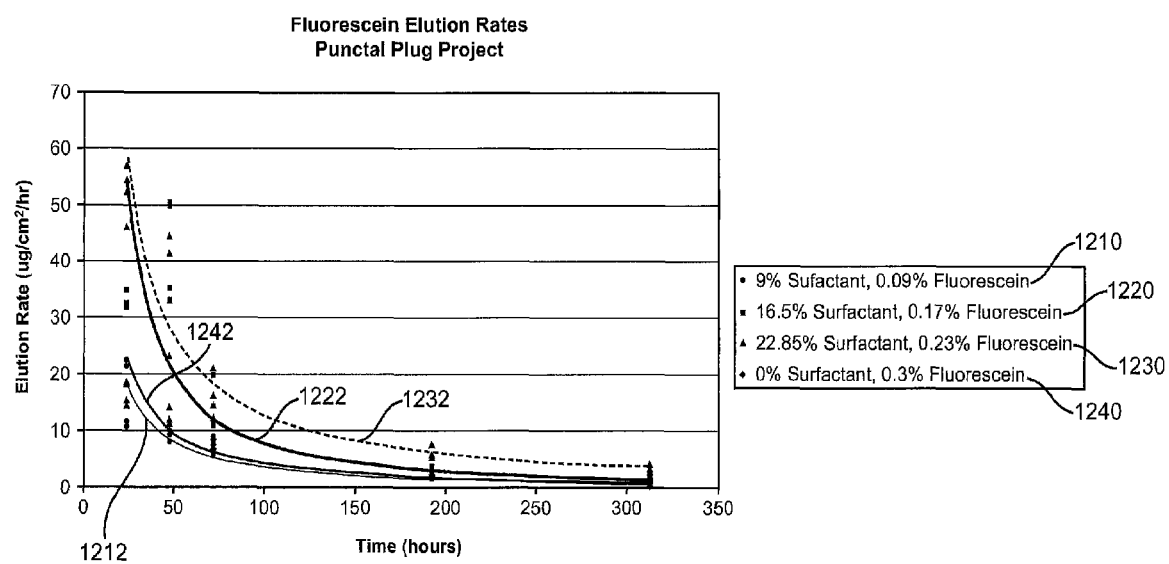
FIG. 12 shows the elution of fluorescein and the effect of surfactant on fluorescein elution, according to embodiments of the present invention.

FIG. 12A shows the elution of fluorescein and the effect of surfactant on fluorescein elution, according to embodiments of the present invention. The elution data for fluorescein show the flexibility of the above drug core and manufacturing processes for the sustained release of many therapeutic agents, including both water soluble and water insoluble therapeutic agents, and relatively low molecular weight and high molecular weight therapeutic agents. Fluorescein has a molecular mass of 332.32 g/mol, is soluble in water, and can serve as a model for the release water soluble therapeutic agents released from the eye. Work in relation with embodiments of the present invention indicates that molecular weight and solubility in water can each effect the release rate of the drug from the solid drug core matrix. For example, lower molecular weight may increase diffusion through the solid matrix material, i.e. through silicone, such that low molecular weight compounds may be released more quickly. Also, solubility in water can also effect the release rate of the drug, and in some instances increased water solubility of the drug may increase the rate of release from the solid drug core matrix, for example via transport from the solid matrix material to the bodily liquid, such as tear liquid. In accordance with these embodiments, therapeutic agents with higher molecular weight than fluorescein and with lower water solubility than fluorescein, for example cyclosporin and prostaglandins as shown above, may be released from the solid core at lower rates. Surfactants may also effect the rate of release of the therapeutic agent from the drug core into the surrounding bodily tissue and/or fluid, for example tear film fluid.

Each drug core tested comprised MED 4011 silicone. In one embodiments, a drug core formulation 1210 comprised 9% surfactant and 0.09% fluorescein. An exponential fit 1212 is shown for the elution rate of drug core formulation 1210. In another embodiment, a drug core formulation 1220 comprised 16.5% surfactant and 0.17% fluorescein. An exponential fit 1222 is shown for the elution rate of drug core formulation 1220. In another embodiment, a drug core formulation 1230 comprised 22.85% surfactant and 0.23% fluorescein. An exponential fit 1232 is shown for the elution rate of drug core formulation 1230. In an embodiment without surfactant, a drug core formulation 1240 comprised 0% surfactant and 0.3% fluorescein. An exponential fit 1242 is shown for the elution rate of drug core formulation 1240.

The drug cores were manufactured with key formulations comprising: Silicone Surfactant "190 Fluid" (Dow Corning); Surfactant Mix: "190 Fluid"+Fluorescein; Silicone (Nusil): MED 4011 Part A, MED 4011 Part B; Centrifuge Tubes; 3 mL Syringe; 20 ga. Needle; 0.031 inch inner diameter Teflon Tube; and Buffer.

Key parameters included: Prepare a mixture of 2.5 g of silicone surfactant and 0.025 g of fluorescein; Prepare silicone compositions of Nusil MED 4011 containing 3.5 g Part A and 0.37 g Part B (10:1 ratio); Prepare four (4) centrifuge tubes each with 0.5 g of silicone and varying surfactant mixture weights as follows: A. 0.05 g surfactant mix: 9% surfactant, 0.09% fluorescein; B. 0.1 g surfactant mix: 16.5% surfactant, 0.17% fluorescein; C. 0.15 surfactant mix: 22.85% surfactant, 0.23% fluorescein; D. 0.0015 g fluorescein: 0% surfactant, 0.3% fluorescein; Inject each of the four formulations into respective teflon tubes using the syringe and needle; Cure the injected tube at 140° C. for 45 minutes in the oven; Cut each tube into 3 pieces in length to 4 mm; and Immerse each cut piece into a centrifuge tube containing 0.3 mL of buffer.

Data collection comprised: Collect samples at time points 24, 48, 72, 192, and 312 hours; Submit each sample for UV spectrometry analysis; Convert each elution rate from µg/mL/hr to µg/cm2/hr by using the dimensions of the teflon tube (4 mm length, 0.031 inch inner diameter); Plot data for elution rate vs. time to compare the rates of each surfactant mix formulation.

Analysis comprised fitting trendlines for each elution rate to an exponential curve, as shown in Table 4.

TABLE 4

Trendlines for each elution rate fit to exponential curves.

| Sample # | % Surfactant | % Fluorescein | R2 | Trendline Equation |
|---|---|---|---|---|
| A | 9.0 | 0.09 | 0.9497 | 636.66x − 1.1161 |
| B | 16.5 | 0.17 | 0.8785 | 4289.6x − 1.3706 |
| C | 22.85 | 0.23 | 0.9554 | 1762.0x − 1.0711 |
| D | 0 | 0.30 | 0.9478 | 1142.1x − 1.2305 |

The trendline equations of table 4 indicate the following: The data fit experimental curves well with R2 values of 0.8785 to 0.9554. The trendline equations shows exponent coefficients of −1.0711 to −1.3706. Elution rates increased with increasing surfactant levels. Despite relatively similar amounts of fluorescein, there is a dramatic increase in elution rates between Samples C and D—this demonstrates that the addition of surfactant to the silicone matrix dramatically affects the elution rate of the water-soluble compound. The elution rate of Sample A is comparable to that of Sample D, even though Sample A contains only one-third the amount of fluorescein. This also demonstrates that the rate of elution can be affected by the addition of surfactant to the silicone matrix.

Although the trendline equation exponent coefficients of −1.0711 to −1.3706 are consistent with first order release, the data include an initial 48 hour period in which bolus release of fluorescein from the core is observed. Such an initial washout period of 2 to 3 days with high levels of the therapeutic agent delivered followed by a period of sustained release at therapeutic levels can be helpful in some embodiments, for example where elevated levels for a short period of time are tolerated and can lead to an accelerated effect on the eye. Work in relation with embodiments of the present invention suggests that after 48 hours the elution data can be closer to zero order, for example within a range from about zero order to about first order. In some embodiments, the level of release therapeutic agent can be decreased with a decreased exposed surface area of the drug core, for example as described above, to release the drug at therapeutic levels for sustained periods.

Example 9

The Effect of Sterilization on Elution of Therapeutic Agent

Work in relation to embodiments of the present invention suggests that radicals generated in the sterilization process may crosslink the drug core matrix material so as to inhibit the initial release rate of therapeutic agent from the drug core matrix material. In specific embodiments with e-beam sterilization, this cross-linking may be limited to the surface and/or near the surface of the drug core matrix. In some embodiments, a known Mylar bag can be penetrated with the e-beam to sterilize the surface of the drug core. In some embodiments, other sterilization techniques that effect sterilization can be used, for example gamma ray sterilization, and that are not limited to the surface of the drug core and fully and/or uniformly penetrate the drug core material.

Figure 13:
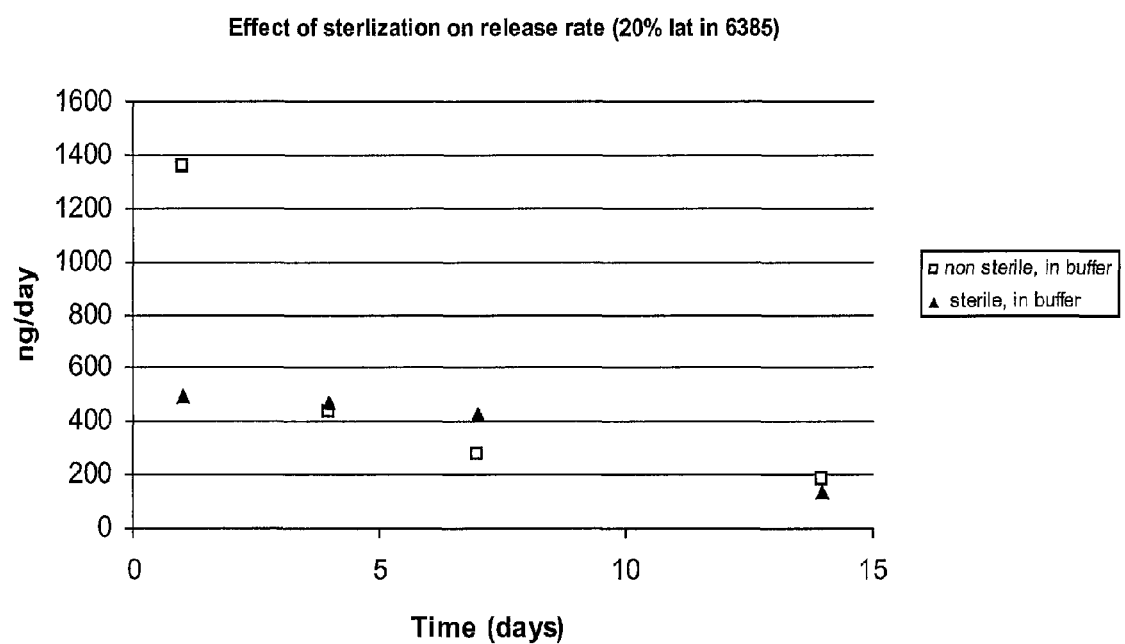
FIG. 13 shows the elution of sterilized and non-sterilized drug cores, according to embodiments of the present invention.

Drug cores were synthesized and e-beam sterilized in Mylar packaging, as described above. FIG. 13A shows the elution of sterilized and non-sterilized drug cores. The sterile and non-sterile drug cores each comprised 20% latanoprost in 6385 synthesized as described above. The drug cores were e-beam sterilized and the elution rates measured as described above. The sterile and non-sterile drug cores show elution rates for the first day of about 450 and 1400 ng/day, respectively. At days 4 and 7, the sterile and non-sterile drug cores show similar elution rates at about 400 ng/day. At 14 day the sterile and non-sterile drug cores show elution rates of 200 and about 150 ng/day, respectively. These data show that sterilization may decrease an initial release, or bolus, of the therapeutic agent, and that sterilization may be used to provide a more uniform rate of release of the therapeutic agent, for example in combination with embodiments described above.

Example 10

The Effect of Salt on Elution of Therapeutic Agent

Work in relation to embodiments of the present invention suggests that known salts, for example sodium chloride can effect the rate of elution from the drug core.

Figure 14:
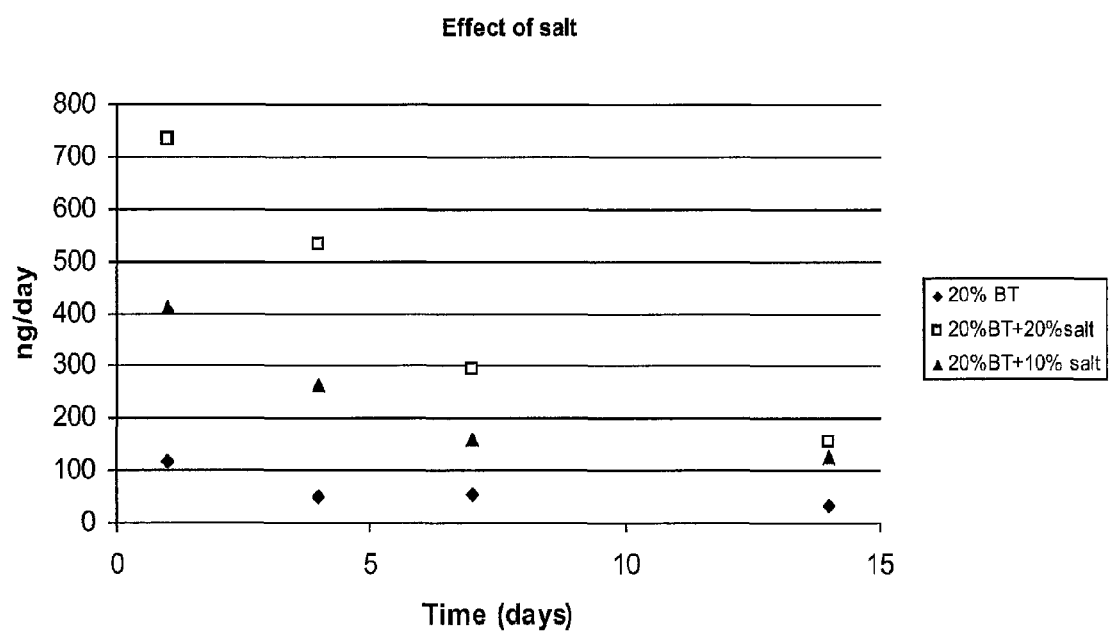
FIG. 14 shows the effect of salt on the elution of therapeutic agent, according to embodiments of the present invention.

FIG. 14A shows the effect of salt on the elution of therapeutic agent. Drug cores comprising 20% bimatoprost (BT) and silicone drug core matrix comprising NuSil 6385 were manufactured as described above. Drug cores were manufactured with salt concentrations of 0%, 10% and 20%. At 1 day the drug cores showed elution rates of about 750 ng/day, 400 ng per day and about 100 ng per day for 20%, 10% and 0%, respectively. At all time periods measured to two weeks, the 20% salt data showed the highest elution rate and the 0% salt data showed the lowest elution rate. This data shows that salt, for example many known salts such as sodium chloride, can be added to the matrix to increase the order of the elution rate of therapeutic agent.

Example 11

Extraction of Therapeutic Agent from Drug Cores to Determine Therapeutic Agent Yield Drug core inserts comprising MED-6385 and 20% and 40% latanoprost were synthesized as described above. Each drug core was weighed and the weight of solid drug core material determined with correction for the weight of the drug tube and adhesive. The amount of therapeutic agent present in each sample was determined based on the weight of drug core material and percentage of therapeutic agent in the drug core material as described above. The therapeutic agent was extracted from the drug cores with 1 ml aliquots of methyl acetate. The concentration of therapeutic agent in the solution for each sample was measured with reverse phase gradient HPLC with optical detection and peak integration at 210 nm. Measurements were taken for 6 drug cores with 20% latanoprost and 4 drug cores with 40% latanoprost. For the 20% samples, the average extraction of latanoprost was 104.8% with a standard deviation of about 10%. For the 40% samples, the average extraction of latanoprost was 96.8% with a standard deviation of about 13%.

Example 12

High Pressure Filling

A two part silicone formulation (MED6385, Nusil Technologies) was used in the preparation of a composite resin containing latanoprost, which was used to fill a section of polyimide sheathing. The sheathing containing the polymerized silicone incorporates discrete latanoprost domains, existing in the form of droplets of less than about 25 µm maximum diameter, within the matrix. Several experiments were conducted.

Part A of the MED6385 silicone formulation was mixed with 0.43 µL of Part B, the tin catalyst, using syringes, to bring about partial coagulation of the polymer over 30 minutes. Then, 37 mg of that material was mixed with a premixed solution of 0.144 additional catalyst and 13 mg latanoprost, and that mixture could be further mixed by sonication with an ultrasonic probe. The resulting mixture was transferred to a syringe needle connected to a HP7x syringe adapter, which is connected to an EFD pump, which is in turn connected to a compressed air system and the delivery pressure set to 40 psi. The silicone-latanoprost mixture is then extruded down the length (10 cm) of polyimide tubing (IWG High Performance Conductors, Inc.). When the viscous mixture reached the bottom of polyimide tubing, clamps were applied at the bottom of the tubing and at the top connection with the syringe adapter, then pressure is released and the tubing section removed. The clamped section of tubing was placed in a humidity chamber (Thunder Scientific) for curing at 40° C. and 80% relative humidity (RH) for approximately 16-24 hrs.

To process the filled polyimide tubing containing the now-solid matrix containing the latanoprost into individual drug inserts, the filled precursor sheath was then cut into 1 mm segments with a jig and a razor blade. One end of each of the 1 mm segments was then sealed with Loctite 4305 UV Flash cure adhesive, and cured with a Loctite UV wand. Each of the segments at this point was ready for insertion into a punctual plug (Quintess) adapted to receive the insert, sealed end inward.

Results

Scanning electron micrographs of the sheath containing the cured matrix, i.e., the filled precursor sheath, are shown in FIG. 15A-D at the magnifications indicated. The inserts were sectioned cryogenically. FIGS. 15A and 15B, respectively, show the insert cores wherein the extrusion was carried at 40° C. (A) or 25° C. (B).

Example 13

The temperature of the mixture, and of the associated apparatus involved in filling the polyimide sheath was held at various temperatures during the injection process. Among the temperatures used were a slightly elevated temperature (40° C.), approximate room temperature (25° C.), and subambient temperatures, such as 0° C., −5° C., and −25° C. The subambient injection procedures are provided in this Example.

Manufacture of Latanprost/Silicone Mixture

The silicone formulation (MED6385) is a two part system. Part A contains the silicone and crosslinker while Part B contains the tin catalyst to promote crosslinking. The two parts are combined in a final ratio of 200:1 (Part A:Part B). The required amounts of Latanoprost, MED6385 Part A and B are weighed onto a glass slide and mixed for approximately 2 minutes using a plastic mini spatula. The weight or volume of components required to prepare 50 mg of mixture to be extruded is presented in the Table below.

Ratio of Components

| Strength (µg latanoprost/'plug) | Part A (mg) | Part B (µL) | Latanoprost (mg) |
|---|---|---|---|
| 3.5 | 47.8 | 0.21 | 2.2 |
| 14 | 41.1 | 0.18 | 8.9 |
| 21 | 36.7 | 0.16 | 13.3 |

Extrusion into Polyimide Tubing
Preparation of Syringe Extrusion System 15 cm sections are threaded through a plastic luer adaptor and glued in place using Loctite 4304 UV flash cure adhesive (FIG. 2). A 1 mL syringe (Henke Sass Wolf NORMJect) is modified by cutting the tip of the plunger flush. The previously assembled tubing/adaptor piece is inserted into the syringe barrel and threaded through the luer outlet and fitted in place.

Extrusion

After the silicone/latanoprost mixing is complete, the mixture is loaded in the barrel of the syringe extrusion system. The plunger is inserted and excess air is removed. The syringe is then ready to be loaded into the chilled extrusion apparatus. The apparatus is an all stainless steel jacketed tube in a tube sanitary welded heat exchanger and includes a gas purge that is internally cooled by coiling inside the coolant side of the heat exchanger. The operating temperature setpoint of the cooling system shall be −10° C. The temperature inside the heat exchanger shall be uniform +/−2.5° C. over the useable length of the polyimide tubing. The steady state temperature of the cooling system is to be verified prior to insertion of syringe and tubing.

After setup, the EFD is activated and a silicone latanoprost mixture is extruded down the length of the polyimide tubing.

Once the mixture reaches the bottom of the tubing, it can be visually detected. The syringe including tubing is quickly removed from the cooling system. The syringe is removed by cutting the tubing with a razor blade; then the tubing is clamped on both ends.

Curing

The clamped section of tubing is placed in a humidity chamber (Thunder Scientific) to be cured at 40° C. and 80% RH for approximately 16-24 hours.

Results

Scanning electron micrographs of the sheath containing the cured matrix, i.e., the filled precursor sheath, are shown in FIG. 15A-D at the magnifications indicated. The inserts were sectioned cryogenically. FIGS. 15C and 15D show the results of extrusions carried out at 0° C. and −25° C. respectively. They can be compared with FIGS. 15A and 15B that were carried out at ambient temperature (25° C.) or above (40° C.).

Measurements of average inclusion diameters, and standard deviation thereof, are as shown:

Cold extrusion (−5° C.): 0.006±0.002 mm (n=40 inclusion)

Room temp (22° C.): 0.019±0.019 mm (n=40 inclusion)

Measurements of average latanoprost content (μg) per 1 mm section (core) divided (razor blade) from a filled precursor tube are as shown:

Cold extrusion (−5° C.): 20.9±0.5 (Average±SD) RSD=2.4

Room temperature (22° C.): 20.2±1.9 (Average±SD) RSD=9.4

Further Embodiments

While described above primarily with reference to treatment of an eye, embodiments of the drug release structures described herein may also find applications for treatment of a wide variety of tissues to treat a range of differing disease states. In some embodiments, these structures may be used for systemic and/or (more commonly) localized elution of a therapeutic agent to treat cancer. In embodiments used for chemotherapy, the matrix may be configured to release of a therapeutic cocktail that is dependent upon the primary tumor type. Use of a local delivery may be particularly beneficial for treating a tumor site post-surgically, and may help minimizing side effects and collateral damage to healthy tissues of the body. In some embodiments, a lumpectomy for breast tumor and/or surgical treatment of prostate cancer can be treated. In many embodiments, a tumor is targeted with positioning of the matrix within and/or adjacent the targeted tumor. In some embodiments, the implant may comprise a radioactive agent to treat the tumor in combination with the therapeutic agent.

Still further alternative embodiments may facilitate elution of a therapeutic agent into a tissue of an ear, into a mouth, into a urethra, into a skin, into a knee joint (or other joint) of a patient, or the like. Conditions of joints that can be treated include arthritis and other joint diseases, and the therapeutic agents that may be used may comprise (for example) at least one COX II inhibitor, NSAIDs, and/or the like. Such localized use of NSAIDs and COX II inhibitors may reduce the risks associated with systemic use of these compounds. In some embodiments, the matrix may comprise nutritional supplements like glucosamine to effect a positive physiological response in local tissue of and/or near the joint. Implants for elution of therapeutic agents into or adjacent an intervertebral joint may be particularly advantageous. Similar (or other) pain relievers, antibiotics, antimicrobials, and/or the like may also be included in an implant for elution of one or more therapeutic agent into a localized trauma. Implants (optionally implants having structures derived from the punctual implants described above may allow elution of one or more therapeutic agent into a nasal cavity. Modifications or differences between such nasal implants and the punctual implants described above may include providing a passage for controlled release of medicated tear fluid through the canilicular lumen. Alternative nasal tissue structures may be quite different in overall form, optionally including any of a variety of known nasal cavity drug release shapes, but optionally taking advantage of one or more aspects of the drug cores or other drug release structures described above for long term release of one or more appropriate therapeutic agents.

Still further alternative embodiments find application in cosmetic uses. For example, these uses include administration of a prostaglandin to enhance eye lash growth.

While the exemplary embodiments have been described in some detail, by way of example and for clarity of understanding, those of skill in the art will recognize that a variety of modification, adaptations, and changes may be employed. For example, multiple delivery mechanisms may be employed, and each device embodiment may be adapted to include features or materials of the other, and further multiple features or multiple materials may be employed in a single device. Hence, the scope of the present invention may be limited solely by the appending claims.

What is claimed is:

1. A method of manufacturing a drug insert for an implant body adapted for disposition within or adjacent to a body cavity, tissue, duct or fluid of a patient, the method comprising injecting into a precursor sheath body, at an extrusion temperature of less than about 15° C., a mixture comprising latanoprost and a silicone matrix such that the precursor sheath body is substantially filled therewith, the precursor sheath body being substantially impermeable to the latanoprost, curing the mixture, at a curing temperature greater than about 25° C., in the precursor sheath body to provide a cured, filled precursor sheath body containing a precursor drug core; and dividing the cured filled precursor sheath body to form a plurality of drug inserts, wherein the drug inserts comprise inclusions of the latanoprost with an average diameter of less than about 10 μm.

2. The method of claim 1, wherein each of the plurality of drug inserts is of substantially the same length, and wherein an amount of the latanoprost in a first insert of the plurality is similar to the amount of agent in any other insert of the plurality.

3. The method of claim 1, wherein the implant is adapted for disposition in or adjacent to an eye of a patient.

4. The method of claim 1, wherein the amount of the latanoprost in a volumetric portion of the cured mixture varies from the amount of the latanoprost in any other equal volumetric portion of the cured mixture by no greater than about 10%.

5. The method of claim 1, wherein the amount of the latanoprost in a volumetric portion of the cured mixture varies from the amount of the latanoprost in any other equal volumetric portion of the cured mixture by no greater than about 5%.

6. The method of claim 1, wherein the amount of the latanoprost in each of the plurality of drug inserts varies by no greater than about 10% therebetween.

7. The method of claim 1, wherein the amount of the latanoprost in each of the plurality of drug inserts varies by no greater than about 5% therebetween.

8. The method of claim 1, wherein said dividing the cured filled precursor sheath body comprises cutting the cured filled precursor sheath body with a blade or with a laser.

9. The method of claim 1, wherein the implant body comprises a punctal plug adapted to be disposed within the punctum of the patient.

10. The method of claim 1, wherein said curing comprises placing the precursor sheath body in a humidity chamber, heating, or vacuum treatment.

11. The method of claim 1, wherein said curing the mixture comprises heating the mixture to the curing temperature, at a relative humidity, for a period of time.

12. The method of claim 11, wherein the curing temperature is in a range from about 25° C. to about 100° C., the relative humidity is in a range from about 30% to about 100%, and the period of time is in a range from about 1 minute to about 48 hours.

13. The method of claim 12, wherein the curing temperature is at least about 40° C., or the relative humidity is at least about 80%, or both.

14. The method of claim 1, wherein said injecting comprises injecting under a pressure of at least about 40 psi.

15. The method of claim 1, wherein the extrusion temperature is in a range of about −50° C. to about 15° C.

16. The method of claim 15, wherein the extrusion temperature is in a range of about −10° C. to about 10° C.

17. The method of claim 1, wherein the mixture is injected such that the precursor sheath body is filled at a rate of no greater than about 0.5 cm/sec.

18. The method of claim 1, further comprising sealing each drug insert at one end thereof, a second end providing the exposed surface.

19. The method of claim 18, wherein each drug insert is sealed at one end thereof with a UV-curable adhesive, a cyanoacrylate, an epoxy, by pinching, with a heat weld, or with a cap.

20. The method of claim 19, further comprising irradiating the drug insert with a UV-curable adhesive with UV light.

21. The method of claim 19, further comprising, after sealing one end thereof, inserting each drug insert into a channel of an implant body adapted to receive the insert therein.

22. The method of claim 1, wherein the insert comprises about 0.1 wt % to about 50 wt % of the latanoprost.

23. The method of claim 1, wherein the precursor sheath body comprises at least one of polyimide, PMMA, PET, stainless steel, or titanium.

24. The method of claim 1, wherein the latanoprost is dispersed within the silicone as droplets thereof.

25. The method of claim 1, wherein the extrusion temperature comprises a temperature of less than about 10° C.

26. The method of claim 1, wherein the extrusion temperature comprises a temperature of less than about 5° C.

27. A method for manufacturing a punctual plug, the method comprising:
- injecting into a precursor sheath body, at an extrusion temperature of less than about 15° C., a mixture comprising latanoprost and a silicone matrix such that the precursor sheath body is substantially filled therewith, the precursor sheath body being substantially impermeable to the latanoprost,
- curing the mixture, at a curing temperature greater than about 25° C., in the precursor sheath body to provide a cured, filled precursor sheath body containing a precursor drug core;
- dividing the cured filled precursor sheath to form a plurality of drug inserts;
- sealing each drug insert at one end of the drug insert; and
- inserting each drug insert into a channel of an implant body adapted to receive the insert therein, wherein the drug inserts comprise inclusions of the latanoprost with an average diameter of less than about 10 μm.

* * * * *